United States Patent
Stokes et al.

(10) Patent No.: US 10,856,897 B2
(45) Date of Patent: *Dec. 8, 2020

(54) FEATURES TO DRIVE FLUID TOWARD AN ULTRASONIC BLADE OF A SURGICAL INSTRUMENT

(71) Applicant: ETHICON LLC, Guaynabo, PR (US)

(72) Inventors: Michael J. Stokes, Cincinnati, OH (US); Ryan M. Asher, Cincinnati, OH (US); Charles J. Scheib, Loveland, OH (US); Rudolph H. Nobis, Mason, OH (US); Frederick L. Estera, Cincinnati, OH (US); Benjamin D. Dickerson, Cincinnati, OH (US); Carl J. Draginoff, Jr., Mason, KY (US); Jeffrey D. Messerly, Cincinnati, OH (US); David J. Cagle, Cincinnati, OH (US); Jacob S. Gee, Cincinnati, OH (US); William B. Weisenburgh, II, Maineville, OH (US); Omar E. Rios Perez, Beaumont, TX (US); Chester O. Baxter, III, Loveland, OH (US); Benjamin M. Boyd, Fairborn, OH (US); Rafael J. Ruiz Ortiz, Mason, OH (US); Joël Fontannaz, Bulle (CH); Lukas Glutz, Bern (CH); Amir Feriani, Auvernier (CH); Emmanuel Gremion, Echarlens (CH)

(73) Assignee: Ethicon LLC, Guaynabo, PR (US)

( * ) Notice: Subject to any disclaimer, the term of this patent is extended or adjusted under 35 U.S.C. 154(b) by 65 days.

This patent is subject to a terminal disclaimer.

(21) Appl. No.: 15/972,846

(22) Filed: May 7, 2018

(65) Prior Publication Data
US 2019/0000499 A1  Jan. 3, 2019

Related U.S. Application Data

(62) Division of application No. 14/553,329, filed on Nov. 25, 2014, now Pat. No. 10,004,529.

(51) Int. Cl.
*A61B 17/32* (2006.01)
*A61B 17/28* (2006.01)
(Continued)

(52) U.S. Cl.
CPC ........... *A61B 17/320092* (2013.01); *A61B 2017/2825* (2013.01); *A61B 2017/2929* (2013.01);
(Continued)

(58) Field of Classification Search
CPC .. A61B 17/320092; A61B 2018/00011; A61B 2017/320084
See application file for complete search history.

(56) References Cited

U.S. PATENT DOCUMENTS

| 5,322,055 A | 6/1994 | Davison et al. |
| 5,324,299 A | 6/1994 | Davison et al. |

(Continued)

FOREIGN PATENT DOCUMENTS

| JP | 2014-000311 A | 1/2014 |
| WO | WO 2012/116957 A1 | 9/2012 |

(Continued)

OTHER PUBLICATIONS

International Search Report and Written Opinion dated Feb. 24, 2016 for Application No. PCT/US2015/061554, 11 pgs.

(Continued)

*Primary Examiner* — Anh T Dang
(74) *Attorney, Agent, or Firm* — Frost Brown Todd LLC

(57) ABSTRACT

A surgical apparatus comprises a body, a user input feature, a shaft assembly, an end effector, and a blade cooling system. The end effector comprises a clamp arm and an ultrasonic blade that may be coupled with an ultrasonic transducer. The clamp arm is configured to pivot toward and away from the ultrasonic blade. The cooling system is (Continued)

operable to deliver liquid coolant to the ultrasonic blade to thereby cool the ultrasonic blade. The user input feature is operable to both actuate the clamp arm and actuate the cooling system.

20 Claims, 85 Drawing Sheets

(51) Int. Cl.
*A61B 17/29* (2006.01)
*A61B 18/00* (2006.01)

(52) U.S. Cl.
CPC ............ *A61B 2017/320084* (2013.01); *A61B 2017/320093* (2017.08); *A61B 2017/320094* (2017.08); *A61B 2017/320095* (2017.08); *A61B 2018/00011* (2013.01)

(56) References Cited

U.S. PATENT DOCUMENTS

| | | | |
|---|---|---|---|
| 5,873,873 A | 2/1999 | Smith et al. |
| 5,980,510 A | 11/1999 | Tsonton et al. |
| 6,056,735 A | 5/2000 | Okada et al. |
| 6,193,709 B1 | 2/2001 | Miyawaki et al. |
| 6,283,981 B1 | 9/2001 | Beaupre |
| 6,309,400 B2 | 10/2001 | Beaupre |
| 6,325,811 B1 | 12/2001 | Messerly |
| 6,358,267 B1 | 3/2002 | Murakami et al. |
| 6,423,082 B1 | 7/2002 | Houser et al. |
| 6,773,444 B2 | 8/2004 | Messerly |
| 6,783,524 B2 | 8/2004 | Anderson et al. |
| 7,066,936 B2 | 6/2006 | Ryan |
| 7,074,219 B2 | 7/2006 | Levine et al. |
| 7,235,073 B2 | 6/2007 | Levine et al. |
| 7,344,533 B2 | 3/2008 | Pearson et al. |
| 7,563,269 B2 | 7/2009 | Hashiguchi |
| 7,780,659 B2 | 8/2010 | Okada et al. |
| 8,057,498 B2 | 11/2011 | Robertson |
| 8,328,834 B2 | 12/2012 | Isaacs et al. |
| 8,348,880 B2 | 1/2013 | Messerly et al. |
| 8,388,647 B2 | 3/2013 | Nau, Jr. et al. |
| 8,444,663 B2 | 5/2013 | Houser et al. |
| 8,461,744 B2 | 6/2013 | Wiener et al. |
| 8,591,459 B2 | 11/2013 | Clymer et al. |
| 8,591,536 B2 | 11/2013 | Robertson |
| 8,623,027 B2 | 1/2014 | Price et al. |
| 8,652,132 B2 | 2/2014 | Tsuchiya et al. |
| 8,662,745 B2 | 3/2014 | Misuchenko et al. |
| 8,685,020 B2 | 4/2014 | Weizman et al. |
| 8,911,460 B2 | 12/2014 | Neurohr et al. |
| 8,974,447 B2 | 3/2015 | Kimball et al. |
| 8,974,478 B2 | 3/2015 | Ross et al. |
| 8,986,302 B2 | 3/2015 | Aldridge et al. |
| 9,005,199 B2 | 4/2015 | Beckman et al. |
| 9,023,071 B2 | 5/2015 | Miller et al. |
| 9,044,261 B2 | 6/2015 | Houser |
| 9,050,100 B2 | 6/2015 | Yates et al. |
| 9,084,878 B2 | 7/2015 | Kawaguchi et al. |
| 9,095,367 B2 | 8/2015 | Olson et al. |
| 9,113,943 B2 | 8/2015 | Ross et al. |
| 9,283,045 B2 | 3/2016 | Rhee et al. |
| 9,375,230 B2 | 6/2016 | Ross et al. |
| 9,381,058 B2 | 7/2016 | Houser et al. |
| 9,393,037 B2 | 7/2016 | Olson et al. |
| 9,795,379 B2 | 10/2017 | Leimbach et al. |
| 9,993,260 B2 | 6/2018 | Stokes et al. |
| 10,004,527 B2 | 6/2018 | Gee et al. |
| 10,004,528 B2 | 6/2018 | Faller et al. |
| 10,004,529 B2 | 6/2018 | Stokes et al. |
| 10,034,685 B2 | 7/2018 | Boudreaux et al. |
| 2006/0079874 A1 | 4/2006 | Faller et al. |
| 2006/0265035 A1 | 11/2006 | Yachi et al. |
| 2007/0191713 A1 | 8/2007 | Eichmann et al. |
| 2007/0282333 A1 | 12/2007 | Fortson et al. |
| 2008/0200940 A1 | 8/2008 | Eichmann et al. |
| 2010/0331873 A1 | 12/2010 | Dannaher et al. |
| 2012/0116265 A1 | 5/2012 | Houser et al. |
| 2013/0090576 A1 | 4/2013 | Stulen et al. |
| 2014/0012298 A1 | 1/2014 | Cunningham et al. |
| 2014/0012299 A1 | 1/2014 | Stoddard et al. |
| 2014/0135804 A1 | 5/2014 | Weisenburgh et al. |
| 2014/0180002 A1 | 6/2014 | Voic |
| 2015/0080924 A1 | 3/2015 | Stulen et al. |
| 2016/0143657 A1 | 5/2016 | Estera et al. |
| 2016/0143659 A1 | 5/2016 | Glutz et al. |

FOREIGN PATENT DOCUMENTS

| | | |
|---|---|---|
| WO | WO 2013/183715 A1 | 12/2013 |
| WO | WO 2013/190937 A1 | 12/2013 |
| WO | WO 2013/062103 A1 | 4/2015 |

OTHER PUBLICATIONS

U.S. Appl. No. 61/410,603, filed Nov. 5, 2010.
U.S. Appl. No. 61/908,920, filed Nov. 26, 2013.
Chinese Office Action, The First Office Action, and First Search Report, dated May 24, 2019 for Application No. CN 201580064146.5, 10 pgs.
Chinese Search Report, Supplementary, dated Dec. 12, 2019 for Application No. CN 201580064146.5, 1 pg.

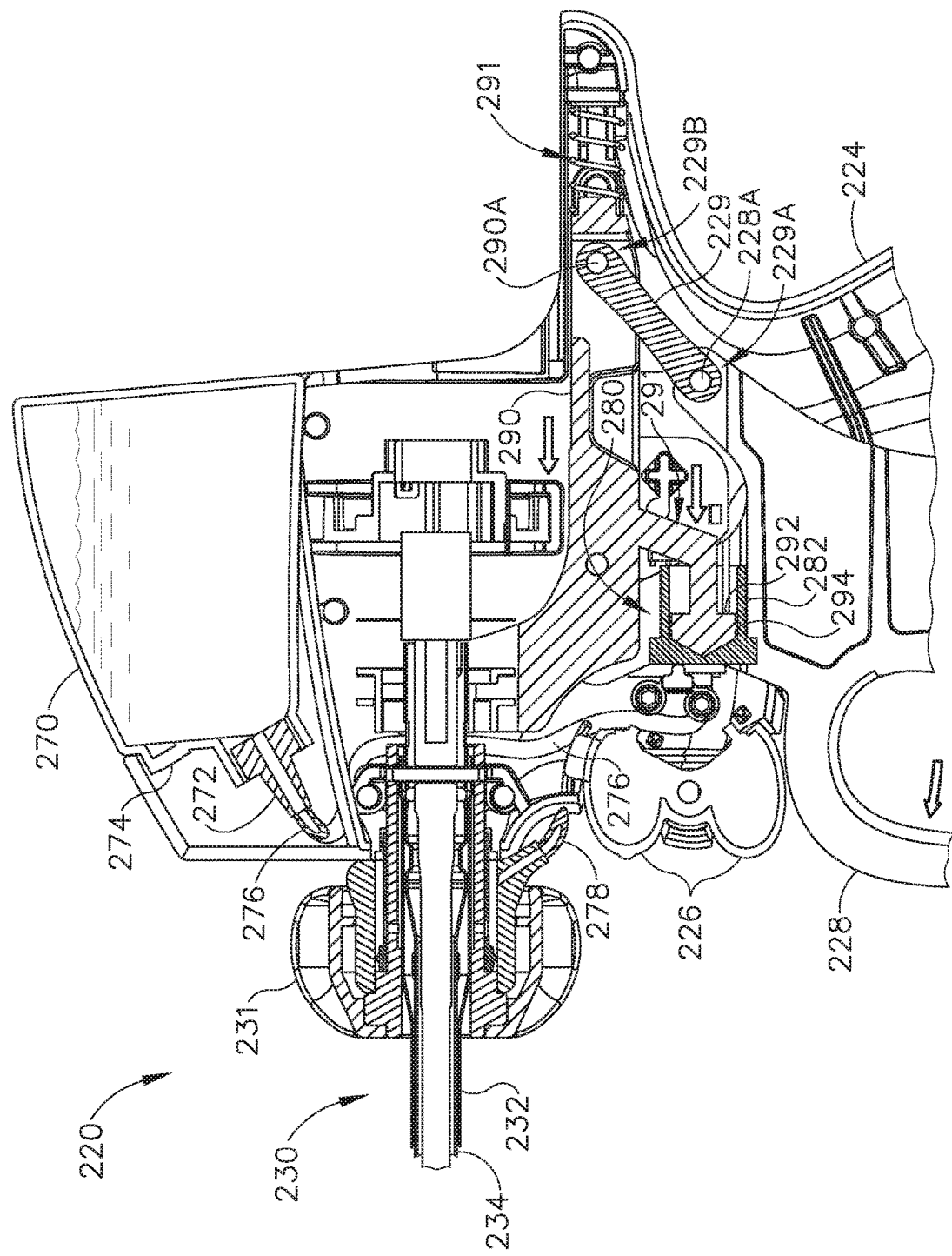

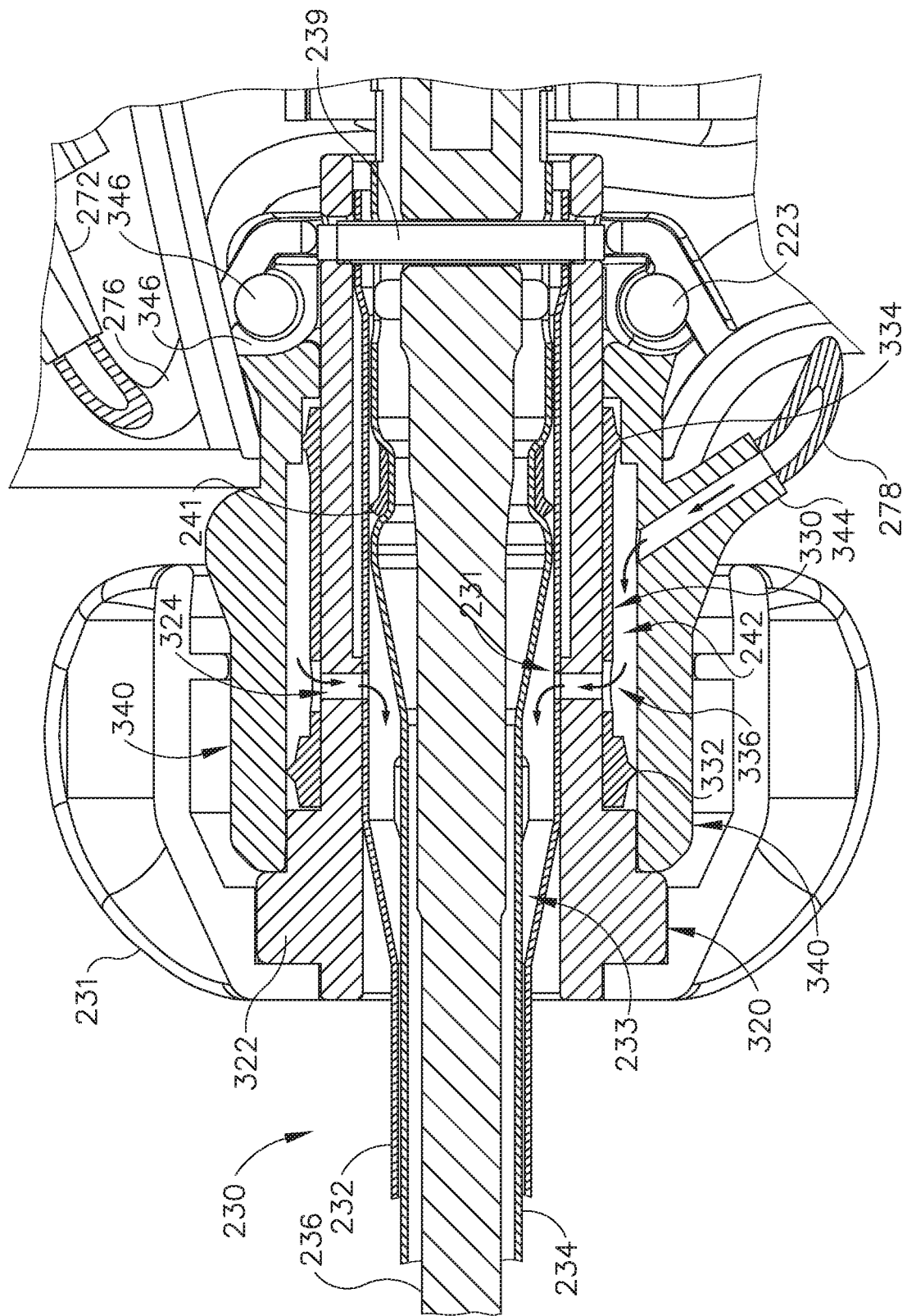

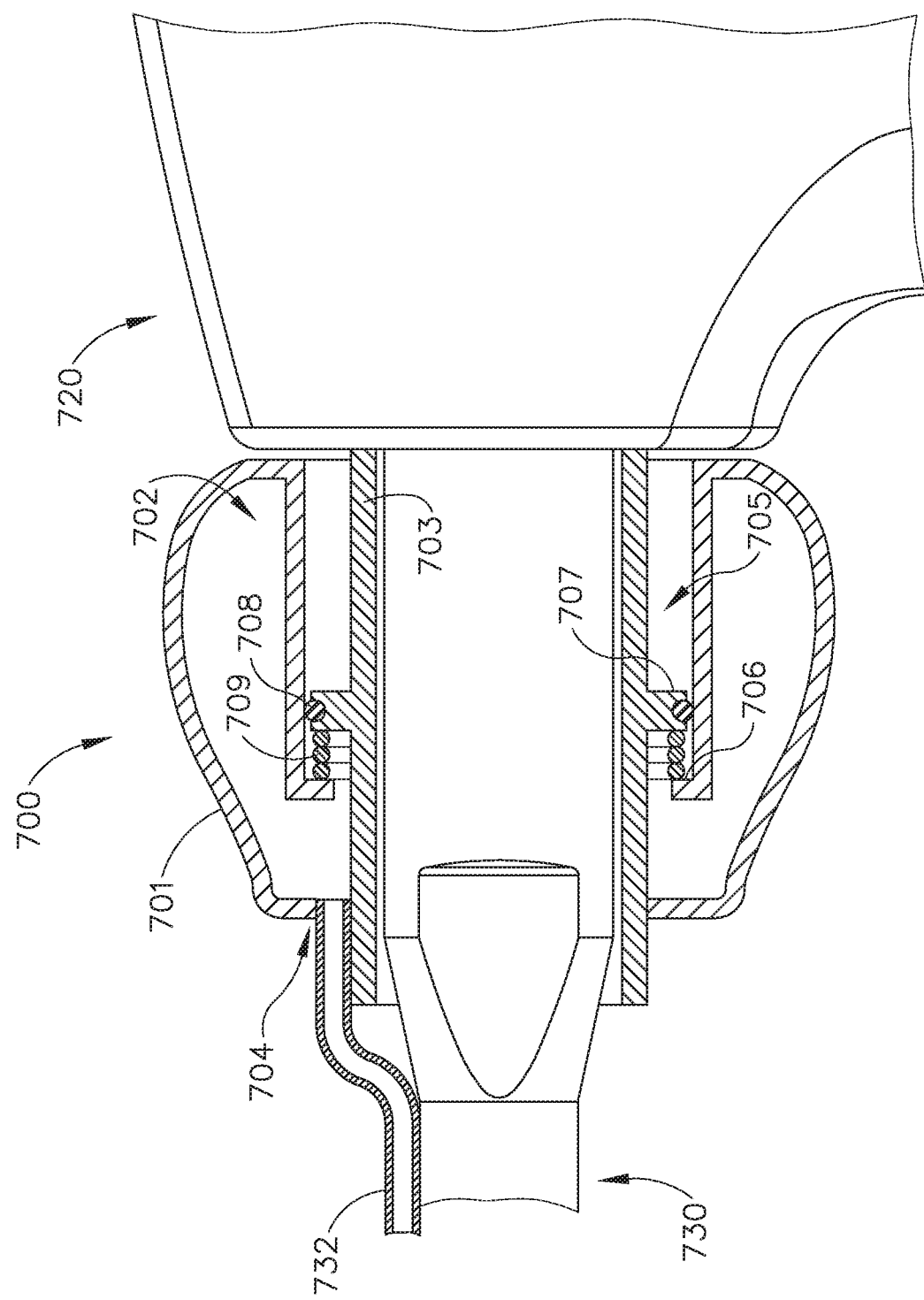

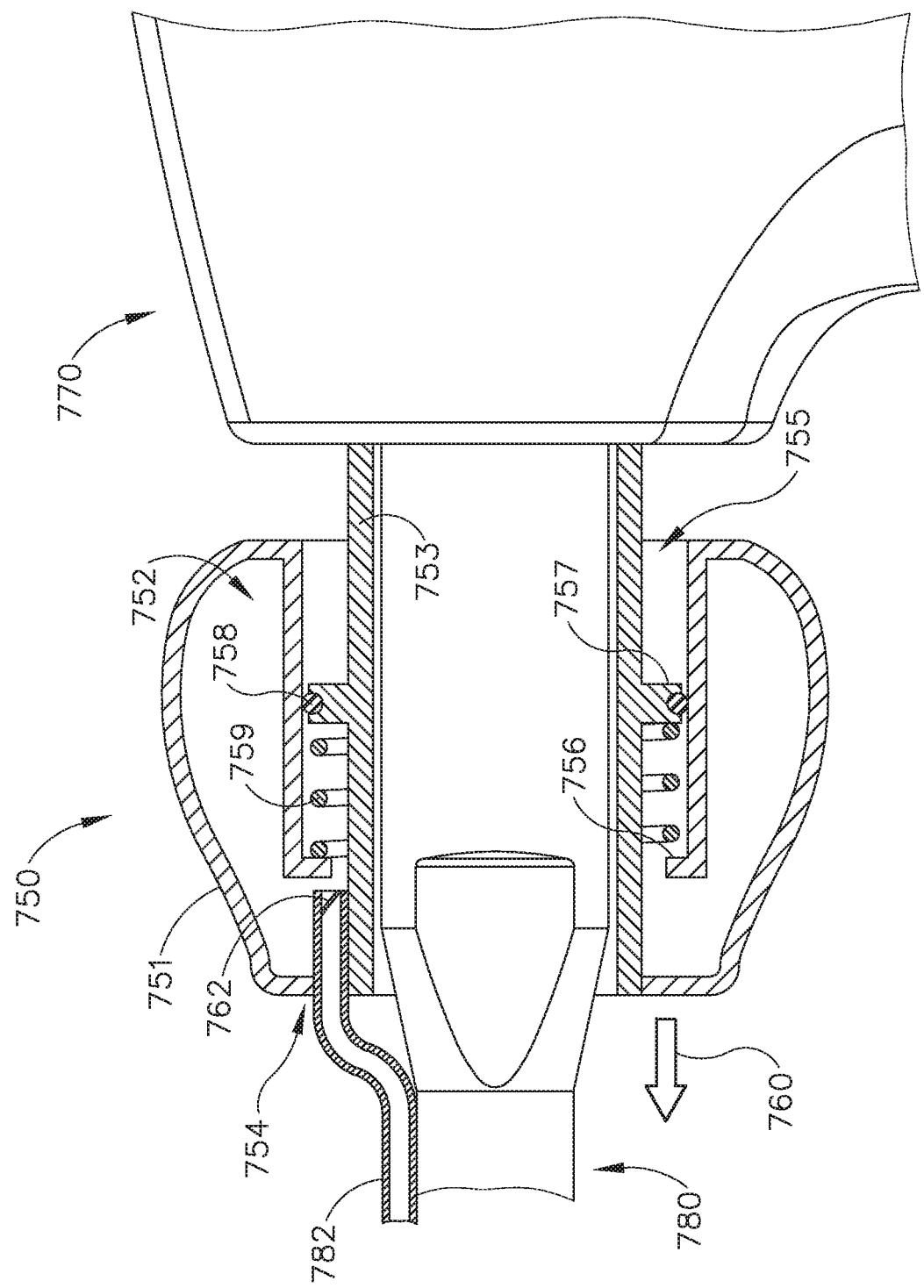

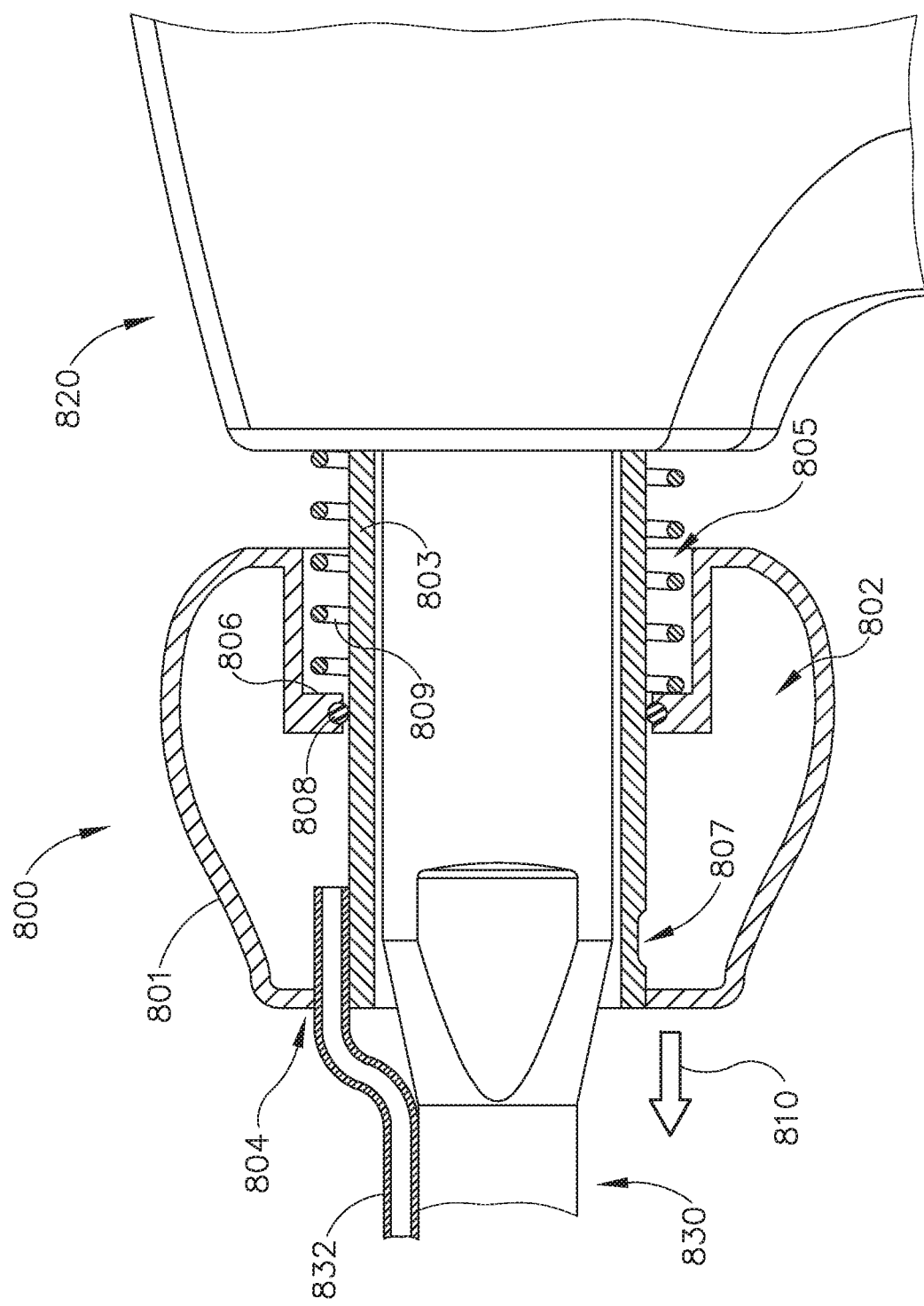

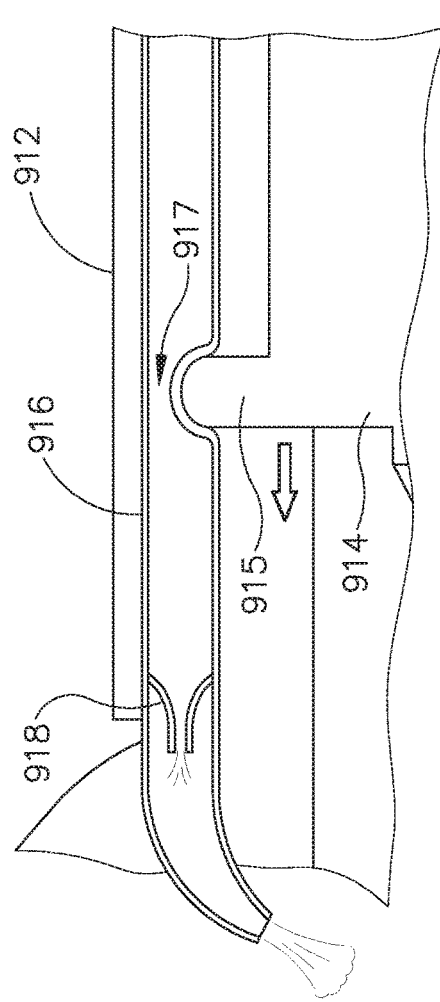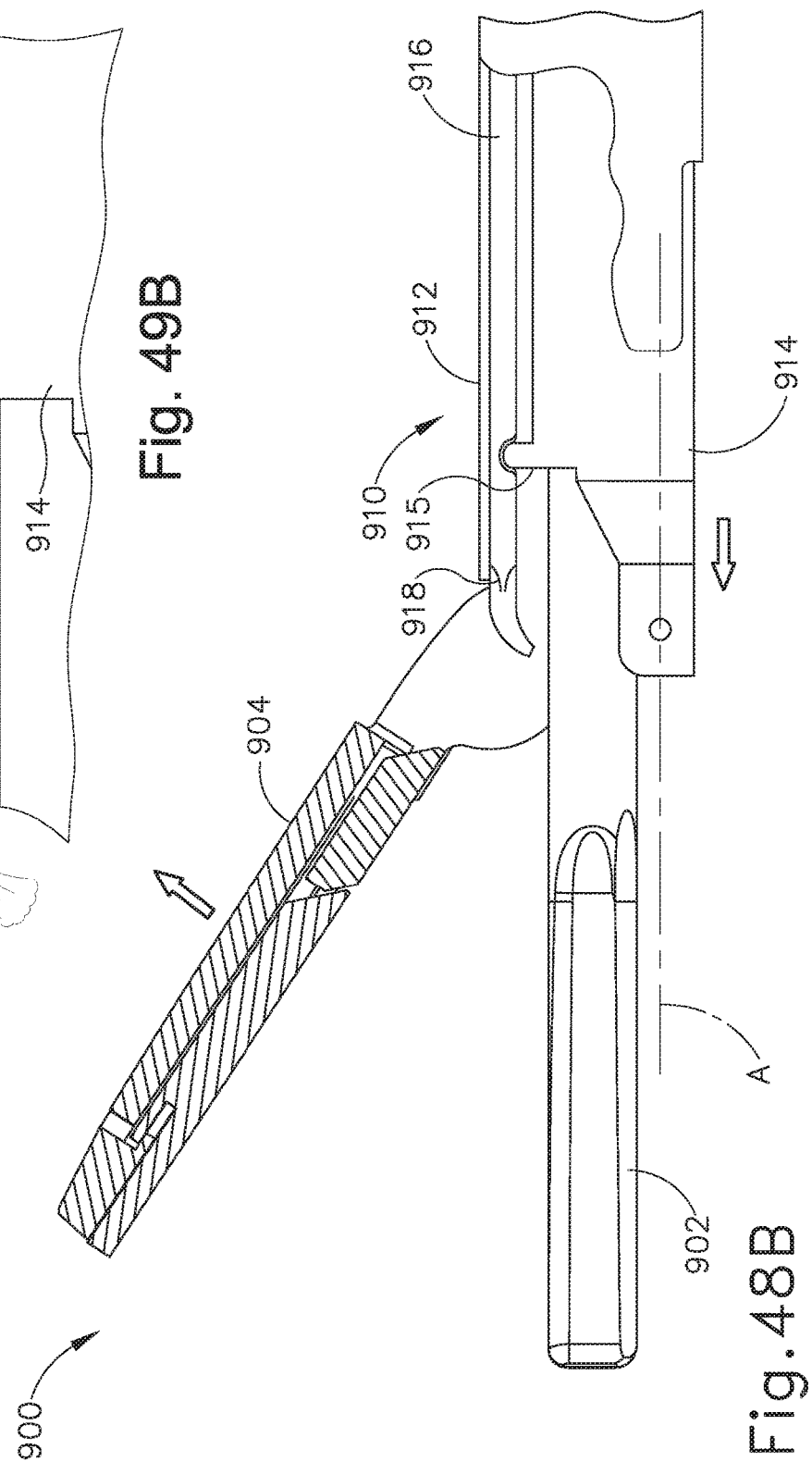

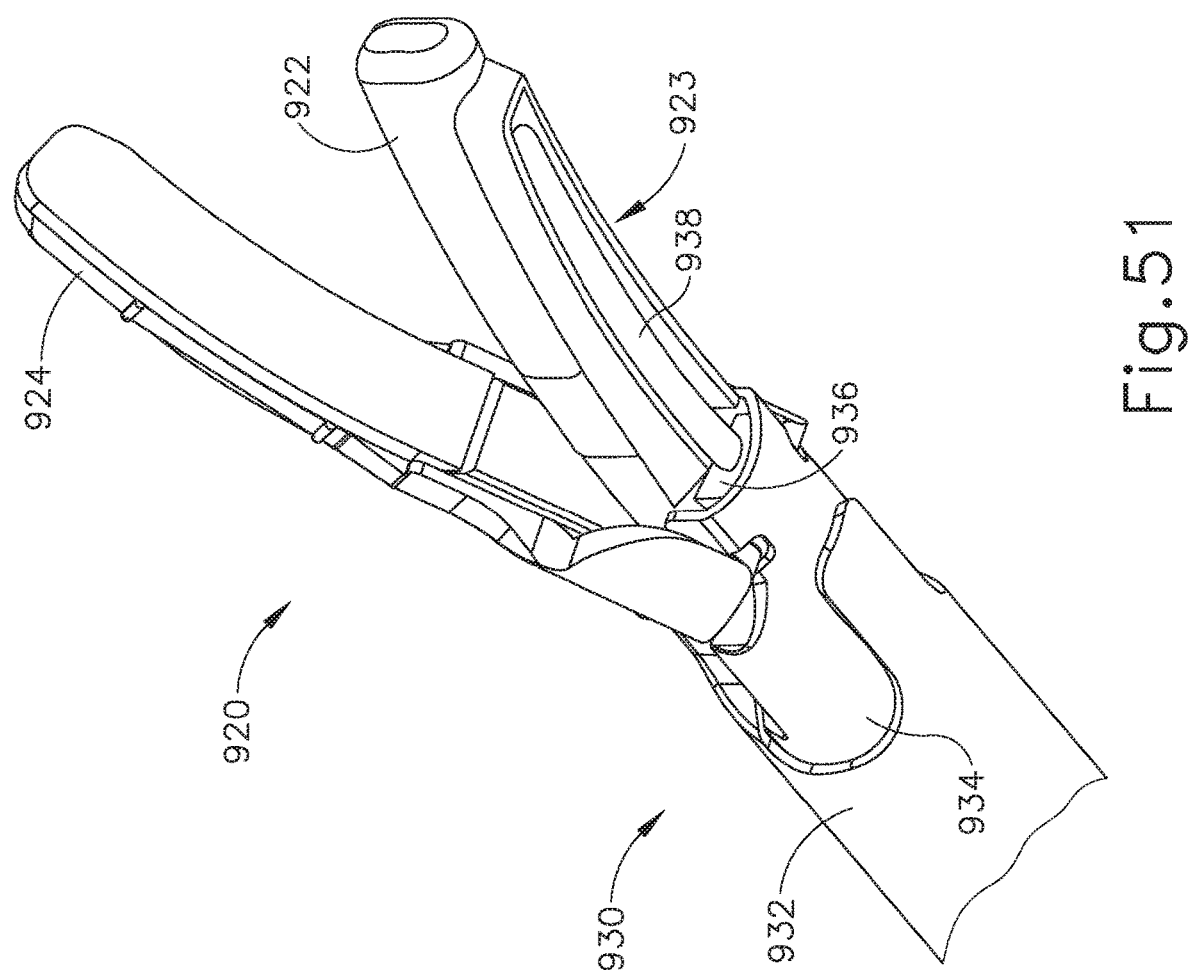

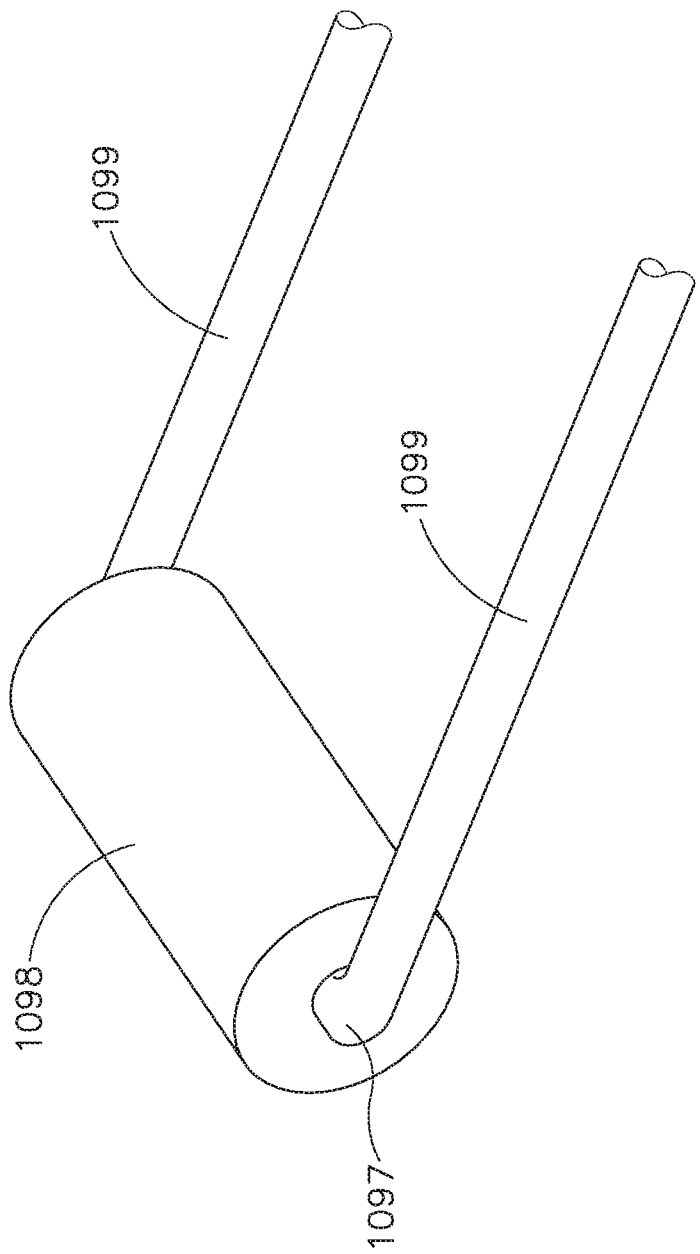

FEATURES TO DRIVE FLUID TOWARD AN ULTRASONIC BLADE OF A SURGICAL INSTRUMENT

This application is a divisional of U.S. patent application Ser. No. 14/553,329, entitled "Features to Drive Fluid Toward an Ultrasonic Blade of a Surgical Instrument," filed Nov. 25, 2014 and issued as U.S. Pat. No. 10,004,529 on Jun. 26, 2018.

BACKGROUND

A variety of surgical instruments include an end effector having a blade element that vibrates at ultrasonic frequencies to cut and/or seal tissue (e.g., by denaturing proteins in tissue cells). These instruments include one or more piezoelectric elements that convert electrical power into ultrasonic vibrations, which are communicated along an acoustic waveguide to the blade element. The precision of cutting and coagulation may be controlled by the operator's technique and adjusting the power level, blade edge angle, tissue traction, and blade pressure.

Examples of ultrasonic surgical instruments include the HARMONIC ACE® Ultrasonic Shears, the HARMONIC WAVE® Ultrasonic Shears, the HARMONIC FOCUS® Ultrasonic Shears, and the HARMONIC SYNERGY® Ultrasonic Blades, all by Ethicon Endo-Surgery, Inc. of Cincinnati, Ohio. Further examples of such devices and related concepts are disclosed in U.S. Pat. No. 5,322,055, entitled "Clamp Coagulator/Cutting System for Ultrasonic Surgical Instruments." issued Jun. 21, 1994, the disclosure of which is incorporated by reference herein; U.S. Pat. No. 5,873,873, entitled "Ultrasonic Clamp Coagulator Apparatus Having Improved Clamp Mechanism," issued Feb. 23, 1999, the disclosure of which is incorporated by reference herein; U.S. Pat. No. 5,980,510, entitled "Ultrasonic Clamp Coagulator Apparatus Having Improved Clamp Arm Pivot Mount," issued Nov. 9, 1999, the disclosure of which is incorporated by reference herein; U.S. Pat. No. 6,283,981, entitled "Method of Balancing Asymmetric Ultrasonic Surgical Blades," issued Sep. 4, 2001, the disclosure of which is incorporated by reference herein; U.S. Pat. No. 6,309,400, entitled "Curved Ultrasonic Blade having a Trapezoidal Cross Section," issued Oct. 30, 2001, the disclosure of which is incorporated by reference herein; U.S. Pat. No. 6,325,811, entitled "Blades with Functional Balance Asymmetries for use with Ultrasonic Surgical Instruments," issued Dec. 4, 2001, the disclosure of which is incorporated by reference herein; U.S. Pat. No. 6,423,082, entitled "Ultrasonic Surgical Blade with Improved Cutting and Coagulation Features," issued Jul. 23, 2002, the disclosure of which is incorporated by reference herein; U.S. Pat. No. 6,773,444, entitled "Blades with Functional Balance Asymmetries for Use with Ultrasonic Surgical Instruments," issued Aug. 10, 2004, the disclosure of which is incorporated by reference herein; U.S. Pat. No. 6,783,524, entitled "Robotic Surgical Tool with Ultrasound Cauterizing and Cutting Instrument," issued Aug. 31, 2004, the disclosure of which is incorporated by reference herein; U.S. Pat. No. 8,057,498, entitled "Ultrasonic Surgical Instrument Blades," issued Nov. 15, 2011, the disclosure of which is incorporated by reference herein; U.S. Pat. No. 8,461,744, entitled "Rotating Transducer Mount for Ultrasonic Surgical Instruments," issued Jun. 11, 2013, the disclosure of which is incorporated by reference herein; U.S. Pat. No. 8,591,536, entitled "Ultrasonic Surgical Instrument Blades," issued Nov. 26, 2013, the disclosure of which is incorporated by reference herein; and U.S. Pat. No. 8,623,027, entitled "Ergonomic Surgical Instruments," issued Jan. 7, 2014, the disclosure of which is incorporated by reference herein.

Still further examples of ultrasonic surgical instruments are disclosed in U.S. Pub. No. 2006/0079874, entitled "Tissue Pad for Use with an Ultrasonic Surgical Instrument," published Apr. 13, 2006, now abandoned, the disclosure of which is incorporated by reference herein; U.S. Pub. No. 2007/0191713, entitled "Ultrasonic Device for Cutting and Coagulating," published Aug. 16, 2007, now abandoned, the disclosure of which is incorporated by reference herein; U.S. Pub. No. 2007/0282333, entitled "Ultrasonic Waveguide and Blade," published Dec. 6, 2007, now abandoned, the disclosure of which is incorporated by reference herein; U.S. Pub. No. 2008/0200940, entitled "Ultrasonic Device for Cutting and Coagulating," published Aug. 21, 2008, now abandoned, the disclosure of which is incorporated by reference herein; U.S. Pub. No. 2008/0234710, entitled "Ultrasonic Surgical Instruments," published Sep. 25, 2008, now U.S. Pat. No. 8,911,460, issued Dec. 16, 2014, the disclosure of which is incorporated by reference herein; and U.S. Pub. No. 2010/0069940, entitled "Ultrasonic Device for Fingertip Control," published Mar. 18, 2010, now U.S. Pat. No. 9,023,071, issued May 5, 2015, the disclosure of which is incorporated by reference herein.

Some ultrasonic surgical instruments may include a cordless transducer such as that disclosed in U.S. Pub. No. 2012/0112687, entitled "Recharge System for Medical Devices," published May 10, 2012, now U.S. Pat. No. 9,381,058, issued Jul. 5, 2016, the disclosure of which is incorporated by reference herein; U.S. Pub. No. 2012/0116265, entitled "Surgical Instrument with Charging Devices," published May 10, 2012, now abandoned, the disclosure of which is incorporated by reference herein; and/or U.S. Pat. App. No. 61/410,603, filed Nov. 5, 2010, entitled "Energy-Based Surgical Instruments," the disclosure of which is incorporated by reference herein.

Additionally, some ultrasonic surgical instruments may include an articulating shaft section. Examples of such ultrasonic surgical instruments are disclosed in U.S. Pub. No. 2014/0005701, published Jan. 2, 2014, entitled "Surgical Instruments with Articulating Shafts," now U.S. Pat. No. 9,393,037, issued Jul. 19, 2016, the disclosure of which is incorporated by reference herein; and U.S. Pub. No. 2014/0114334, published Apr. 24, 2014, entitled "Flexible Harmonic Waveguides/Blades for Surgical Instruments," now U.S. Pat. No. 9,095,367, issued Aug. 4, 2015, the disclosure of which is incorporated by reference herein.

While several surgical instruments and systems have been made and used, it is believed that no one prior to the inventors has made or used the invention described in the appended claims.

BRIEF DESCRIPTION OF THE DRAWINGS

While the specification concludes with claims which particularly point out and distinctly claim this technology, it is believed this technology will be better understood from the following description of certain examples taken in conjunction with the accompanying drawings, in which like reference numerals identify the same elements and in which:

FIG. 25C depicts a side elevational view of the handle assembly of FIG. 7 with the housing shroud of FIG. 17 removed, with the yoke of FIG. 23 moved back into the first longitudinal position by movement of the trigger back to the first rotational position to thereby force fluid from the pump of FIG. 21;

FIG. 26 depicts a detailed cross-sectional side elevational view of the handle assembly of FIG. 7 and a shaft assembly of the instrument of FIG. 5, with fluid forced from the pump of FIG. 21 passing into an interior passageway of the shaft assembly;

FIG. 45B depicts a cross-sectional side view of the fluid pump of FIG. 44, with the rotation knob of FIG. 44 moved to a second longitudinal position;

FIG. 46A depicts a cross-sectional side view of another exemplary fluid pump operable for use with any of the instruments described herein, with a rotation knob of the fluid pump in a first longitudinal position, and with a flapper valve of the fluid pump in a closed position;

FIG. 47A depicts a cross-sectional side view of yet another exemplary fluid pump operable for use with any of the instruments described herein, with a rotation knob of the fluid pump in a first longitudinal position;

FIG. 48B depicts a cross-sectional side view of the fluid pump of FIG. 48A, with the roller of FIG. 48A moved to a second longitudinal position;

FIG. 49B depicts a detailed cross-sectional side view of the fluid pump of FIG. 48A, with the roller of FIG. 48A moved to the second longitudinal position;

FIG. 51 depicts a perspective view of the fluid pump of FIG. 50A;

FIG. 59 depicts a perspective view of a roller of yet another exemplary fluid delivery system;

Figure 1:
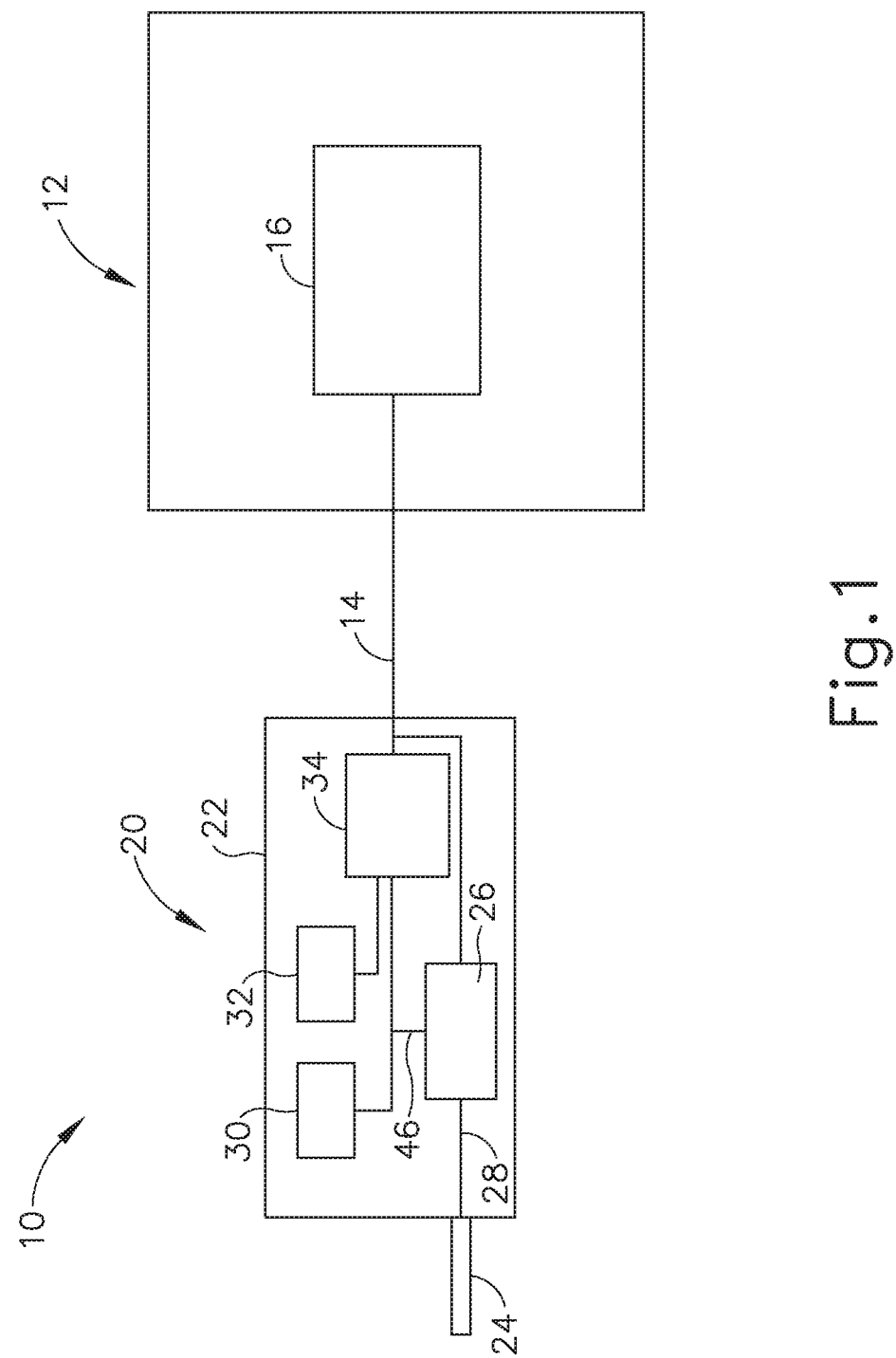
FIG. 1 depicts a block schematic view of an exemplary surgical system.

The drawings are not intended to be limiting in any way, and it is contemplated that various embodiments of the technology may be carried out in a variety of other ways, including those not necessarily depicted in the drawings. The accompanying drawings incorporated in and forming a part of the specification illustrate several aspects of the present technology, and together with the description serve to explain the principles of the technology; it being understood, however, that this technology is not limited to the precise arrangements shown.

DETAILED DESCRIPTION

The following description of certain examples of the technology should not be used to limit its scope. Other examples, features, aspects, embodiments, and advantages of the technology will become apparent to those skilled in the art from the following description, which is by way of illustration, one of the best modes contemplated for carrying out the technology. As will be realized, the technology described herein is capable of other different and obvious aspects, all without departing from the technology. Accordingly, the drawings and descriptions should be regarded as illustrative in nature and not restrictive.

It is further understood that any one or more of the teachings, expressions, embodiments, examples, etc. described herein may be combined with any one or more of the other teachings, expressions, embodiments, examples, etc. that are described herein. The following-described teachings, expressions, embodiments, examples, etc. should therefore not be viewed in isolation relative to each other. Various suitable ways in which the teachings herein may be combined will be readily apparent to those of ordinary skill in the art in view of the teachings herein. Such modifications and variations are intended to be included within the scope of the claims.

For clarity of disclosure, the terms "proximal" and "distal" are defined herein relative to an operator or other operator grasping a surgical instrument having a distal surgical end effector. The term "proximal" refers the position of an element closer to the operator or other operator and the term "distal" refers to the position of an element closer to the surgical end effector of the surgical instrument and further away from the operator or other operator.

I. Overview of Exemplary Ultrasonic Surgical System

FIG. 1 shows components of an exemplary surgical system (10) in diagrammatic block form. As shown, system (10) comprises an ultrasonic generator (12) and an ultrasonic surgical instrument (20). As will be described in greater detail below, instrument (20) is operable to cut tissue and seal or weld tissue (e.g., a blood vessel, etc.) substantially simultaneously, using ultrasonic vibrational energy. Generator (12) and instrument (20) are coupled together via cable (14). Cable (14) may comprise a plurality of wires; and may provide unidirectional electrical communication from generator (12) to instrument (20) and/or bidirectional electrical communication between generator (12) and instrument (20). By way of example only, cable (14) may comprise a "hot" wire for electrical power to surgical instrument (20), a ground wire, and a signal wire for transmitting signals from surgical instrument (20) to ultrasonic generator (12), with a shield surrounding the three wires. In some versions, separate "hot" wires are used for separate activation voltages (e.g., one "hot" wire for a first activation voltage and another "hot" wire for a second activation voltage, or a variable voltage between the wires proportional to the power requested, etc.). Of course, any other suitable number or configuration of wires may be used. It should also be understood that some versions of system (10) may incorporate generator (12) into instrument (20), such that cable (14) may simply be omitted.

By way of example only, generator (12) may comprise the GEN04, GEN11, or GEN 300 sold by Ethicon Endo-Surgery, Inc. of Cincinnati, Ohio. In addition or in the alternative, generator (12) may be constructed in accordance with at least some of the teachings of U.S. Pub. No. 2011/0087212, entitled "Surgical Generator for Ultrasonic and Electrosurgical Devices," published Apr. 14, 2011, now U.S. Pat. No. 8,986,302, issued Mar. 24, 2015, the disclosure of which is incorporated by reference herein. Alternatively, any other suitable generator (12) may be used. As will be described in greater detail below, generator (12) is operable to provide power to instrument (20) to perform ultrasonic surgical procedures.

Instrument (20) comprises a handpiece (22), which is configured to be grasped in one hand (or two hands) of an operator and manipulated by one hand (or two hands) of the operator during a surgical procedure. For instance, in some versions, handpiece (22) may be grasped like a pencil by the operator. In some other versions, handpiece (22) may include a scissor grip that may be grasped like scissors by the operator. In some other versions, handpiece (22) may include a pistol grip that may be grasped like a pistol by the operator. Of course, handpiece (22) may be configured to be gripped in any other suitable fashion. Furthermore, some versions of instrument (20) may substitute handpiece (22) with a body that is coupled to a robotic surgical system that is configured to operate instrument (20) (e.g., via remote control, etc.). In the present example, a blade (24) extends distally from the handpiece (22). Handpiece (22) includes an ultrasonic transducer (26) and an ultrasonic waveguide (28), which couples ultrasonic transducer (26) with blade (24). Ultrasonic transducer (26) receives electrical power from generator (12) via cable (14). By virtue of its piezoelectric properties, ultrasonic transducer (26) is operable to convert such electrical power into ultrasonic vibrational energy.

Ultrasonic waveguide (28) may be flexible, semi-flexible, rigid, or have any other suitable properties. As noted above, ultrasonic transducer (26) is integrally coupled with blade (24) via ultrasonic waveguide (28). In particular, when ultrasonic transducer (26) is activated to vibrate at ultrasonic frequencies, such vibrations are communicated through ultrasonic waveguide (28) to blade (24), such that blade (24) will also vibrate at ultrasonic frequencies. When blade (24) is in an activated state (i.e., vibrating ultrasonically), blade (24) is operable to effectively cut through tissue and seal tissue. Ultrasonic transducer (26), ultrasonic waveguide (28), and blade (24) together thus form an acoustic assembly providing ultrasonic energy for surgical procedures when powered by generator (12). Handpiece (22) is configured to substantially isolate the operator from the vibrations of the acoustic assembly formed by transducer (26), ultrasonic waveguide (28), and blade (24).

In some versions, ultrasonic waveguide (28) may amplify the mechanical vibrations transmitted through ultrasonic waveguide (28) to blade (24). Ultrasonic waveguide (28) may further have features to control the gain of the longitudinal vibration along ultrasonic waveguide (28) and/or features to tune ultrasonic waveguide (28) to the resonant frequency of system (10). For instance, ultrasonic waveguide (28) may have any suitable cross-sectional dimensions/configurations, such as a substantially uniform cross-section, be tapered at various sections, be tapered along its entire length, or have any other suitable configuration. Ultrasonic waveguide (28) may, for example, have a length substantially equal to an integral number of one-half system wavelengths (n$\lambda$/2). Ultrasonic waveguide (28) and blade (24) may be fabricated from a solid core shaft constructed out of a material or combination of materials that propagates ultrasonic energy efficiently, such as titanium alloy (i.e., Ti-6Al-4V), aluminum alloys, sapphire, stainless steel, or any other acoustically compatible material or combination of materials.

In the present example, the distal end of blade (24) is located at a position corresponding to an anti-node associated with resonant ultrasonic vibrations communicated through waveguide (28) (i.e., at an acoustic anti-node), in order to tune the acoustic assembly to a preferred resonant frequency $f_o$ when the acoustic assembly is not loaded by tissue. When transducer (26) is energized, the distal end of blade (24) is configured to move longitudinally in the range of, for example, approximately 10 to 500 microns peak-to-peak, and in some instances in the range of about 20 to about 200 microns at a predetermined vibratory frequency $f_o$ of, for example, 55.5 kHz. When transducer (26) of the present example is activated, these mechanical oscillations are transmitted through waveguide (28) to reach blade (24), thereby providing oscillation of blade (24) at the resonant ultrasonic frequency. Thus, the ultrasonic oscillation of blade (24) may simultaneously sever the tissue and denature the proteins in adjacent tissue cells, thereby providing a coagulative effect with relatively little thermal spread. In some versions, an electrical current may also be provided through blade (24) to also cauterize the tissue.

By way of example only, ultrasonic waveguide (28) and blade (24) may comprise components sold under product codes SNGHK and SNGCB by Ethicon Endo-Surgery, Inc. of Cincinnati, Ohio. By way of further example only, ultrasonic waveguide (28) and/or blade (24) may be constructed and operable in accordance with the teachings of U.S. Pat. No. 6,423,082, entitled "Ultrasonic Surgical Blade with Improved Cutting and Coagulation Features," issued Jul. 23, 2002, the disclosure of which is incorporated by reference herein. As another merely illustrative example, ultrasonic waveguide (28) and/or blade (24) may be constructed and operable in accordance with the teachings of U.S. Pat. No. 5,324,299, entitled "Ultrasonic Scalpel Blade and Methods of Application," issued Jun. 28, 1994, the disclosure of which is incorporated by reference herein. Other suitable properties and configurations of ultrasonic waveguide (28) and blade (24) will be apparent to those of ordinary skill in the art in view of the teachings herein.

Handpiece (22) of the present example also includes a control selector (30) and an activation switch (32), which are each in communication with a circuit board (34). By way of example only, circuit board (34) may comprise a conventional printed circuit board, a flex circuit, a rigid-flex circuit, or may have any other suitable configuration. Control selector (30) and activation switch (32) may be in communication with circuit board (34) via one or more wires, traces formed in a circuit board or flex circuit, and/or in any other suitable fashion. Circuit board (34) is coupled with cable (14), which is in turn coupled with control circuitry (16) within generator (12). Activation switch (32) is operable to selectively activate power to ultrasonic transducer (26). In particular, when switch (32) is activated, such activation provides communication of appropriate power to ultrasonic transducer (26) via cable (14). By way of example only, activation switch (32) may be constructed in accordance with any of the teachings of the various references cited herein. Other various forms that activation switch (32) may take will be apparent to those of ordinary skill in the art in view of the teachings herein.

In the present example, surgical system (10) is operable to provide at least two different levels or types of ultrasonic energy (e.g., different frequencies and/or amplitudes, etc.) at blade (24). To that end, control selector (30) is operable to permit the operator to select a desired level/amplitude of ultrasonic energy. By way of example only, control selector (30) may be constructed in accordance with any of the teachings of the various references cited herein. Other various forms that control selector (30) may take will be apparent to those of ordinary skill in the art in view of the teachings herein. In some versions, when an operator makes a selection through control selector (30), the operator's selection is communicated back to control circuitry (16) of generator (12) via cable (14), and control circuitry (16) adjusts the power communicated from generator (12) accordingly the next time the operator actuates activation switch (32).

It should be understood that the level/amplitude of ultrasonic energy provided at blade (24) may be a function of characteristics of the electrical power communicated from generator (12) to instrument (20) via cable (14). Thus, control circuitry (16) of generator (12) may provide electrical power (via cable (14)) having characteristics associated with the ultrasonic energy level/amplitude or type selected through control selector (30). Generator (12) may thus be operable to communicate different types or degrees of electrical power to ultrasonic transducer (26), in accordance with selections made by the operator via control selector (30). In particular, and by way of example only, generator (12) may increase the voltage and/or current of the applied signal to increase the longitudinal amplitude of the acoustic assembly. As a merely illustrative example, generator (12) may provide selectability between a "level 1" and a "level 5," which may correspond with a blade (24) vibrational resonance amplitude of approximately 50 microns and approximately 90 microns, respectively. Various ways in which control circuitry (16) may be configured will be apparent to those of ordinary skill in the art in view of the teachings herein. It should also be understood that control selector (30) and activation switch (32) may be substituted with two or more activation switches (32). In some such versions, one activation switch (32) is operable to activate blade (24) at one power level/type while another activation switch (32) is operable to activate blade (24) at another power level/type, etc.

In some alternative versions, control circuitry (16) is located within handpiece (22). For instance, in some such versions, generator (12) only communicates one type of electrical power (e.g., just one voltage and/or current available) to handpiece (22), and control circuitry (16) within handpiece (22) is operable to modify the electrical power (e.g., the voltage of the electrical power), in accordance with selections made by the operator via control selector (30), before the electrical power reaches ultrasonic transducer (26). Furthermore, generator (12) may be incorporated into handpiece (22) along with all other components of surgical system (10). For instance, one or more batteries (not shown) or other portable sources of power may be provided in handpiece (22). Still other suitable ways in which the components depicted in FIG. 1 may be rearranged or otherwise configured or modified will be apparent to those of ordinary skill in the art in view of the teachings herein.

II. Overview of Exemplary Ultrasonic Surgical Instrument

The following discussion relates to various exemplary components and configurations of instrument (20). It should be understood that the various examples of instrument (20) described below may be readily incorporated into surgical system (10) as described above. It should also be understood that the various components and operabilities of instrument (20) described above may be readily incorporated into the exemplary versions of instrument (20) described below. Various suitable ways in which the above and below teachings may be combined will be apparent to those of ordinary skill in the art in view of the teachings herein. It should also be understood that the below teachings may be readily combined with the various teachings of the references that are cited herein.

Figure 2:
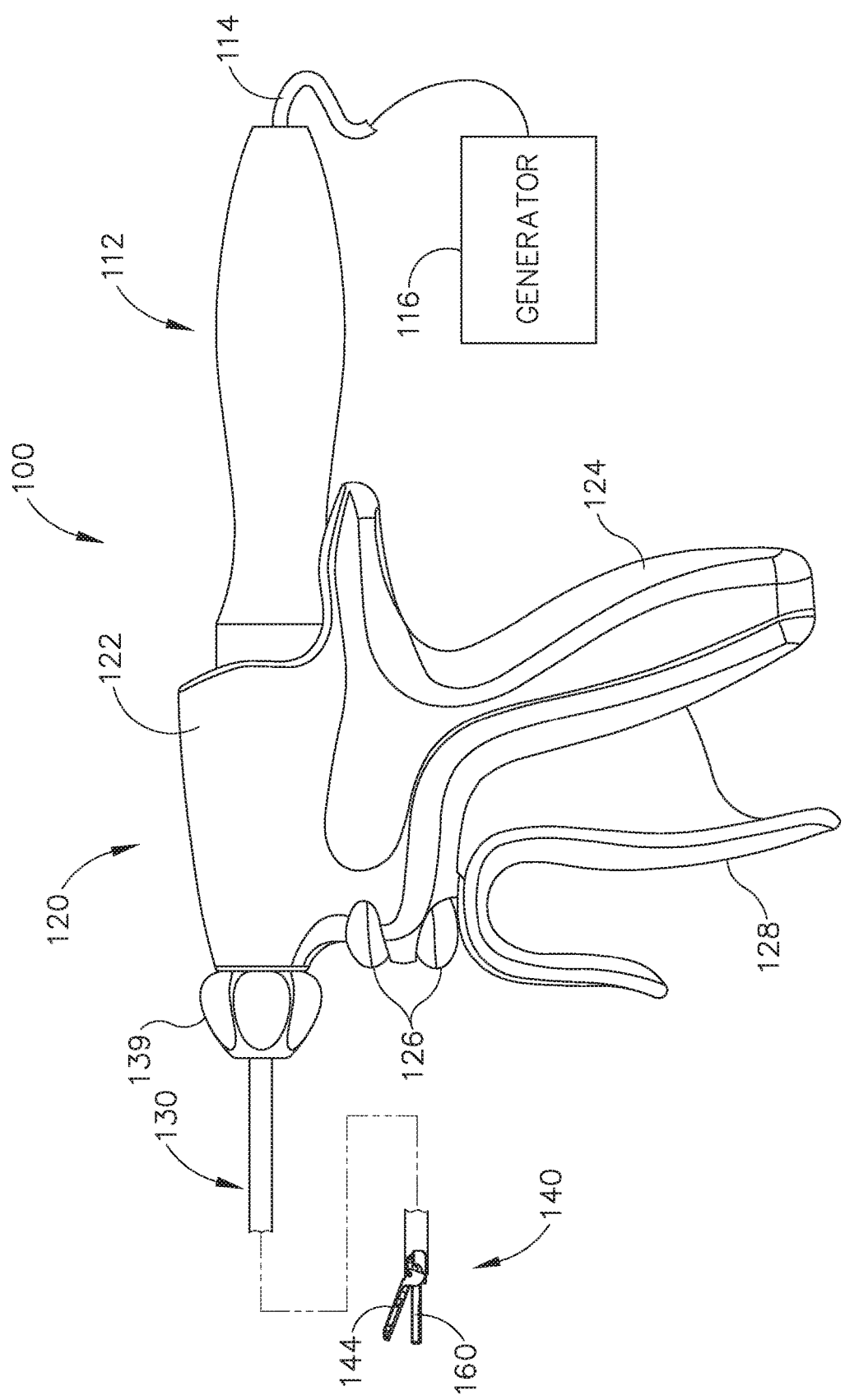
FIG. 2 depicts a side elevational view of an exemplary surgical instrument.

FIG. 2 illustrates an exemplary ultrasonic surgical instrument (100). At least part of instrument (100) may be constructed and operable in accordance with at least some of the teachings of U.S. Pat. Nos. 5,322,055; 5,873,873; 5,980,510; 6,325,811; 6,773,444; 6,783,524; 8,461,744; 8,623,027; U.S. Pub. No. 2006/0079874, now abandoned; U.S. Pub. No. 2007/0191713, now abandoned; U.S. Pub. No. 2007/0282333, now abandoned; U.S. Pub. No. 2008/0200940, now abandoned; U.S. Pub. No. 2010/0069940, now U.S. Pat. No. 9,023,071, issued May 5, 2015; U.S. Pub. No. 2012/0112687, now U.S. Pat. No. 9,381,058, issued Jul. 5, 2016; U.S. Pub. No. 2012/0116265, now abandoned; U.S. Pub. No. 2014/0005701, now U.S. Pat. No. 9,393,037, issued Jul. 19, 2016; U.S. Pub. No. 2014/0114334, now U.S. Pat. No. 9,095,367, issued Aug. 4, 2015; U.S. Pat. App. No. 61/410,603; and/or U.S. Pub. No. 2015/0080924, published Jul. 24, 2014, issued as U.S. Pat. No. 10,172,636 on Jan. 8, 2019. The disclosures of each of the foregoing patents, publications, and applications are incorporated by reference herein. As described therein and as will be described in greater detail below, instrument (100) is operable to cut tissue and seal or weld tissue (e.g., a blood vessel, etc.) substantially simultaneously. It should also be understood that instrument (100) may have various structural and functional similarities with the HARMONIC ACE® Ultrasonic Shears, the HARMONIC WAVE® Ultrasonic Shears, the HARMONIC FOCUS® Ultrasonic Shears, and/or the HARMONIC SYNERGY® Ultrasonic Blades. Furthermore, instrument (100) may have various structural and functional similarities with the devices taught in any of the other references that are cited and incorporated by reference herein.

To the extent that there is some degree of overlap between the teachings of the references cited herein, the HARMONIC ACE® Ultrasonic Shears, the HARMONIC WAVE® Ultrasonic Shears, the HARMONIC FOCUS® Ultrasonic Shears, and/or the HARMONIC SYNERGY® Ultrasonic Blades, and the following teachings relating to instrument (100), there is no intent for any of the description herein to be presumed as admitted prior art. Several teachings herein will in fact go beyond the scope of the teachings of the references cited herein and the HARMONIC ACE® Ultrasonic Shears, the HARMONIC WAVE® Ultrasonic Shears, the HARMONIC FOCUS® Ultrasonic Shears, and the HARMONIC SYNERGY® Ultrasonic Blades.

Instrument (100) of the present example comprises a handle assembly (120), a shaft assembly (130), and an end effector (140). Handle assembly (120) comprises a body (122) including a pistol grip (124) and a pair of buttons (126). Handle assembly (120) also includes a trigger (128) that is pivotable toward and away from pistol grip (124). It should be understood, however, that various other suitable configurations may be used, including but not limited to a pencil-grip configuration or a scissor-grip configuration. End effector (140) includes an ultrasonic blade (160) and a pivoting clamp arm (144). Clamp arm (144) is coupled with trigger (128) such that clamp arm (144) is pivotable toward ultrasonic blade (160) in response to pivoting of trigger (128) toward pistol grip (124); and such that clamp arm (144) is pivotable away from ultrasonic blade (160) in response to pivoting of trigger (128) away from pistol grip (124). Various suitable ways in which clamp arm (144) may be coupled with trigger (128) will be apparent to those of ordinary skill in the art in view of the teachings herein. In some versions, one or more resilient members are used to bias clamp arm (144) and/or trigger (128) to the open position shown in FIG. 4A.

An ultrasonic transducer assembly (112) extends proximally from body (122) of handle assembly (120). Transducer assembly (112) is coupled with a generator (116) via a cable (114). Transducer assembly (112) receives electrical power from generator (116) and converts that power into ultrasonic vibrations through piezoelectric principles. Generator (116) may include a power source and control module that is configured to provide a power profile to transducer assembly (112) that is particularly suited for the generation of ultrasonic vibrations through transducer assembly (112). By way of example only, generator (116) may comprise a GEN 300 sold by Ethicon Endo-Surgery, Inc. of Cincinnati, Ohio. In addition or in the alternative, generator (116) may be constructed in accordance with at least some of the teachings of U.S. Pub. No. 2011/0087212, entitled "Surgical Generator for Ultrasonic and Electrosurgical Devices," published Apr. 14, 2011, now U.S. Pat. No. 8,986,302, issued Mar. 24, 2015, the disclosure of which is incorporated by reference herein. It should also be understood that at least some of the functionality of generator (116) may be integrated into handle assembly (120), and that handle assembly (120) may even include a battery or other on-board power source such that cable (114) is omitted. Still other suitable forms that generator (116) may take, as well as various features and operabilities that generator (116) may provide, will be apparent to those of ordinary skill in the art in view of the teachings herein.

Shaft assembly (130) of the present example comprises an outer sheath (132) and an inner tube (176). Inner tube (176) is slidably disposed within outer sheath (132). As will be discussed in more detail below inner tube (176) is operable to translate longitudinally within outer sheath (132) relative to outer sheath (132) to selectively pivot clamp arm (144) toward and away from blade (160). Shaft assembly (130) of the present example further includes a rotation knob (139). Rotation knob (139) is operable to rotate the entire shaft assembly (130) and end effector (140) relative to handle assembly (120) about a longitudinal axis of shaft assembly (130). In some versions, rotation knob (139) is operable to selectively lock the angular position of shaft assembly (130) and end effector (140) relative to handle assembly (120) about the longitudinal axis of shaft assembly (130). For instance, rotation knob (139) may be translatable between a first longitudinal position, in which shaft assembly (130) and end effector (140) are rotatable relative to handle assembly (120) about the longitudinal axis of shaft assembly (130); and a second longitudinal position, in which shaft assembly (130) and end effector (140) are not rotatable relative to handle assembly (120) about the longitudinal axis of shaft assembly (130). Of course, shaft assembly (130) may have a variety of other components, features, and operabilities, in addition to or in lieu of any of those noted above. By way of example only, at least part of shaft assembly (130) may be constructed in accordance with at least some of the teachings of U.S. Pub. No. 2014/0239038, entitled "Surgical Instrument with Multi-Diameter Shaft," published Aug. 28, 2014, now U.S. Pat. No. 9,795,379, issued Oct. 24, 2017, the disclosure of which is incorporated by reference herein. Other suitable configurations for shaft assembly (130) will be apparent to those of ordinary skill in the art in view of the teachings herein.

Figure 3:
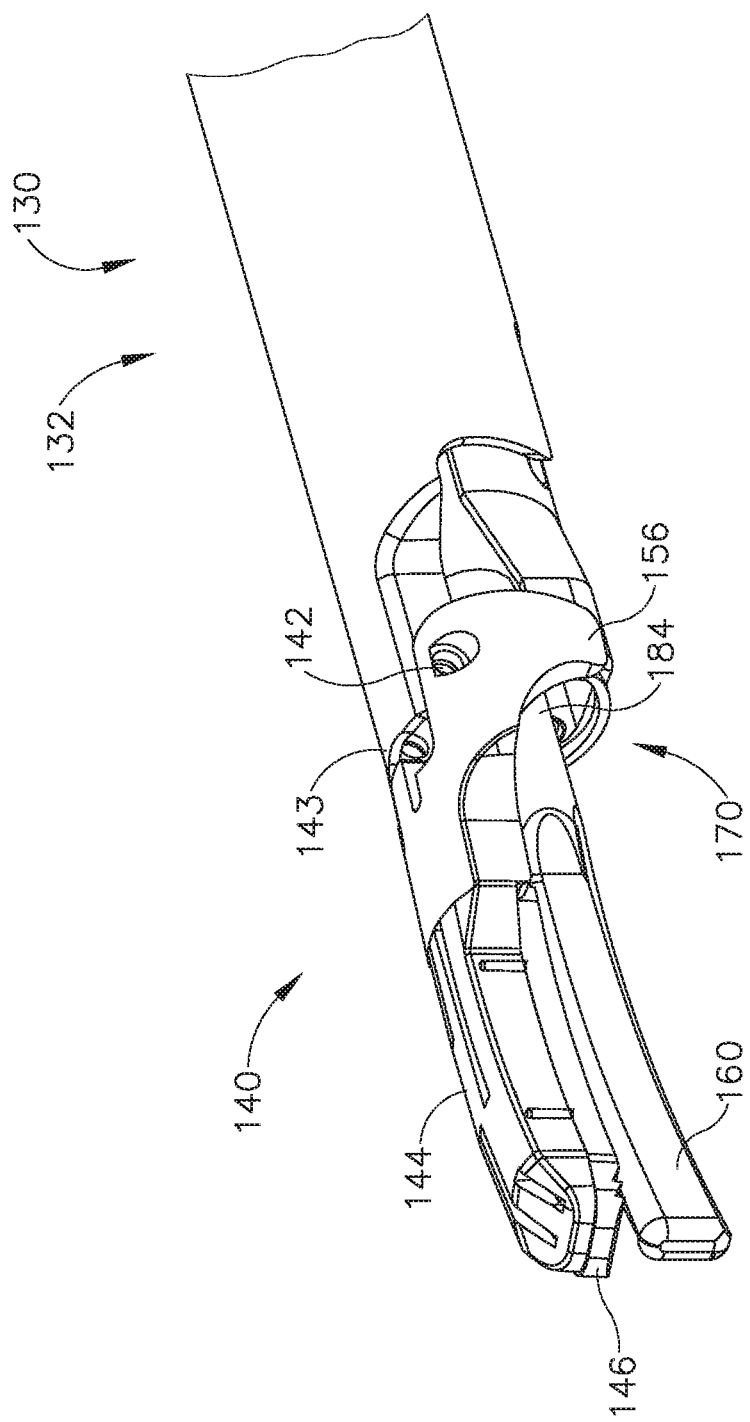
FIG. 3 depicts a perspective view of an end effector and a shaft assembly of the instrument of FIG. 2.

As best seen in FIG. 3, end effector (140) of the present example comprises clamp arm (144) and ultrasonic blade (160). Clamp arm (144) includes a primary clamp pad (146) and a secondary clamp pad (148) that are secured to the underside of clamp arm (144), facing blade (160). Clamp arm (144) is pivotably secured to a distally projecting tongue (143) of outer sheath (132) via a pin (142). Clamp arm (144) is operable to selectively pivot toward and away from blade (160) to selectively clamp tissue between clamp arm (144) and blade (160). A pair of arms (156) extend transversely from clamp arm (144) and are secured to a distal portion (170) of inner tube (176) that extends laterally between arms (156). Arms (156) are secured to distal portion (170) via a pair of integral, inwardly extending pins (151), which are rotatably disposed within a pair of through holes (not shown) of distal portion (170). Inner tube (176) is operable to translate longitudinally within outer sheath (132) relative to outer sheath (132) to selectively pivot clamp arm (144) toward and away from blade (160). In particular, inner tube (176) is coupled with trigger (128) such that clamp arm (144) pivots toward blade (160) in response to pivoting of trigger (128) toward pistol grip (124); and such that clamp arm (144) pivots away from blade (160) in response to pivoting of trigger (128) away from pistol grip (124). Clamp arm (144) may be biased toward the open position, such that (at least in some instances) the operator may effectively open clamp arm (144) by releasing a grip on trigger (128).

Figure 4A:
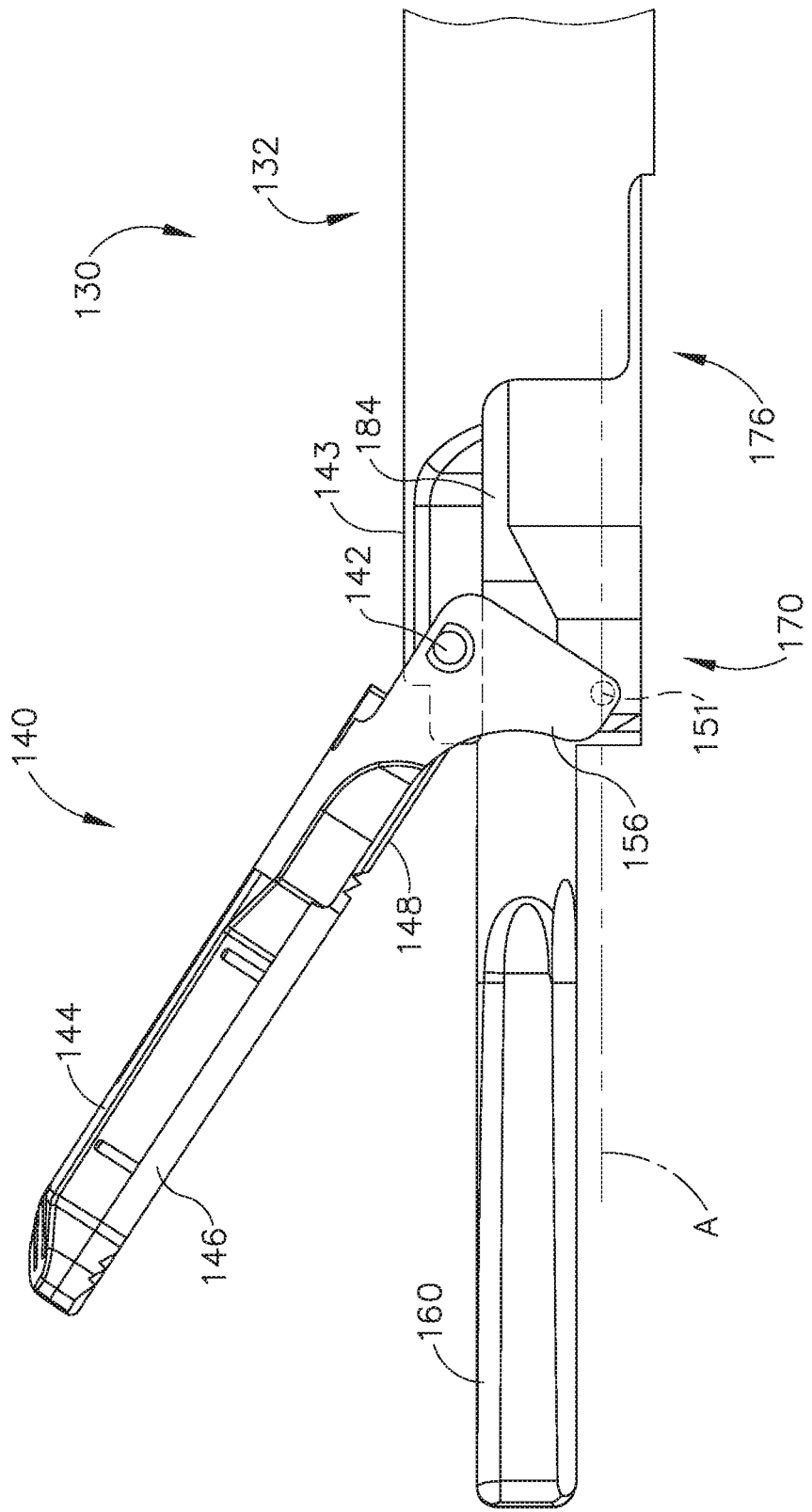
FIG. 4A depicts a side elevational view of the end effector of FIG. 3 with a clamp arm in a first rotational position and with an inner tube in a first longitudinal position.
Figure 4B:
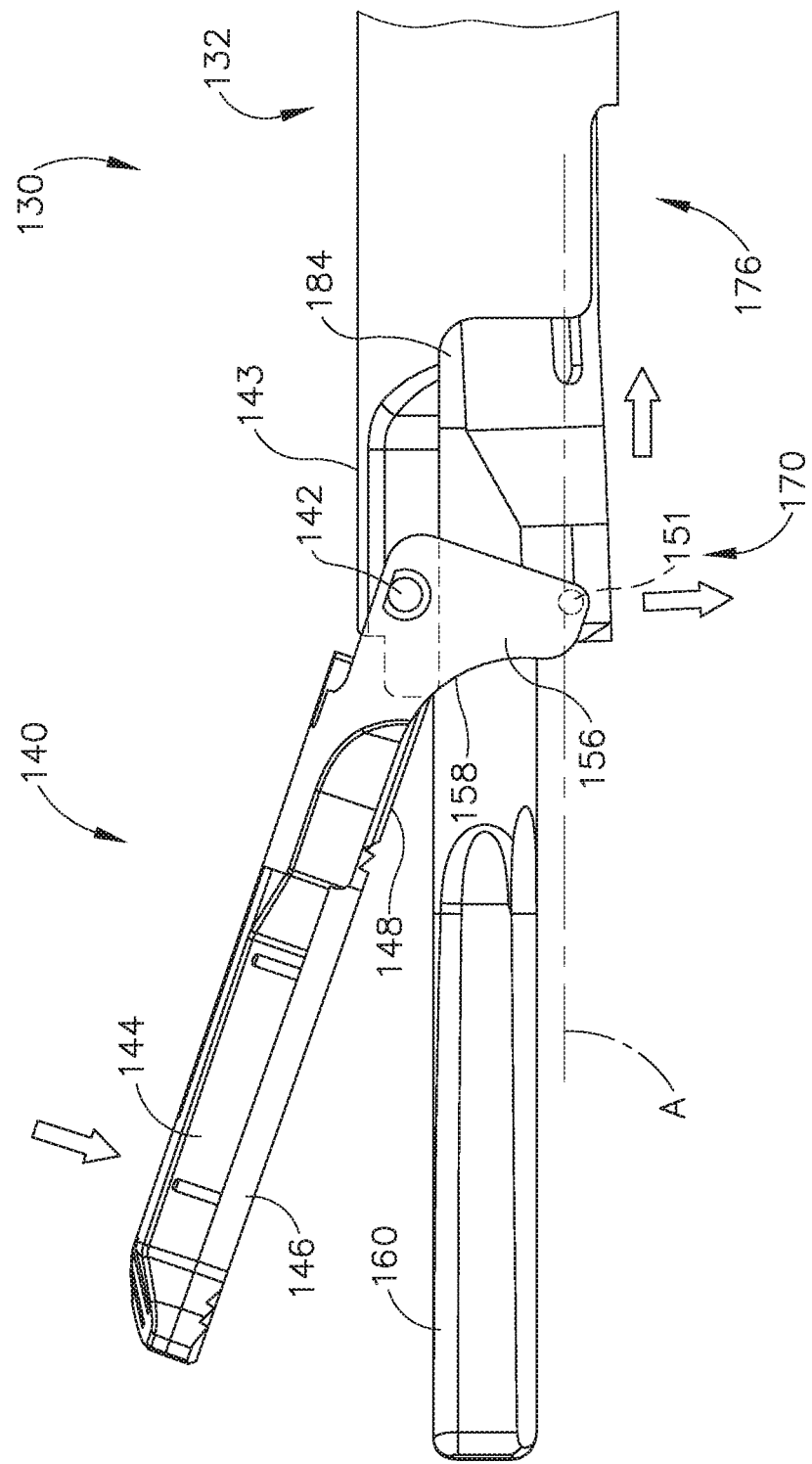
FIG. 4B depicts a side elevational view of the end effector of FIG. 3 with the clamp arm of FIG. 4A moved to a second rotational position by movement of the inner tube of FIG. 4A to a second longitudinal position.
Figure 4C:
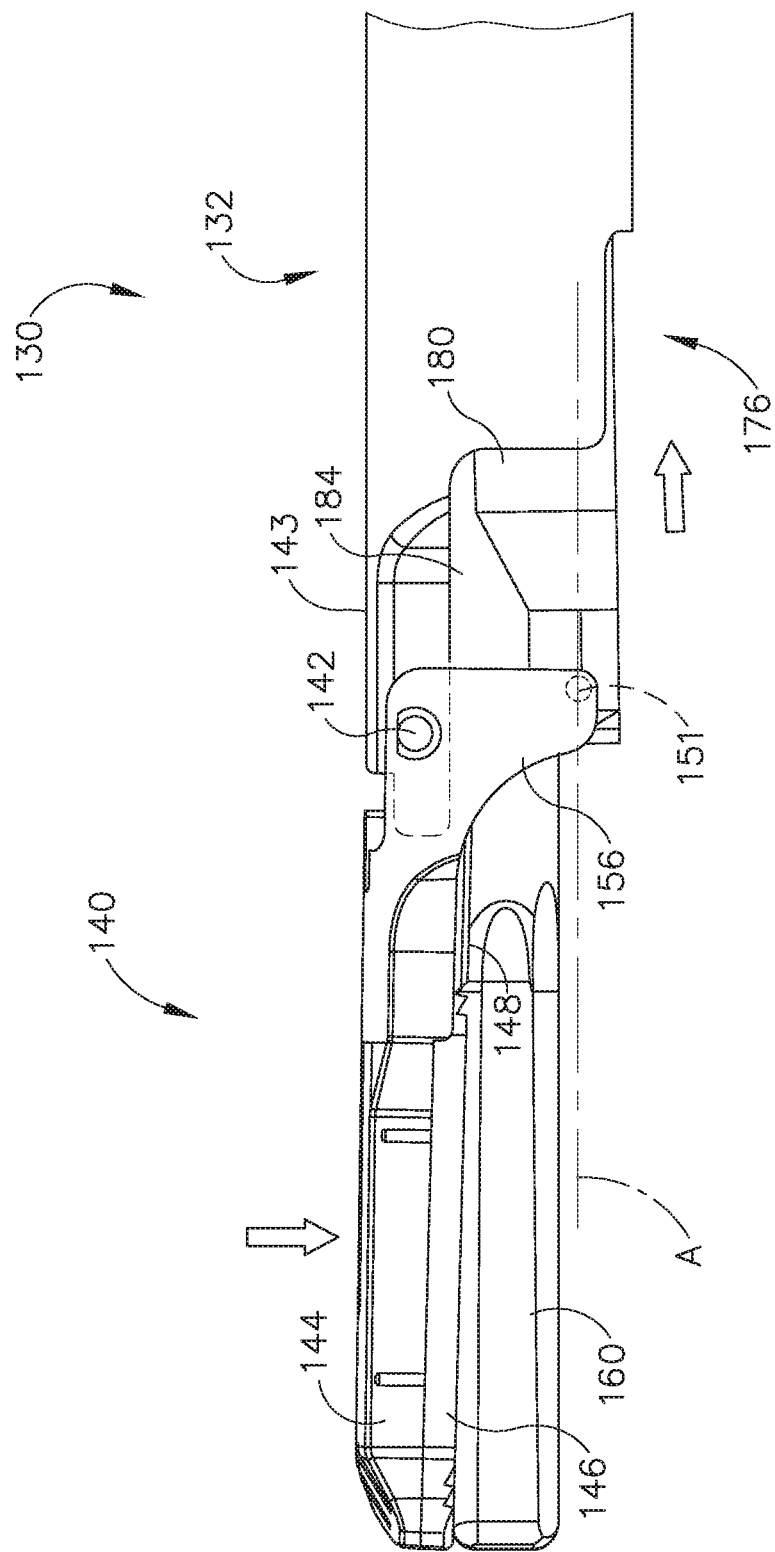
FIG. 4C depicts a side elevational view of the end effector of FIG. 3 with the clamp arm of FIG. 4A moved to a third rotational position by movement of the inner tube of FIG. 4A to a third longitudinal position.
Figure 5:
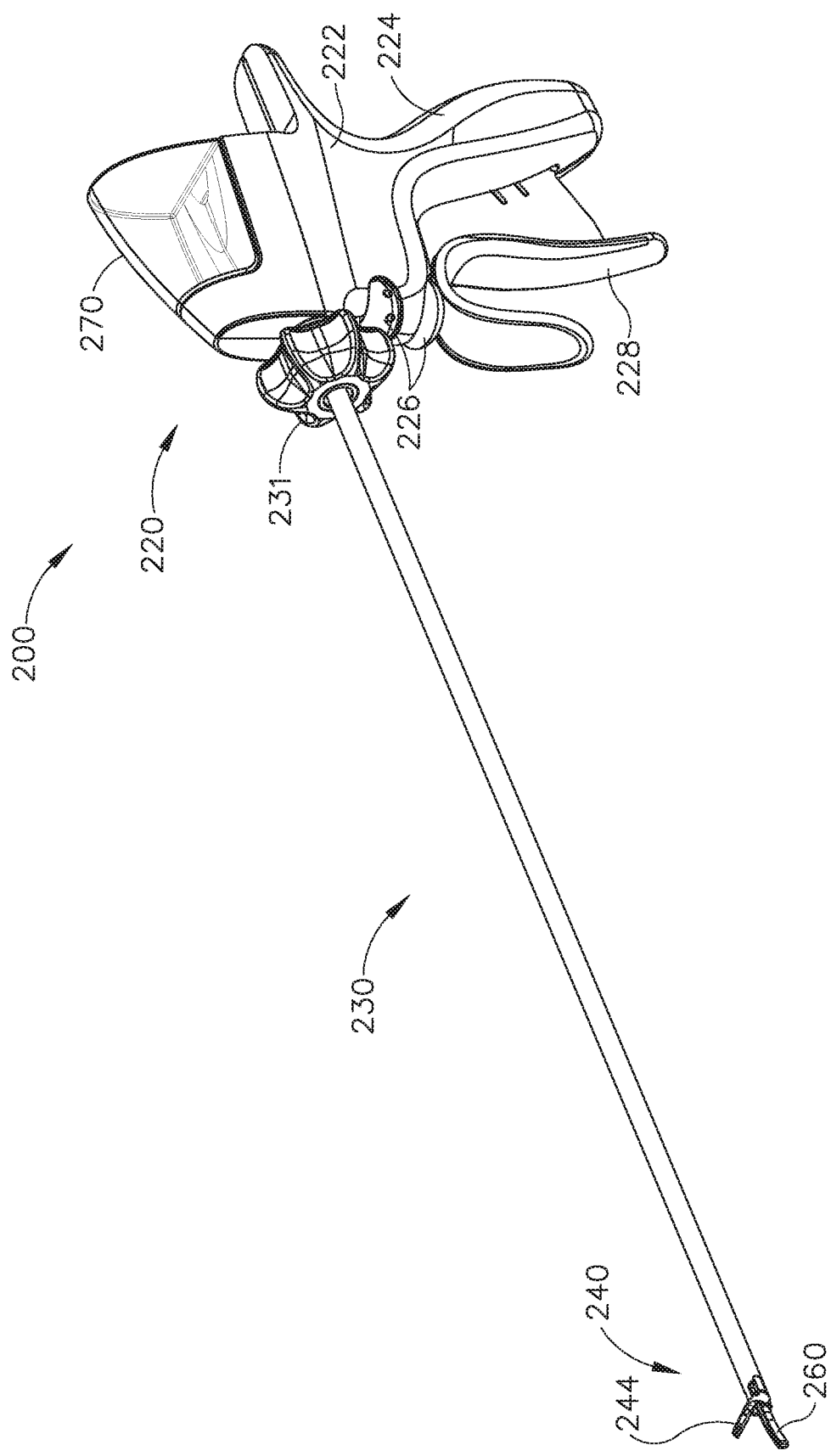
FIG. 5 depicts a perspective view of an exemplary alternative ultrasonic surgical instrument.
Figure 6:
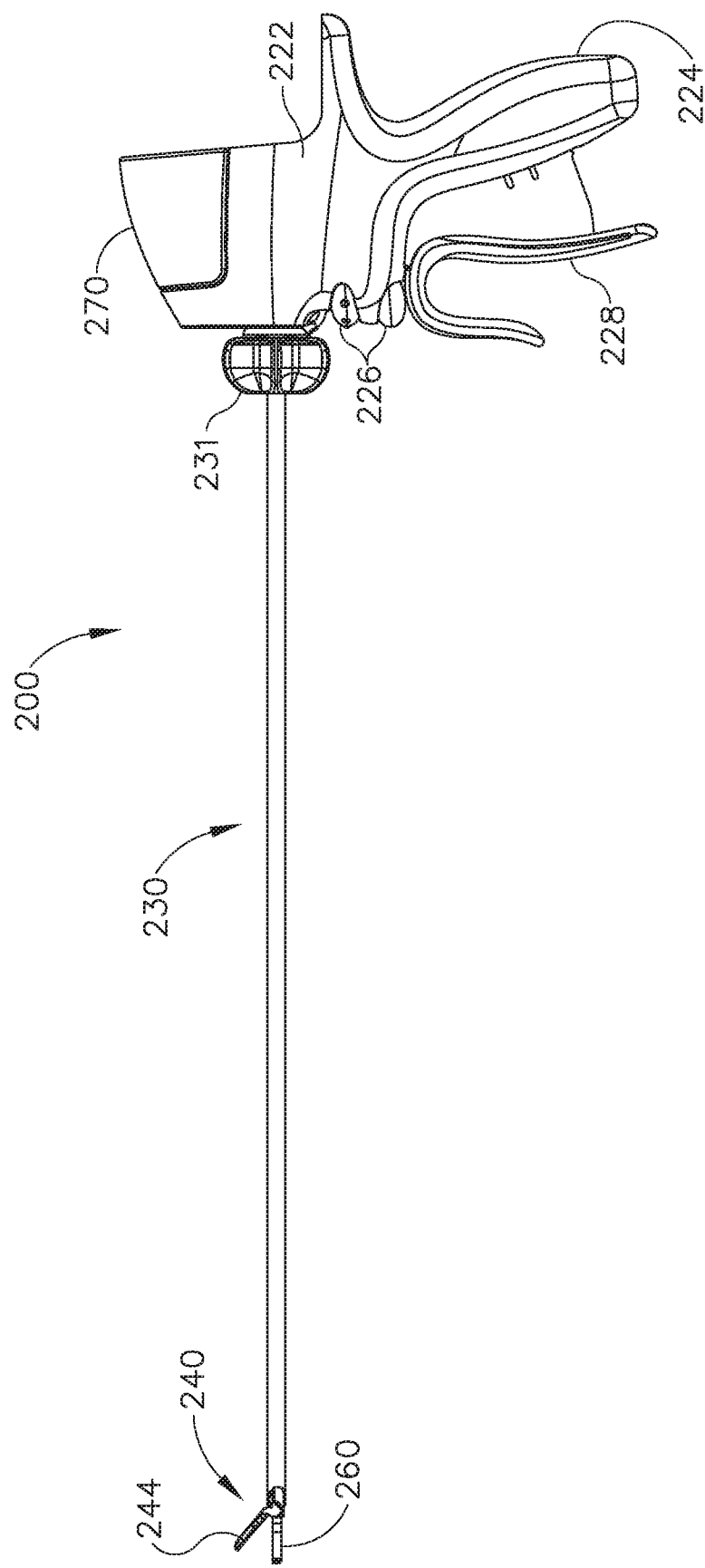
FIG. 6 depicts a side elevational view of the instrument of FIG. 5.
Figure 7:
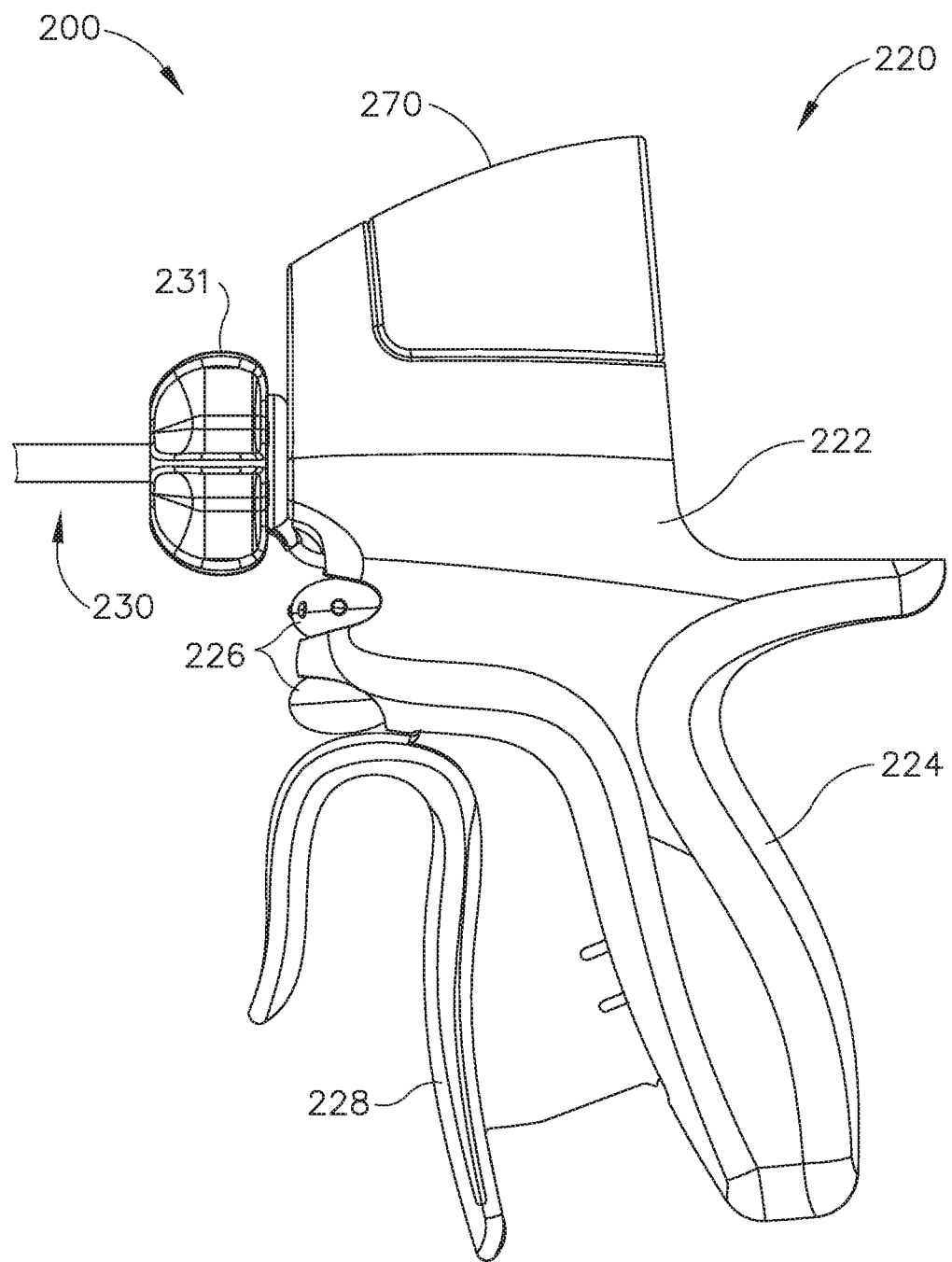
FIG. 7 depicts a side elevational view of a handle assembly of the instrument of FIG. 5.

FIGS. 4A-4C show the operation of clamp arm (144) between an open position (FIG. 4A) and a closed position (FIG. 4C). As shown in FIG. 4A, when inner tube (176) is in a distal position relative to outer sheath (132), clamp arm (144) is in the open position. As shown in FIG. 4B, as inner tube (176) is moved proximally into an intermediate position, clamp arm (144) is pivoted toward blade (160) into an intermediate position. As shown in FIG. 4C, as inner tube (176) is moved further proximally into a proximal position, clamp arm (144) is pivoted toward blade (160) into the closed position.

Blade (160) of the present example is operable to vibrate at ultrasonic frequencies in order to effectively cut through and seal tissue, particularly when the tissue is being clamped between clamp pads (146, 148) and blade (160). Blade (160) is positioned at the distal end of an acoustic drivetrain. This acoustic drivetrain includes transducer assembly (112) and an acoustic waveguide (184). Transducer assembly (112) includes a set of piezoelectric discs (not shown) located proximal to a horn (not shown) of rigid acoustic waveguide (184). The piezoelectric discs are operable to convert electrical power into ultrasonic vibrations, which are then transmitted along acoustic waveguide (184) to blade (160) in accordance with known configurations and techniques. By way of example only, this portion of the acoustic drivetrain may be configured in accordance with various teachings of various references that are cited herein.

In the present example, the distal end of blade (160) is located at a position corresponding to an anti-node associated with resonant ultrasonic vibrations communicated through acoustic waveguide (184), in order to tune the acoustic assembly to a preferred resonant frequency $f_o$ when the acoustic assembly is not loaded by tissue. When transducer assembly (112) is energized, the distal end of blade (160) is configured to move longitudinally in the range of, for example, approximately 10 to 500 microns peak-to-peak, and in some instances in the range of about 20 to about 200 microns at a predetermined vibratory frequency $f_o$ of, for example, 55.5 kHz. When transducer assembly (112) of the present example is activated, these mechanical oscillations are transmitted through acoustic waveguide (184) to reach blade (160), thereby providing oscillation of blade (160) at the resonant ultrasonic frequency. Thus, when tissue is secured between blade (160) and clamp pads (146, 148), the ultrasonic oscillation of blade (160) may simultaneously sever the tissue and denature the proteins in adjacent tissue cells, thereby providing a coagulative effect with relatively little thermal spread. In some versions, an electrical current may also be provided through blade (160) and clamp arm (144) to also cauterize the tissue. While some configurations for an acoustic transmission assembly and transducer assembly (112) have been described, still other suitable configurations for an acoustic transmission assembly and transducer assembly (112) will be apparent to one or ordinary skill in the art in view of the teachings herein. Similarly, other suitable configurations for end effector (140) will be apparent to those of ordinary skill in the art in view of the teachings herein.

III. Exemplary Ultrasonic Surgical Instrument with Blade Cooling System

In some instances, one or more regions of instrument (20, 100) may heat up during extended operation of instrument (20, 100) in a surgical procedure. By way of example only, blade (24, 160), clamp arm (144), and/or other portions of instrument (20, 100) may eventually heat up over time. Such heating may be caused by friction and/or other factors. To the extent that the heat is initially generated in one particular component of instrument (20, 100) (e.g., blade (24, 160) or clamp arm (144), etc.), such heat may be gradually transmitted to other portions of instrument (20, 100). It may be desirable to minimize such heating and/or otherwise manage such heating in order to avoid having heated portions of instrument (20, 100) contact tissue that should not be heated. For instance, the operator may wish for end effector (140) to be relatively cool when the operator wishes to use end effector (140) to perform spreading blunt dissections and/or simple tissue grasping, etc. It may also be desirable to minimize heat and/or otherwise manage heat in a way that does not significantly increase the size or operability of instrument (20, 100).

One merely exemplary way in which heat may be managed in instrument (20, 100) is to use a fluid to cool blade (24, 160). For instance, a cooling liquid (e.g., saline, etc.) may be applied to the proximal end of blade (24, 160). The cooling fluid may then be communicated distally along the rest of the length of blade (24, 160) to thereby cool blade (24, 160). The examples described below provide various structures and techniques through which a cooling fluid may be communicated to a blade such as blade (24, 160). While various examples of features configured to cool blade (24, 160) will be described in greater detail below, other examples will be apparent to those of ordinary skill in the art according to the teachings herein.

A. Exemplary Ultrasonic Surgical Instrument with Piston Pump

FIGS. 5-27 illustrate an exemplary ultrasonic surgical instrument (200) that is configured to operate substantially similar to instrument (100) discussed above except for the differences discussed below. It should therefore be understood that instrument (200) may include the same components and operabilities as instrument (20, 100), in addition to including the components and operabilities described below. Instrument (200) of the present example comprises a handle assembly (220), a shaft assembly (230), and an end effector (240). Handle assembly (220) comprises a body (222) including a pistol grip (224) and a pair of buttons (226). As with instrument (100) discussed above, body (222) of handle assembly (220) is configured to receive an ultrasonic transducer assembly (not shown). Handle assembly (220) also includes a trigger (228) that is pivotable toward and away from pistol grip (224). End effector (240) includes an ultrasonic blade (260) and a pivoting clamp arm (244). Clamp arm (244) is coupled with trigger (228) such that clamp arm (244) is pivotable toward ultrasonic blade (260) in response to pivoting of trigger (228) toward pistol grip (224); and such that clamp arm (244) is pivotable away from ultrasonic blade (260) in response to pivoting of trigger (228) away from pistol grip (224). In some versions, one or more resilient members are used to bias clamp arm (244) and/or trigger (228) to an open position.

Figure 8:
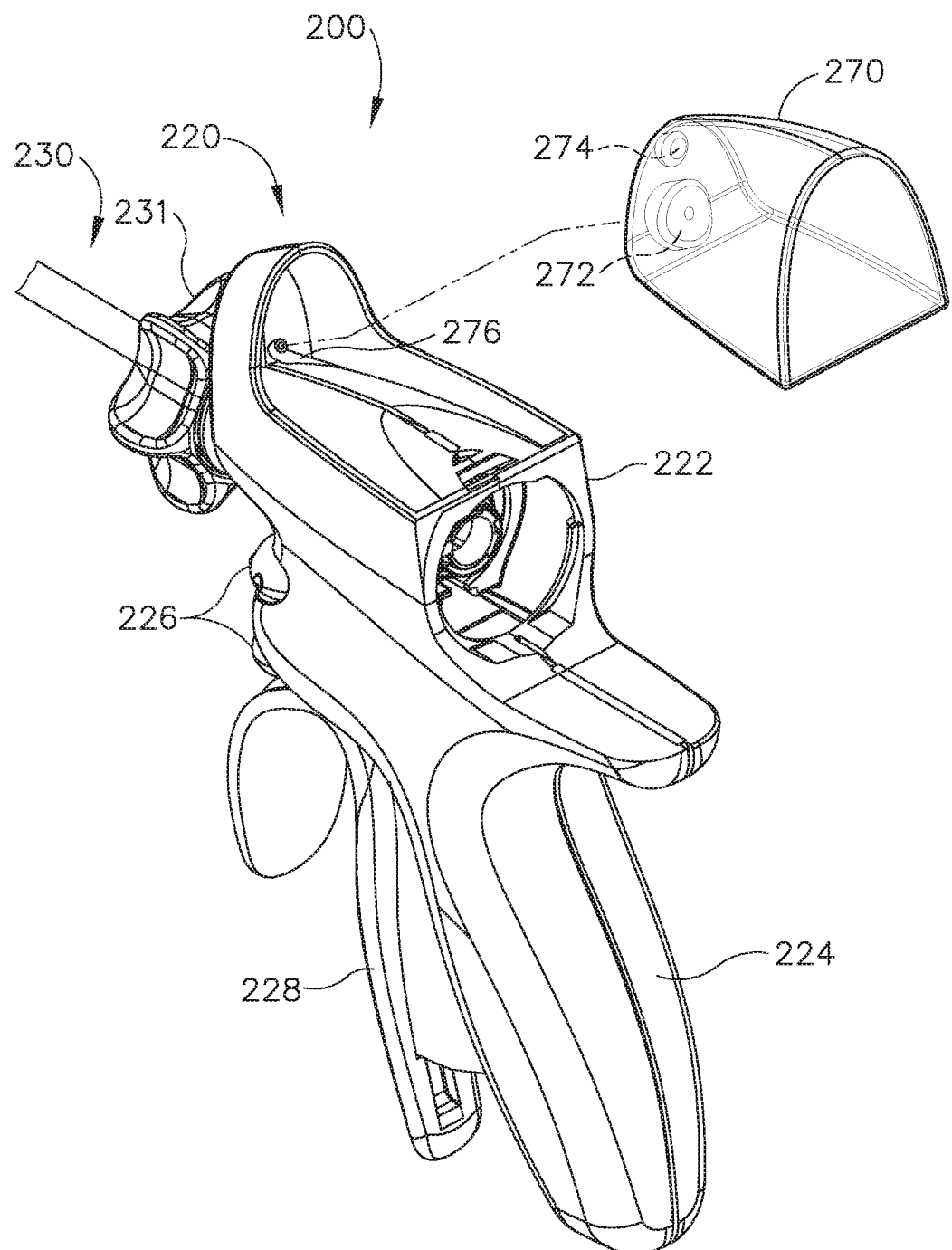
FIG. 8 depicts a perspective view of the handle assembly of FIG. 7 with a fluid reservoir of the handle assembly detached from the handle assembly.
Figure 9:
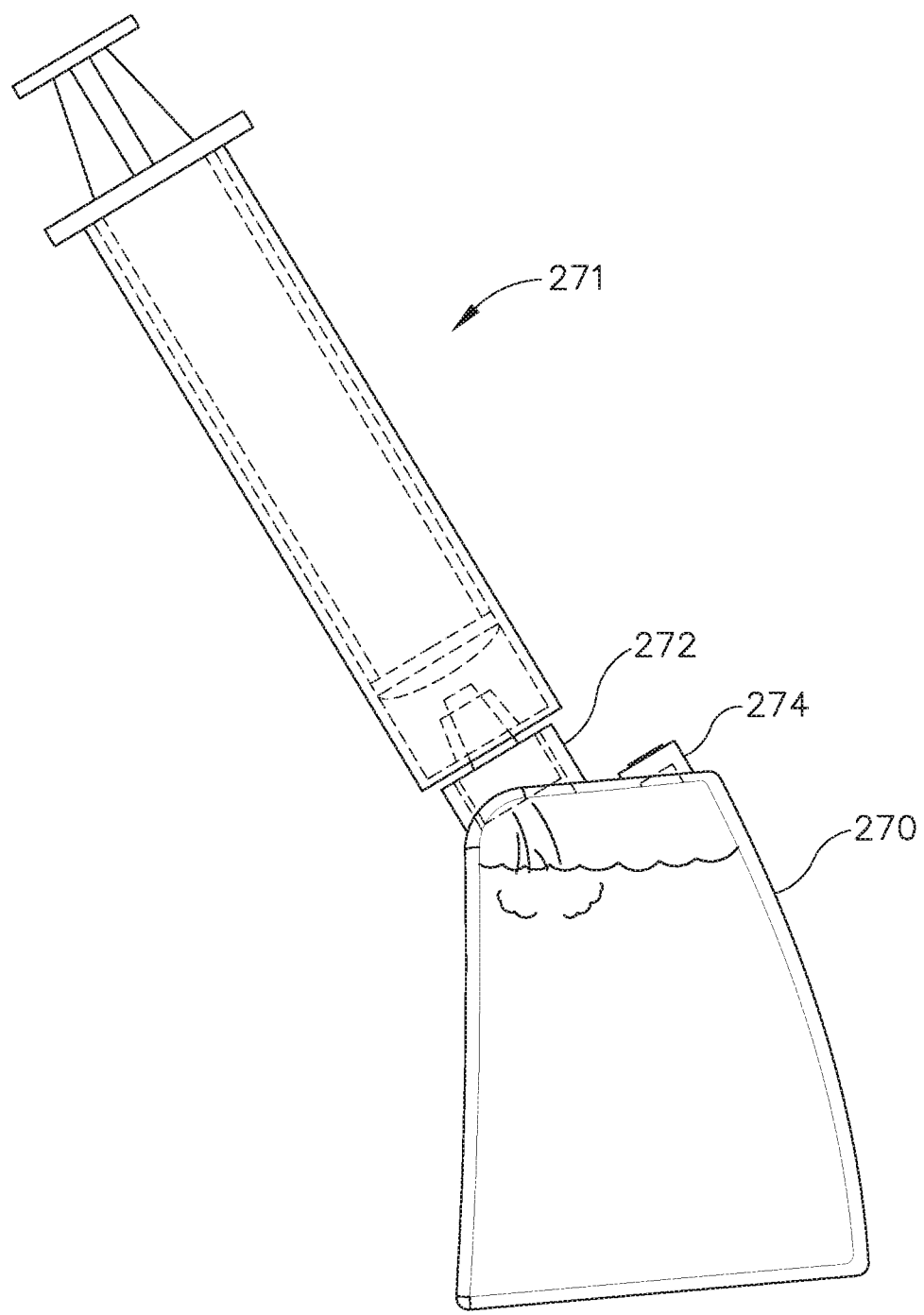
FIG. 9 depicts a side elevational view of the fluid reservoir of FIG. 8 being filled with fluid by a syringe.

Handle assembly (220) of the present example further comprises a fluid reservoir (270). Fluid reservoir (270) is configured to be filled with liquid coolant and to selectively retain the liquid coolant therein. By way of example only, fluid reservoir (270) may be configured to hold approximately 26 cubic centimeters of fluid. Alternatively, fluid reservoir (270) may have any other suitable capacity. Fluid reservoir (270) is selectively coupleable with a top portion of body (222) of handle assembly (220). In some instances, fluid reservoir (270) may couple with body (222) in a snap-fit manner. Alternatively, fluid reservoir (270) may be coupled with body (222) in any other suitable manner as would be apparent to one of ordinary skill in the art. As best seen in FIGS. 8-9, fluid reservoir (270) comprises a valve (272) and a vent (274) formed in a distal portion of fluid reservoir (270). With fluid reservoir (270) coupled to body (222), valve (272) is configured to couple with a first tube (276), as best seen in FIGS. 17-20. As will be discussed in more detail below, fluid reservoir (270) is configured to provide liquid coolant to a fluid pump (280) via first tube (276). As liquid coolant is communicated from fluid reservoir (270), vent (274) permits atmospheric air to flow into fluid reservoir (270) to thereby to prevent formation of a vacuum within fluid reservoir (270).

Figure 10:
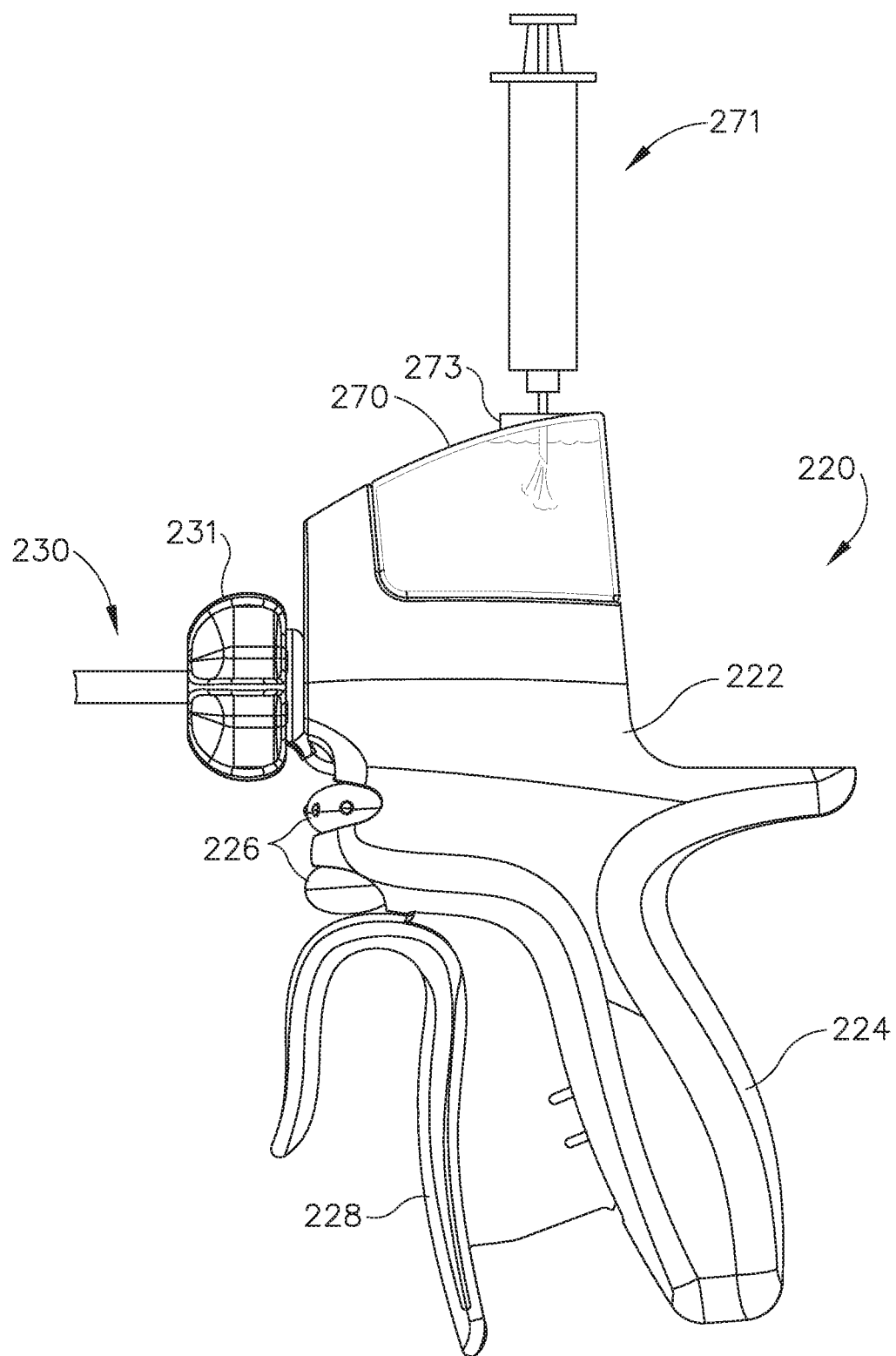
FIG. 10 depicts a side elevational view of the handle assembly of FIG. 7 with an exemplary alternative fluid reservoir being filled with fluid by a syringe.

As shown in FIG. 8, fluid reservoir (270) may be detached from body (222) in order to refill fluid reservoir (270) with liquid coolant. For instance, as shown in FIG. 9, a syringe (271) filled with liquid coolant may be coupled with valve (272) such that the liquid coolant may be passed into fluid reservoir (270) via valve (272). As fluid reservoir (270) is filled with liquid coolant, vent (274) permits air to flow out of fluid reservoir (270) to thereby prevent pressurization of the liquid coolant within fluid reservoir (270). In some versions of fluid reservoir (270), it may be desirable to provide fluid reservoir (270) with features that permit refilling of fluid reservoir (270) without fluid reservoir (270) having to be detached from body (222). For instance, as shown in FIG. 10, fluid reservoir (270) may comprise a septum (273) that provides fluid access to the interior of fluid reservoir (270). A syringe (271) filled with liquid coolant may pierce septum (273) such that the liquid coolant may be passed into fluid reservoir (270) via septum (273). As discussed above, as fluid reservoir (270) is filled with liquid coolant, vent (274) permits air to flow out of fluid reservoir (270) to thereby prevent pressurization of the liquid coolant within fluid reservoir (270). Other suitable ways in which reservoir (270) may be configured will be apparent to those of ordinary skill in the art in view of the teachings herein. Similarly, other suitable ways in which reservoir (270) may be coupled with body (222) will be apparent to those of ordinary skill in the art in view of the teachings herein. By way of example only, in some alternative versions reservoir (270) may be located separately from body (222) and may be coupled with body via a flexible conduit, etc.

Figure 11:
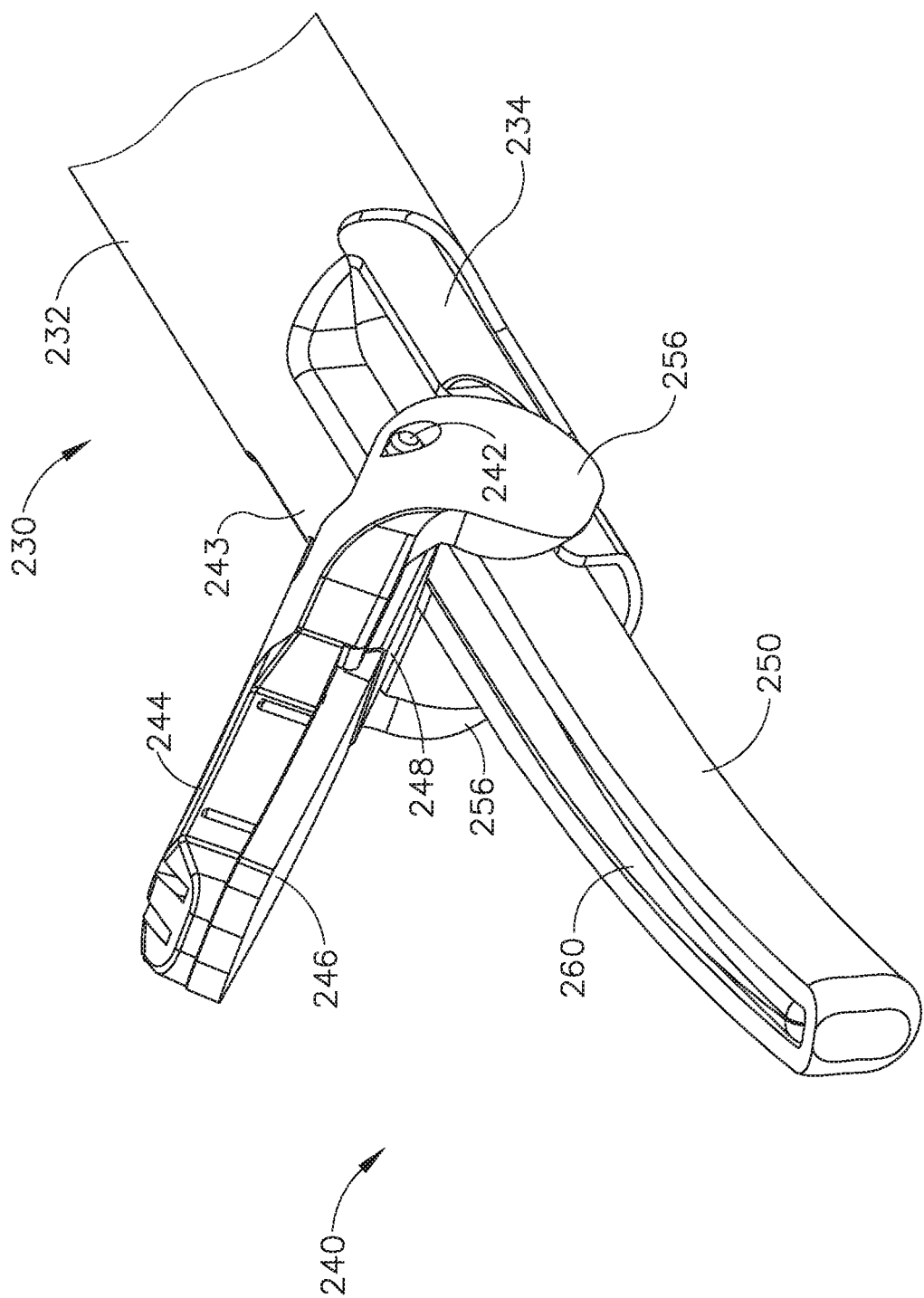
FIG. 11 depicts a perspective view of an end effector of the instrument of FIG. 5.
Figure 12:
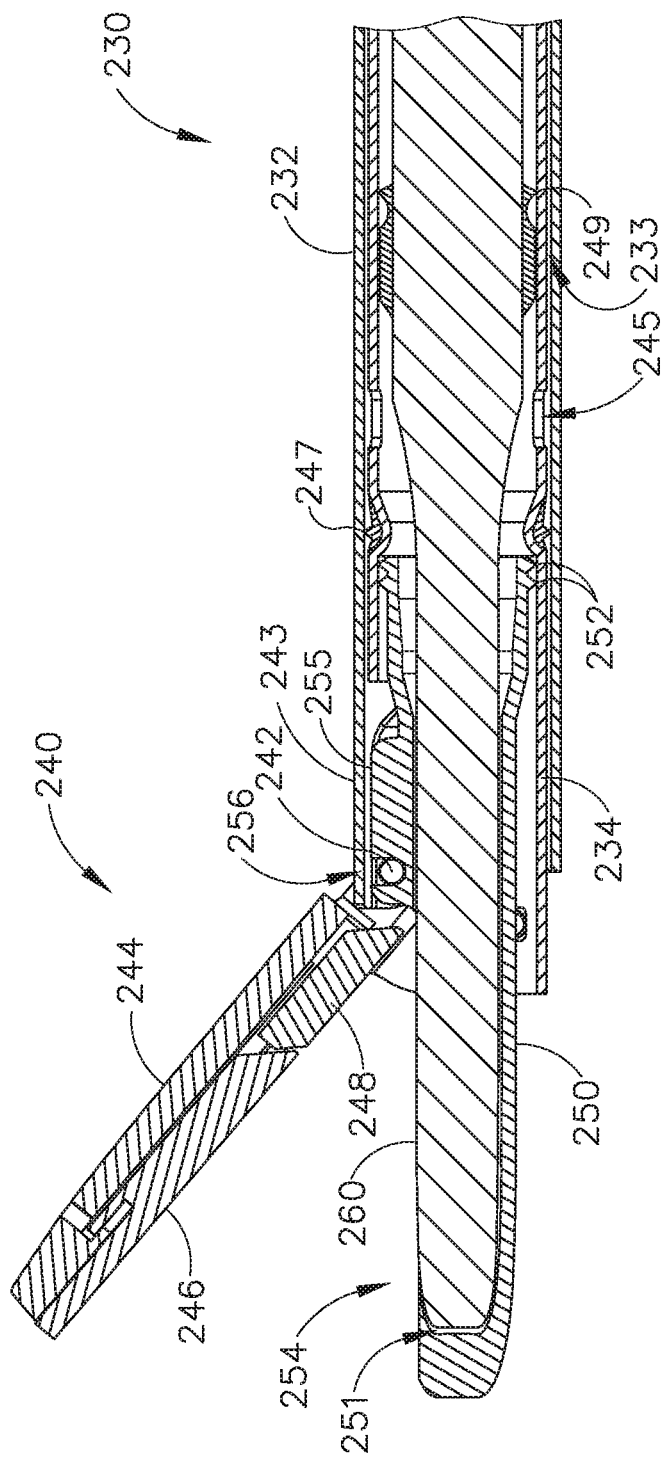
FIG. 12 depicts a cross-sectional side view of the end effector of FIG. 11.

Shaft assembly (230) of the present example comprises an outer sheath (232) and an inner tube (234). Inner tube (234) is slidably disposed within outer sheath (232). As with shaft assembly (130) discussed above, inner tube (234) is operable to translate longitudinally within outer sheath (232) relative to outer sheath (232) to selectively pivot clamp arm (244) toward and away from blade (260). As best seen in FIGS. 11 and 12, end effector (240) of the present example comprises clamp arm (244) and ultrasonic blade (260). Clamp arm (244) includes a primary clamp pad (246) and a secondary clamp pad (248) that are secured to the underside of clamp arm (244), facing blade (260). Clamp arm (244) is pivotably secured to a distally projecting tongue (243) of outer sheath (232) via a pin (242). Clamp arm (244) is operable to selectively pivot toward and away from blade (260) to selectively clamp tissue between clamp arm (244) and blade (260). A pair of arms (256) extend transversely from clamp arm (244) and are secured to a distal portion (270) of inner tube (276) that extends laterally between arms (256). Thus, as with shaft assembly (130) discussed above, longitudinal translation of inner tube (234) causes rotation of clamp arm (244) toward and away from blade (260).

Figure 13:
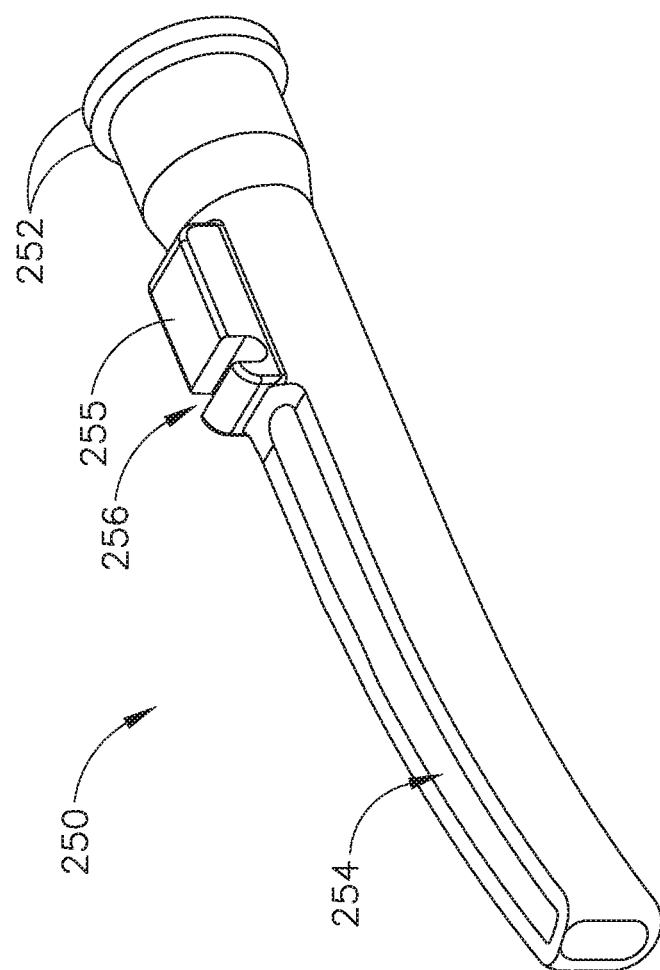
FIG. 13 depicts a perspective view of a sleeve of the end effector of FIG. 11.
Figure 14:
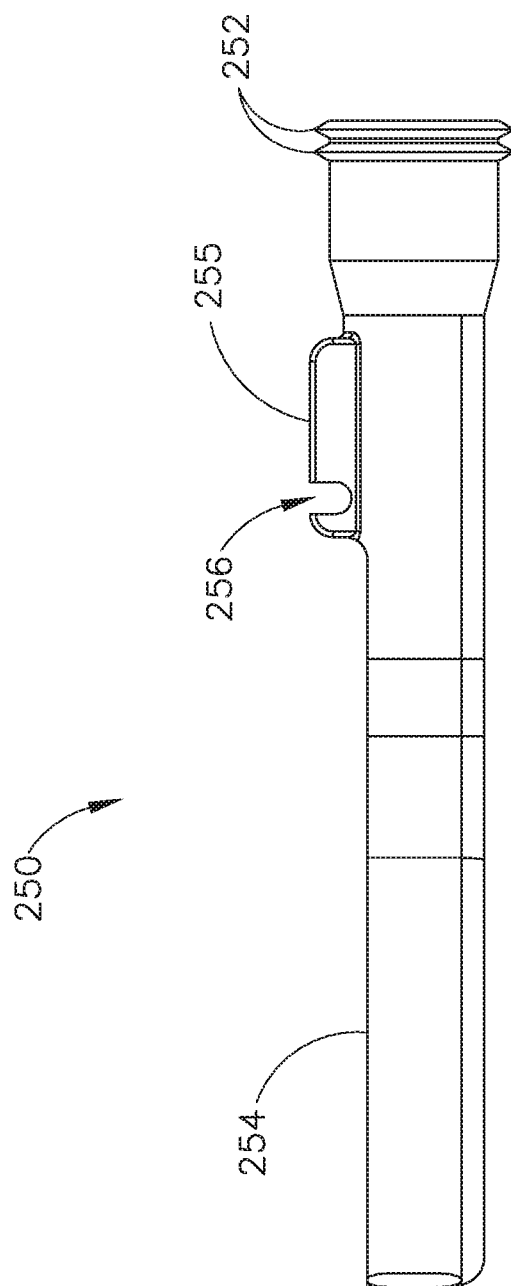
FIG. 14 depicts a side elevational view of the sleeve of FIG. 13.

End effector (240) of the present example further comprises a sleeve (250). As shown in FIG. 12, a proximal end of sleeve (250) is disposed within a distal end of inner tube (234). As best seen in FIGS. 13 and 14, a proximal end of sleeve (250) comprises a pair of annular seals (252) that are configured to engage an interior surface of inner tube (234) to thereby provide a fluid seal between inner tube (234) and sleeve (250). Annular seals (252) further provide a friction fit between inner tube (234) and sleeve (250) such that sleeve (250) is selectively secured within inner tube (234). Sleeve (250) further comprises a projection (255) having a slot (256) formed therein. Slot (256) is configured to receive pin (242) to thereby longitudinally retain sleeve (250) relative to inner tube (234). Thus, sleeve (250) remains stationary as inner tube (234) translates longitudinally to drive clamp arm (244) toward and away from blade (260). Sleeve (250) also defines a curved channel (254) having a closed distal end. Channel (254) is configured to receive blade (260). Channel (254) is sized slightly larger than blade (260) in order to provide a gap (251) between the inner surface of sleeve (250) that defines gap (251) and the outer surface of blade (260). As will be discussed in more detail below, channel (254) is configured to receive liquid coolant from fluid pump (280) such that the liquid coolant is placed in contact with blade (260) via gap (251) to thereby cool blade (260).

In some versions, sleeve (250) may comprise a silicone material. In some such versions, one or more features are included to provide structural reinforcement to sleeve (250), to reduce or eliminate deflection of sleeve (250) relative to the longitudinal axis of blade (260). By way of example only, sleeve (250) may be configured and operable in accordance with at least some of the teachings of U.S. Pub. No. 2015/0148833, published May 28, 2015, issued as U.S. Pat. No. 9,993,260 on Jun. 12, 2018, entitled "Shielding Features for Ultrasonic Blade of a Surgical Instrument," the disclosure of which is incorporated by reference herein; and/or U.S. Pub. No. 2015/0148835, published May 28, 2015, issued as U.S. Pat. No. 10,004,528 on Jun. 26, 2018, entitled "Sleeve Features for Ultrasonic Blade of a Surgical Instrument," the disclosure of which is incorporated by reference herein. It should therefore be understood that sleeve (250) may serve as a heat shield for blade (260) in addition to providing structure to assist in liquid cooling of blade (260).

Figure 15:
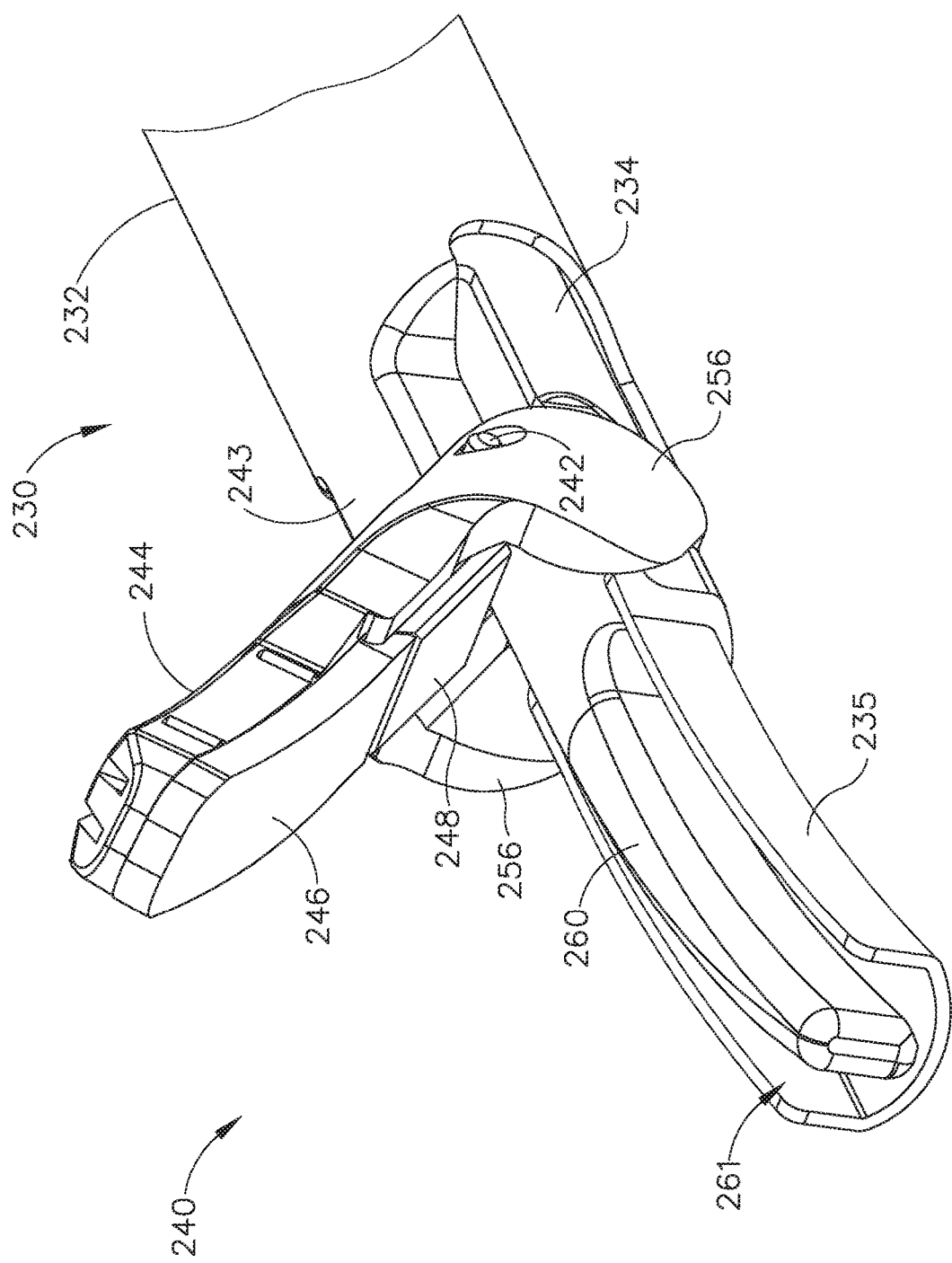
FIG. 15 depicts a perspective view of the end effector of FIG. 11 with an exemplary alternative sleeve.
Figure 16:
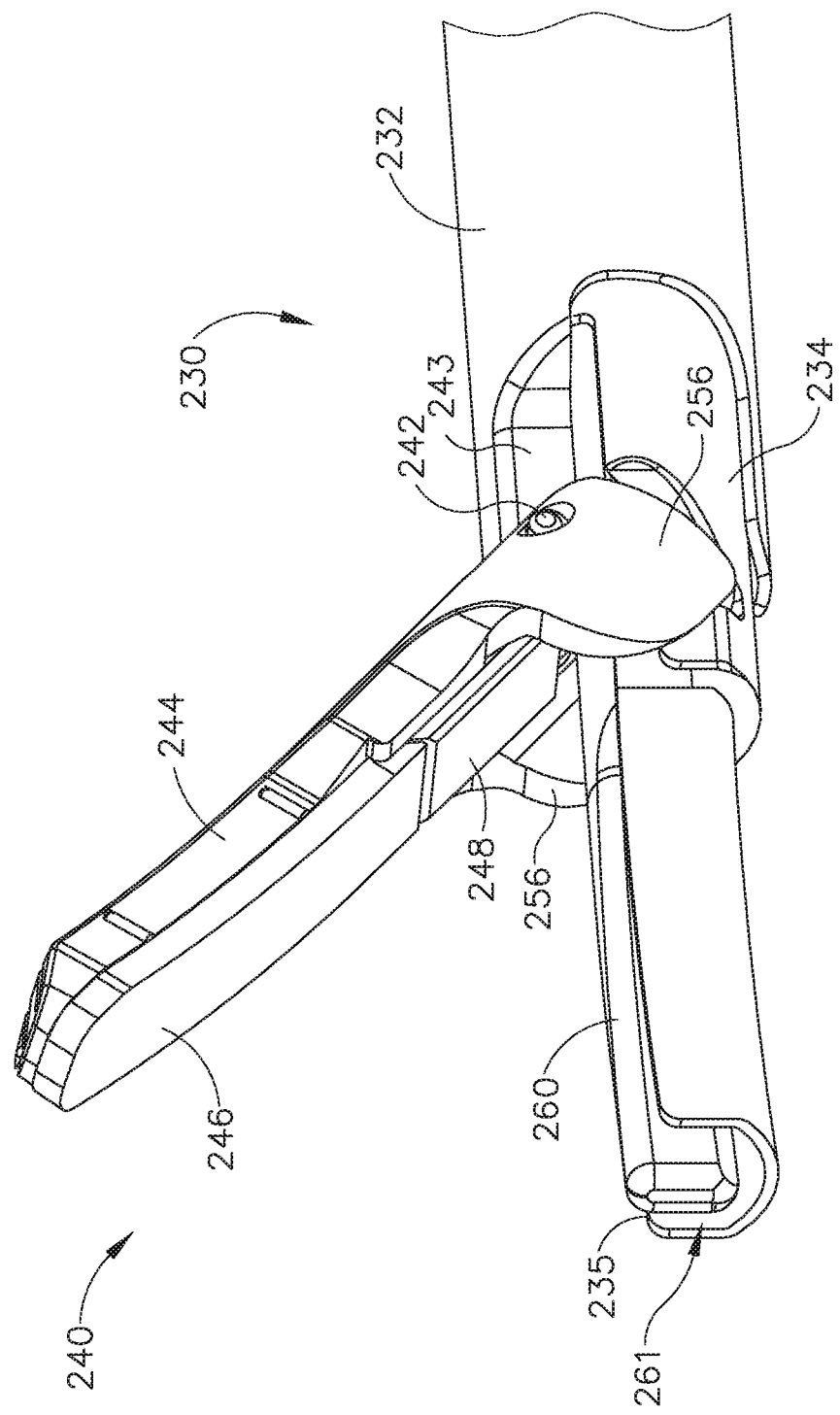
FIG. 16 depicts another perspective view of the end effector of FIG. 11 with the sleeve of FIG. 15.

As shown in FIGS. 15 and 16, in lieu of sleeve (250), inner tube (234) may comprise an integral tongue (235) having an open distal end. Tongue (235) is configured to receive blade (260). Tongue (235) is sized to provide a gap (261) between the inner surface of tongue (235) and the outer surface of blade (260). As with channel (254) of sleeve (250), tongue (235) is configured to receive liquid coolant from fluid pump (280) such that the liquid coolant is placed in contact with blade (260) via gap (261) to thereby cool blade (260).

Figure 17:
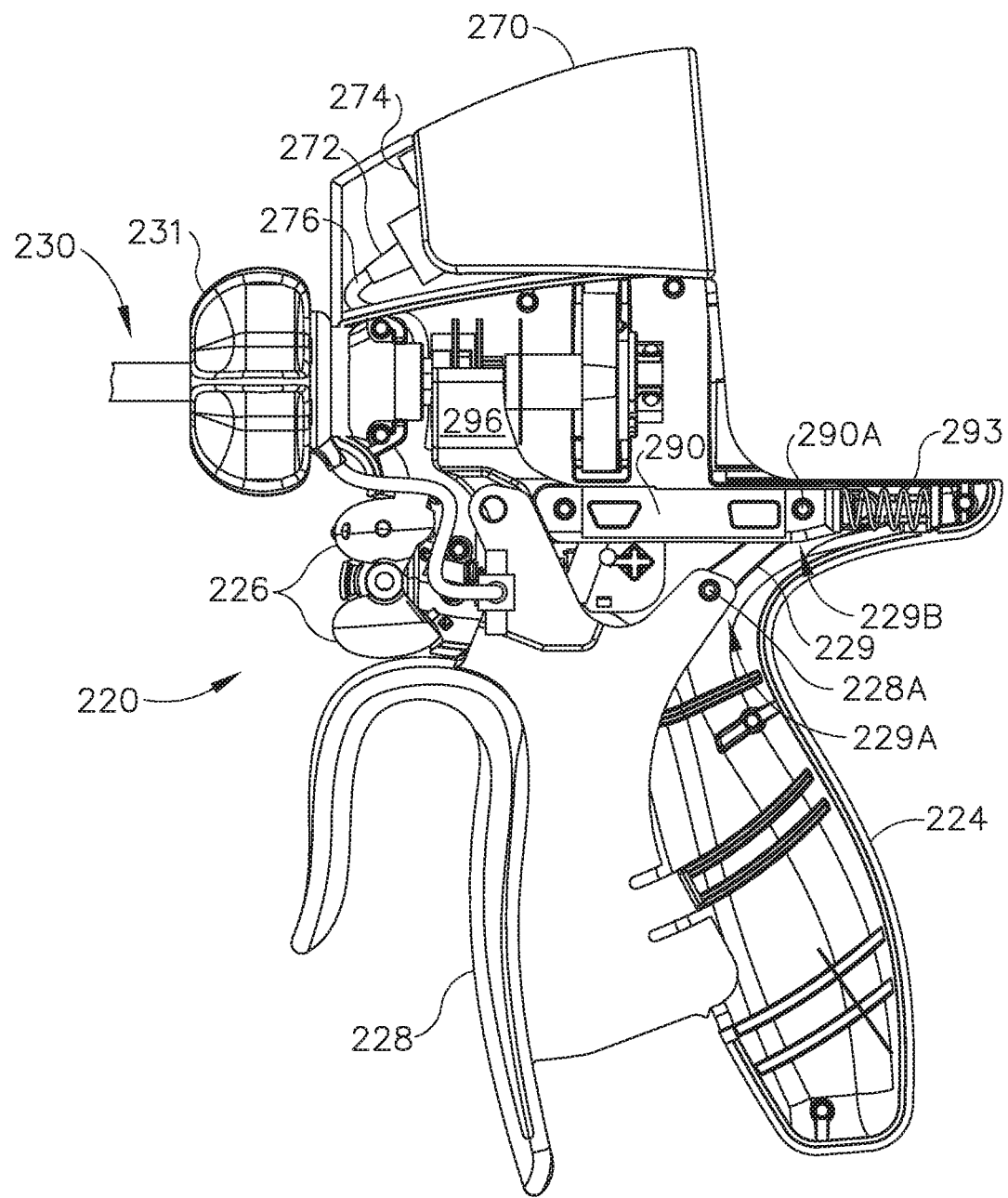
FIG. 17 depicts a side elevational view of the handle assembly of FIG. 7 with a housing shroud removed.
Figure 18:
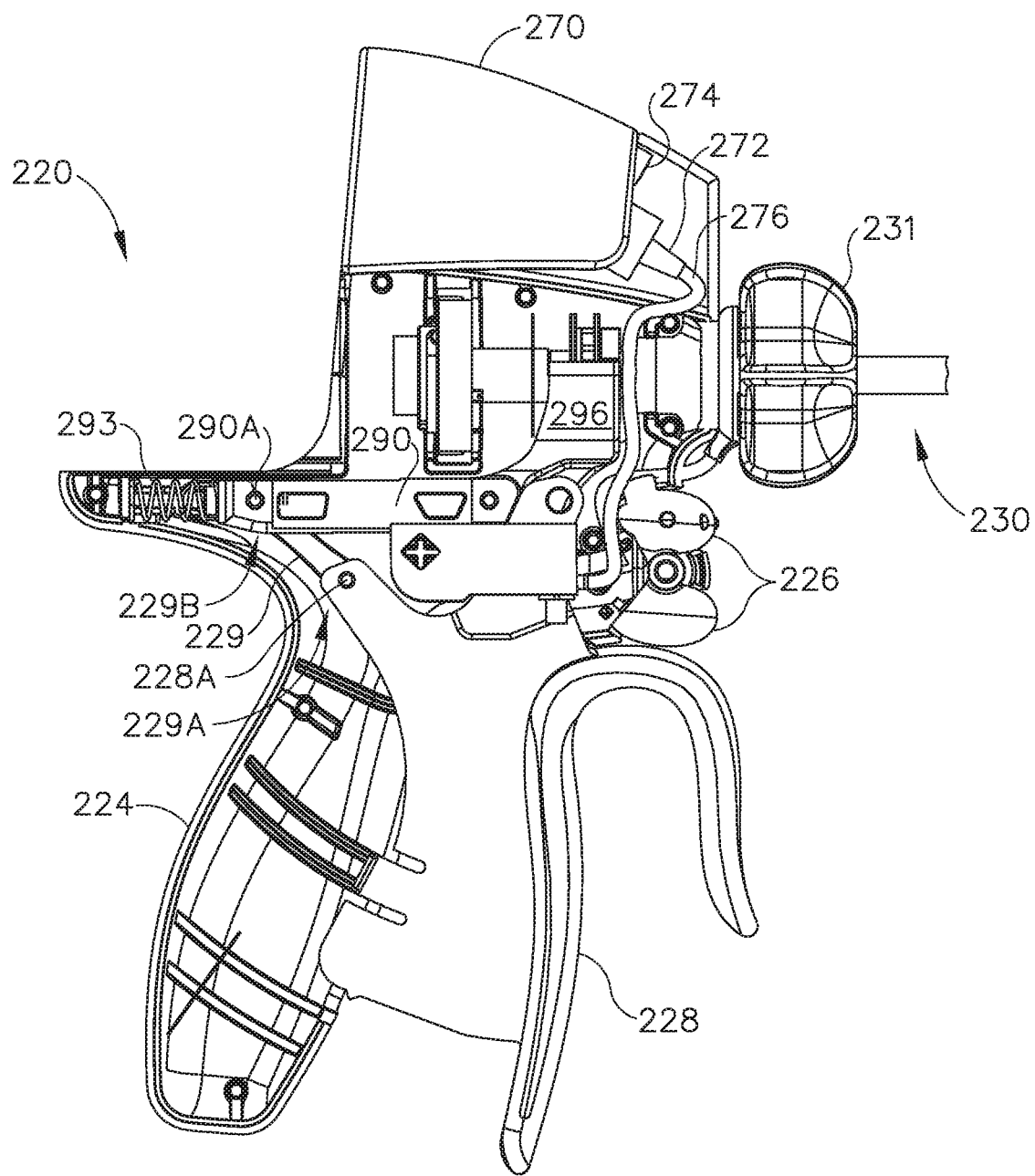
FIG. 18 depicts another side elevational view of the handle assembly of FIG. 7 with another housing shroud removed.
Figure 19:
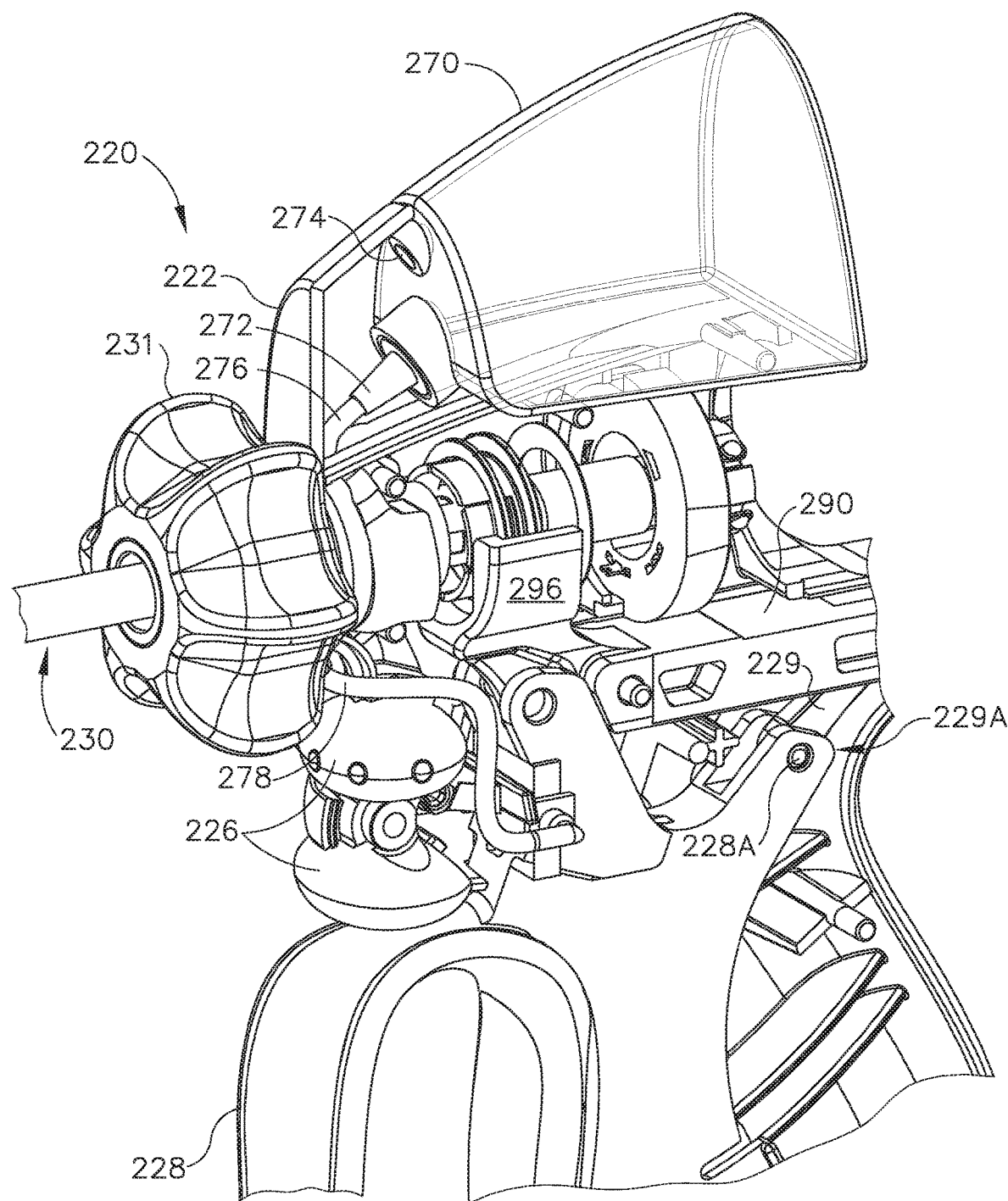
FIG. 19 depicts a detailed perspective view of the handle assembly of FIG. 7 with the housing shroud of FIG. 17 removed.
Figure 20:
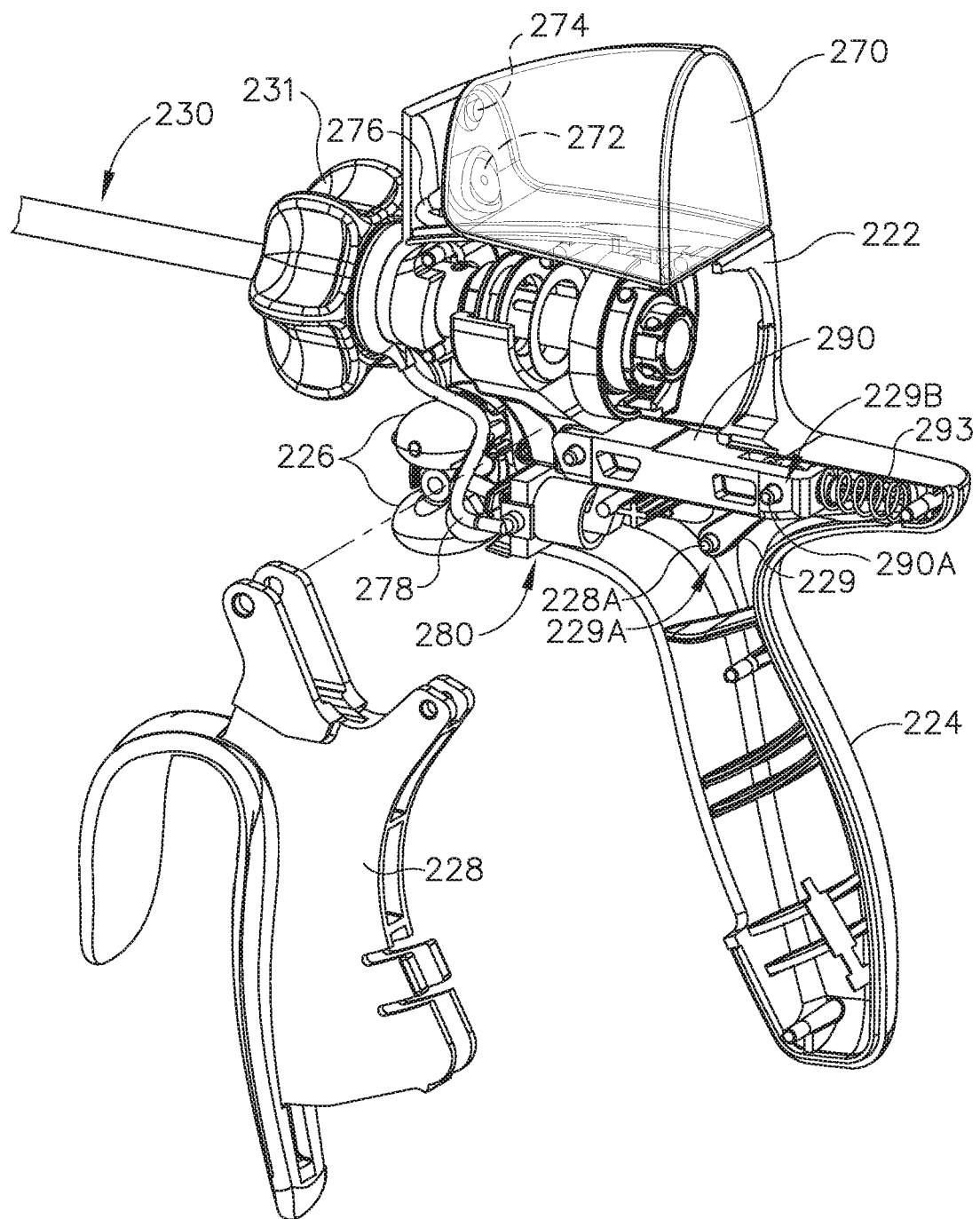
FIG. 20 depicts a perspective view of the handle assembly of FIG. 7 with the housing shroud of FIG. 17 removed and with a trigger of the handle assembly detached from the handle assembly.

FIGS. 17-19 show interior components of handle assembly (220). Trigger (228) of handle assembly (220) is pivotably coupled to body (222) of handle assembly (220) such that trigger (228) is operable to pivot toward and away from pistol grip (224). Trigger (228) is coupled with a yoke (290) via a linkage (229) such that rotation of trigger (228) causes longitudinal translation of yoke (229). A first end (229A) of linkage (229) is rotatably coupled with a proximal portion of trigger (228) via a pin (228A). A second end (229B) of linkage (229) is rotatably coupled with a proximal portion of yoke (290) via a pin (290A). Yoke (290) is longitudinally translatable within body (222) between a proximal longitudinal position and a distal longitudinal position. Yoke (290) is supported in handle assembly (220) by rails (not shown) formed in body (222) of handle assembly (220), such that yoke (290) is constrained to longitudinal movement within handle assembly (220). Because the proximal portion of trigger (228) is coupled with yoke (290) via linkage (229), it should be understood that pivoting of trigger (228) toward pistol grip (224) will cause proximal longitudinal translation of yoke (290) within body (222); and that pivoting of trigger (228) away from pistol grip (224) will cause distal longitudinal translation of yoke (290) within body (222). As will be discussed in more detail below, longitudinal translation of yoke (290) between the proximal longitudinal position and the distal longitudinal position pumps liquid coolant from fluid reservoir (270) to sleeve (250) via fluid pump (280).

Figure 21:
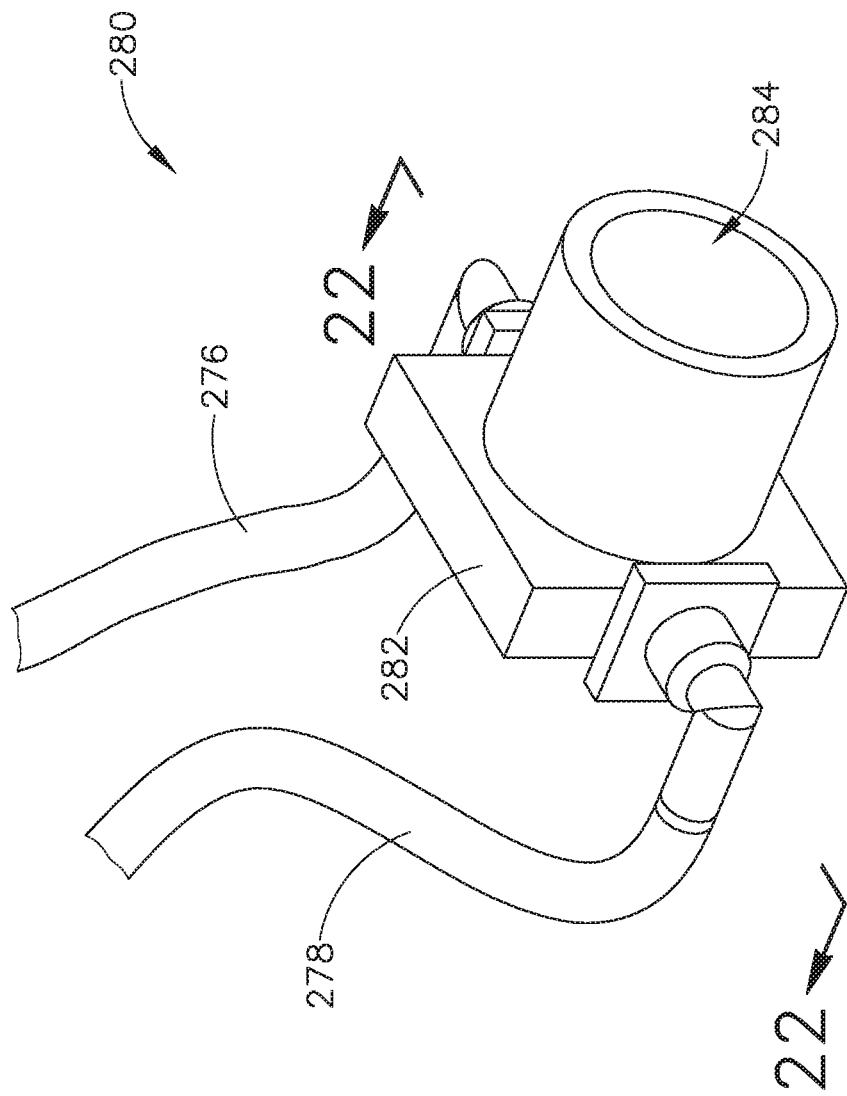
FIG. 21 depicts a perspective view of a pump of the instrument of FIG. 5.
Figure 22:
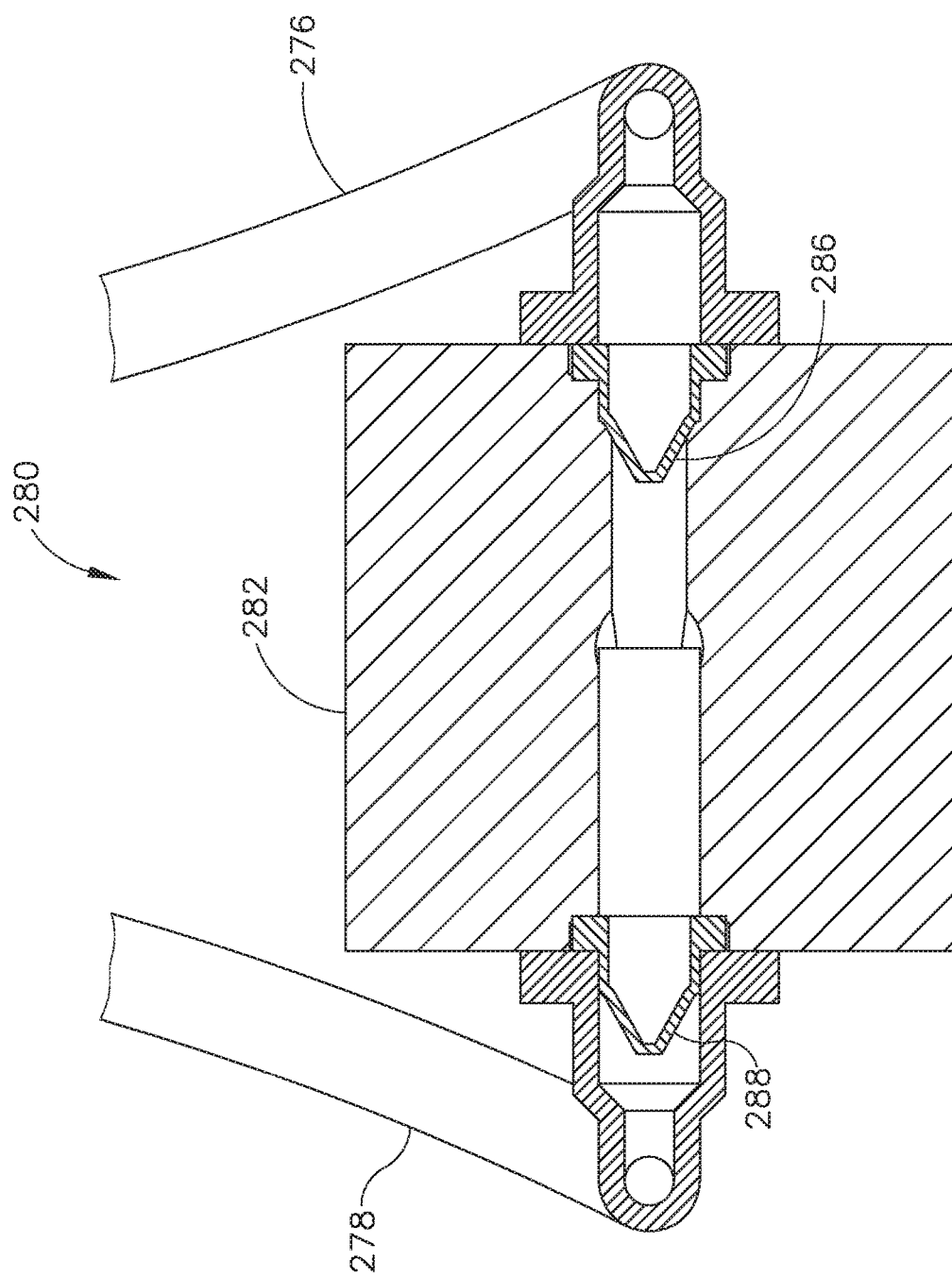
FIG. 22 depicts a cross-sectional end view of the pump of FIG. 21 taken along line 22-22 of FIG. 21.

FIGS. 21-22 depict fluid pump (280). Fluid pump (280) comprises a pump body (282) coupled to first tube (276) and a second tube (278). First tube (276) is further coupled with fluid reservoir (270). As will be discussed in more detail below, second tube (278) is in fluid communication with shaft assembly (230) such that second tube (278) is operable to deliver coolant fluid to shaft assembly (230). Pump body (282) defines a hollow cylindrical interior (284) that is configured to receive a piston (292) of a plunger (291) of yoke (290). As best seen in FIG. 22, hollow cylindrical interior (284) is in fluid communication with first tube (276) and second tube (278) via a pair of one-way valves (286, 288). A first one-way valve (286) permits the flow of liquid coolant from first tube (276) into hollow cylindrical interior (284) of pump body (282) but not in the opposite direction. A second one-way valve (288) permits the flow of liquid coolant from hollow cylindrical interior (284) of pump body (282) into second tube (278) but not in the opposite direction. Thus, one-way valves (286, 288) permit the flow of liquid coolant from first tube (276) through pump body (282) and from pump body (282) into second tube (278); but prohibit the flow of liquid coolant from second tube (278) into pump body (282) and from pump body (282) into first tube (276). It should therefore be understood that one-way valves (286, 288) permit the flow of liquid coolant from fluid reservoir (270) to shaft assembly (230) via fluid pump (280), but not vice versa. Although one-way valves (286, 288) of the present example are shown as a pair of duckbill valves, one-way valves (286, 288) may comprise any appropriate type of one-way valve as would be appreciated by one of ordinary skill in the art.

Figure 23:
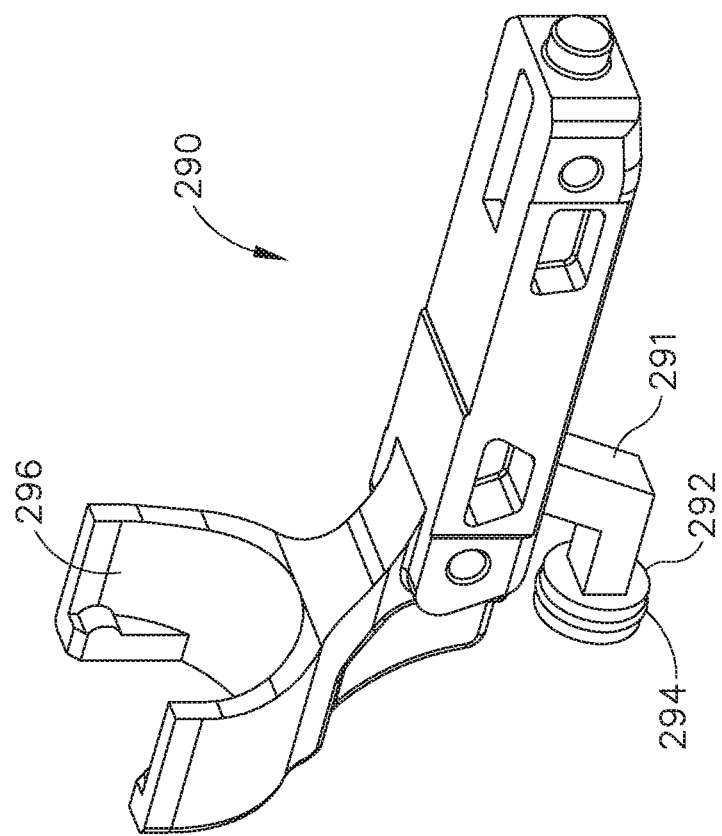
FIG. 23 depicts a perspective view of a yoke of the instrument of FIG. 5.
Figure 24:
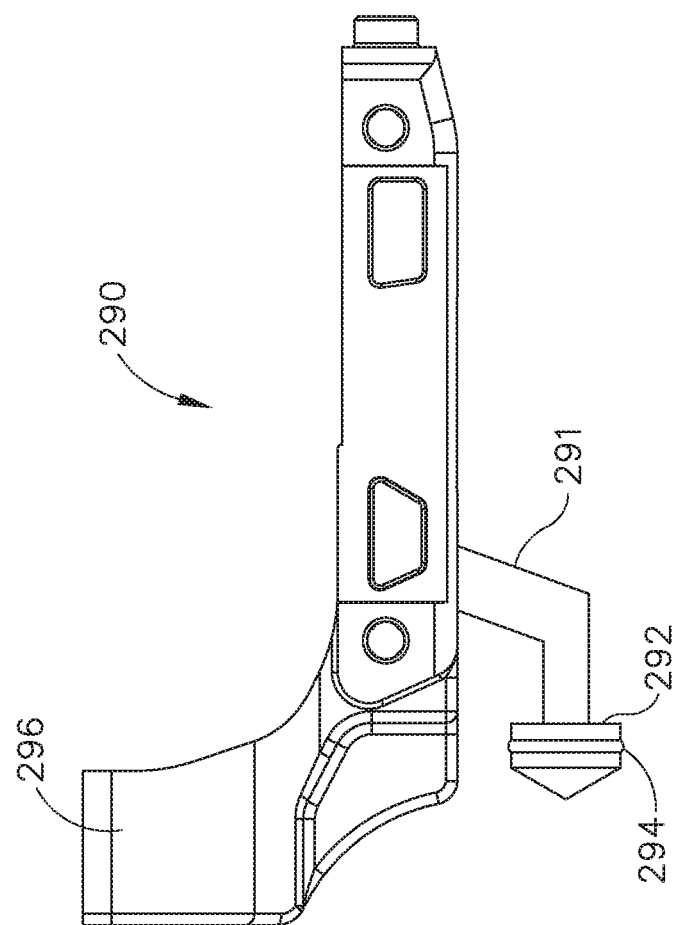
FIG. 24 depicts a side elevational view of the yoke of FIG. 23.

As shown in FIGS. 23 and 24, yoke (290) comprises a fork feature (296) and a plunger (291). Fork feature (296) is configured to couple with complementary feature at the proximal end of inner tube (176), such that yoke (290) and inner tube (176) longitudinally translate together unitarily. Plunger (291) extends from a bottom surface of yoke (290) and includes an integral piston (292). As mentioned above, hollow cylindrical interior (284) of pump body (282) is configured to receive piston (292) of plunger (291). Piston (292) comprises a circular seal ring (294) configured to engage an interior surface of hollow cylindrical interior (284) to thereby provide a fluid seal between an interior surface of pump body (282) and piston (292). As discussed above, yoke (290) is longitudinally translatable within body (222) between a proximal longitudinal position and a distal longitudinal position. Longitudinal translation of yoke (290) between the proximal longitudinal position and the distal longitudinal position causes concurrent longitudinal translation of piston (292) within pump body (282). As will be described in more detail below, this longitudinal translation of piston (292) is configured to cause a pumping effect within pump body (282). In the present example, a coil spring (293) is positioned proximal to yoke (290) and resiliently biases yoke (290) distally. Of course, yoke (290) may be resiliently biased in any other suitable fashion; or may be non-biased if desired.

Figure 25A:
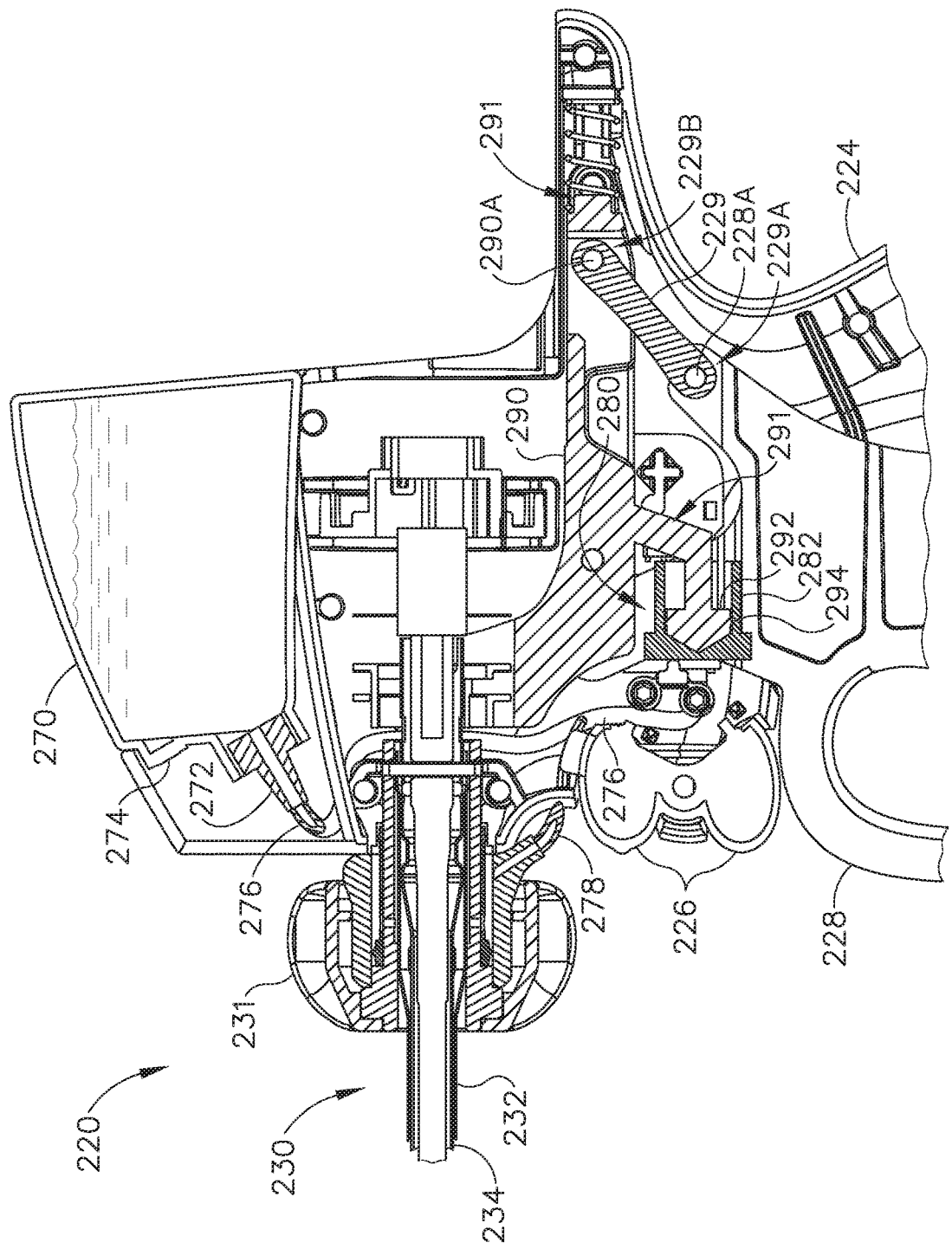
FIG. 25A depicts a side elevational view of the handle assembly of FIG. 7 with the housing shroud of FIG. 17 removed, with the trigger of the handle assembly in a first rotational position, and with the yoke of FIG. 23 in a first longitudinal position.
Figure 25B:
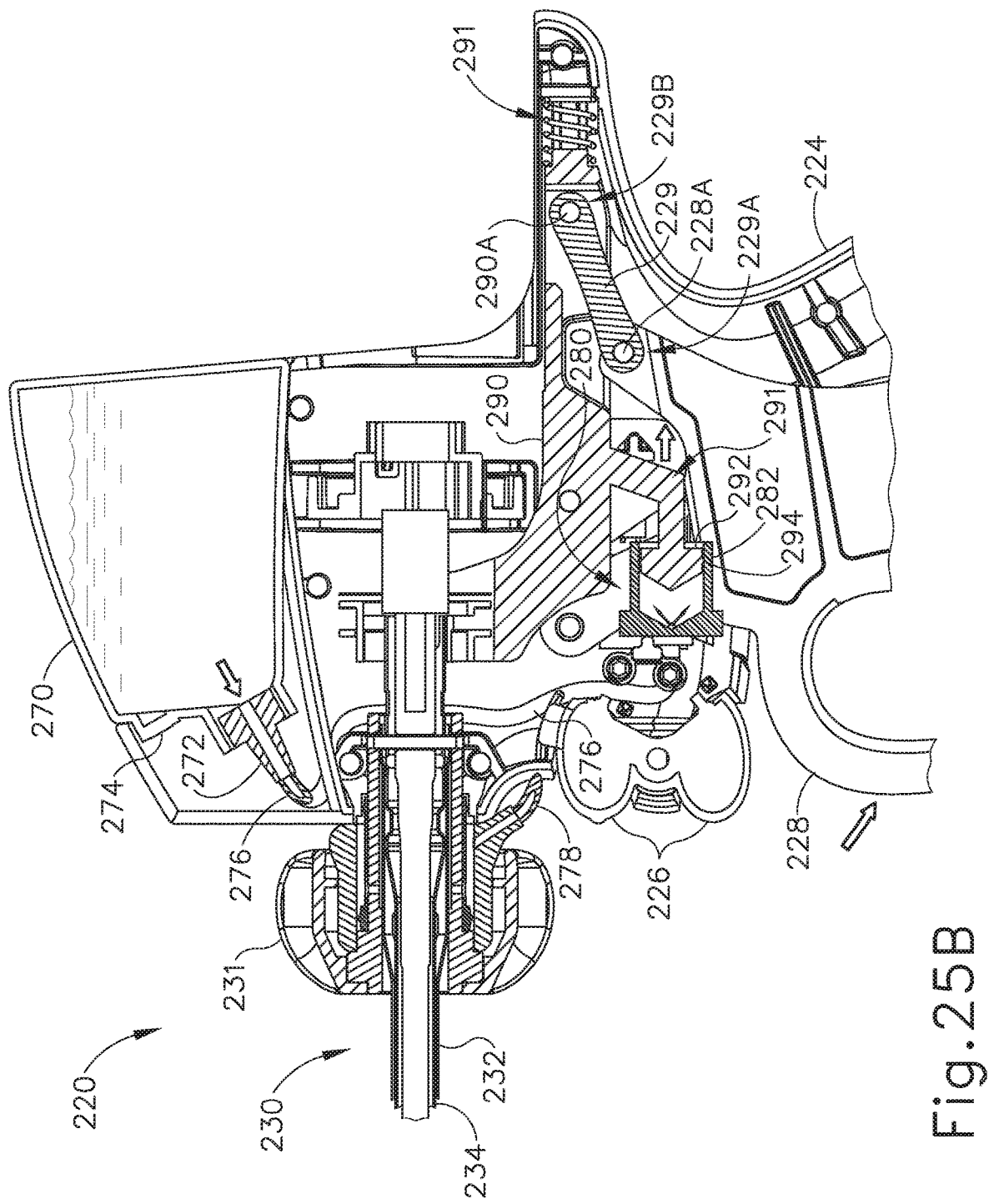
FIG. 25B depicts a side elevational view of the handle assembly of FIG. 7 with the housing shroud of FIG. 17 removed, with the yoke of FIG. 23 moved into a second longitudinal position by movement of the trigger to a second rotational position to thereby draw fluid from the fluid reservoir of FIG. 8 into the pump of FIG. 21.

FIGS. 25A-25C depict the operation of fluid pump (280). FIG. 25A shows instrument (200) in an initial position. As shown in FIG. 25B, and as discussed above, pivoting of trigger (228) toward pistol grip (224) causes proximal longitudinal translation of yoke (290) within body (222) which in turn causes proximal longitudinal translation of piston (292) within pump body (282). The proximal translation of yoke (290) within body (222) also causes proximal translation of inner tube (234), which in turn causes clamp arm (244) to pivot toward blade (260). The proximal longitudinal translation of piston (292) within pump body (282) causes a vacuum to be drawn within pump body (282) thereby drawing liquid coolant from fluid reservoir (270) into pump body (282) via first tube (276) and one-way valve (286). It should be appreciated that one-way valve (288) prohibits liquid coolant from being drawn from second tube (278) into pump body (282) as piston (292) draws a vacuum within pump body (282).

As shown in FIG. 25C, and as discussed above, pivoting of trigger (228) away from pistol grip (224) causes distal longitudinal translation of yoke (290) within body (222) which in turn causes distal longitudinal translation of piston (292) within pump body (282). The distal translation of yoke (290) within body (222) also causes distal translation of inner tube (234), which in turn causes clamp arm (244) to pivot away from blade (260). The distal longitudinal translation of piston (292) within pump body (282) pressurizes the liquid coolant within hollow cylindrical interior (284) of pump body (282) thereby forcing liquid coolant from pump body (282) into second tube (278) via one-way valve (288). It should be appreciated that one-way valve (286) prohibits liquid coolant being forced into first tube (276) as piston (292) pressurizes the liquid coolant within pump body (282). Thus, it should be understood that pivoting of trigger (228) toward and away from pistol grip (224) will pump liquid coolant from fluid reservoir (270) to shaft assembly (230) via fluid pump (280); while simultaneously pivoting clamp arm (244) toward and away from blade (260).

As discussed above, shaft assembly (230) comprises outer sheath (232) and inner tube (234). Shaft assembly (230) of the present example further includes a rotation knob (231). Rotation knob (231) is operable to rotate the entire shaft assembly (230) and end effector (240) relative to handle assembly (220) about a longitudinal axis of shaft assembly (230). By way of example only, rotation knob (231) and associated components and features may be configured and operable in accordance with at least some of the teachings of U.S. Pub. No. 2016/0143657, published May 26, 2016, issued as U.S. Pat. No. 10,206,705 on Feb. 19, 2019, entitled "Features for Communication of Fluid through Shaft Assembly of Ultrasonic Surgical Instrument," the disclosure of which is incorporated by reference herein.

As best seen in FIG. 26, rotation knob (231) of shaft assembly (230) comprises a rotatable housing (236) that is rotatably disposed about outer sheath (232); and a stationary housing (238) disposed about rotatable housing (236). An interior space (237) is defined between an interior surface of stationary housing (238) and rotatable housing (236). As shown in FIG. 26, second tube (278) is coupled to stationary housing (238) such that as liquid coolant is forced through second tube (278), second tube (278) passes the liquid coolant through stationary housing (283) and into interior space (237). An interior space (233) is formed between outer sheath (232) and inner tube (234) and extends the length of shaft assembly (230). As will be discussed in more detail below, liquid coolant is configured to pass within interior space (233) to sleeve (250) to thereby cool blade (260). A pair of openings (239) are formed in rotatable housing (236). Another pair of openings (231) are formed in outer sheath (232). Openings (239, 231) are aligned to provide fluid communication between interior space (237) and interior space (233) such that the liquid coolant is able to pass from interior space (237) into interior space (233) formed between outer sheath (232) and inner tube (234). A pair of fluid seals (235) prevent fluid from inadvertently escaping interior space (237); while still permitting rotatable housing (236) to rotate relative to stationary housing (238). A fluid seal (241) prevents fluid from inadvertently escaping interior space (233) proximally. While openings (239, 231) are described as being formed in respective pairs, it should be understood that any suitable number of openings (239, 231) may be provided.

Figure 27:
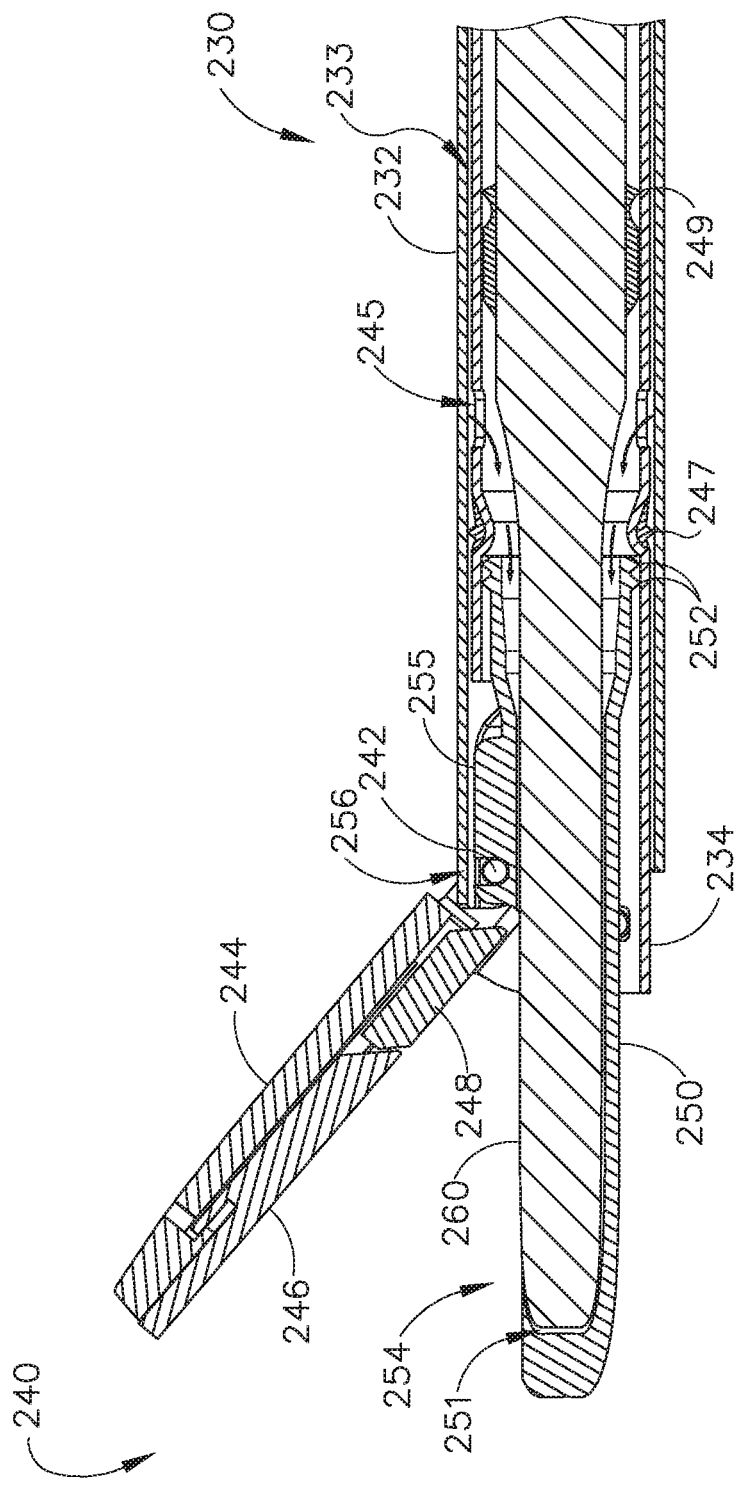
FIG. 27 depicts a cross-sectional side view of the end effector of FIG. 11, with fluid forced from the pump of FIG. 21 passing through the interior passageway of the shaft assembly of FIG. 26 and into the sleeve of FIG. 13.
Figure 28:
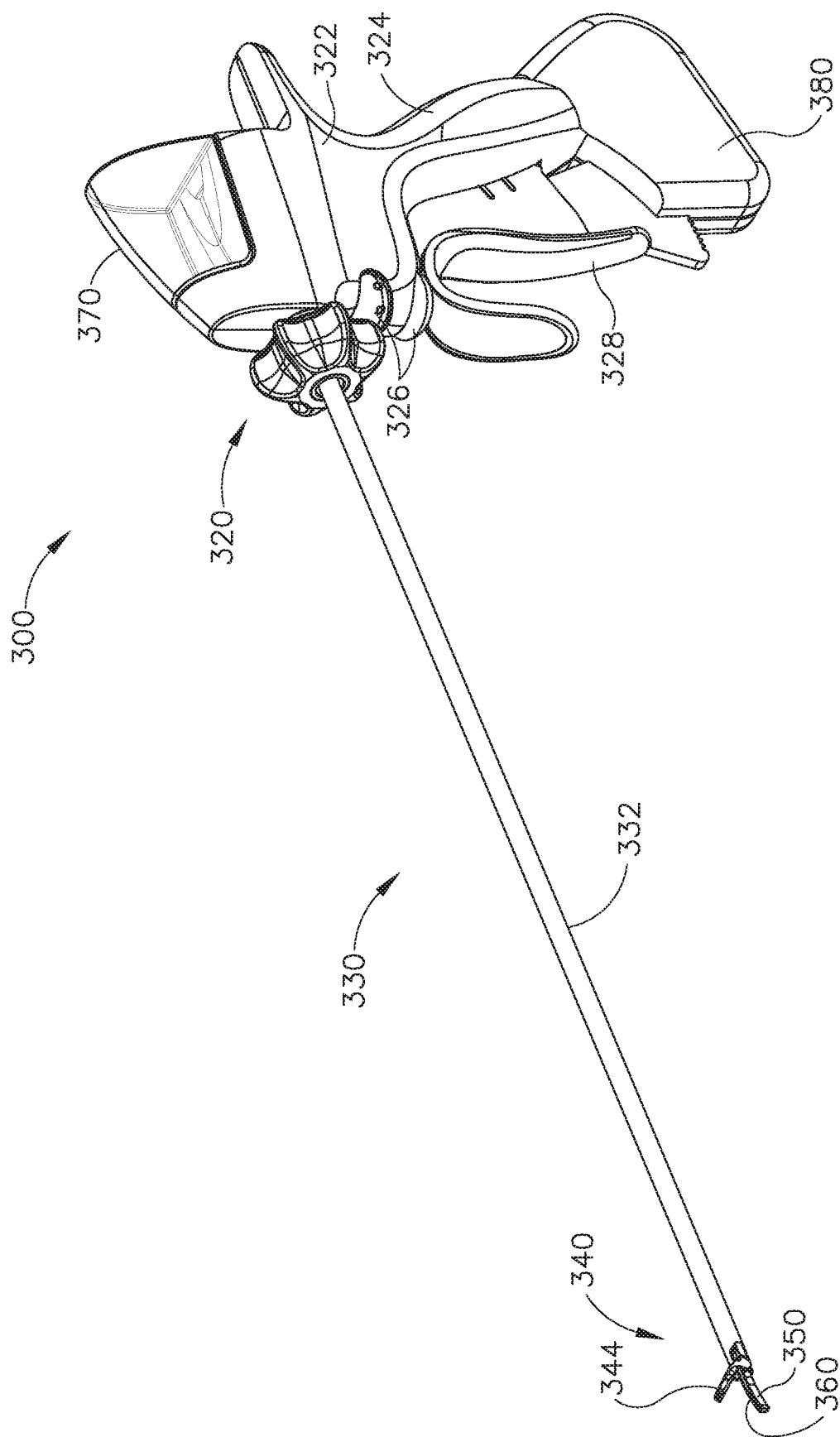
FIG. 28 depicts a perspective view of another exemplary alternative ultrasonic surgical instrument.
Figure 29:
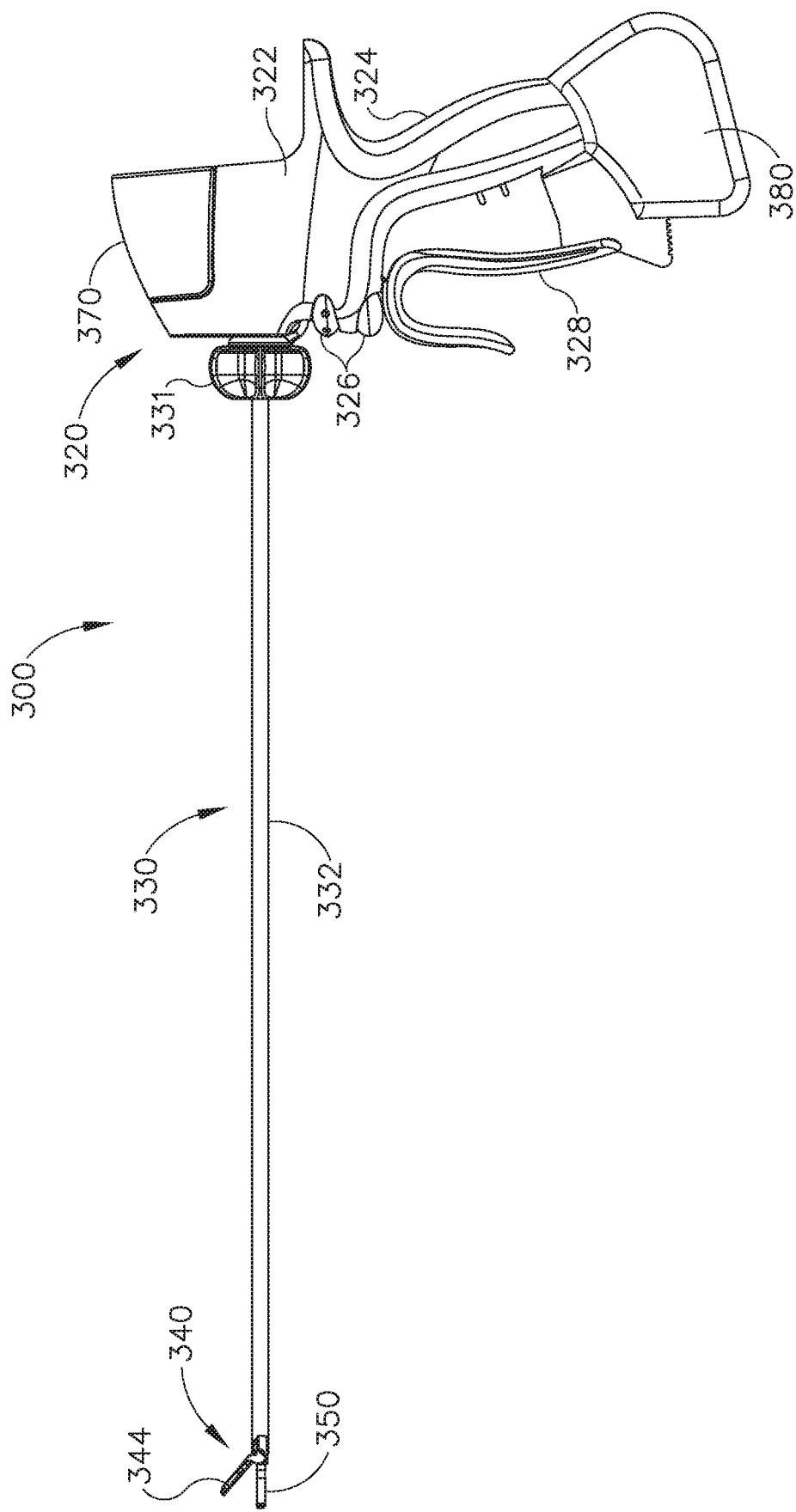
FIG. 29 depicts a side elevational view of the instrument of FIG. 28.
Figure 30:
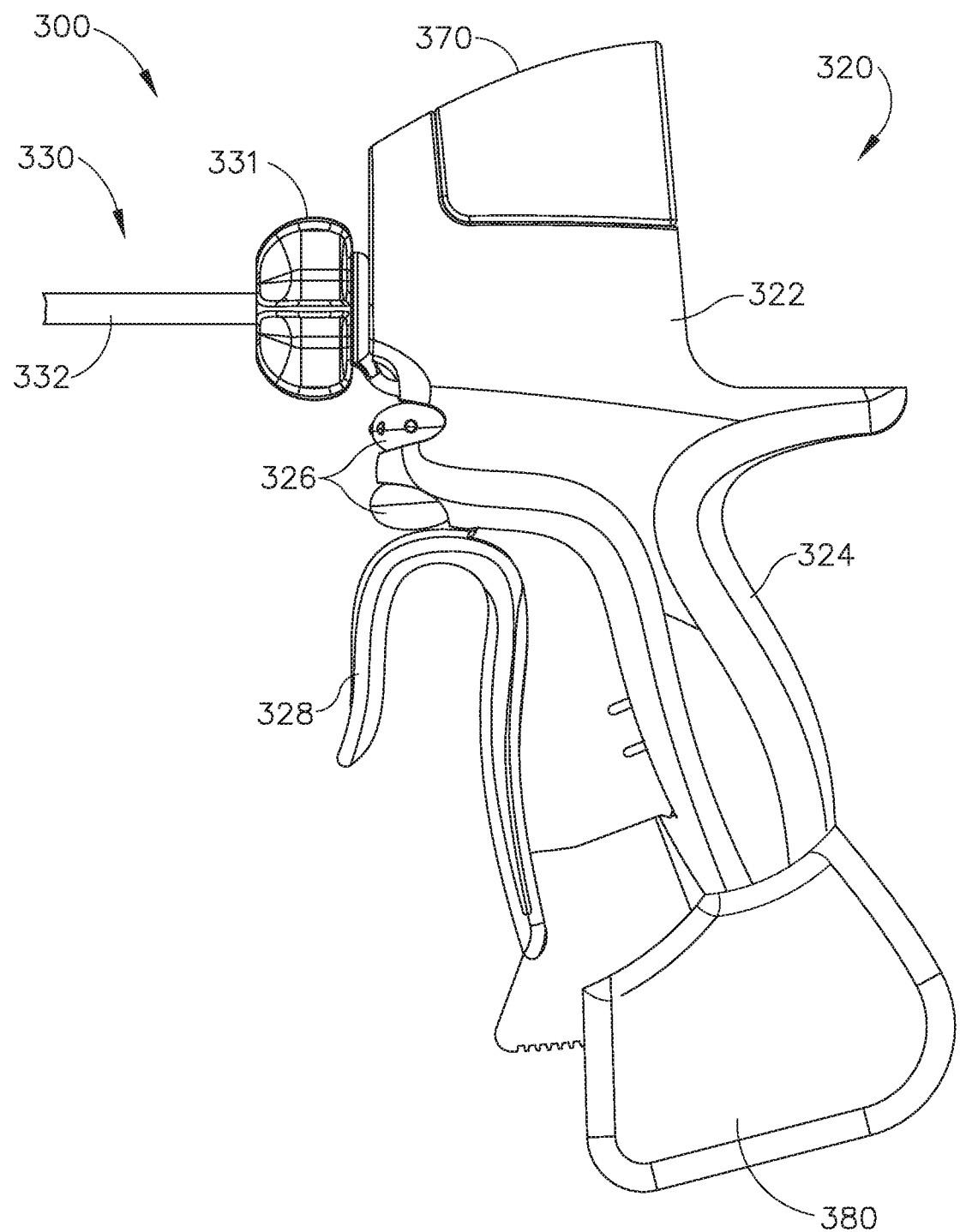
FIG. 30 depicts a side elevational view of a handle assembly of the instrument of FIG. 28.

As shown in FIG. 27, as liquid coolant is passed within interior space (233) of shaft assembly (230), the liquid coolant travels the length of shaft assembly (230) and eventually passes from interior space (233) into an interior of inner tube (234) via a set of openings (245) that are formed in a distal portion of inner tube (234). Again, any suitable number of openings (245) may be provided. A fluid seal (247) prevents the fluid from inadvertently escaping interior space (233) distally. As discussed above, a proximal end of sleeve (250) is disposed within a distal end of inner tube (234). Annular seals (252) are configured to engage an interior surface of inner tube (234) to thereby provide a fluid seal between inner tube (234) and sleeve (250) such that liquid coolant is configured to pass from the interior of inner tube (234) to the gap (251) in channel (254) of sleeve (250). A fluid seal (249) prevents fluid from inadvertently escaping the interior of inner tube (234) proximally. As gap (251) of channel (254) receives liquid coolant, the liquid coolant contacts blade (260) to thereby provide a cooling effect to blade (260). Thus, from the discussion above, it should be understood that pivoting of trigger (228) toward and away from pistol grip (224) will pump liquid coolant from fluid reservoir (270) to sleeve (250) via fluid pump (280). In some versions, each actuation of trigger (228) delivers approximately 280 microliters of liquid coolant to sleeve (250). Alternatively, any other suitable volume of liquid coolant may be delivered to sleeve (250) with each actuation of trigger (220).

B. Exemplary Ultrasonic Surgical Instrument with Peristaltic Pump

FIGS. 28-34B illustrate another exemplary ultrasonic surgical instrument (300) that is configured to operate substantially similar to instruments (100, 200) discussed above except for the differences discussed below. It should therefore be understood that instrument (300) may include the same components and operabilities as instrument (20, 100), in addition to including the components and operabilities described below. Instrument (300) of the present example comprises a handle assembly (320), a shaft assembly (330), and an end effector (340). Handle assembly (320) comprises a body (322) including a pistol grip (324) and a pair of buttons (326). As with instruments (100, 200) discussed above, body (322) of handle assembly (320) is configured to receive an ultrasonic transducer assembly (not shown). Handle assembly (320) of the present example further comprises a fluid reservoir (370) that is configured and operable substantially similar to fluid reservoir (270) discussed above. Handle assembly (320) also includes a trigger (328) that is pivotable toward and away from pistol grip (324). End effector (340) includes an ultrasonic blade (360) and a pivoting clamp arm (344). Clamp arm (344) is coupled with trigger (328) such that clamp arm (344) is pivotable toward ultrasonic blade (360) in response to pivoting of trigger (328) toward pistol grip (324); and such that clamp arm (344) is pivotable away from ultrasonic blade (360) in response to pivoting of trigger (328) away from pistol grip (324). In some versions, one or more resilient members are used to bias clamp arm (344) and/or trigger (328) to the open position.

Shaft assembly (330) of the present example comprises an outer sheath (332) and an inner tube (not shown). Like inner tube (234) described above, the inner tube of this example is slidably disposed within outer sheath (332) such that the inner tube may translate longitudinally within outer sheath (332) relative to outer sheath (332) to selectively pivot clamp arm (344) toward and away from blade (360). As with end effector (240) discussed above, end effector (340) of the present example comprises clamp arm (344), an ultrasonic blade (360), and a sleeve (350). Clamp arm (344) is operable to selectively pivot toward and away from blade (360) to selectively clamp tissue between clamp arm (344) and blade (360). Clamp arm (344), blade (360), and sleeve (350) may be configured and operable substantially identical to clamp arm (244), blade (260), and sleeve (250) described above. In addition, shaft assembly (330) includes a rotation knob (331) that is configured to provide fluid communication just like rotation knob (231) described above. The fluid coupling features of rotation knob (331) are in fluid communication with shaft assembly (330) and peristaltic fluid pump (380). Thus, with blade (360) disposed within a channel (not shown) of sleeve (350), sleeve (350) is configured to receive liquid coolant within channel (354) from a peristaltic fluid pump (380) via rotation knob (331) such that the liquid coolant is placed in contact with blade (360) to thereby cool blade (360).

Figure 31:
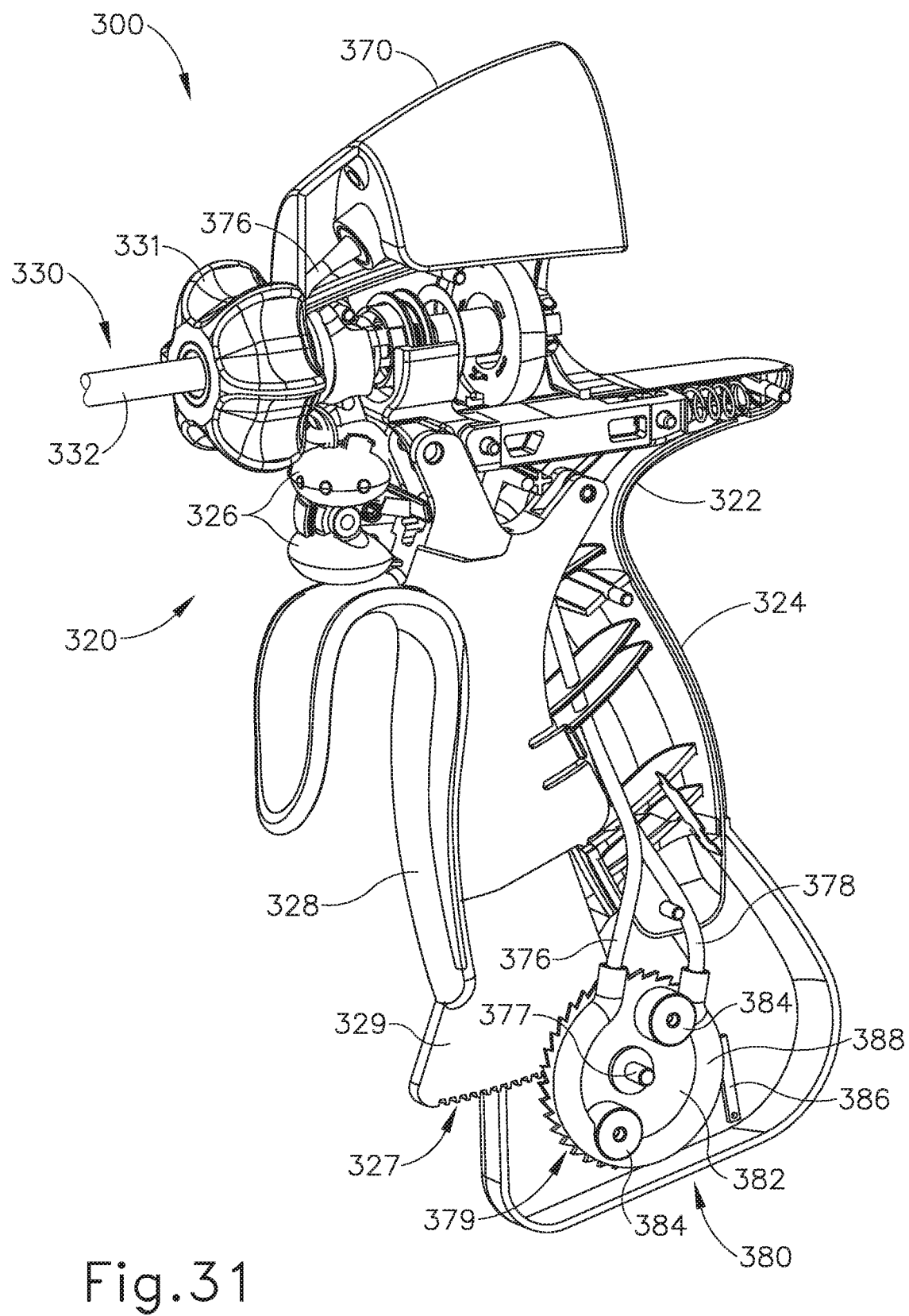
FIG. 31 depicts a perspective view of the handle assembly of FIG. 30 with a housing shroud removed.
Figure 32:
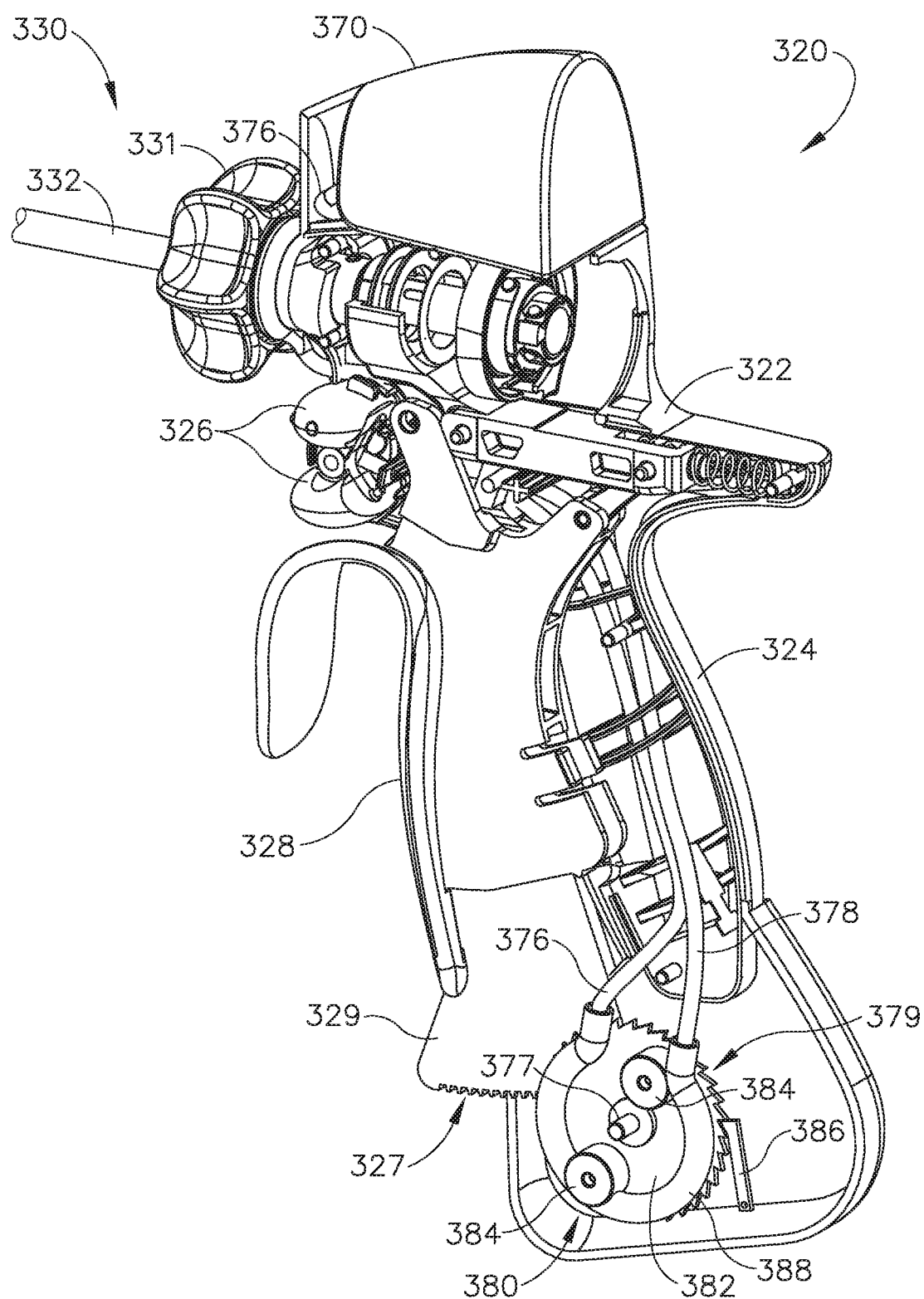
FIG. 32 depicts another perspective view of the handle assembly of FIG. 30 with the housing shroud of FIG. 31 removed.

FIGS. 31 and 32 show interior components of handle assembly (320). Trigger (328) of handle assembly (320) is pivotably coupled to body (322) of handle assembly (320) such that trigger (328) is operable to pivot toward and away from pistol grip (324). A peristaltic pump (380) is disposed within pistol grip (324) of handle assembly (320). Peristaltic pump (380) comprises a wheel (382). Wheel (382) is rotatably coupled to an interior surface of body (322) via a pin (377) such that wheel (382) is operable to rotate about pin (377) within body (322). Wheel (382) comprises a pair of rollers (384) that are rotatably coupled to a lateral surface of wheel (382). Rollers (384) are secured to wheel (382) such that rollers (384) orbit about pin (377) when wheel (382) rotates about pin (377). Rollers (384) are also operable to rotate independently of wheel (382) such that rollers (384) rotate about their own respective axes as rollers (384) orbit about pin (377). Wheel (382) comprises a plurality of teeth (379) disposed about an outer perimeter of wheel (382). Peristaltic pump (380) further comprises an arm (386) that is rotatably coupled to an interior surface of body (322) and that is biased to engage teeth (379) of wheel (382) in a ratcheting fashion, such that arm (386) serves as a pawl. Teeth (379) of wheel (382) are configured such that engagement with lever arm (386) permits counter-clockwise rotation of wheel (382) about pin (377), but prohibits clockwise rotation of wheel (382) about pin (377). In this context, "clockwise" and "counter-clockwise" are only intended to refer to rotation in the view shown in FIGS. 31-33D.

Peristaltic pump (380) further comprises a resilient tube (388). A first end of resilient tube (388) is coupled to a first tube (376). First tube (376) is further coupled with fluid reservoir (370). A second end of resilient tube (388) is coupled to a second tube (378). Second tube (378) is further coupled with shaft assembly (330), which is in fluid communication with sleeve (350) of end effector (340). Body (322) includes one or more boss features (not shown) that are positioned on the radially outermost regions of resilient tube (388), thereby providing structural support and mechanical grounding to resilient tube (388). Resilient tube (388) is positioned adjacent to rollers (384) such that rollers (384) bear against a radially interior surface of resilient tube (388) and cause resilient tube (388) to deform as rollers (384) rotate with wheel (382) about pin (377). In other words, resilient tube (388) is pinched between rollers (384) and the boss features of body (322). The orbital rotation of rollers (384) about pin (377) draws liquid coolant from reservoir (370) through resilient tube (388) through a peristaltic action. In particular, rotation of rollers (384) draws liquid coolant from first tube (376) through resilient tube (388) and drives the liquid coolant into second tube (378). Thus, it should be understood that peristaltic pump (380) is configured to draw liquid coolant from fluid reservoir (370) via first tube (376) and to pump the liquid coolant into sleeve (350) via second tube (378) and shaft assembly (330) by rotation of peristaltic pump (380).

Figure 34A:
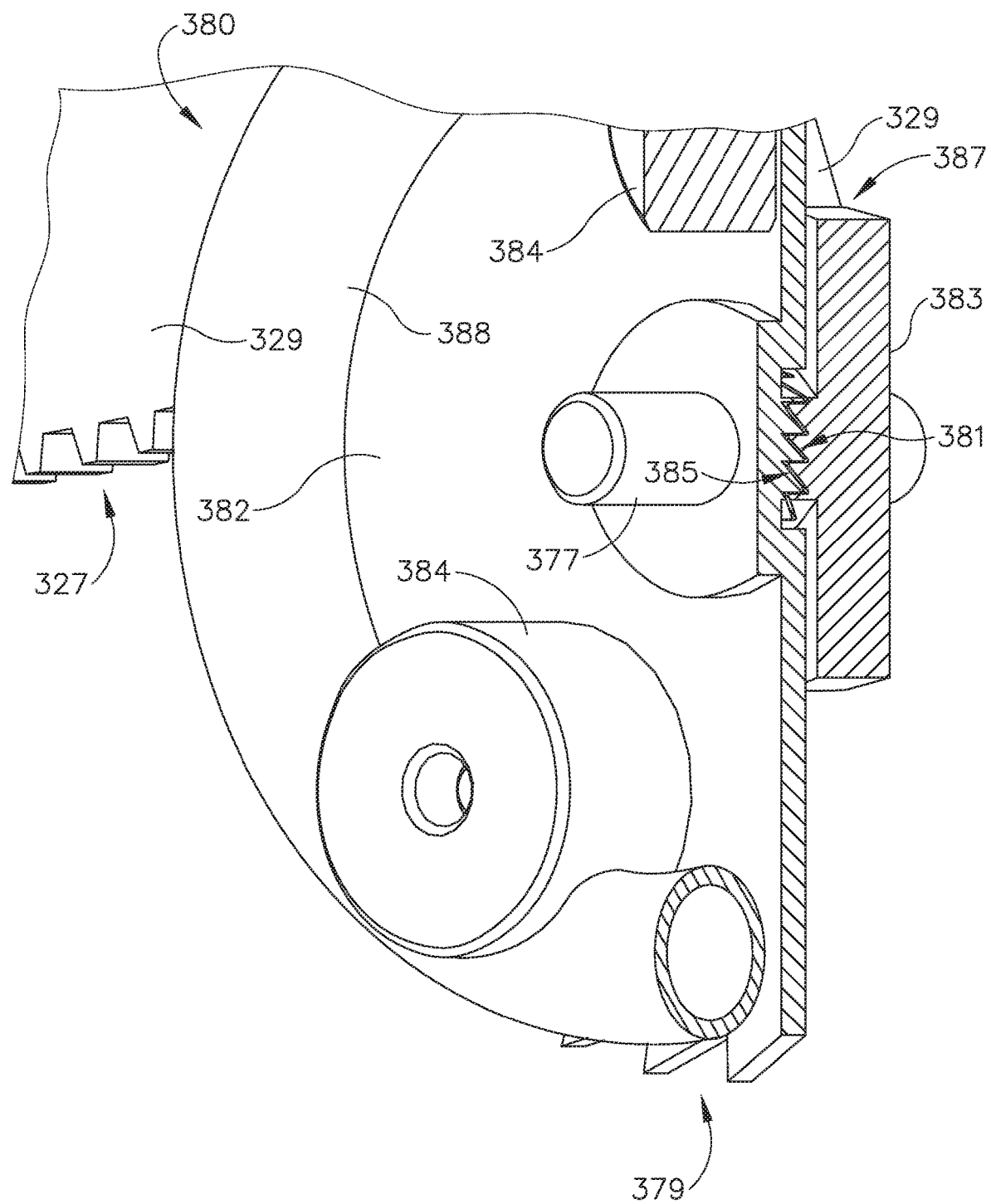
FIG. 34A depicts a cross-sectional perspective view of the peristaltic pump of FIG. 33A with a first gear and a second gear of the peristaltic pump engaged with one another.
Figure 34B:
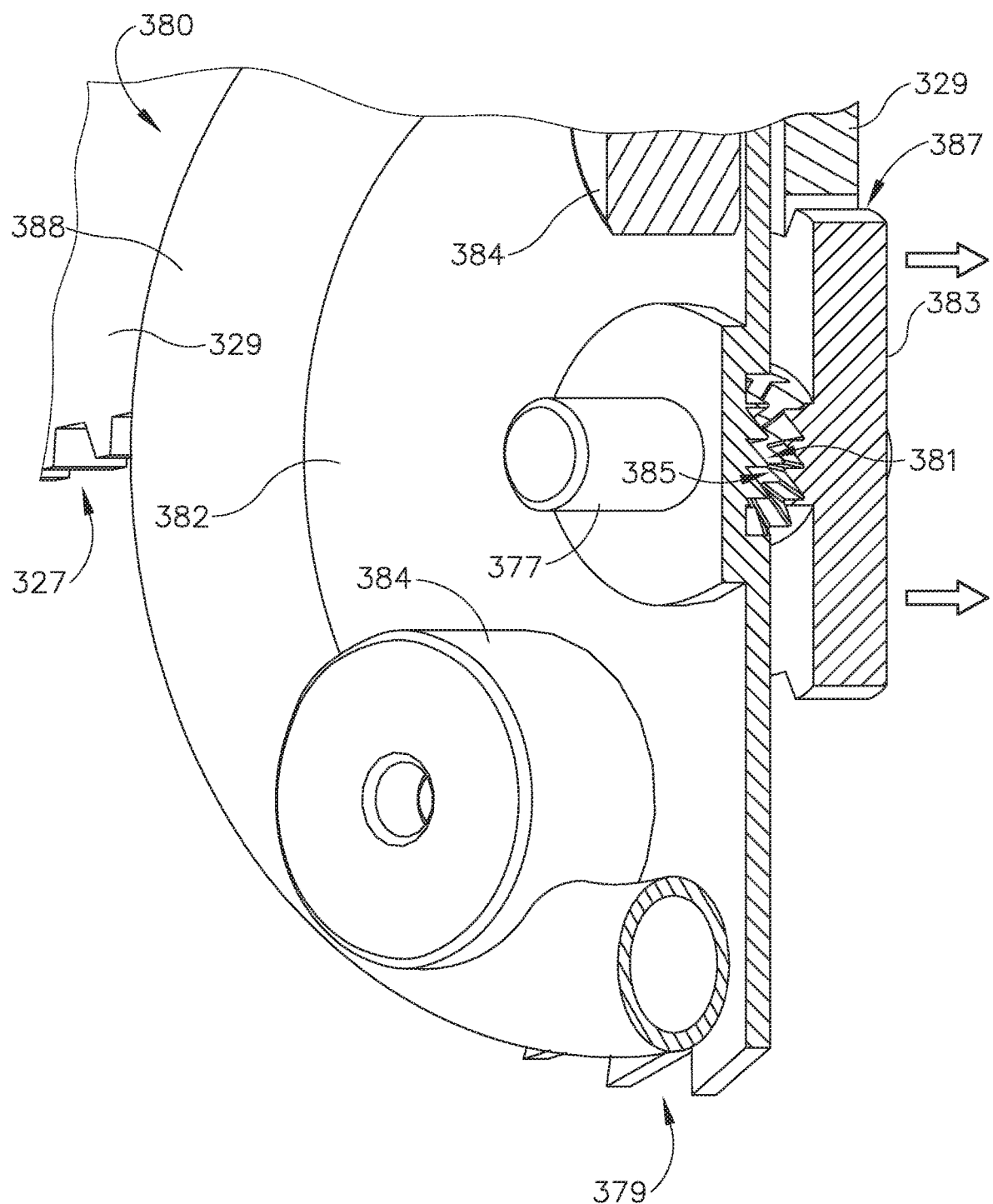
FIG. 34B depicts a cross-sectional perspective view of the peristaltic pump of FIG. 33A with the first gear and the second gear of FIG. 34A disengaged from one another as the trigger of FIG. 33A is moved from the first rotational position to the second rotational position.
Figure 35:
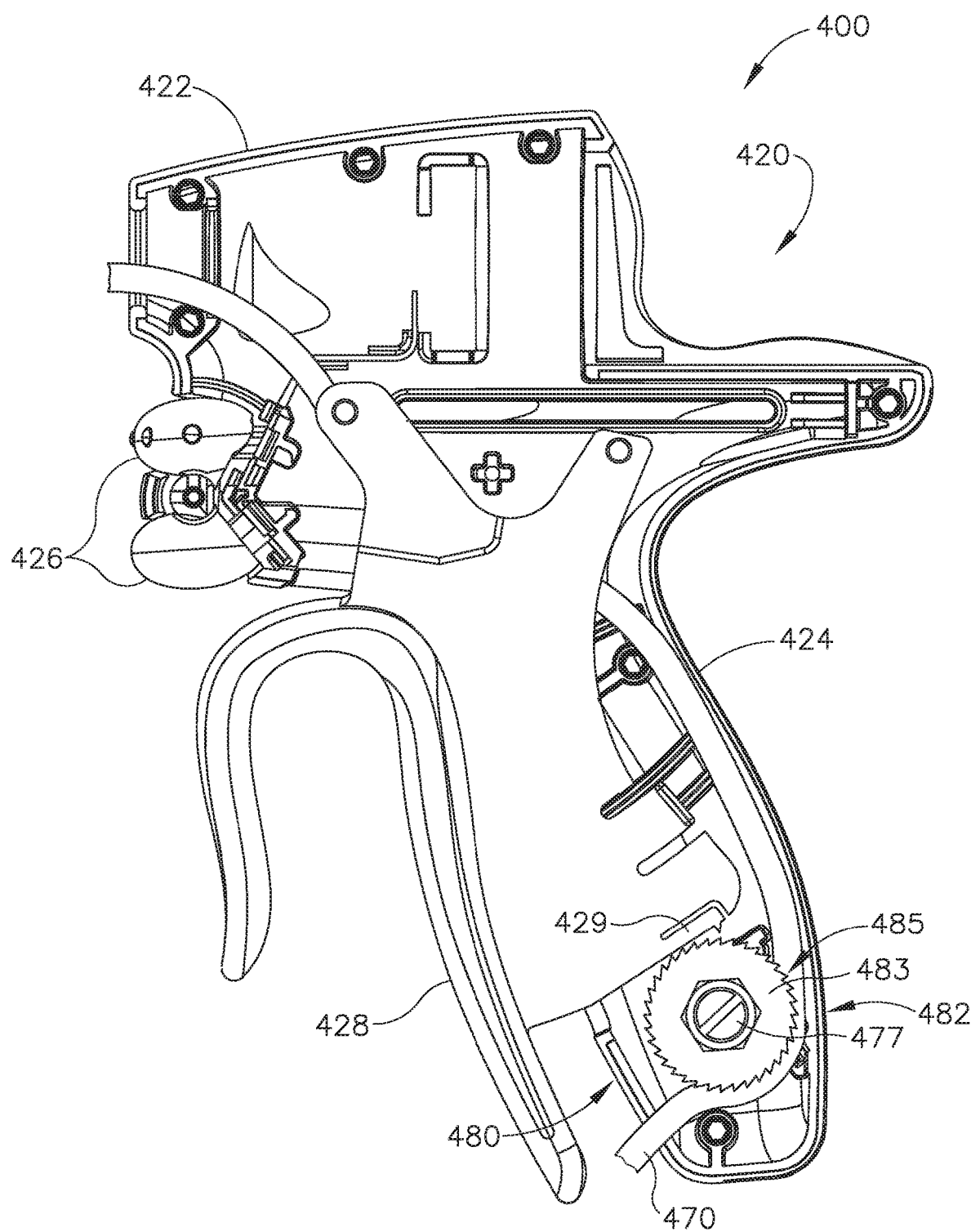
FIG. 35 depicts a side elevational view of yet another exemplary alternative ultrasonic surgical instrument with a housing shroud of a handle assembly removed.

FIGS. 34A and 34B show certain aspects of the operation of peristaltic pump (380). Wheel (382) comprises a plurality of gear teeth (381) formed in a lateral surface of wheel (382) (i.e., in the lateral surface that is opposite to the lateral surface having rollers (384)). Peristaltic pump (380) further comprises a gear (383) that comprises a first plurality of teeth (385) and a second plurality of teeth (387). Teeth (385) are configured to engage teeth (381) of wheel (382). Teeth (387) are disposed about an outer perimeter of gear (383). It should be appreciated that peristaltic pump (380) may comprise a biasing member (not shown) (e.g., a spring disposed about pin (377)) that is configured to bias gear (383) toward wheel (382) such that teeth (385) of gear (383) are biased to engage teeth (381) of wheel (382). Trigger (328) comprises a flange (329) extending from a lower portion of trigger (328). Flange (329) comprises a plurality of teeth (327). Teeth (387) are configured to engage teeth (327) of trigger (328) such that pivoting of trigger (328) toward and away from pistol grip (324) causes rotation of gear (383). However, teeth (385) of gear (383) and teeth (381) of wheel (382) are configured such that as trigger (328) is pivoted toward pistol grip (324), gear (383) translates along pin (377) away from wheel (382) and disengages wheel (382) such that rotation of gear (383) is not communicated to wheel (382). Thus, it should be understood that pivoting of trigger (328) toward pistol grip (324) is not communicated to wheel (382). On the other hand, teeth (385) of gear (383) and teeth (381) of wheel (382) are configured such that as trigger (328) is pivoted away from pistol grip (324), gear (383) remains engaged with wheel (382) such that rotation of gear (383) is communicated to wheel (382). It should therefore be understood that pivoting of trigger (328) away from pistol grip (324) is communicated to wheel (382). Pivoting of trigger (328) away from pistol grip (324) thus actuates peristaltic pump (380) while pivoting of trigger (328) toward pistol grip (324) will not.

Figure 33A:
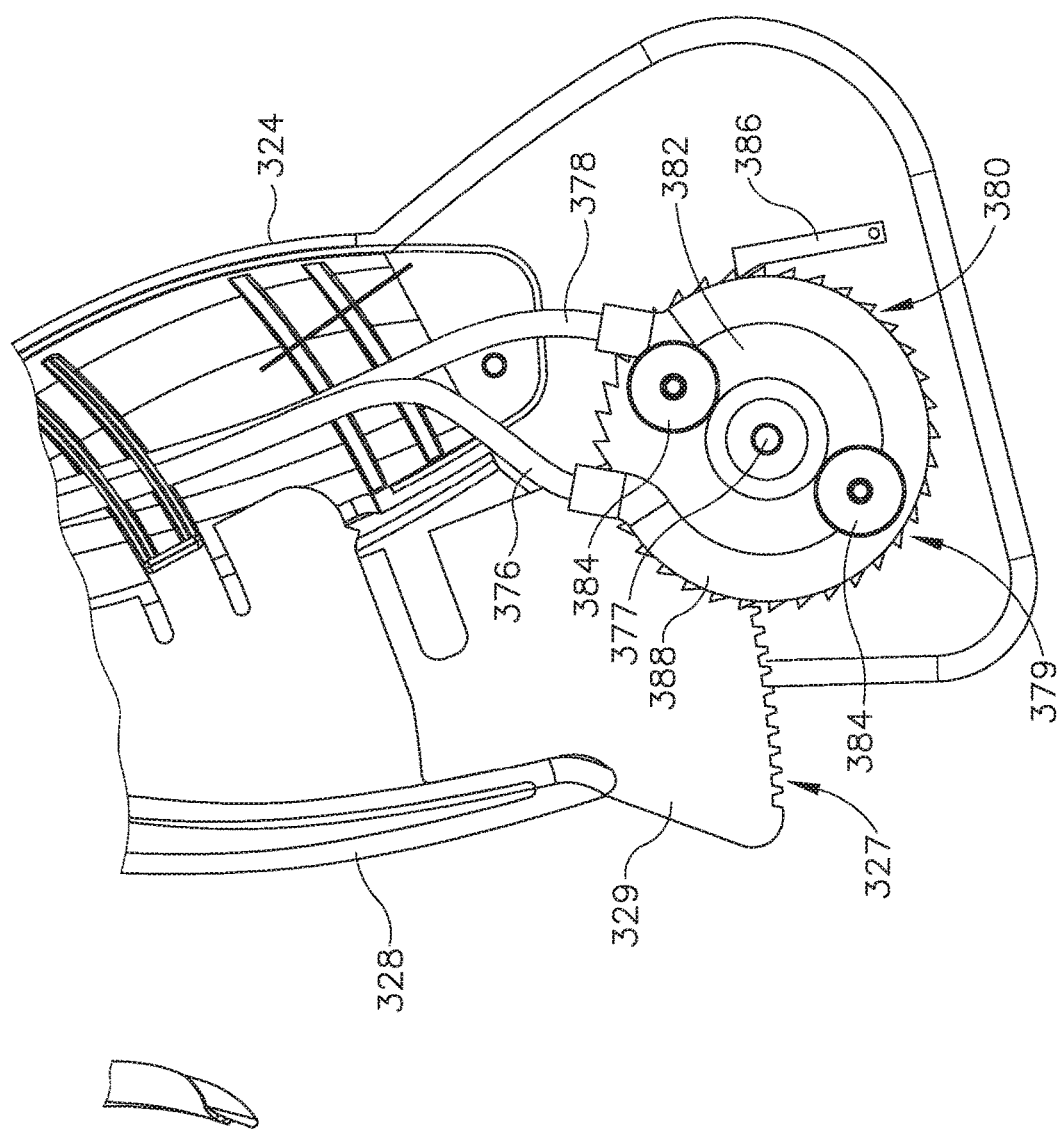
FIG. 33A depicts a detailed side elevational view of the handle assembly of FIG. 30 with the housing shroud removed, with a trigger of the handle assembly in a first rotational position, and with a peristaltic pump in a first rotational position.
Figure 33B:
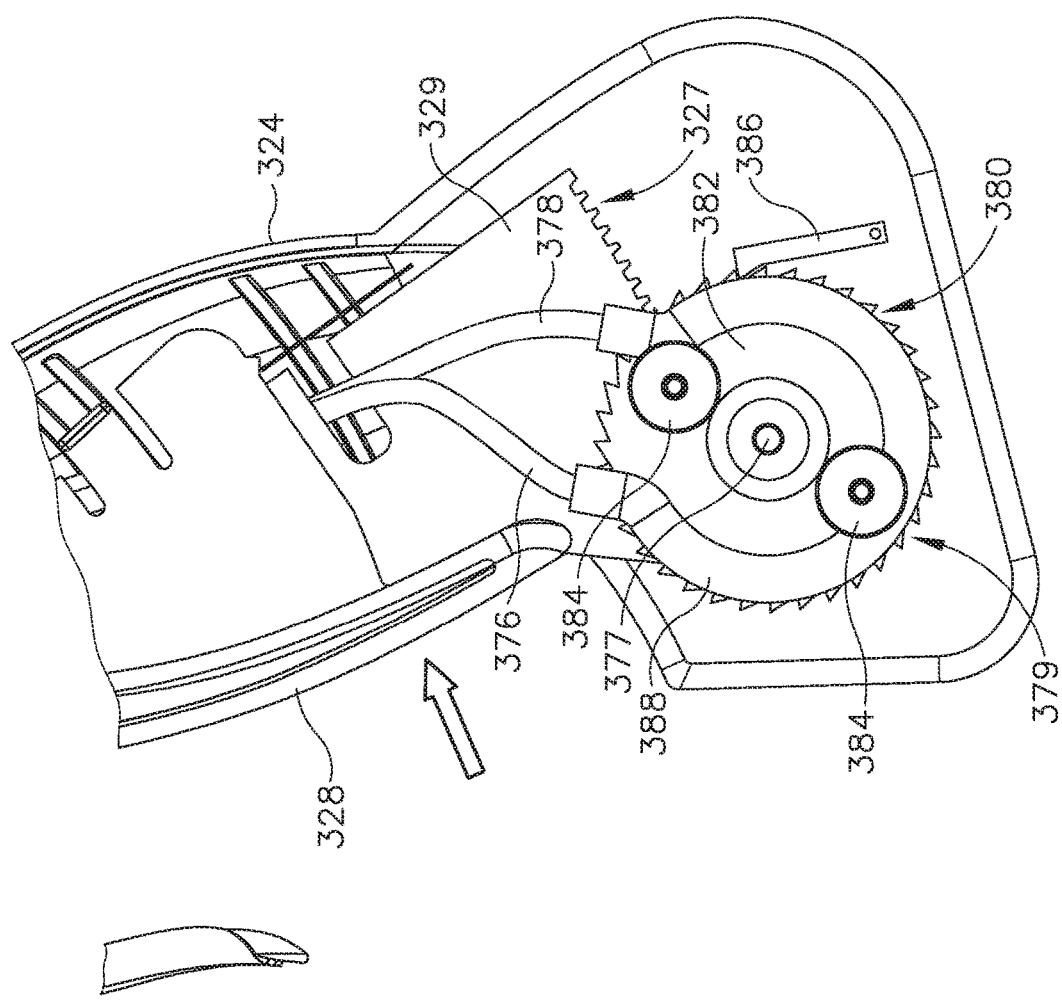
FIG. 33B depicts a detailed side elevational view of the handle assembly of FIG. 30 with the housing shroud removed, with the trigger of FIG. 33A moved to a second rotational position, and with the peristaltic pump of FIG. 33A remaining in the first rotational position.
Figure 33C:
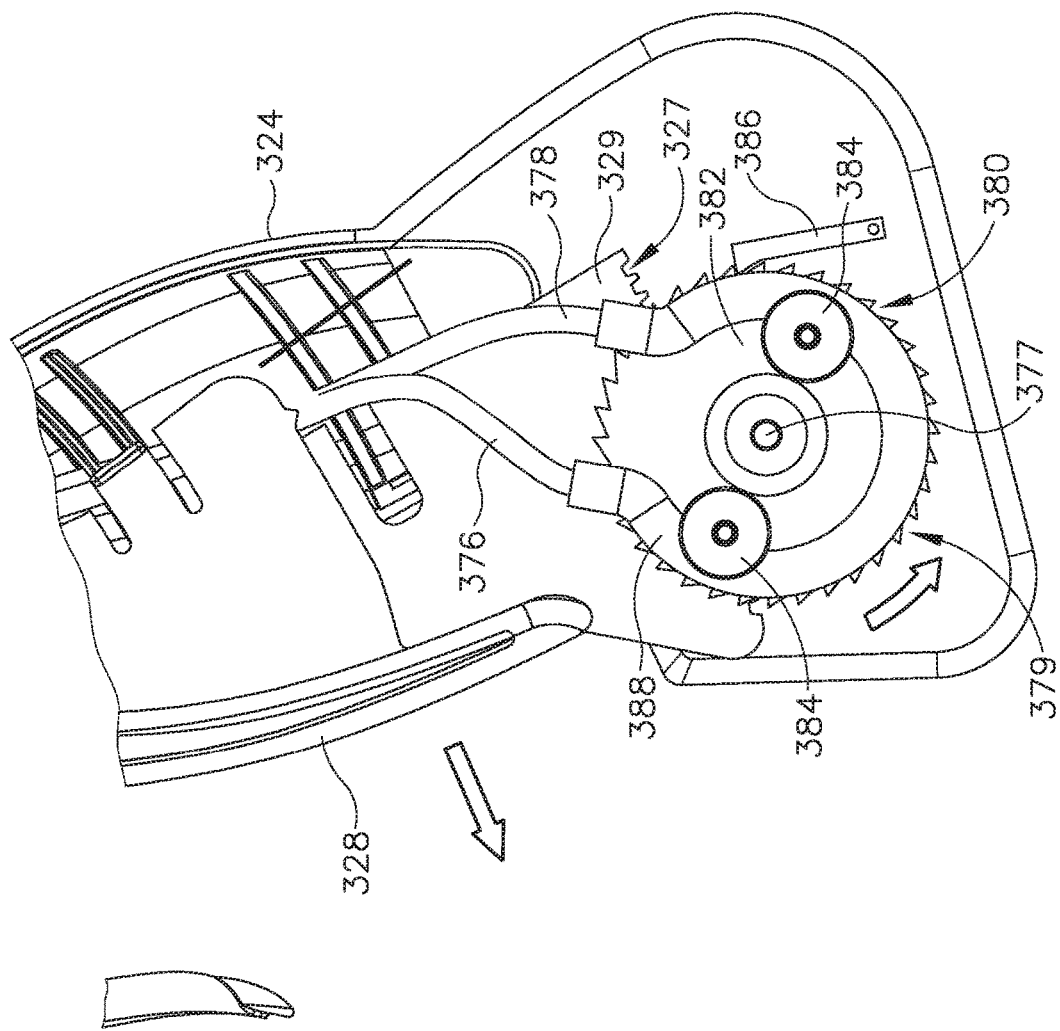
FIG. 33C depicts a detailed side elevational view of the handle assembly of FIG. 30 with the housing shroud removed, with the peristaltic pump of FIG. 33A moved to a second rotational position by movement of the trigger of FIG. 33A to a third rotational position to thereby draw fluid from a fluid reservoir of the handle assembly and pass it into a shaft assembly of the instrument of FIG. 28.
Figure 33D:
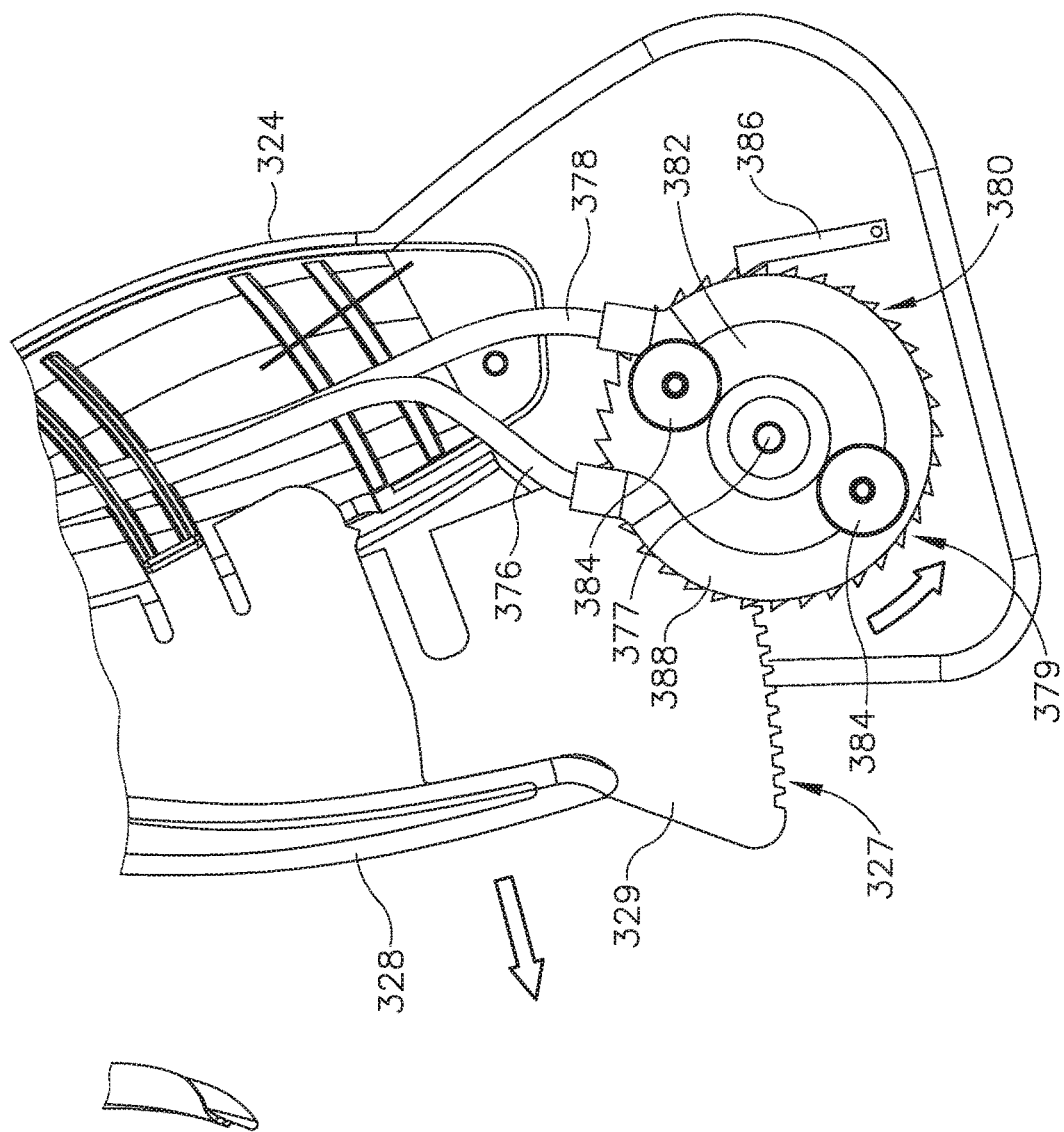
FIG. 33D depicts a detailed side elevational view of the handle assembly of FIG. 30 with the housing shroud removed, with the peristaltic pump of FIG. 33A moved back to the first rotational position by movement of the trigger of FIG. 33A back to a first rotational position to thereby further draw fluid from the fluid reservoir of the handle assembly and pass it into the shaft assembly of the instrument of FIG. 28.

FIGS. 33A-33D further show the operation of peristaltic pump (380). FIG. 33A depicts peristaltic pump (380) in an initial position. As discussed above, and as shown in FIG. 33B, pivoting of trigger (328) toward pistol grip (324) does not cause rotation of wheel (382) of peristaltic pump (380). This is due to the fact that teeth (381) are configured to slip against teeth (381) as gear (383) is rotated during the closure stroke of trigger (324). Moreover, arm (386) serves as a pawl preventing wheel (382) from rotating in response to rotation of gear (383) during the closure stroke of trigger (328). However, as shown in FIGS. 33C and 33D as trigger (328) is pivoted away from pistol grip (324), this rotational movement of trigger (328) is communicated to wheel (382) via gear (383), such that the pivotal movement of trigger (328) causes rotation of wheel (382) of peristaltic pump (380). As wheel (382) rotates, rollers (384) bear against an interior surface of resilient tube (388) and cause resilient tube (388) to deform. This rotation of rollers (384) draws liquid coolant from first tube (376) through resilient tube (388) and drives the liquid coolant into second tube (378). Thus, it should be understood that each return stroke of trigger (328) (i.e., pivoting trigger (328) away from pistol grip (324)) pumps a certain amount of liquid coolant from fluid reservoir (370) via first tube (376) to sleeve (350) via second tube (378) through rotation of peristaltic pump (380).

While peristaltic pump (380) of the present example is described as being actuated by movement of trigger (328), peristaltic pump (380) may additionally or alternatively be actuated by an internal or external motor such that liquid coolant is provided to blade (360) regardless of the movement of trigger (328) as will be apparent to one of ordinary skill in the art in view of the teachings herein. It should also be understood that peristaltic pump (380) may include three rollers (384), four rollers (384), or any other suitable number of rollers (384). The number of rollers (384) and/or angular spacing of rollers (384) may be selected to provide a desired volume of liquid coolant delivery with each return stroke of trigger (328).

C. Exemplary Ultrasonic Surgical Instrument with Peristaltic Pump with External Fluid Source FIGS. 35-38D illustrate another exemplary ultrasonic surgical instrument (400) that is configured to operate substantially similar to instruments (100, 200, 300) discussed above except for the differences discussed below. It should therefore be understood that instrument (400) may include the same components and operabilities as instrument (20, 100), in addition to including the components and operabilities described below. Instrument (400) of the present example comprises a handle assembly (420). Handle assembly (420) comprises a body (422) including a pistol grip (424) and a pair of buttons (426). As with instruments (100, 200, 300) discussed above, body (422) of handle assembly (420) is configured to receive an ultrasonic transducer assembly (not shown). Handle assembly (420) also includes a trigger (428) that is pivotable toward and away from pistol grip (424). While not shown, it should be understood that instrument (400) may include a shaft assembly just like shaft assemblies (230, 330) described above; as well as a rotation knob with fluid coupling features just like rotation knobs (231, 331) described above.

Figure 36:
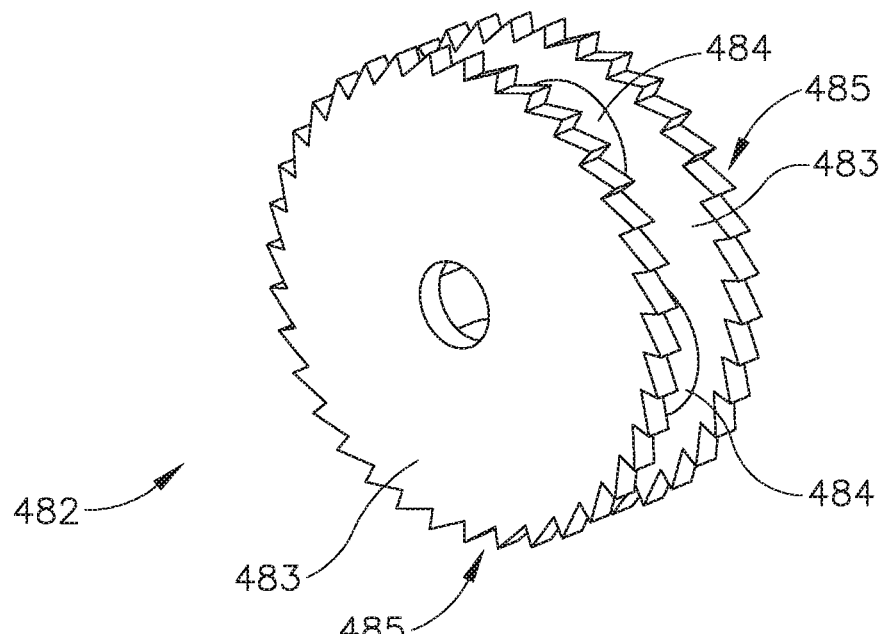
FIG. 36 depicts a perspective view of a peristaltic pump of the instrument of FIG. 35.
Figure 37:
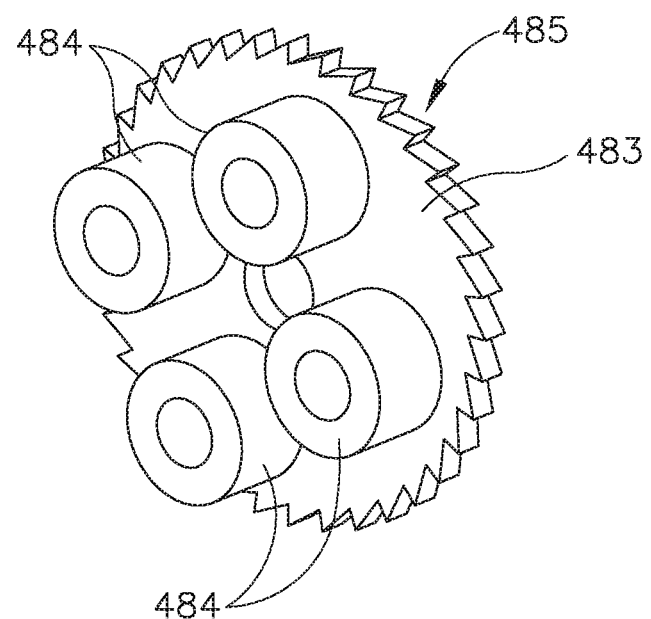
FIG. 37 depicts a perspective view of the peristaltic pump of FIG. 36 with a gear of the peristaltic pump removed.

Trigger (428) of handle assembly (420) is pivotably coupled to body (422) of handle assembly (420) such that trigger (428) is operable to pivot toward and away from pistol grip (424). A peristaltic pump (480) is disposed within body (422) of handle assembly (420). Peristaltic pump (480) comprises a gear assembly (482). Gear assembly (482) is rotatably coupled to an interior surface of body (422) via a pin (477) such that gear assembly (482) is operable to rotate about pin (477) within body (422). As best seen in FIGS. 36 and 37, gear assembly (482) comprises a pair of ratchet gears (483) and plurality of rollers (484) that are rotatably disposed between gears (483). Rollers (484) are secured to gears (483) such that rollers (484) orbit about pin (477) when gears (483) rotate about pin (477). Rollers (484) are also operable to rotate independently of gears (483) such that rollers (484) rotate about their own respective axes as rollers (484) orbit about pin (477).

A resilient tube (470) extends from an external fluid reservoir (not shown) and passes through handle assembly (420). The resilient tube (470) is operable to provide liquid coolant to an ultrasonic blade (not shown) of an end effector (not shown). A portion of resilient tube (470) is arranged in a semi-circular fashion within pistol grip (424), adjacent to gear assembly (482). Body (422) includes one or more boss features (not shown) that are positioned on the radially outermost regions of resilient tube (470), thereby providing structural support and mechanical grounding to resilient tube (470). Resilient tube (470) is positioned adjacent to rollers (484) such that rollers (484) bear against a radially interior surface of resilient tube (470) and cause resilient tube (470) to deform as rollers (484) rotate with gears (483) about pin (477). In other words, resilient tube (470) is pinched between rollers (484) and the boss features of body (422). This orbital rotation of rollers (484) draws liquid coolant from the fluid source through tube (470) through a peristaltic action. Thus, it should be understood that peristaltic pump (480) is configured to draw liquid coolant from the external fluid source through tube (470) and to pump the liquid coolant through tube (470) to the end effector to thereby cool the ultrasonic blade by rotation of peristaltic pump (480).

Figure 38A:
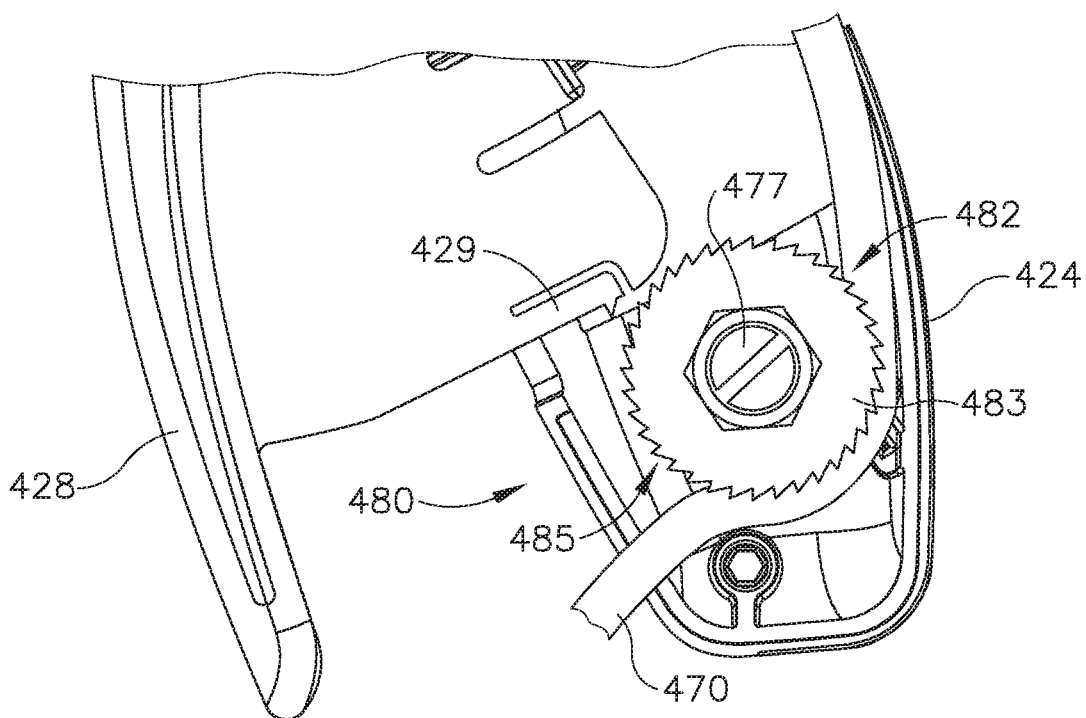
FIG. 38A depicts a side elevational view of the handle assembly of FIG. 35, with a trigger of the handle assembly in a first rotational position, and with the peristaltic pump of FIG. 36 in a first rotational position.
Figure 38B:
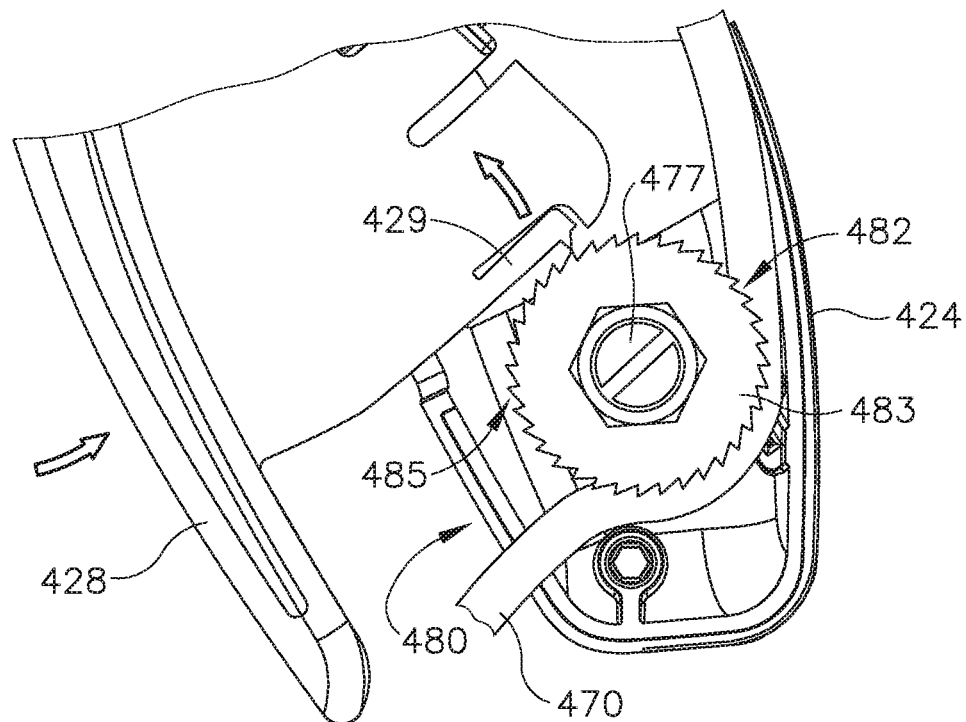
FIG. 38B depicts a side elevational view of the handle assembly of FIG. 35, with the trigger of FIG. 38A moved to a second rotational position, and with the peristaltic pump of FIG. 36 remaining in a first rotational position.
Figure 38C:
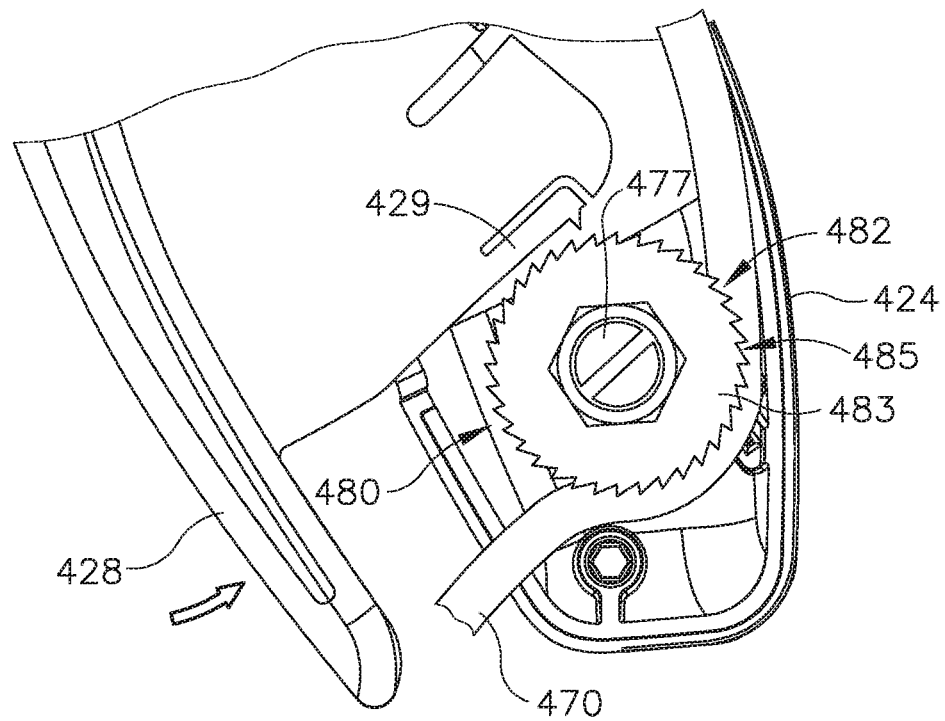
FIG. 38C depicts a side elevational view of the handle assembly of FIG. 35, with the trigger of FIG. 38A moved to a third rotational position, and with the peristaltic pump of FIG. 36 remaining in a first rotational position.
Figure 38D:
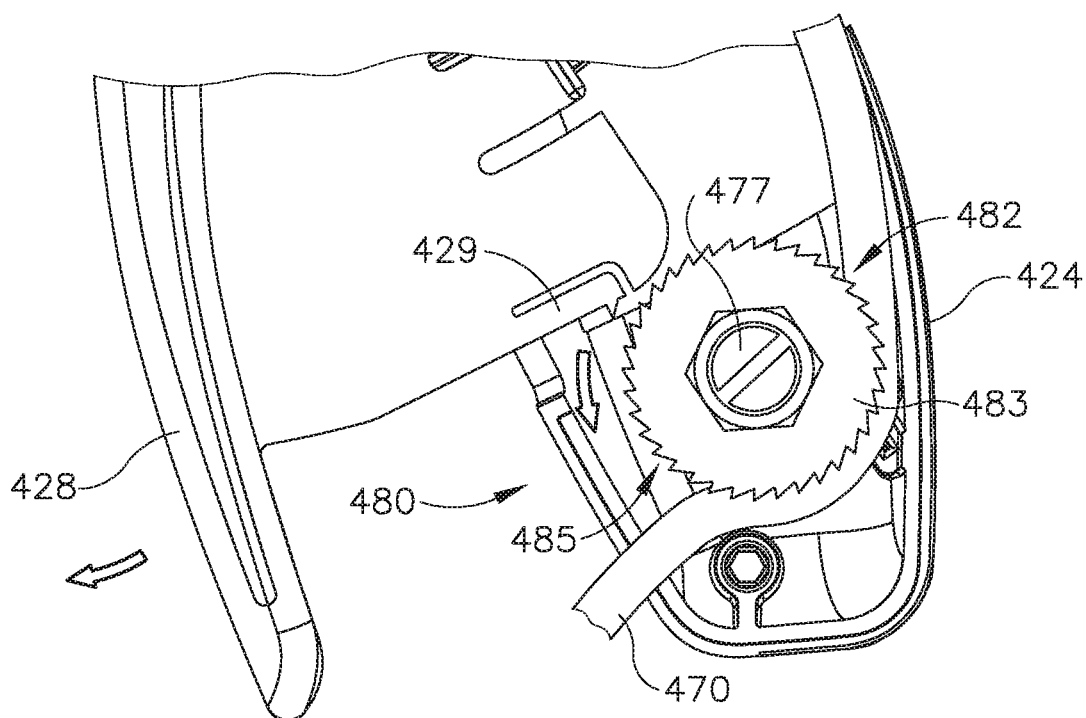
FIG. 38D depicts a side elevational view of the handle assembly of FIG. 35, with the peristaltic pump of FIG. 36 moved to a second rotational position by movement of the trigger of FIG. 38A back to the first rotational position.

FIGS. 38A-38D, show the operation of peristaltic pump (480). Trigger (428) comprises a pawl arm (429) that is resiliently biased to engage a plurality of teeth (485) of gears (483). As shown in FIG. 38B, teeth (485) of gears (483) are configured and angled such that as trigger (428) is pivoted toward pistol grip (424) in a closure stroke, teeth (485) cause pawl arm (429) to flex away from gear assembly (482) such that pawl arm (429) slides along teeth (485) of gears (483). Thus, movement of trigger (428) toward pistol grip (424) is not communicated to gear assembly (482), such that pivoting of trigger (428) toward pistol grip (424) during a closure stroke does not actuate peristaltic pump (480). On the other hand, as shown in FIGS. 38C and 38D, teeth (485) of gear (483) are configured and angled such that as trigger (428) is pivoted away from pistol grip (424), pawl arm (429) remains engaged with teeth (485) of gears (483). Thus, movement of trigger (428) is communicated to gear assembly (482) during the return stroke of trigger (428), such that pivoting of trigger (428) away from pistol grip (424) actuates peristaltic pump (480). It should therefore be understood that pivoting of trigger (428) away from pistol grip (424) actuates peristaltic pump (480) to thereby provide liquid coolant to the end effector to thereby cool the ultrasonic blade; while pivoting of trigger (428) toward pistol grip (424) will not.

It should be appreciated that although peristaltic pump (480) of the present example is described as being actuated by movement of trigger (428), peristaltic pump (480) may additionally or alternatively be actuated by an internal or external motor such that liquid coolant is provided to the ultrasonic blade regardless of the movement of trigger (428) as would be apparent to one of ordinary skill in the art. It should also be understood that peristaltic pump (480) may include two rollers (484), three rollers (484), or any other suitable number of rollers (484). The number of rollers (484) and/or angular spacing of rollers (484) may be selected to provide a desired volume of liquid coolant delivery with each return stroke of trigger (428). While peristaltic pump (480) is described as being coupled with an external source of liquid coolant, peristaltic pump (480) may also be used with an on-board source of liquid coolant, such as fluid reservoir (370), etc. Likewise, peristaltic pump (380) described above may be coupled with an external source of liquid coolant in lieu of using an on-board source of liquid coolant, such as fluid reservoir (370).

D. Exemplary Ultrasonic Surgical Instrument with Syringe Pump

Figure 39:
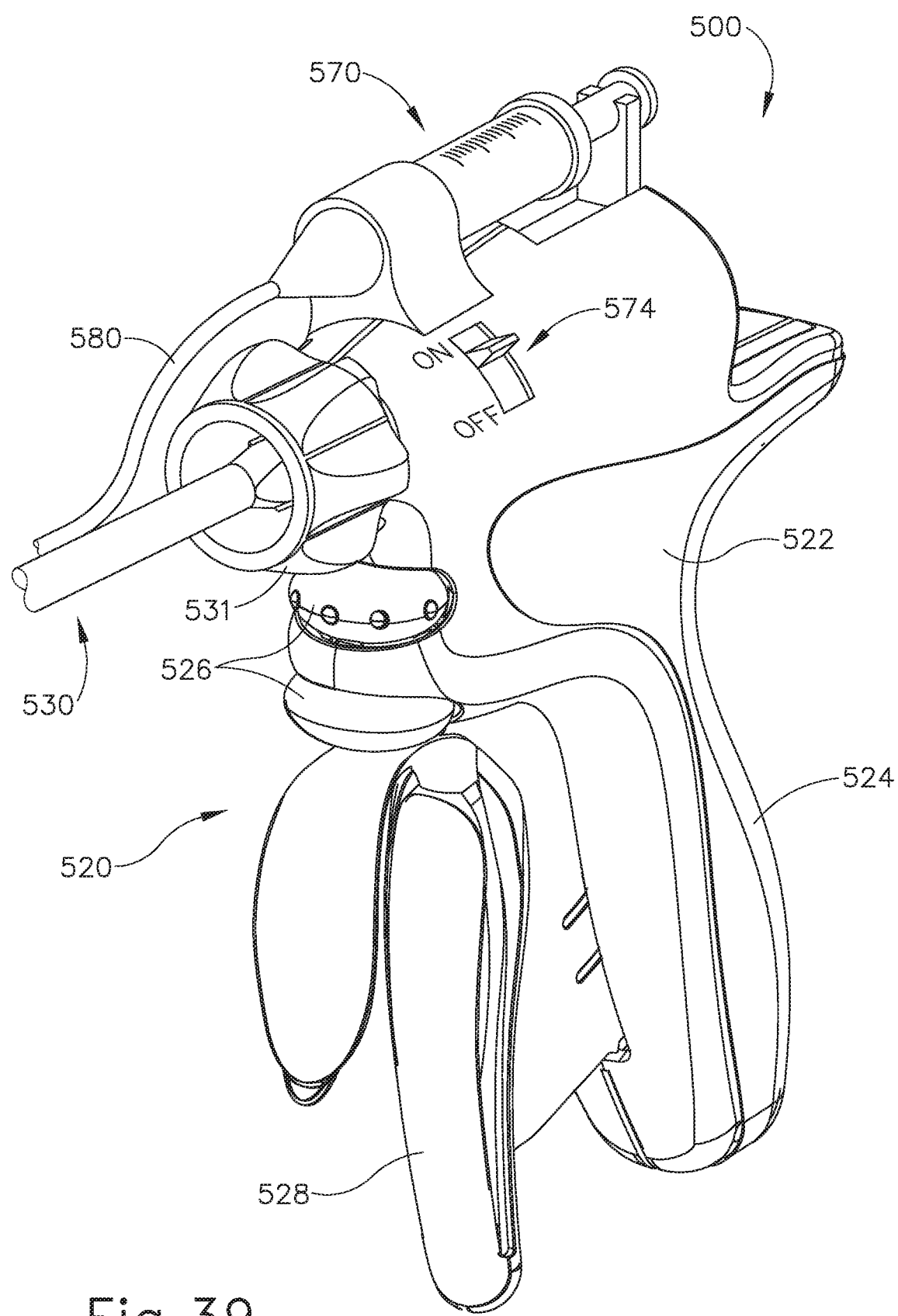
FIG. 39 depicts a perspective view of yet another exemplary alternative ultrasonic surgical instrument.
Figure 40A:
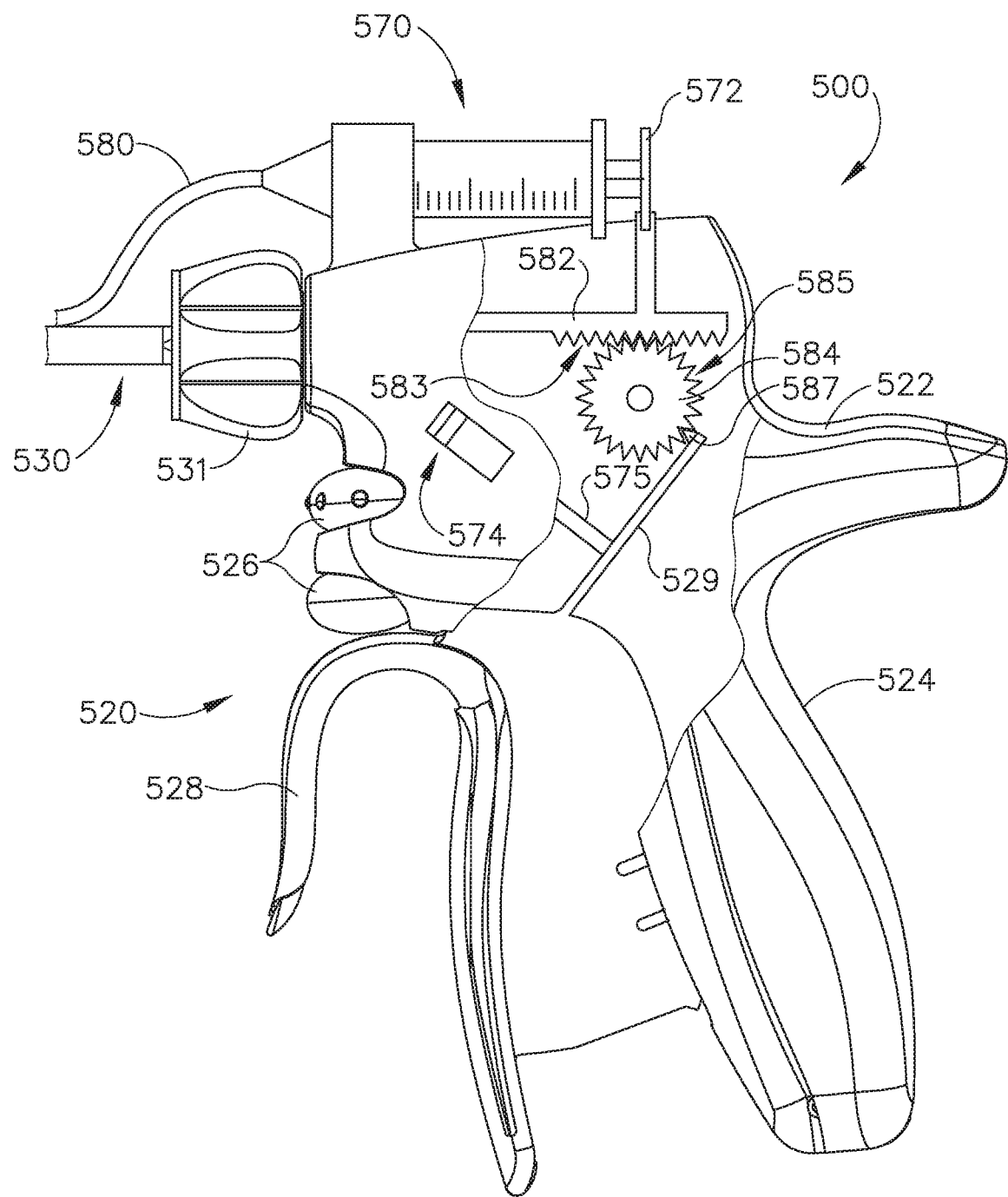
FIG. 40A depicts a side elevational view of the instrument of FIG. 39, with a portion of a shroud housing of a handle assembly of the instrument removed, with a trigger of the handle assembly in a first rotational position, and with a plunger of a syringe of the instrument in a first longitudinal position.
Figure 40B:
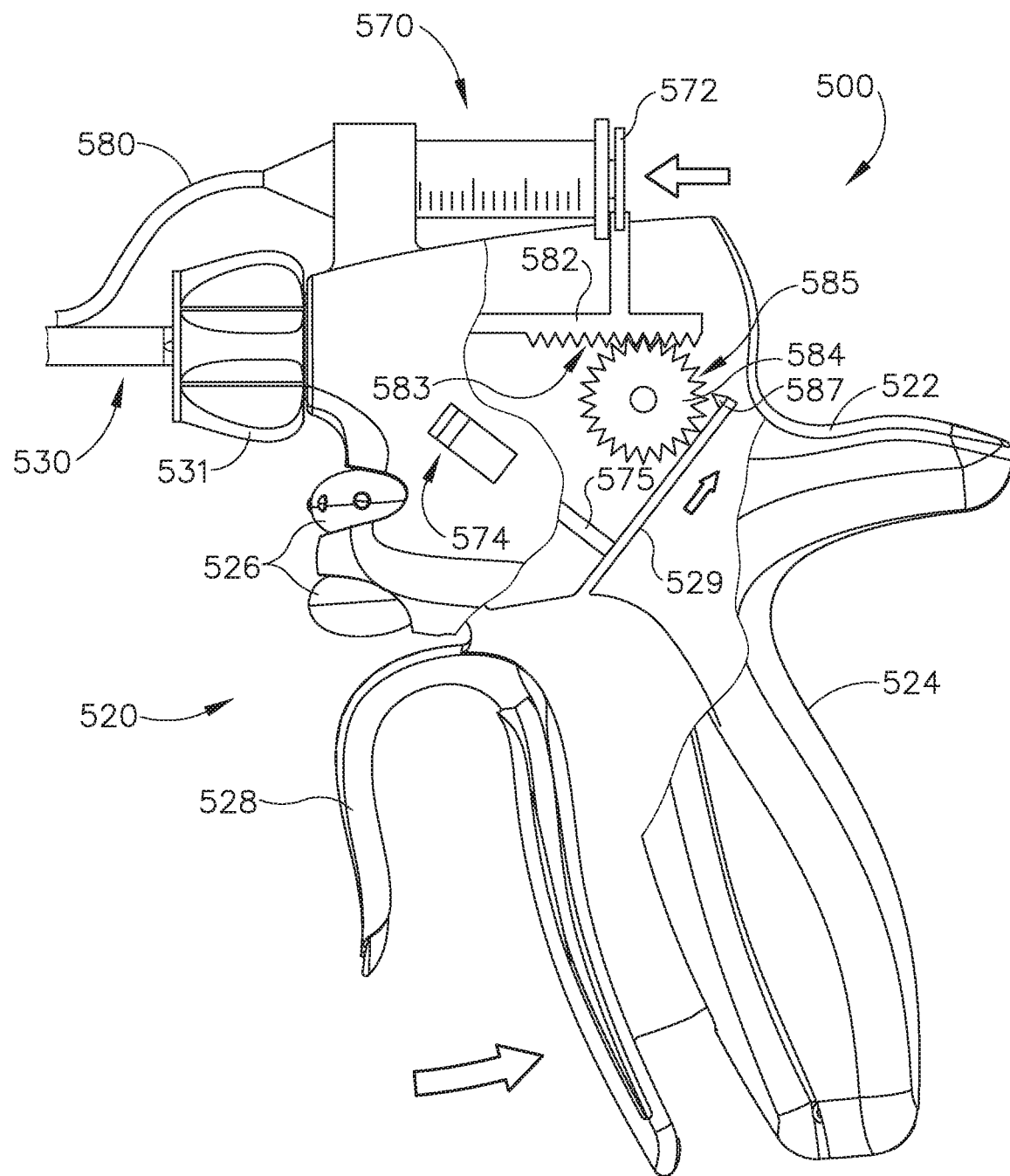
FIG. 40B depicts a side elevational view of the instrument of FIG. 39, with a portion of the shroud housing of the handle assembly of FIG. 40A removed, with the plunger of the syringe of FIG. 40A moved to a second longitudinal position by movement of the trigger of FIG. 40A to a second rotational position.
Figure 41:
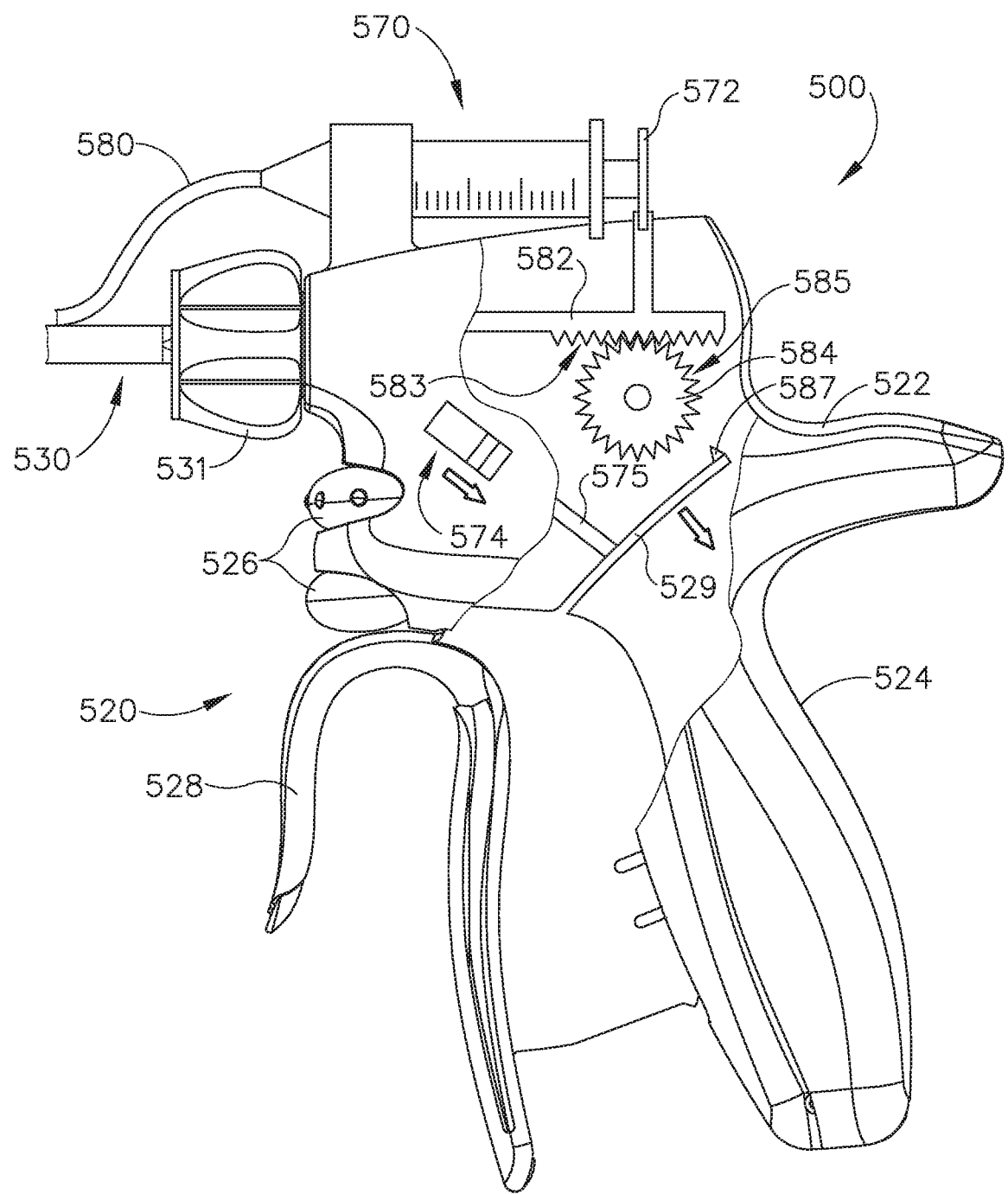
FIG. 41 depicts a side elevational view of the instrument of FIG. 39, with the trigger of FIG. 40A in an "OFF" position.

FIGS. 39-41 illustrate another exemplary ultrasonic surgical instrument (500) that is configured to operate substantially similar to instruments (100, 200, 300, 400) discussed above except for the differences discussed below. It should therefore be understood that instrument (500) may include the same components and operabilities as instrument (20, 100), in addition to including the components and operabilities described below. Instrument (500) of the present example comprises a handle assembly (520), a shaft assembly (530), and an end effector (not shown). Handle assembly (520) comprises a body (522) including a pistol grip (524) and a pair of buttons (526). As with instruments (100, 200, 300, 400) discussed above, body (522) of handle assembly (520) is configured to receive an ultrasonic transducer assembly (not shown). Handle assembly (520) also includes a trigger (528) that is pivotable toward and away from pistol grip (524).

Handle assembly (520) of the present example further comprises a syringe (570) that is selectively coupled with a top portion of body (522) of handle assembly (520). Syringe (570) is fluidly coupled with a tube (580). Tube (580) extends along shaft assembly (530) to the end effector and is configured to provide liquid coolant to an ultrasonic blade (not shown). In some other versions, tube (580) is coupled with a rotation knob (531) of shaft assembly (530). Rotation knob (531) may have fluid coupling features like rotation knob (331) described above, such that rotation knob (531) is operable to provide fluid communication between syringe (570) and the end effector of shaft assembly (530). It should therefore be understood that tube (580) need not extend along the length of shaft assembly (580).

As shown in FIGS. 40A-41, handle assembly (520) comprises a rack (582) and a pinion gear (584). Rack (582) is longitudinally translatable within body (522) between a proximal longitudinal position (FIG. 40A) and a distal longitudinal position (FIG. 40B). A proximal end of a plunger (572) of syringe (570) is coupled with rack (582) such that longitudinal translation of rack (582) causes concurrent longitudinal translation of plunger (572). A plurality of teeth (583) of rack (582) mesh with a plurality of teeth (585) of pinion gear (584) such that rotation of pinion gear (584) causes longitudinal translation of rack (582). Trigger (528) includes an integral, proximally extending pawl arm (529). Pawl arm (529) includes a tooth (587) that is configured to engage teeth (585) of pinion gear (584). Pawl arm (529) is resiliently biased to urge tooth (587) into engagement with teeth (585).

FIGS. 40A-41, show the operation of syringe (570). In particular. FIG. 40A shows instrument (500) in an initial position. As trigger (528) is pivoted toward pistol grip (524), resilient arm (529) engages teeth (585) of gear (584) to thereby cause counter-clockwise rotation of gear (584). As shown in FIG. 40B, this rotation of gear (584) causes distal longitudinal translation of rack (582) and plunger (572) of syringe (570) via engagement between teeth (583) of rack (582) and teeth (585) of gear (584). As plunger (572) is translated longitudinally distally, plunger (572) drives fluid from syringe (570), such that liquid coolant is forced through first tube (580) to the ultrasonic blade, thereby cooling the ultrasonic blade. Since pawl arm (529) only has one tooth (587), pinion gear (584) only rotates through a relatively small angular range when trigger (528) is pivoted to the closed position. Thus, syringe (570) communicates a small, predetermined volume of liquid coolant to the ultrasonic blade when trigger (528) is actuated through a closure stroke. In the present example, teeth (585) are configured such that tooth (587) slides along teeth (585) in a ratcheting fashion as trigger (528) pivots away from pistol grip (524) during a return stroke. Gear (584) therefore does not rotate when trigger (528) pivots away from pistol grip (524) during a return stroke, such that syringe (570) does not expel any liquid coolant when trigger (528) pivots away from pistol grip (524) during a return stroke. It should therefore be understood that syringe (570) may incrementally expel predetermined amounts of liquid coolant toward the end effector each time trigger (528) is actuated to move the clamp arm of the end effector toward the ultrasonic blade.

Handle assembly (520) comprises a switch (574) in the present example. A post (575) is coupled to switch (574) such that movement of switch (574) causes concurrent movement of post (575). In FIGS. 40A and 40B, switch (574) is in an "ON" position. In this position, resilient arm (529) is permitted to engage teeth (585) of gear (584). FIG. 41 shows switch moved into an "OFF" position. In this position, post (575) has been moved to engage resilient arm (529) so as to cause resilient arm (529) to flex away from gear (584) such that resilient arm (529) no longer engages teeth (585) of gear (584). Thus, it should be understood that in the "OFF" position, trigger (528) may be freely pivoted toward and away from pistol grip (524) without actuating syringe (570). An operator may wish to use switch (574) to select this mode of operation when the operator does not wish to communicate liquid coolant to the end effector.

It should be appreciated that although syringe (570) is described as being coupled with a top portion of body (522) of handle assembly (520), syringe (570) may alternatively be positioned within body (522) of handle assembly (520) as would be apparent to one of ordinary skill in the art. It should also be understood that gear (584) and pawl arm (529) may be modified such that pawl arm (529) only rotates gear (584) during the return stroke of trigger (528), such that pawl arm (529) does not rotate gear (584) during the closure stroke of trigger (528). In other words, in some versions, syringe (570) may expel fluid toward the end effector when the clamp arm is being pivoted away from the ultrasonic blade. Other suitable variations will be apparent to those of ordinary skill in the art in view of the teachings herein.

E Exemplary Ultrasonic Surgical Instrument with Spring-Loaded Pump

Figure 42:
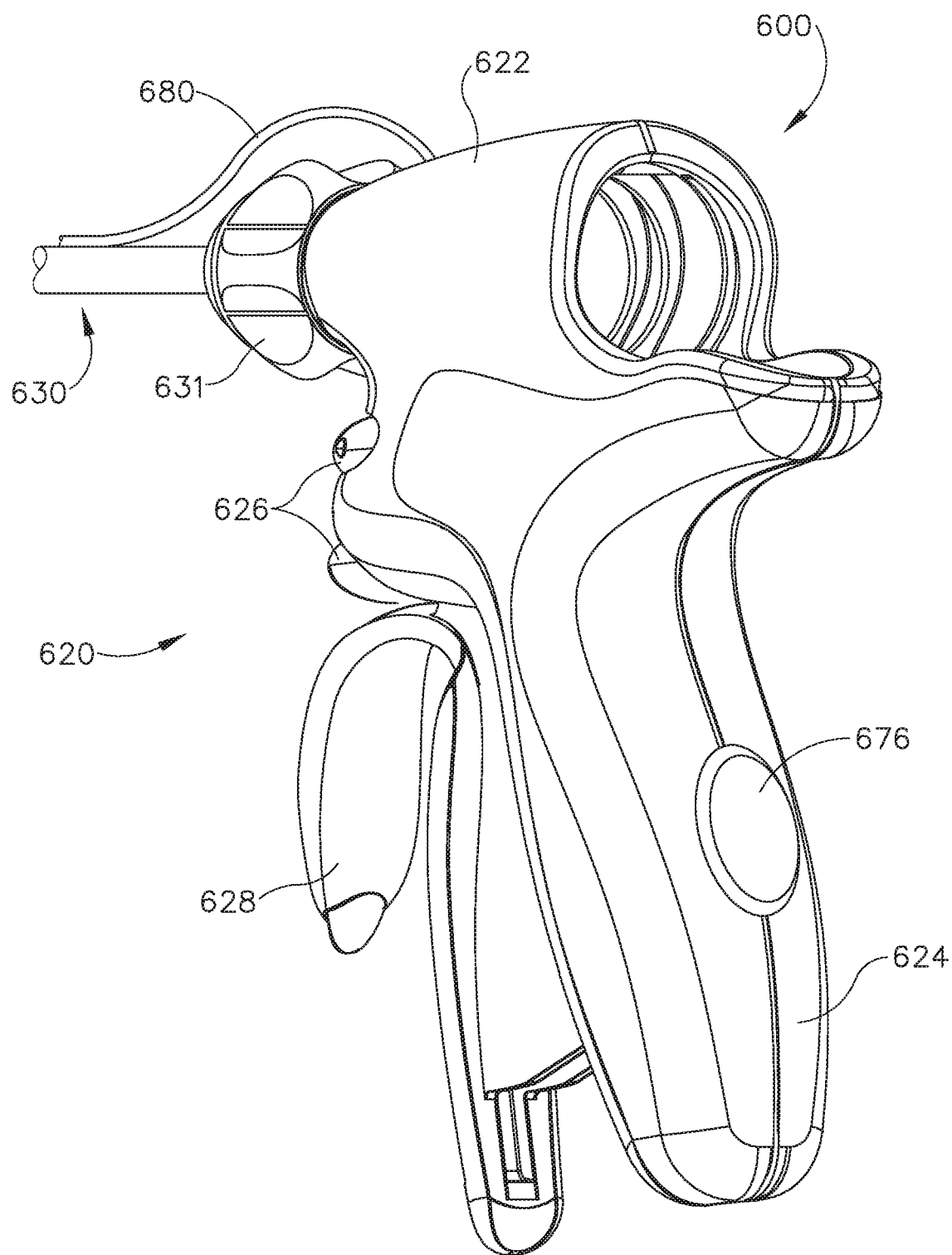
FIG. 42 depicts a perspective view of yet another exemplary alternative ultrasonic surgical instrument.
Figure 43A:
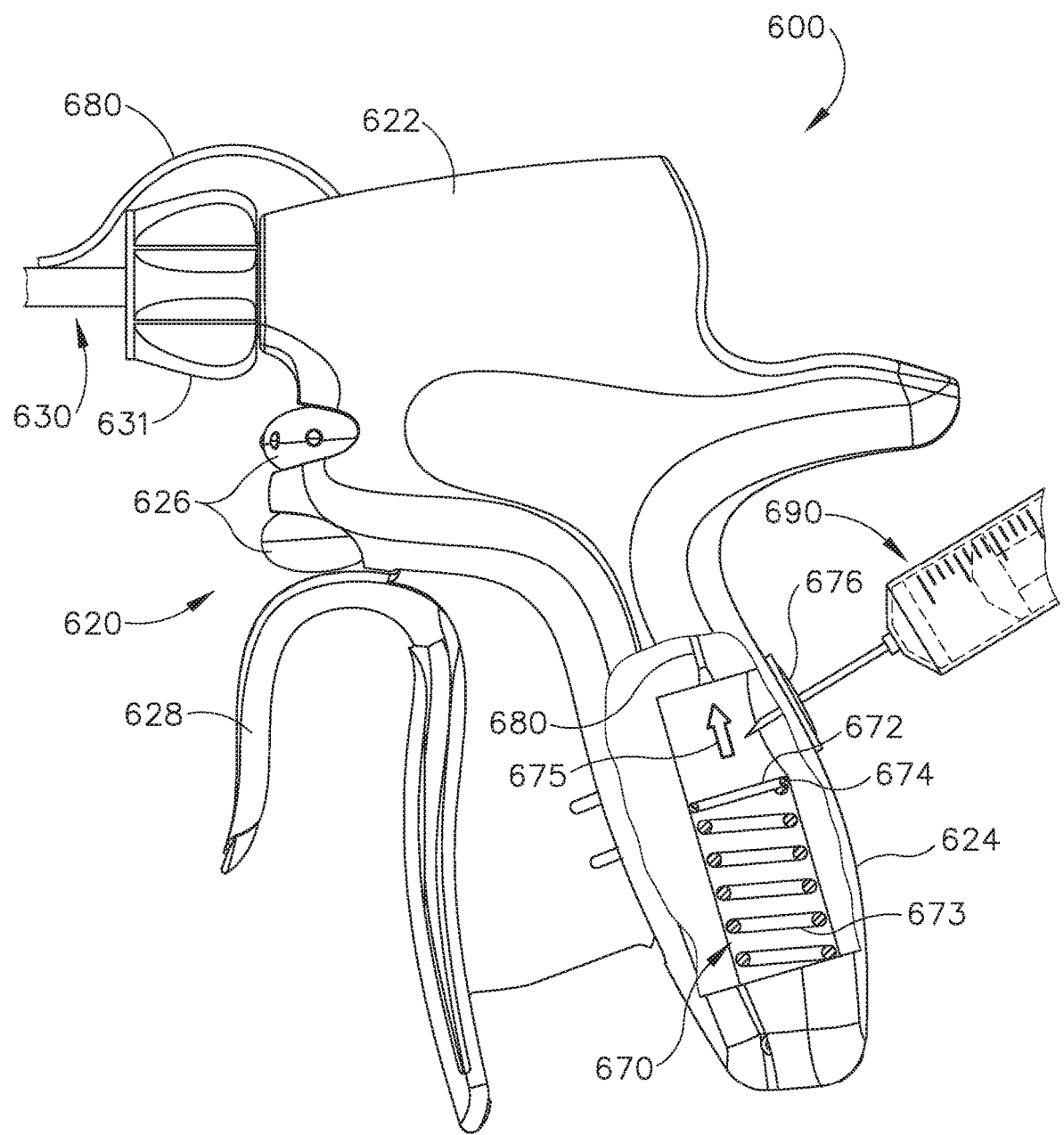
FIG. 43A depicts a side elevational view of the instrument of FIG. 42, with a portion of a shroud housing of a handle assembly of the instrument removed, and with a piston of a fluid pump of the instrument in a first position.
Figure 43B:
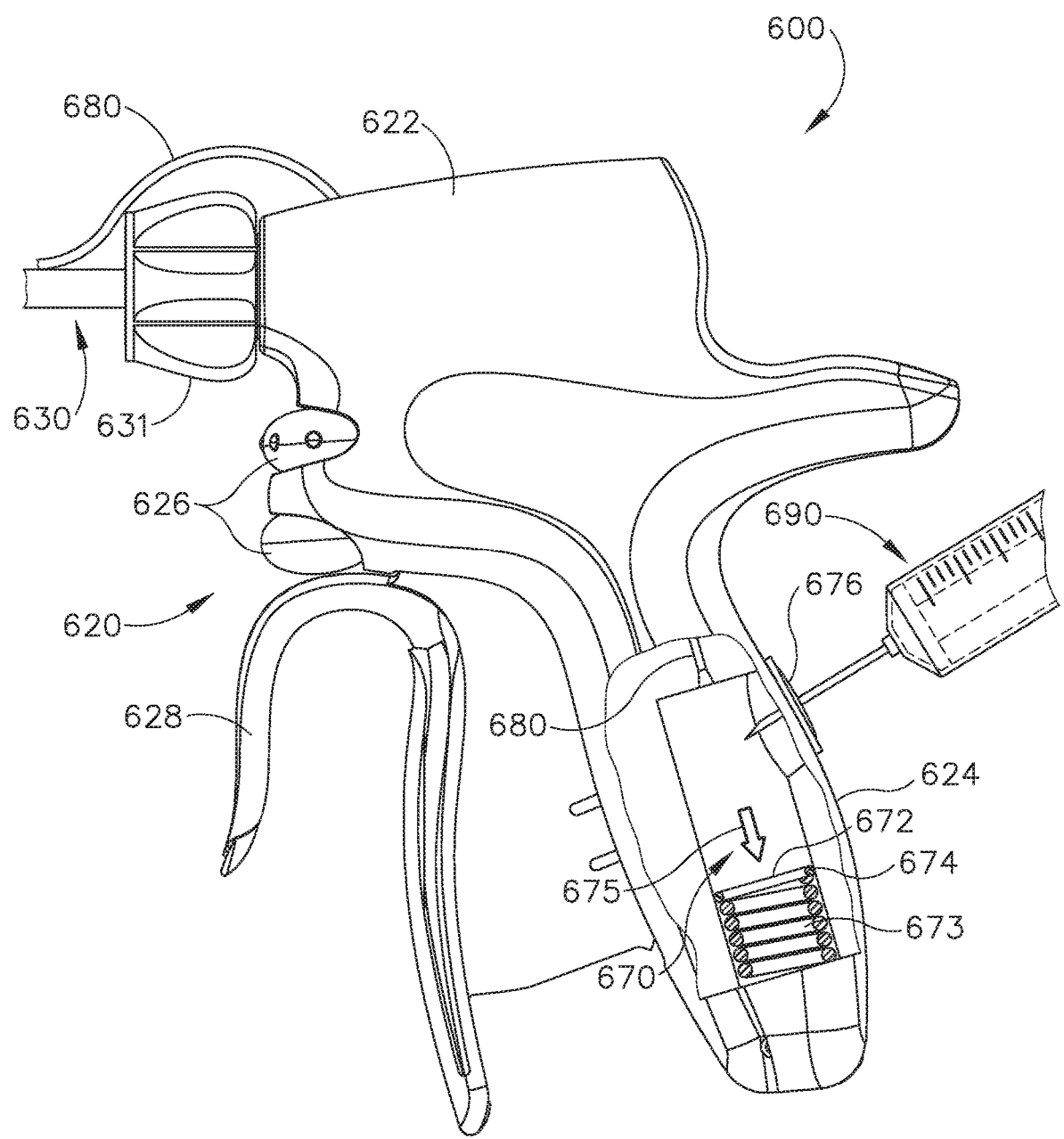
FIG. 43B depicts a side elevational view of the instrument of FIG. 42, with a portion of the shroud housing of the handle assembly of FIG. 43A removed, with the piston of the fluid pump of FIG. 43A moved to a second position by injection of fluid into the pump via a syringe.

FIGS. 42-43B illustrate another exemplary ultrasonic surgical instrument (600) configured to operate substantially similar to instruments (100, 200, 300, 400, 500) discussed above except for the differences discussed below. It should therefore be understood that instrument (500) may include the same components and operabilities as instrument (20, 100), in addition to including the components and operabilities described below. Instrument (600) of the present example comprises a handle assembly (620), a shaft assembly (630), and an end effector (not shown). Handle assembly (620) comprises a body (622) including a pistol grip (624) and a pair of buttons (626). As with instruments (100, 200, 300, 400, 500) discussed above, body (622) of handle assembly (620) is configured to receive an ultrasonic transducer assembly (not shown). Handle assembly (620) also includes a trigger (628) that is pivotable toward and away from pistol grip (624).

Handle assembly (620) of the present example further comprises a cylindrical bore (670) formed in pistol grip (624). Cylindrical bore (670) is fluidly coupled with a tube (680). Tube (680) extends through handle assembly (620) and along shaft assembly (630) to the end effector and is configured to provide liquid coolant to an ultrasonic blade (not shown). In some other versions, tube (680) is coupled with a rotation knob (631) of shaft assembly (630). Rotation knob (631) may have fluid coupling features like rotation knob (331) described above, such that rotation knob (631) is operable to provide fluid communication between cylindrical bore (670) and the end effector of shaft assembly (630). It should therefore be understood that tube (680) need not extend along the length of shaft assembly (680).

A piston (672) is slidably disposed within cylindrical bore (670) such that piston (672) is operable to translate within cylindrical bore (670). Piston (672) comprises a circular seal ring (674) disposed about an exterior surface of piston (672). Seal ring (674) is configured to engage an interior surface of cylindrical bore (670) to thereby provide a fluid seal between piston (672) and cylindrical bore (670). A spring (673) is disposed within cylindrical bore (670) between piston (672) and a bottom surface of cylindrical bore (670). Spring (673) is configured to resiliently bias piston (672) upwardly in the direction of arrow (675) as shown in FIG. 43A. Handle assembly (620) further comprises a self-sealing septum (676) that provides fluid access to cylindrical bore (670). A syringe (690) filled with liquid coolant may pierce septum (676) such that the liquid coolant may be passed into cylindrical bore (670) via septum (676). As cylindrical bore (670) is filled with liquid coolant, the liquid coolant provides sufficient pressure within cylindrical bore (670) so as to drive piston (672) downwardly in the direction of arrow (677) as shown in FIG. 43B.

Once cylindrical bore (670) has been completely filled with liquid coolant as shown in FIG. 43B, the upward bias of spring (673) imparted upon piston (672) pressurizes the liquid coolant such that the liquid coolant is driven through tube (680) to the end effector top thereby provide liquid coolant to the ultrasonic blade. It should be appreciated that this flow of liquid coolant caused by force from spring (673) through tube (680) may be continuously or selectively permitted by an actuation mechanism. For instance, a metering assembly may be coupled with trigger (628) such that the metering assembly allows a predetermined volume of fluid to flow from cylindrical bore (670) toward the end effector each time trigger (628) is actuated. In some such versions, the metering assembly provides the incremental communication of fluid each time trigger (628) completes a closure stroke (i.e., each time trigger (628) is pivoted toward pistol grip (624)). In addition or in the alternative, the metering assembly may provide the incremental communication of fluid each time trigger (628) completes a return stroke (i.e., each time trigger (628) is pivoted away from pistol grip (624)). Various suitable forms that a metering assembly may take will be apparent to those of ordinary skill in the art in view of the teachings herein.

It should also be understood that pistol grip (624) may comprise a vent (not shown) in fluid communication with a portion of cylindrical bore (670) between piston (672) and the bottom surface of cylindrical bore (670). Such a vent may be configured to permit air to flow into and out of this portion of cylindrical bore (670) to thereby prevent drawing of a vacuum or pressurization within this portion of cylindrical bore (670) due to translation of piston (672) within cylindrical bore (670).

F. Exemplary Rotation Knob Pump

Figure 44:
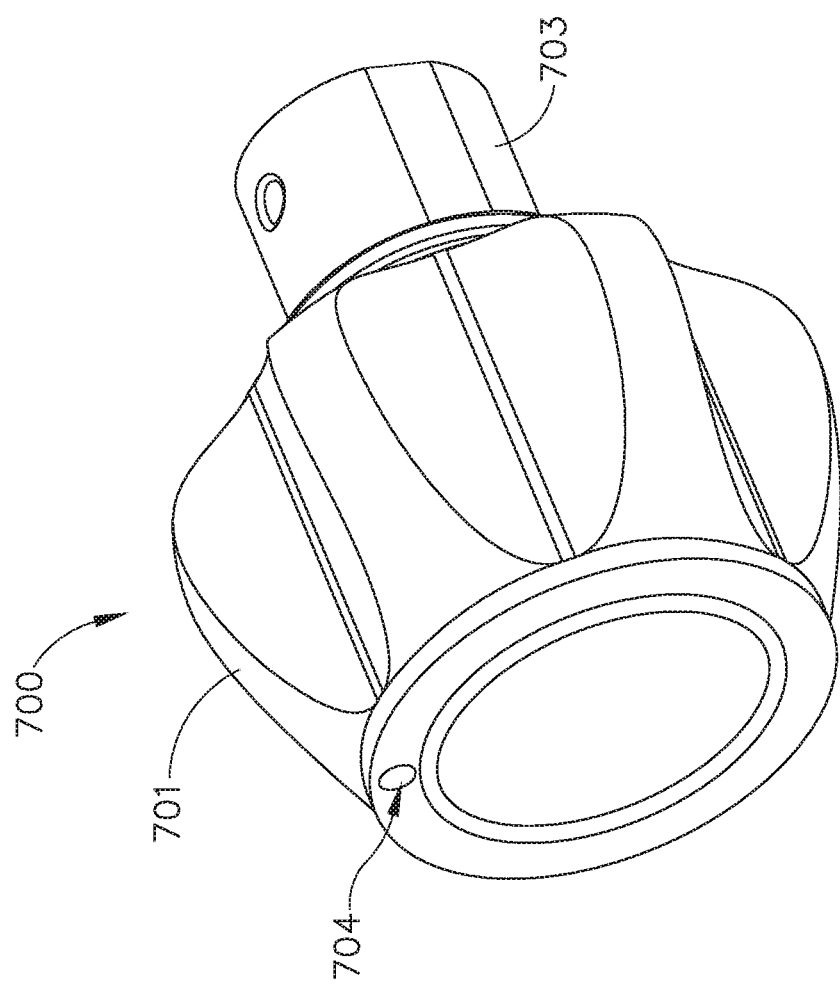
FIG. 44 depicts a perspective view of a rotation knob of an exemplary fluid pump operable for use with any of the instruments described herein.

FIGS. 44-45B illustrate an exemplary rotation knob assembly (700) that is configured to provide liquid coolant to an ultrasonic blade (not shown). Rotation knob assembly (700) is configured to operate substantially similar to rotation knob (139) discussed above except for the differences discussed below. It should therefore be understood that rotation knob assembly (700) may be readily substituted for rotation knob (139) in instrument (100). Rotation knob assembly (700) is operable to rotate an entire shaft assembly (730) and end effector (not shown) relative to handle assembly (720) about a longitudinal axis of shaft assembly (730). In this example, shaft assembly (730), the end effector, and handle assembly (720) are substantially identical to the similarly named components of instrument (100).

Figure 45A:
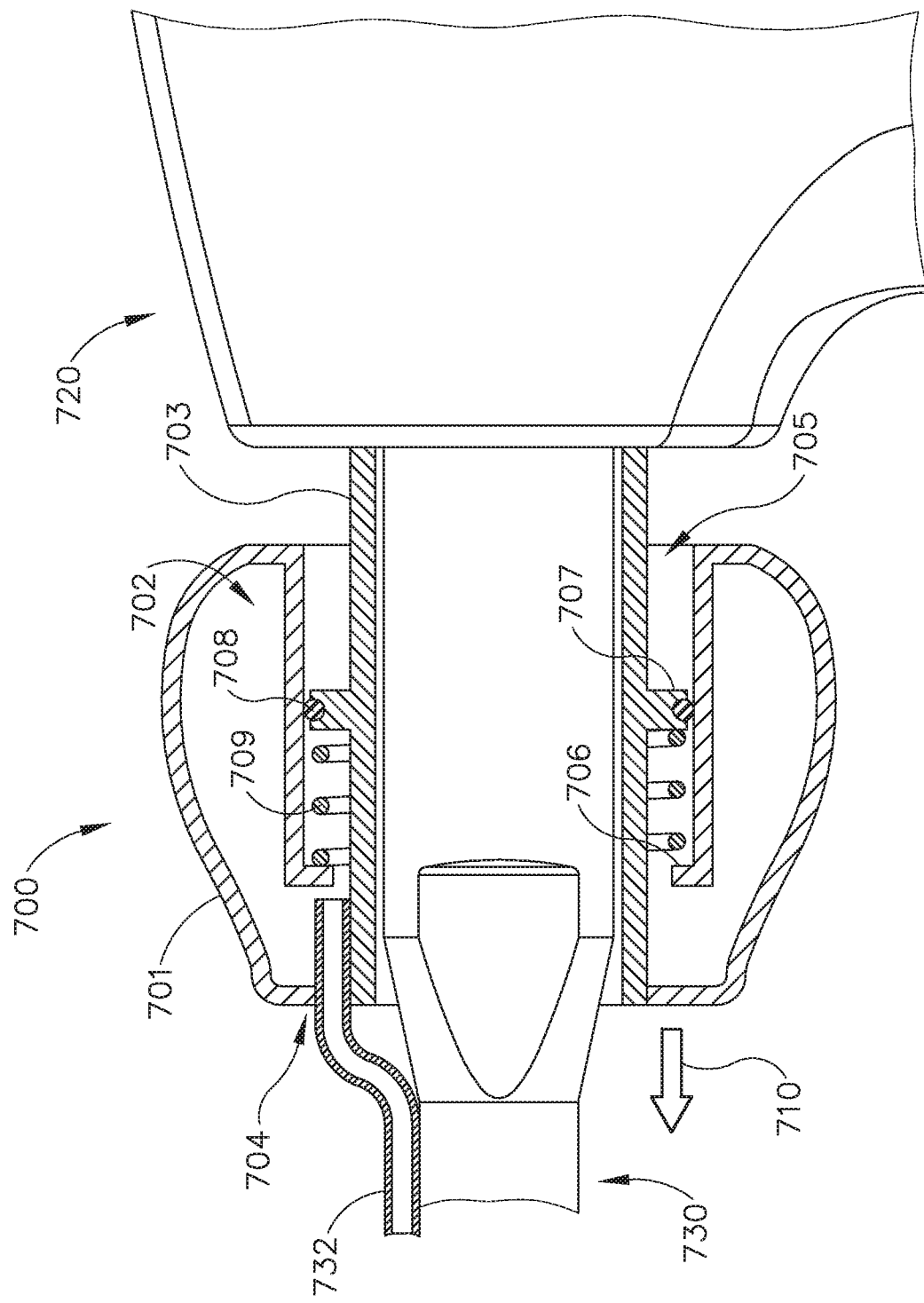
FIG. 45A depicts a cross-sectional side view of the fluid pump of FIG. 44, with the rotation knob of FIG. 44 in a first longitudinal position.

Rotation knob assembly (700) comprises a rotatable knob (701) and a stationary housing (703). Rotatable knob (701) is rotatably and slidably disposed about stationary housing (703) such that rotatable knob (701) may be rotated about stationary housing (703) and translated longitudinally between a distal longitudinal position (FIG. 45A) and a proximal longitudinal position (FIG. 45B). Rotatable knob (701) defines a cylindrical bore (705). A distal end of cylindrical bore (705) defines an annular flange (706) extending inwardly from an interior surface of cylindrical bore (705). Stationary housing (703) comprises an annular flange (707) extending outwardly from an exterior surface of stationary housing (703). Annular flange (707) comprises a circular seal ring (708) disposed about an exterior surface of annular flange (707). Seal ring (708) is configured to engage the interior surface of cylindrical bore (705) of rotatable knob (701) to thereby provide a fluid seal between annular flange (707) of stationary housing (703) and cylindrical bore (705) of rotatable knob (701). A spring (709) is disposed within cylindrical bore (705) between a proximal surface of annular flange (706) and distal surface of annular flange (707). Spring (709) is configured to resiliently bias rotatable knob (701) distally in the direction of arrow (710) toward the distal longitudinal position shown in FIG. 45A.

Rotatable knob (701) further defines a hollow interior (702) that may be filled with liquid coolant. Rotatable knob (701) includes a distal opening (704). Rotatable knob (701) is fluidly coupled with a tube (732) via opening (704). Tube (732) extends along shaft assembly (730) to the end effector and is configured to provide liquid coolant to the ultrasonic blade. In some other versions, hollow interior (702) is in fluid communication with a space defined between an exterior of an inner tube of shaft assembly and an interior of an outer sheath of shaft assembly, such that liquid coolant reaches the end effector via this space. It should therefore be understood that tube (732) may be shortened or even omitted, such that tube (732) need not extend along the length of shaft assembly (730).

FIGS. 45A and 45B depict the operation of rotation knob assembly (700). As discussed above, rotatable knob (701) is translatable between the distal longitudinal position (FIG. 45A) and the proximal longitudinal position (FIG. 45B). As shown in FIG. 45B, as rotatable knob (701) is driven proximally by overcoming the distal bias of spring (709), annular flange (707) pressurizes the liquid coolant within rotatable knob (701). This pressurized liquid coolant is then driven through tube (732) to the end effector to thereby provide liquid coolant to the ultrasonic blade. Upon release of rotatable knob (701), spring (709) drives rotatable knob (701) distally to the distal longitudinal position shown in FIG. 45A. As rotatable knob (701) translates longitudinally distally, a vacuum may be drawn within hollow interior (702) of rotatable knob (701). Such a vacuum, if permitted to be drawn, may cause fluid from within tube (732) to be drawn into hollow interior (702) of rotatable knob (701). It should be understood that rotatable knob (701) may comprise a one-way vent (not shown) in fluid communication with hollow interior (702) of rotatable knob (701). Such a vent may be configured to permit air to flow into hollow interior (702) of rotatable knob (701) to thereby prevent drawing of a vacuum within hollow interior (702) upon distal longitudinal translation of rotatable knob (701).

G. Exemplary Rotation Knob Pump with One-Way Valve

Figure 46B:
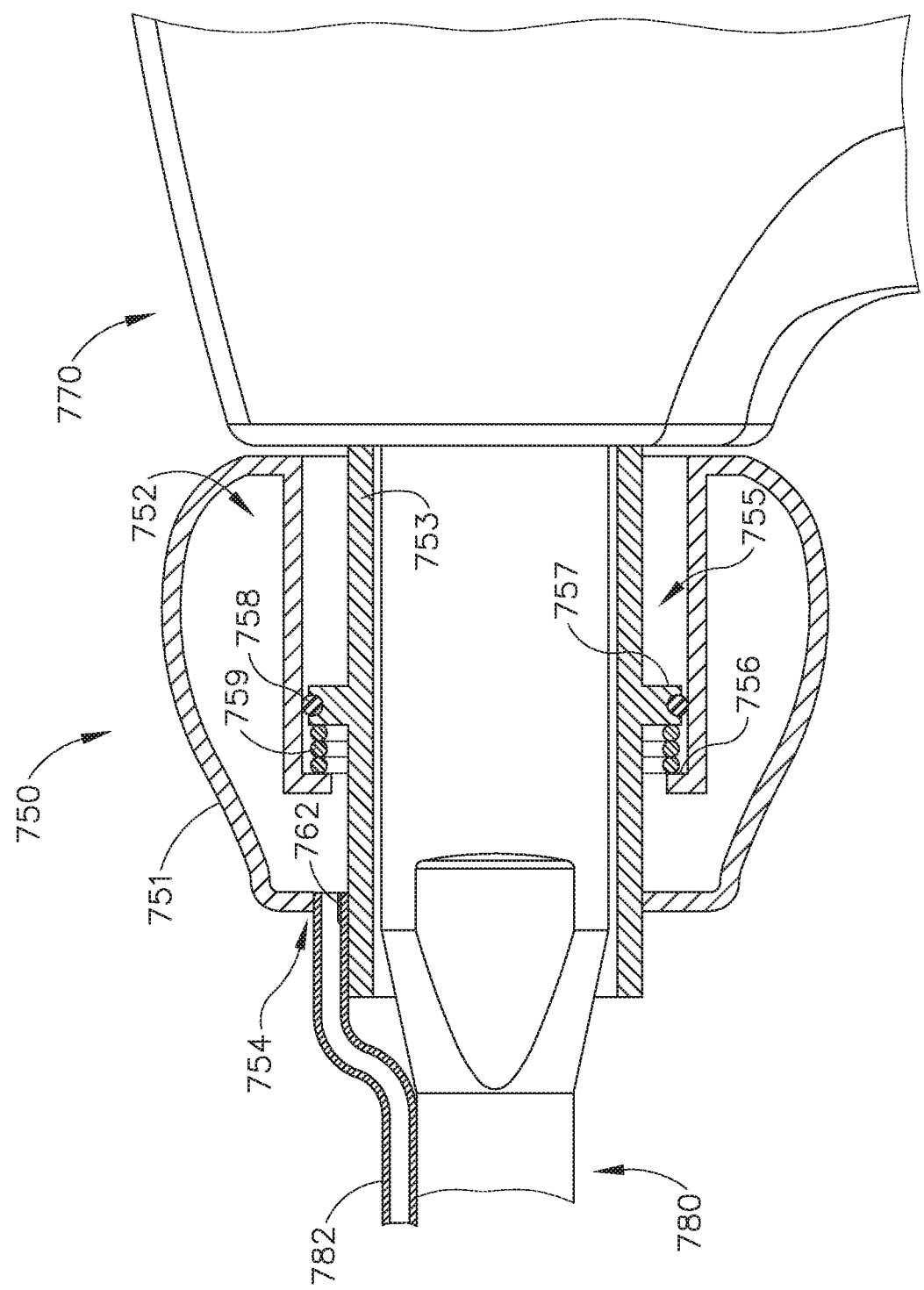
FIG. 46B depicts a cross-sectional side view of the fluid pump of FIG. 46A, with the rotation knob of FIG. 46A moved to a second longitudinal position, and with the flapper valve of FIG. 46A in an open position.

FIGS. 46A and 46B illustrate another exemplary rotation knob assembly (750) that is configured to provide liquid coolant to an ultrasonic blade (not shown). Rotation knob assembly (750) is configured to operate substantially similar to rotation knob (139) discussed above except for the differences discussed below. It should therefore be understood that rotation knob assembly (750) may be readily substituted for rotation knob (139) in instrument (100). Rotation knob assembly (750) is operable to rotate an entire shaft assembly (780) and end effector (not shown) relative to handle assembly (770) about a longitudinal axis of shaft assembly (780). In this example, shaft assembly (780), the end effector, and handle assembly (770) are substantially identical to the similarly named components of instrument (100).

Rotation knob assembly (750) comprises a rotatable knob (751) and a stationary housing (753). Rotatable knob (751) is rotatably and slidably disposed about stationary housing (753) such that rotatable knob (751) may be rotated about stationary housing (753) and translated longitudinally between a distal longitudinal position (FIG. 46A) and a proximal longitudinal position (FIG. 46B). Rotatable knob (751) defines a cylindrical bore (755). A distal end of cylindrical bore (755) defines an annular flange (756) extending inwardly from an interior surface of cylindrical bore (755). Stationary housing (753) comprises an annular flange (757) extending outwardly from an exterior surface of stationary housing (753). Annular flange (757) comprises a circular seal ring (758) disposed about an exterior surface of annular flange (757). Seal ring (758) is configured to engage the interior surface of cylindrical bore (755) of rotatable knob (751) to thereby provide a fluid seal between annular flange (757) of stationary housing (753) and cylindrical bore (755) of rotatable knob (751). A spring (759) is disposed within cylindrical bore (755) between a proximal surface of annular flange (756) and distal surface of annular flange (757). Spring (759) is configured to resiliently bias rotatable knob (751) distally in the direction of arrow (760) toward the distal longitudinal position shown in FIG. 46A.

Rotatable knob (751) further defines a hollow interior (752) that may be filled with liquid coolant. Rotatable knob (751) includes a distal opening (754). Rotatable knob (751) is fluidly coupled with a tube (782) via opening (754). Tube (782) extends along shaft assembly (780) to the end effector and is configured to provide liquid coolant to the ultrasonic blade. In some other versions, hollow interior (752) is in fluid communication with a space defined between an exterior of an inner tube of shaft assembly and an interior of an outer sheath of shaft assembly, such that liquid coolant reaches the end effector via this space. It should therefore be understood that tube (782) may be shortened or even omitted, such that tube (782) need not extend along the length of shaft assembly (780). In the present example, a proximal end of tube (782) comprises a one-way valve (762). One-way valve (762) is configured to permit liquid coolant to flow from within hollow interior (752) of rotatable knob (751) to the end effector via tube (782); but to prohibit the flow of liquid coolant from tube (782) into rotatable knob (751).

FIGS. 46A and 46B depict the operation of rotation knob assembly (750). As discussed above, rotatable knob (751) is translatable between the distal longitudinal position (FIG. 46A) and the proximal longitudinal position (FIG. 46B). As shown in FIG. 46B, as rotatable knob (751) is driven proximally by overcoming the distal bias of spring (759), annular flange (757) pressurizes the liquid coolant within rotatable knob (751). This pressurized liquid coolant is then driven through tube (782) to the end effector to thereby provide liquid coolant to the ultrasonic blade. As shown in FIG. 46A, one-way valve (762) permits liquid coolant to flow from within rotatable knob (751) to the end effector via tube (782). Upon release of rotatable knob (751), spring (709) drives rotatable knob (751) distally to the position shown in FIG. 46A. As rotatable knob (751) translates distally longitudinally, annular flange (757) may cause a vacuum within rotatable knob (751). One-way valve (762) prohibits any backflow of liquid coolant from tube (782) that may be caused by this vacuum. Although one-way valve (762) of the present example is shown as a flapper valve, one-way valve (752) may comprise any appropriate type of one-way valve as would be appreciated by one of ordinary skill in the art. In addition to one-way valve (762), rotatable knob (751) may comprise a one-way vent (not shown) in fluid communication with hollow interior (752) of rotatable knob (751). Such a vent may be configured to permit air to flow into hollow interior (752) of rotatable knob (751) to thereby prevent drawing of a vacuum within hollow interior (752) upon distal longitudinal translation of rotatable knob (751).

H. Exemplary Rotation Knob Pump with Pressure Equalizing Features

Figure 47B:
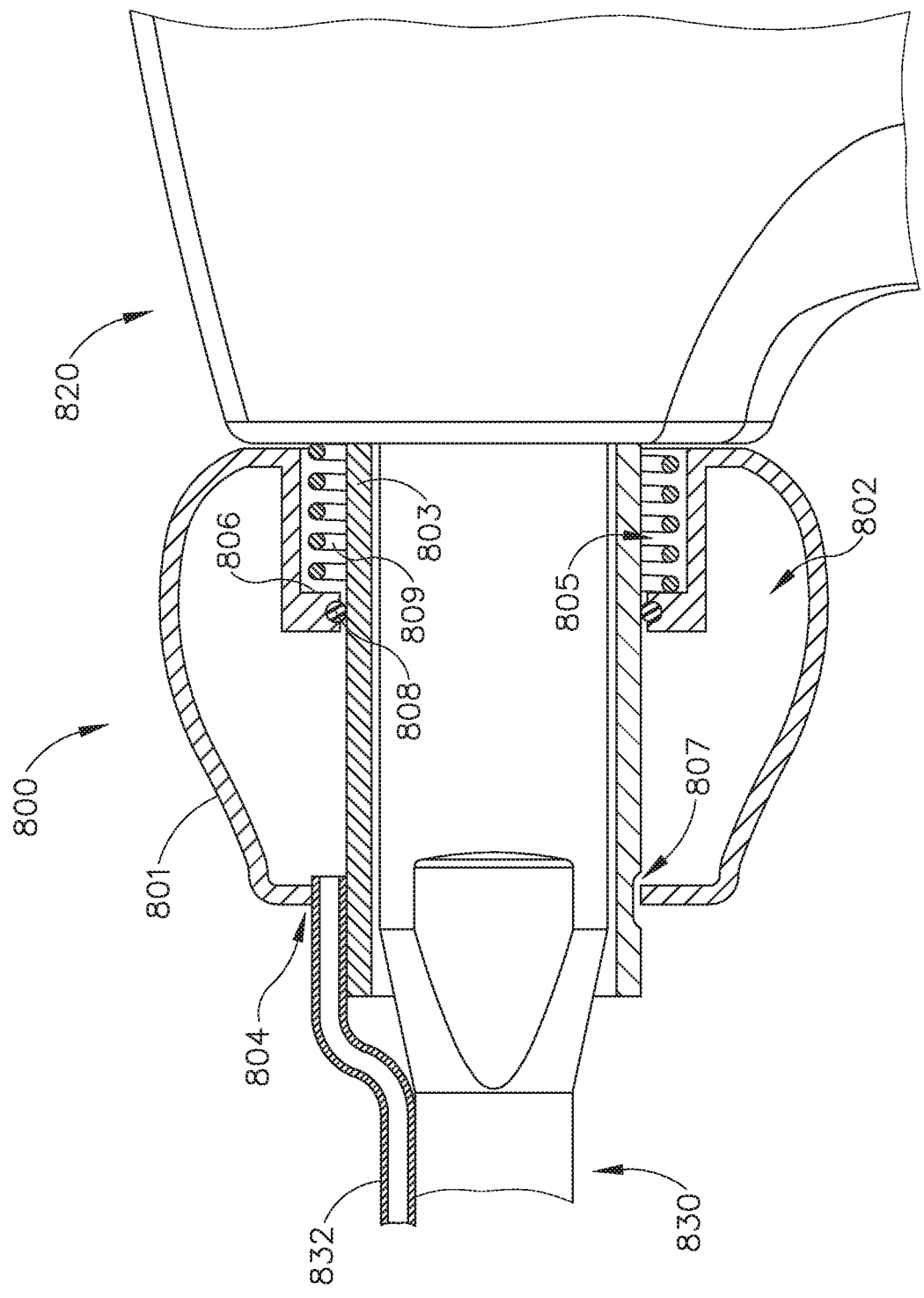
FIG. 47B depicts a cross-sectional side view of the fluid pump of FIG. 47A, with the rotation knob of FIG. 47A moved to a second longitudinal position.

FIGS. 47A and 47B illustrate another exemplary rotation knob assembly (800) that is configured to provide liquid coolant to an ultrasonic blade (not shown). Rotation knob assembly (800) is configured to operate substantially similar to rotation knob (139) discussed above except for the differences discussed below. It should therefore be understood that rotation knob assembly (800) may be readily substituted for rotation knob (139) in instrument (100). Rotation knob assembly (800) is operable to rotate an entire shaft assembly (830) and end effector (not shown) relative to handle assembly (820) about a longitudinal axis of shaft assembly (830). In this example, shaft assembly (830), the end effector, and handle assembly (820) are substantially identical to the similarly named components of instrument (100).

Rotation knob assembly (800) comprises a rotatable knob (801) and a stationary housing (803). Rotatable knob (801) is rotatably and slidably disposed about stationary housing (803) such that rotatable knob (801) may be rotated about stationary housing (803) and translated longitudinally between a distal longitudinal position (FIG. 47A) and a proximal longitudinal position (FIG. 47B). Rotatable knob (801) defines a cylindrical bore (805). A distal end of cylindrical bore (805) defines an annular flange (806) extending inwardly from an interior surface of cylindrical bore (805). Annular flange (806) comprises a circular seal ring (808) disposed about an interior surface of annular flange (806). Seal ring (808) is configured to engage an exterior surface of stationary housing (803) to thereby provide a fluid seal between annular flange (806) of rotatable knob (801) and stationary housing (803). A spring (809) is disposed within cylindrical bore (805) between a proximal surface of annular flange (806) and a distal surface of handle assembly (820). Spring (809) is configured to resiliently bias rotatable knob (801) distally in the direction of arrow (810) toward the distal longitudinal position shown in FIG. 47A.

Rotatable knob (801) further defines a hollow interior (802) that may be filled with liquid coolant. Rotatable knob (801) includes a distal opening (804). Rotatable knob (801) is fluidly coupled with a tube (832) via opening (804). Tube (832) extends along shaft assembly (830) to the end effector and is configured to provide liquid coolant to the ultrasonic blade. In some other versions, hollow interior (802) is in fluid communication with a space defined between an exterior of an inner tube of shaft assembly and an interior of an outer sheath of shaft assembly, such that liquid coolant reaches the end effector via this space. It should therefore be understood that tube (832) may be shortened or even omitted, such that tube (832) need not extend along the length of shaft assembly (830).

FIGS. 47A and 47B depict the operation of rotation knob assembly (800). FIG. 47A shows rotation knob assembly in an initial position. In this position, hollow interior (802) of rotatable knob (801) is completely fluidly sealed. Thus, at this point, any liquid coolant that is released from a distal end of tube (832) will draw a vacuum within hollow interior (802) of rotatable knob (801). It is for this reason that with hollow interior (802) completely fluidly sealed, liquid coolant may not be released from a distal end of tube (832) without assistance. Rotatable knob (801) is translatable between the distal longitudinal position (FIG. 47A) and the proximal longitudinal position (FIG. 47B).

As shown in FIG. 47B, as rotatable knob (801) is driven proximally by overcoming the distal bias of spring (809), a divot (807) formed in the exterior surface of stationary housing (803) is exposed such that hollow interior (802) is no longer fluidly sealed. At this point, liquid coolant may be released from a distal end of tube (832) without drawing a vacuum within hollow interior (802) of rotatable knob (801). It should be appreciated that, among other forces, liquid coolant may be drawn from the distal end of tube (832) by gravity. It should also be appreciated that a one-way valve may be incorporated to prevent liquid coolant from leaking out through divot (807) when rotatable knob (801) is in the proximal position; while still allowing atmospheric air to be communicated through divot (807) to hollow interior (802) when rotatable knob (801) is in the proximal position. Upon release of rotatable knob (801), spring (809) drives rotatable knob (801) distally to the position shown in FIG. 47A thereby completely fluidly sealing hollow interior (802) of rotatable knob (801).

I. Exemplary End Effector with Fluid Pump

FIGS. 48A-49B illustrate an exemplary end effector (900) and shaft assembly (910) that are configured to provide liquid coolant to an ultrasonic blade (902). End effector (900) is configured to operate substantially similar to end effectors (140, 240) discussed above except for the differences discussed below. It should therefore be understood that end effector (900) may be readily substituted for end effectors (14, 240). End effector (900) of this example includes an ultrasonic blade (902) and a pivoting clamp arm (904) that is selectively pivotable toward and away from blade (902) to selectively clamp tissue between clamp arm (904) and blade (902). Clamp arm (904) is pivotably coupled to an outer sheath (912) of shaft assembly (910). Clamp arm (904) is further pivotably coupled to an inner tube (914) of shaft assembly (910) such that as inner tube (914) translates longitudinally within outer sheath (912) relative to outer sheath (912), clamp arm (904) is selectively pivoted toward and away from blade (902). In particular, clamp arm (904) is coupled with outer sheath (912) and inner tube (914) such that clamp arm (904) is pivotable toward blade (902) in response to proximal longitudinal translation of inner tube (914) relative to outer sheath (912); and such that clamp arm (904) is pivotable away from ultrasonic blade (902) in response to distal longitudinal translation of inner tube (914) relative to outer sheath (912). Various suitable ways in which clamp arm (904) may be coupled with outer sheath (912) and inner tube (914) will be apparent to those of ordinary skill in the art in view of the teachings herein. In some versions, one or more resilient members are used to bias clamp arm (904) to the open position shown in FIG. 48B.

Shaft assembly (910) further comprises a tube (916) disposed within shaft assembly (910) between outer sheath (912) and inner tube (914). Tube (916) is fluidly coupled to a fluid reservoir (not shown) and, as will be described in more detail below, is operable to provide liquid coolant from the fluid reservoir to ultrasonic blade (902). By way of example only, the fluid reservoir may be configured and operable similar to fluid reservoir (270) described above. As another merely illustrative example, the proximal end of tube (916) may be closed by a one-way valve that permits atmospheric air to be drawn into tube (916) yet prevents liquid coolant from escaping the proximal end of tube (916), such that tube (916) may serve as its own fluid reservoir. Alternatively, the fluid reservoir may take any other suitable form.

Figure 49A:
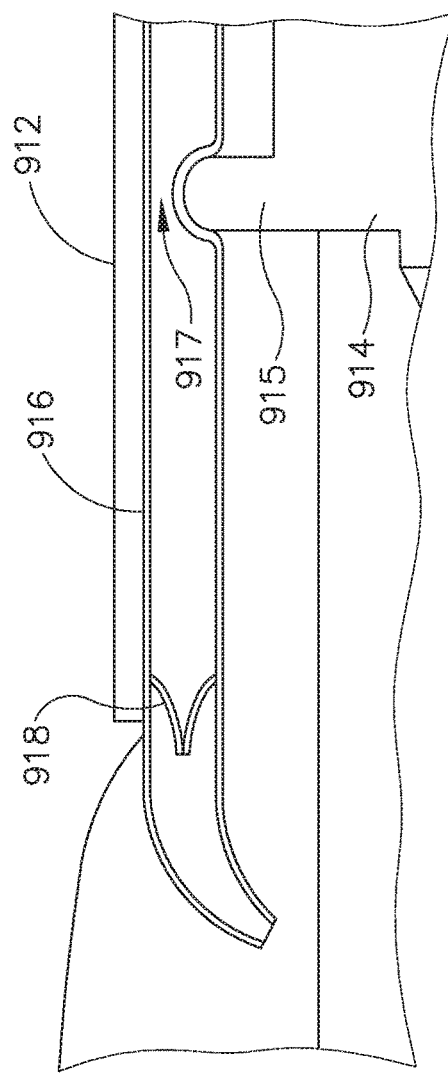
FIG. 49A depicts a detailed cross-sectional side view of the fluid pump of FIG. 48A, with the roller of FIG. 48A in the first longitudinal position.

A distal end of tube (916) is oriented such that as liquid coolant is released from tube (916), the liquid coolant is directed toward ultrasonic blade (902). As best seen in FIGS. 49A and 49B, tube (916) comprises a one-way valve (918). One-way valve (918) is configured to permit liquid coolant to flow distally from within tube (916) to ultrasonic blade (902), but to prohibit any backflow of liquid coolant from within tube (916). Although one-way valve (918) of the present example is shown as a duckbill valve, one-way valve (918) may have any other suitable configuration as will be apparent to those of ordinary skill in the art in view of the teachings herein.

Inner tube (914) comprises a projection (915) extending from a distal portion of inner tube (914). Tube (916) is disposed within shaft assembly (910) adjacent to projection (915) of inner tube (914) such that projection (915) bears against an exterior surface of tube (916) and causes tube (916) to deform as projection (915) translates with inner tube (914). While projection (915) bears into tube (916) and thereby deforms tube (916), projection (915) does not completely pinch tube (916) closed at the point where projection (915) engages tube (916). Instead, projection (915) is configured to leave a small gap (917) in the region where projection (915) engages tube. When inner tube (914) translates distally, projection (915) slides distally along tube (916), such that the deformation of inner tube (914) translates distally. This distal translation urges liquid coolant distally in inner tube (914) and out through one-way valve (918). It should be understood that the liquid coolant may travel distally and out through one-way valve (918) even though there is still a small gap (917) in the region where projection (915) engages tube (916). This is because one-way valve (918) provides less resistance to the flow of liquid coolant than the restriction at gap (917) provides. However, once inner tube (914) is retracted back proximally, liquid coolant will eventually flow distally through gap (917) to fill the region of tube (916) distal to gap (917), placing tube (916) in a state for subsequent dispensation of liquid coolant.

Figure 48A:
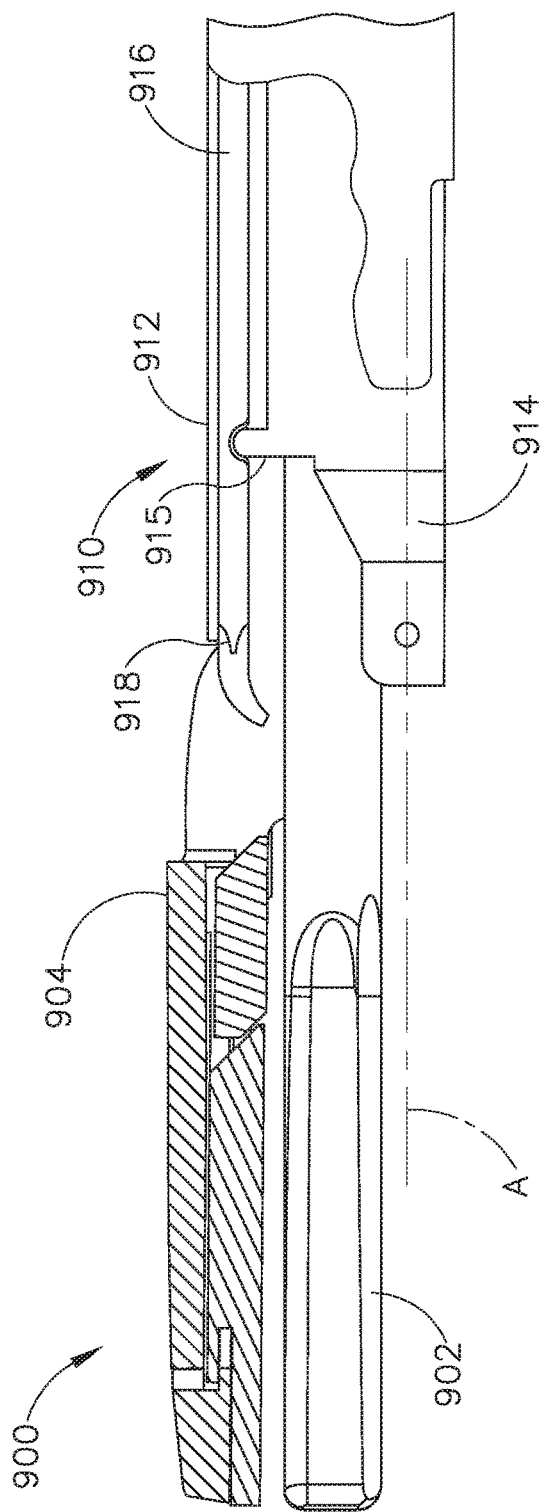
FIG. 48A depicts a cross-sectional side view of yet another exemplary fluid pump operable for use with any of the instruments described herein, with a roller of the fluid pump in a first longitudinal position.

FIGS. 48A-49B depict the operation of end effector (900) and shaft assembly (910). FIGS. 48A and 49A show inner tube (914) in a proximal longitudinal position. In this state, clamp arm (902) is in a closed position. As inner tube (914) is translated longitudinally distally, clamp arm (902) is pivoted away from ultrasonic blade (902) as shown in FIG. 48B. Also as inner tube (914) is translated longitudinally distally, projection (915) bears against the exterior surface of tube (916) and causes the deformation in tube (916) to translate distally as best seen in FIG. 49B. This distal translation of the deformation in tube (916) drives liquid coolant through one-way valve (918), such that the liquid coolant is dispensed onto ultrasonic blade (902). If inner tube (914) is subsequently translated proximally back to the position shown in FIGS. 48A and 49A, projection (915) and the associated deformation in tube (916) also translate proximally back to the position shown in FIGS. 48A and 49A. Additional liquid coolant will eventually seep distally through gap (917), priming tube (916) to dispense additional liquid coolant onto ultrasonic blade (902) when inner tube (914) is subsequently translated distally to pivot clamp arm (902) toward ultrasonic blade (902).

J. Exemplary End Effector with Fluid Sponge

Figure 50A:
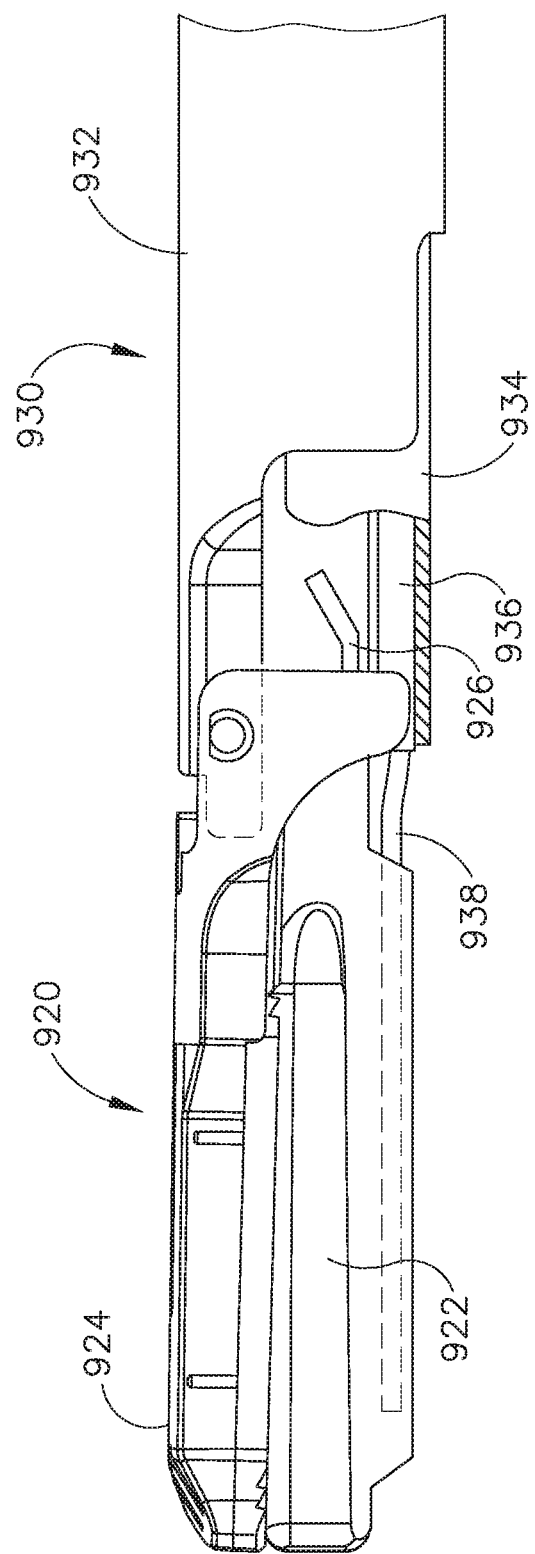
FIG. 50A depicts a partial cross-sectional side view of yet another exemplary fluid pump operable for use with any of the instruments described herein, with a clamp arm of an end effector in a closed position.
Figure 50B:
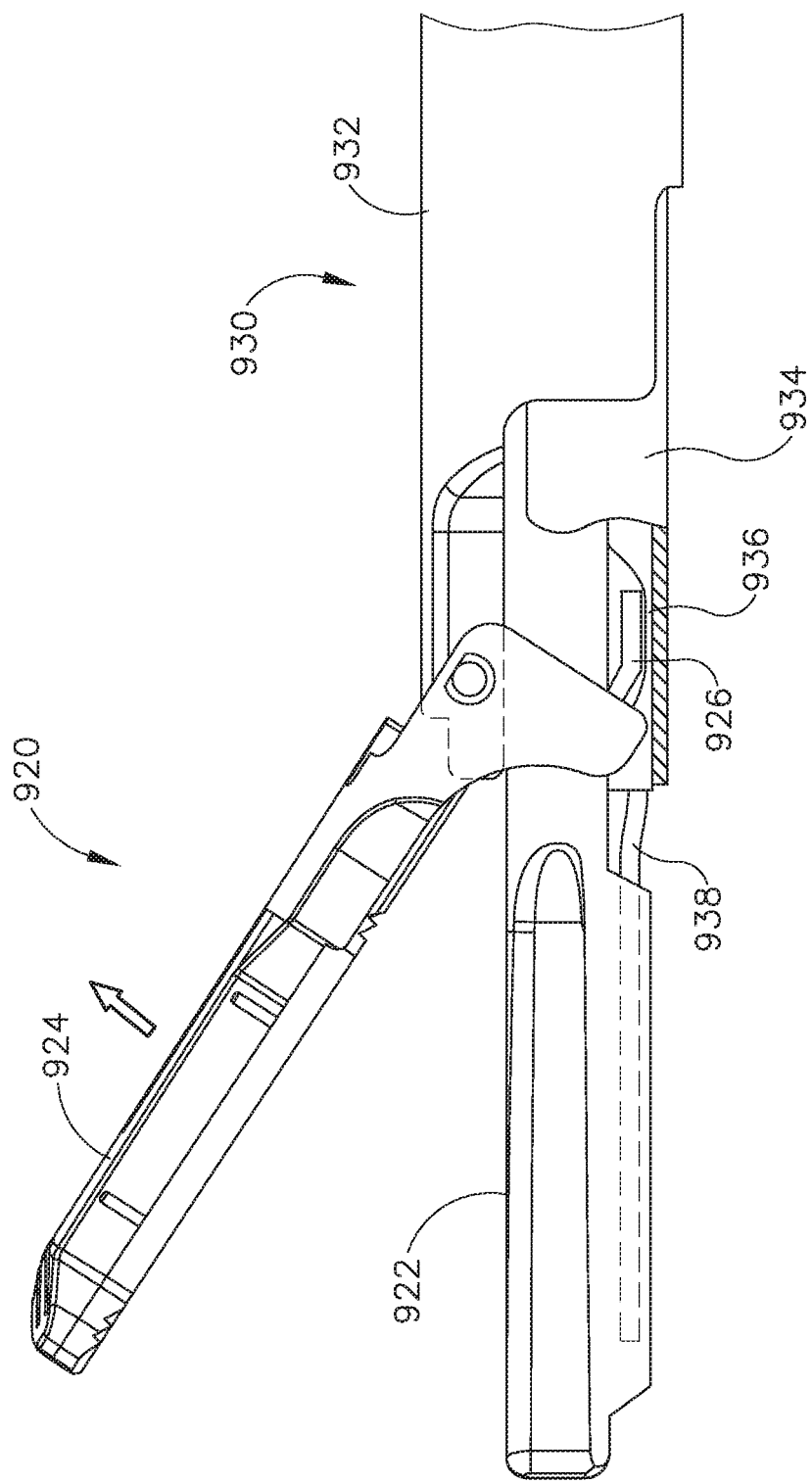
FIG. 50B depicts a partial cross-sectional side view of the fluid pump of FIG. 50A, with the clamp arm of FIG. 50A moved to an open position thereby compressing a fluid source of the fluid pump.

FIGS. 50A-50B illustrate an exemplary end effector (920) and shaft assembly (930) that is configured to provide liquid coolant to an ultrasonic blade (922). End effector (920) is configured to operate substantially similar to end effectors (140, 240) discussed above except for the differences discussed below. It should therefore be understood that end effector (920) may be readily substituted for end effectors (14, 240). End effector (920) of this example includes an ultrasonic blade (922) and a pivoting clamp arm (924) that is selectively pivotable toward and away from blade (922) to selectively clamp tissue between clamp arm (924) and blade (922). Clamp arm (924) is pivotably coupled to an outer sheath (932) of shaft assembly (930). Clamp arm (924) is further pivotably coupled to an inner tube (934) of shaft assembly (930) such that as inner tube (934) translates longitudinally within outer sheath (932) relative to outer sheath (932), clamp arm (924) is selectively pivoted toward and away from blade (922). In particular, clamp arm (924) is coupled with outer sheath (932) and inner tube (934) such that clamp arm (924) is pivotable toward blade (922) in response to proximal longitudinal translation of inner tube (934) relative to outer sheath (932); and such that clamp arm (924) is pivotable away from ultrasonic blade (922) in response to distal longitudinal translation of inner tube (934) relative to outer sheath (932). Various suitable ways in which clamp arm (924) may be coupled with outer sheath (932) and inner tube (934) will be apparent to those of ordinary skill in the art in view of the teachings herein. In some versions, one or more resilient members are used to bias clamp arm (924) to the open position shown in FIG. 50B.

Shaft assembly (930) comprises a porous sponge (936). Sponge (936) is configured to absorb and selectively retain a liquid coolant. Liquid coolant may be introduced to sponge (936) by dipping sponge (936) (i.e., effectively end effector (920) and a distal portion of shaft assembly (930)) into a container of liquid coolant. Additionally or alternatively, sponge (936) may absorb liquid from a surgical site, which may in turn serve as a liquid coolant. Clamp arm (924) comprises a resilient arm (926) extending proximally from a distal end of clamp arm (924). As shown in FIG. 50A, with clamp arm (924) in a closed position, resilient arm (926) is positioned adjacent to a top surface of sponge (936). As shown in FIG. 50B, as clamp arm (924) is pivoted away from blade (922) toward an open position, resilient arm (926) bears down upon sponge (936) and compresses sponge (936). A fluid absorbent filament (938) extends distally from sponge (936). Filament (938) is in fluid communication with sponge (936) such that liquid coolant within sponge (936) is passed from sponge (936) to filament (938) as sponge (936) is compressed by resilient arm (926). It should therefore be understood that liquid coolant is delivered to filament (938) as clamp arm (924) is pivoted into the open position shown in FIG. 50B.

As best seen in FIG. 51, bottom surface of blade (922) comprises a channel (923) formed therein. Filament (938) extends distally from sponge (936) and passes through channel (923) adjacent to blade (922) such that liquid coolant from sponge (936) may passed from sponge (936) to filament (938) and wicked through filament (938) to thereby cool blade (922). It should therefore be understood that liquid coolant is delivered to blade (922) as clamp arm (924) is pivoted into the open position shown in FIG. 50B. In some other versions, sponge (936) may be replaced with a compressible fluid reservoir (e.g., a fluid bladder) that is configured to be compressed by resilient arm (926) and to deliver liquid coolant to filament (938) as clamp arm (924) is pivoted into the open position shown in FIG. 50B. Other suitable variations will be apparent to those of ordinary skill in the art in view of the teachings herein.

K. Exemplary End Effector with Fluid Bladder

Figure 52A:
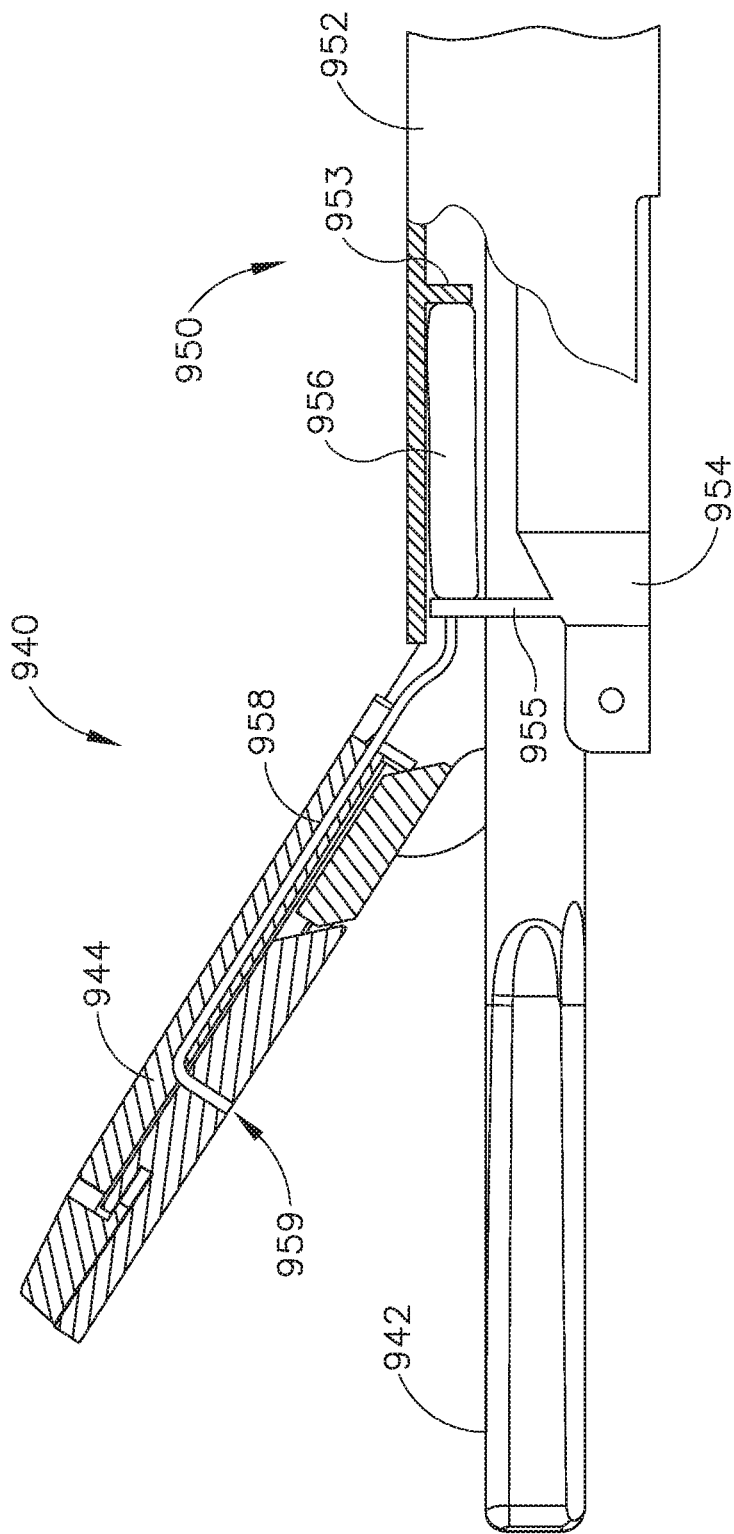
FIG. 52A depicts a partial cross-sectional side view of yet another exemplary fluid pump operable for use with any of the instruments described herein, with an inner tube of a shaft assembly in a first longitudinal position.
Figure 52B:
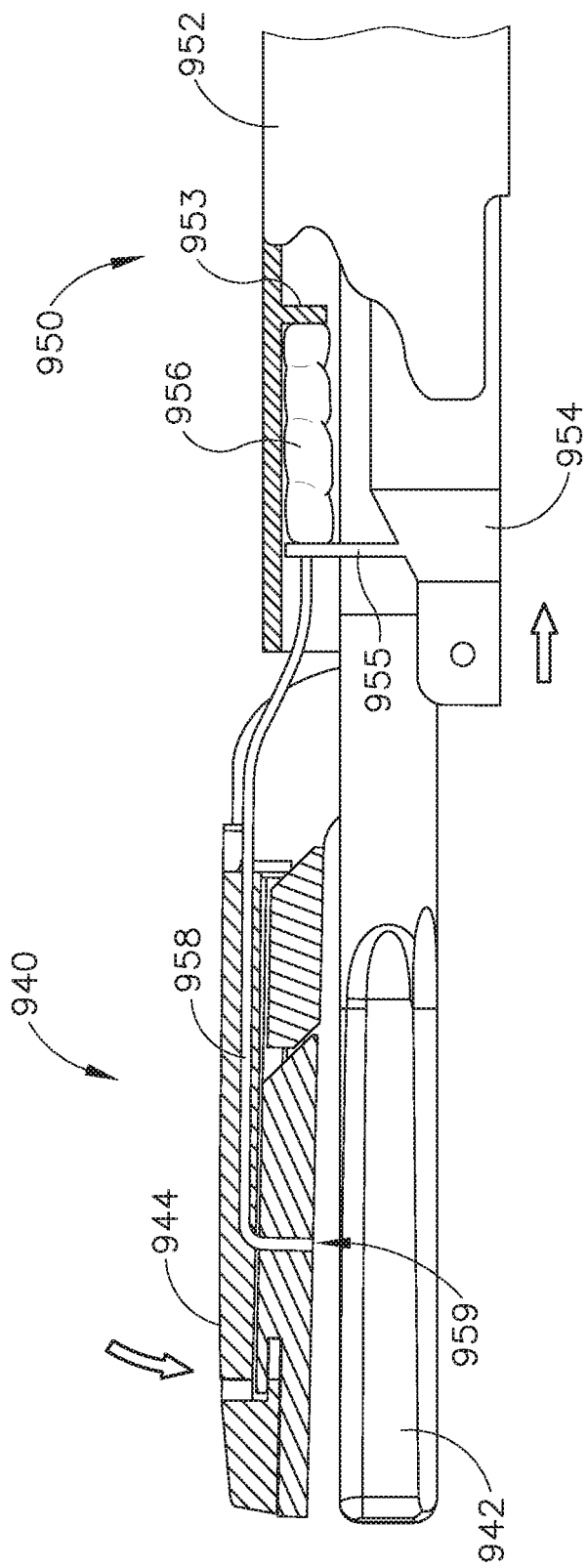
FIG. 52B depicts a partial cross-sectional side view of the fluid pump of FIG. 52A, with the inner tube of FIG. 52A moved to a second longitudinal position thereby compressing a fluid source of the fluid pump.

FIGS. 52A and 52B illustrate an exemplary end effector (940) and shaft assembly (950) that are configured to provide liquid coolant to an ultrasonic blade (942). End effector (950) is configured to operate substantially similar to end effectors (140, 240) discussed above except for the differences discussed below. It should therefore be understood that end effector (950) may be readily substituted for end effectors (14, 240). End effector (940) of this example includes an ultrasonic blade (942) and a pivoting clamp arm (944) that is selectively pivotable toward and away from blade (942) to selectively clamp tissue between clamp arm (944) and blade (942). Clamp arm (944) is pivotably coupled to an outer sheath (952) of shaft assembly (950). Clamp arm (944) is further pivotably coupled to an inner tube (954) of shaft assembly (950) such that as inner tube (954) translates longitudinally within outer sheath (952) relative to outer sheath (952), clamp arm (944) is selectively pivoted toward and away from blade (942). In particular, clamp arm (944) is coupled with outer sheath (952) and inner tube (954) such that clamp arm (944) is pivotable toward blade (942) in response to proximal longitudinal translation of inner tube (954) relative to outer sheath (952); and such that clamp arm (944) is pivotable away from ultrasonic blade (942) in response to distal longitudinal translation of inner tube (954) relative to outer sheath (952). Various suitable ways in which clamp arm (944) may be coupled with outer sheath (952) and inner tube (954) will be apparent to those of ordinary skill in the art in view of the teachings herein. In some versions, one or more resilient members are used to bias clamp arm (944) to the open position shown in FIG. 52A.

Inner tube (954) of the present example comprises a projection (955) extending from a distal portion of inner tube (954). Outer sheath (952) comprises a projection (953) extending inwardly from an interior surface of outer sheath (952). In the present example, projection (955) of inner tube (954) is positioned distally of projection (953) of outer sheath (952). A fluid bladder (956) is disposed between projection (955) of inner tube (954) projection (953) of outer sheath (952). Bladder (956) is configured to be filled with liquid coolant and to selectively retain the liquid coolant therein. Bladder (956) is fluidly coupled with a tube (958). Tube (958) extends distally from bladder (956) and passes through clamp arm (944) such that a distal end of tube (958) is exposed relative to a bottom surface of clamp arm (944). In particular, the distal end of tube (958) provides a fluid outlet (959) above ultrasonic blade (942). While just one fluid outlet (959) is shown, it should be understood that any other suitable number of fluid outlets (959) may be provided (e.g., several fluid outlets (959) along the length of clamp arm (944)). As shown in FIG. 52B, as inner tube (954) is translated longitudinally proximally, clamp arm (944) is pivoted toward blade (942) thereby positioning fluid outlet (959) of tube (958) adjacent to blade (942). Additionally, as inner tube (954) is translated longitudinally proximally, projection (955) of inner tube (954) is translated longitudinally toward projection (953) of outer sheath (952), thereby compressing bladder (956). As bladder (956) is compressed, liquid coolant within bladder (956) is driven through tube (958) to blade (942) via fluid outlet (959) to thereby cool blade (942).

In some versions, bladder (956) is formed of a resilient material and includes a vent opening. The vent opening may include a one-way valve that permits atmospheric air to enter bladder (956) via the vent opening but prevents the liquid coolant from escaping bladder (956) via the vent opening. Thus, when inner tube (954) is translated distally from the position shown in FIG. 52B to the position shown in FIG. 52A, the resilience of bladder (956) causes bladder (956) to expand. This expansion of bladder (956) draws in atmospheric air to take up the capacity that was evacuated by the most recently dispensed volume of liquid coolant. If inner tube (954) is translated proximally again, projections (953, 955) may again cooperate to compress bladder (956) to thereby drive an additional volume of liquid coolant through fluid outlet (959). The above processes may be repeated until the full volume of liquid coolant has been dispensed from bladder (956).

L. Exemplary End Effector with Pinch Arm

Figure 53A:
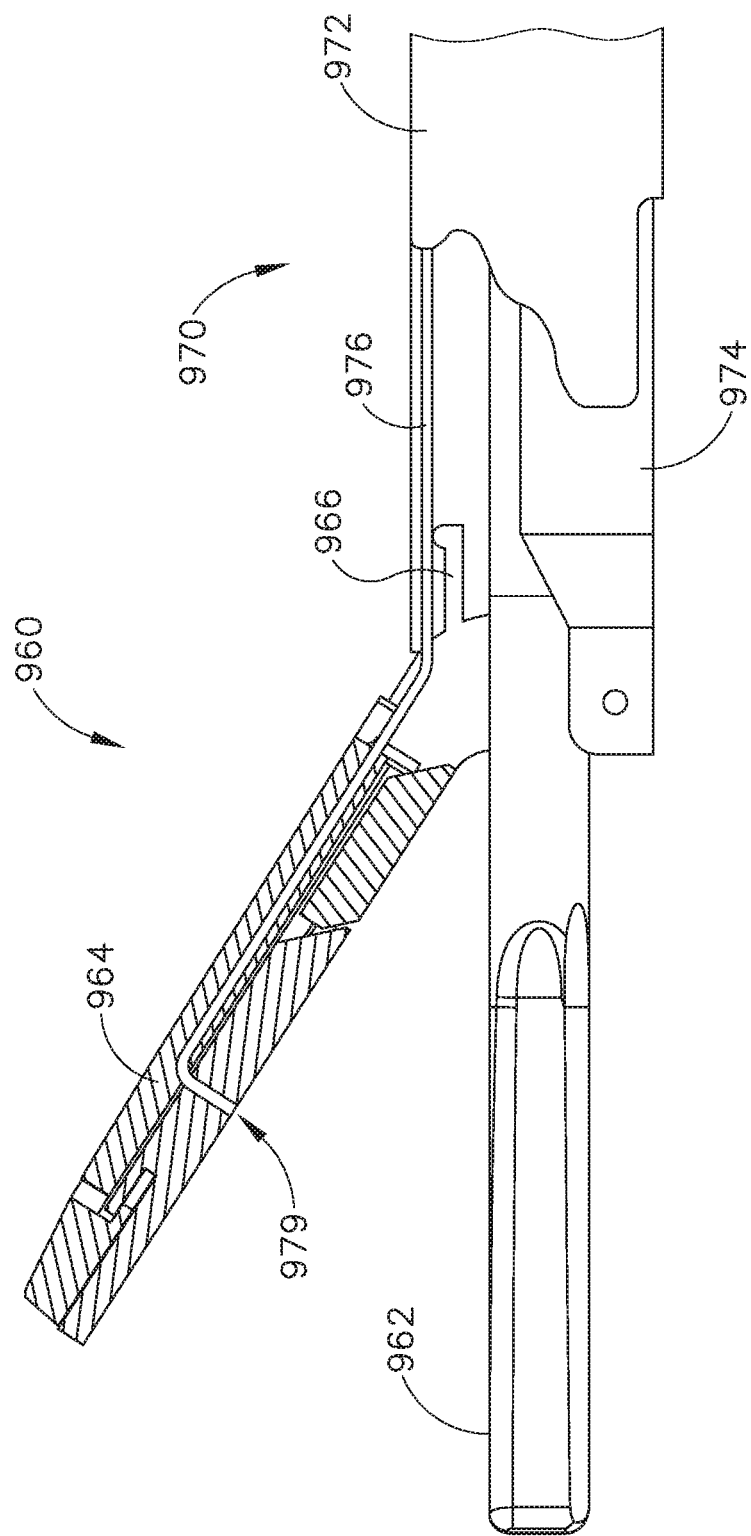
FIG. 53A depicts a partial cross-sectional side view of an exemplary fluid delivery system operable for use with any of the instruments described herein, with a clamp arm of an end effector in an open position.
Figure 53B:
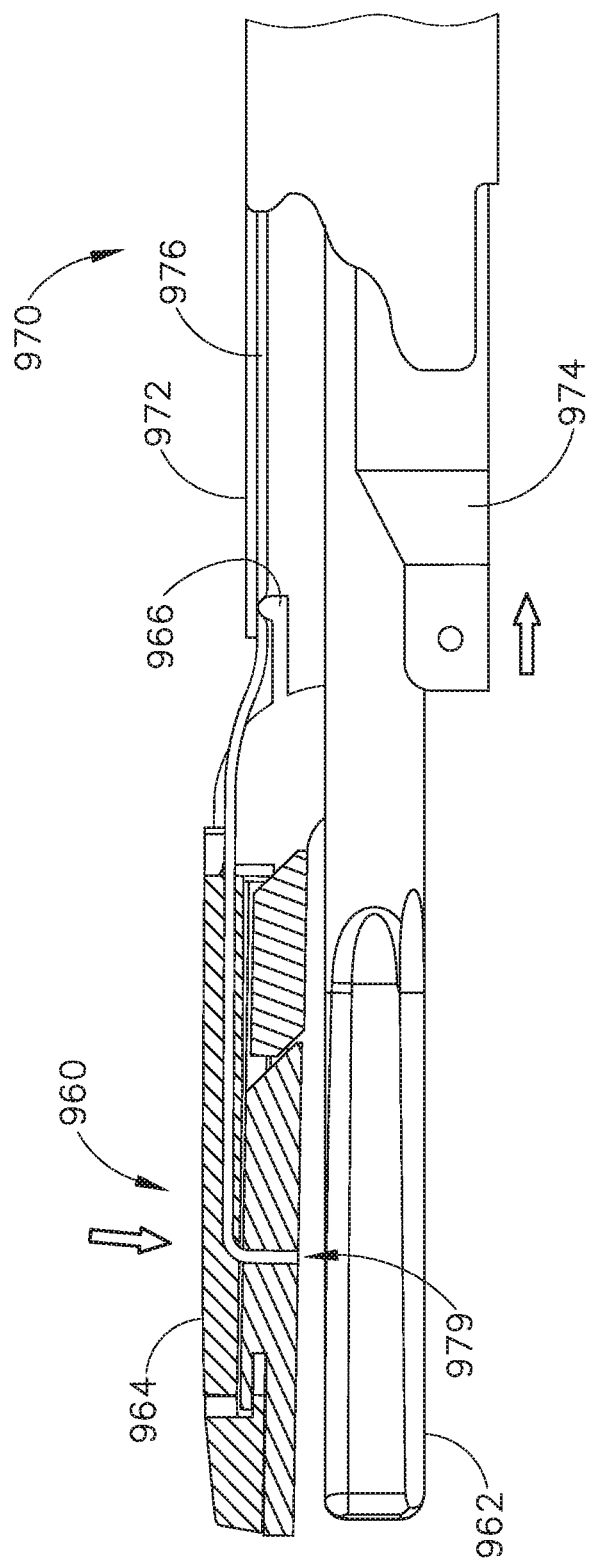
FIG. 53B depicts a partial cross-sectional side view of the fluid delivery system of FIG. 53A, with the clamp arm of FIG. 53A moved to a closed position thereby pinching a fluid line of the fluid delivery system.

FIGS. 53A and 53B illustrate an exemplary end effector (960) and shaft assembly (970) that are configured to provide liquid coolant to an ultrasonic blade (962). End effector (960) is configured to operate substantially similar to end effectors (140, 240) discussed above except for the differences discussed below. It should therefore be understood that end effector (960) may be readily substituted for end effectors (14, 240). End effector (960) of this example includes an ultrasonic blade (962) and a pivoting clamp arm (964) that is selectively pivotable toward and away from blade (962) to selectively clamp tissue between clamp arm (964) and blade (962). Clamp arm (964) is pivotably coupled to an outer sheath (972) of shaft assembly (970). Clamp arm (964) is further pivotably coupled to an inner tube (974) of shaft assembly (970) such that as inner tube (974) translates longitudinally within outer sheath (972) relative to outer sheath (972), clamp arm (964) is selectively pivoted toward and away from blade (962). In particular, clamp arm (964) is coupled with outer sheath (972) and inner tube (974) such that clamp arm (964) is pivotable toward blade (962) in response to proximal longitudinal translation of inner tube (974) relative to outer sheath (972); and such that clamp arm (964) is pivotable away from ultrasonic blade (962) in response to distal longitudinal translation of inner tube (974) relative to outer sheath (972). Various suitable ways in which clamp arm (964) may be coupled with outer sheath (972) and inner tube (974) will be apparent to those of ordinary skill in the art in view of the teachings herein. In some versions, one or more resilient members are used to bias clamp arm (964) to the open position shown in FIG. 53B.

Shaft assembly (970) further comprises a tube (976) that is disposed within shaft assembly (970) adjacent to outer sheath (972). Tube (976) is fluidly coupled to a fluid reservoir (not shown) and is operable to provide liquid coolant from the fluid reservoir to ultrasonic blade (962). By way of example only, the fluid reservoir may be configured and operable similar to fluid reservoir (270) described above. As another merely illustrative example, the proximal end of tube (976) may be closed by a one-way valve that permits atmospheric air to be drawn into tube (976) yet prevents liquid coolant from escaping the proximal end of tube (976), such that tube (976) may serve as its own fluid reservoir. Alternatively, the fluid reservoir may take any other suitable form. Tube (976) extends distally from shaft assembly (970) and passes through clamp arm (964) such that a distal end of tube (976) is exposed relative to a bottom surface of clamp arm (964). In particular, the distal end of tube (976) provides a fluid outlet (979) above ultrasonic blade (962). While just one fluid outlet (979) is shown, it should be understood that any other suitable number of fluid outlets (979) may be provided (e.g., several fluid outlets (979) along the length of clamp arm (964)).

Clamp arm (964) comprises a resilient arm (966) extending proximally from a distal end of clamp arm (964). As shown in FIG. 53A, with clamp arm (964) in an open position, resilient arm (966) is positioned adjacent to an exterior surface of tube (976). As shown in FIG. 53B, as clamp arm (964) is pivoted toward blade (962) into a closed position, resilient arm (966) bears upon tube (976) and pinches tube (976) to thereby prevent the flow of liquid coolant within tube (976). In the present example, the liquid coolant in tube (976) is pressurized. Thus, when clamp arm (964) is opened and resilient arm (966) disengages tube, the pressurized liquid coolant is allowed to flow through fluid outlet (979) to cool ultrasonic blade (962). When clamp arm (964) is closed and resilient arm (966) pinches tube (976) closed, the liquid coolant is prevented from flowing to fluid outlet (979).

M. Exemplary Shaft Assembly with Pinching Divot

Figure 54A:
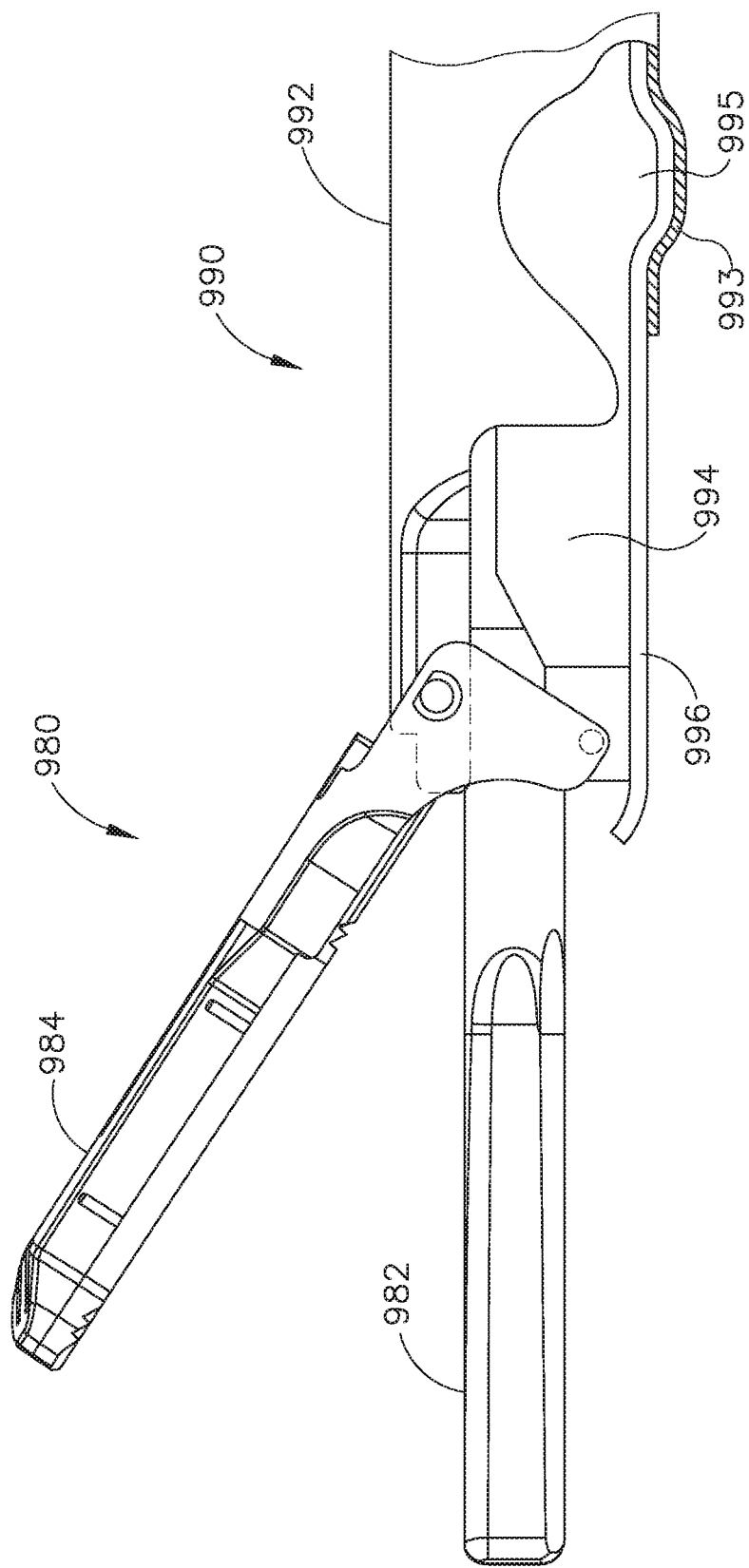
FIG. 54A depicts a partial cross-sectional side view of yet another exemplary fluid delivery system operable for use with any of the instruments described herein, with an inner tube of a shaft assembly in a first longitudinal position.
Figure 54B:
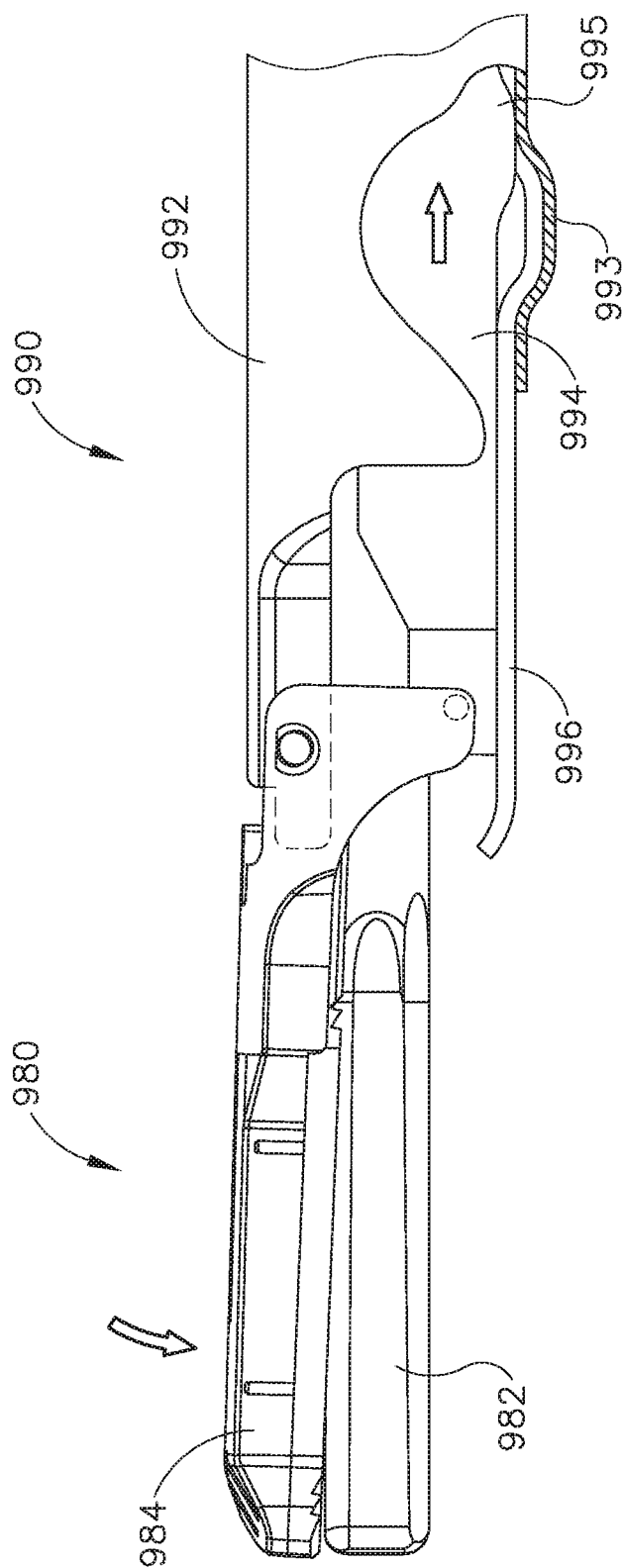
FIG. 54B depicts a partial cross-sectional side view of the fluid delivery system of FIG. 54A, with the inner tube of FIG. 54A moved to a second longitudinal position thereby pinching a fluid line of the fluid delivery system.

FIGS. 54A and 54B illustrate an exemplary end effector (980) and shaft assembly (990) that are configured to provide liquid coolant to an ultrasonic blade (982). End effector (980) is configured to operate substantially similar to end effectors (140, 240) discussed above except for the differences discussed below. It should therefore be understood that end effector (980) may be readily substituted for end effectors (14, 240). End effector (980) of this example includes an ultrasonic blade (982) and a pivoting clamp arm (984) that is selectively pivotable toward and away from blade (982) to selectively clamp tissue between clamp arm (984) and blade (982). Clamp arm (984) is pivotably coupled to an outer sheath (992) of shaft assembly (990). Clamp arm (984) is further pivotably coupled to an inner tube (994) of shaft assembly (990) such that as inner tube (994) translates longitudinally within outer sheath (992) relative to outer sheath (992), clamp arm (984) is selectively pivoted toward and away from blade (982). In particular, clamp arm (984) is coupled with outer sheath (992) and inner tube (994) such that clamp arm (984) is pivotable toward blade (982) in response to proximal longitudinal translation of inner tube (994) relative to outer sheath (992); and such that clamp arm (984) is pivotable away from ultrasonic blade (982) in response to distal longitudinal translation of inner tube (994) relative to outer sheath (992). Various suitable ways in which clamp arm (984) may be coupled with outer sheath (992) and inner tube (994) will be apparent to those of ordinary skill in the art in view of the teachings herein. In some versions, one or more resilient members are used to bias clamp arm (984) to the open position shown in FIG. 54A.

Shaft assembly (990) further comprises a tube (996) that is disposed within shaft assembly (990) between outer sheath (992) and inner tube (994). Tube (996) is fluidly coupled to a fluid reservoir (not shown) and is operable to provide liquid coolant from the fluid reservoir to ultrasonic blade (982). By way of example only, the fluid reservoir may be configured and operable similar to fluid reservoir (270) described above. As another merely illustrative example, the proximal end of tube (996) may be closed by a one-way valve that permits atmospheric air to be drawn into tube (996) yet prevents liquid coolant from escaping the proximal end of tube (996), such that tube (996) may serve as its own fluid reservoir. Alternatively, the fluid reservoir may take any other suitable form. Tube (996) extends distally from shaft assembly (990) such that a distal end of tube (996) is positioned adjacent to blade (982). Thus, as liquid coolant is released from tube (996), the liquid coolant is directed toward ultrasonic blade (982).

Outer sheath (992) comprises a divot (993) formed in a sidewall of outer sheath (992). Inner tube (994) comprises a projection (995) extending from an exterior surface of inner tube (994). Inner tube (994) is oriented such that projection (995) extends within divot (993) of outer sheath (992), and as will be described in more detail below, is configured to translate longitudinally within divot (993) and relative to divot (993). As best seen in FIG. 54A, tube (996) is disposed within divot (993) between an exterior surface of projection (995) of inner tube (994) and an interior surface of divot (993) of outer sheath (992). As shown in FIG. 54A, with clamp arm (984) in an open position, sufficient clearance is provided between the exterior surface of projection (995) and the interior surface of divot (993) such that liquid coolant is able to flow through tube (996). As shown in FIG. 54B, as inner tube (994) is translated longitudinally proximally, clamp arm (984) is pivoted toward blade (982). Additionally, as inner tube (994) is translated longitudinally proximally, projection (995) of inner tube (994) is translated longitudinally proximally within divot (993) thereby pinching tube (996) between the exterior surface of projection (995) and the interior surface of divot (993) to thereby prevent the flow of liquid coolant within tube (996). In the present example, the liquid coolant in tube (996) is pressurized. Thus, when clamp arm (984) is opened, the pressurized liquid coolant is allowed to flow through tube (996) to cool ultrasonic blade (962). When clamp arm (984) is closed, the liquid coolant is prevented from flowing through tube (996).

N. Exemplary Shaft Assembly with Pinching Projection

Figure 55A:
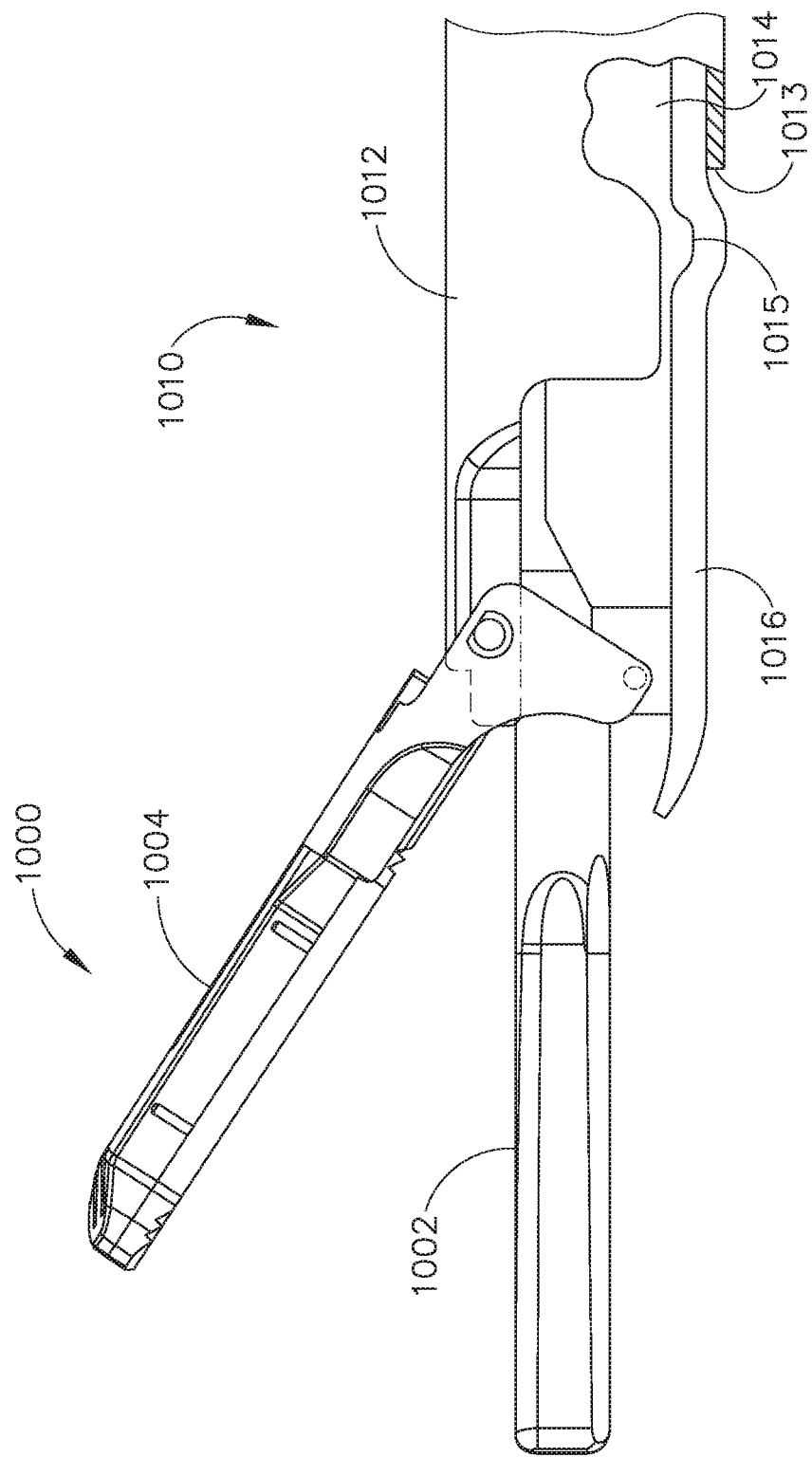
FIG. 55A depicts a partial cross-sectional side view of yet another exemplary fluid delivery system operable for use with any of the instruments described herein, with an inner tube of a shaft assembly in a first longitudinal position.
Figure 55B:
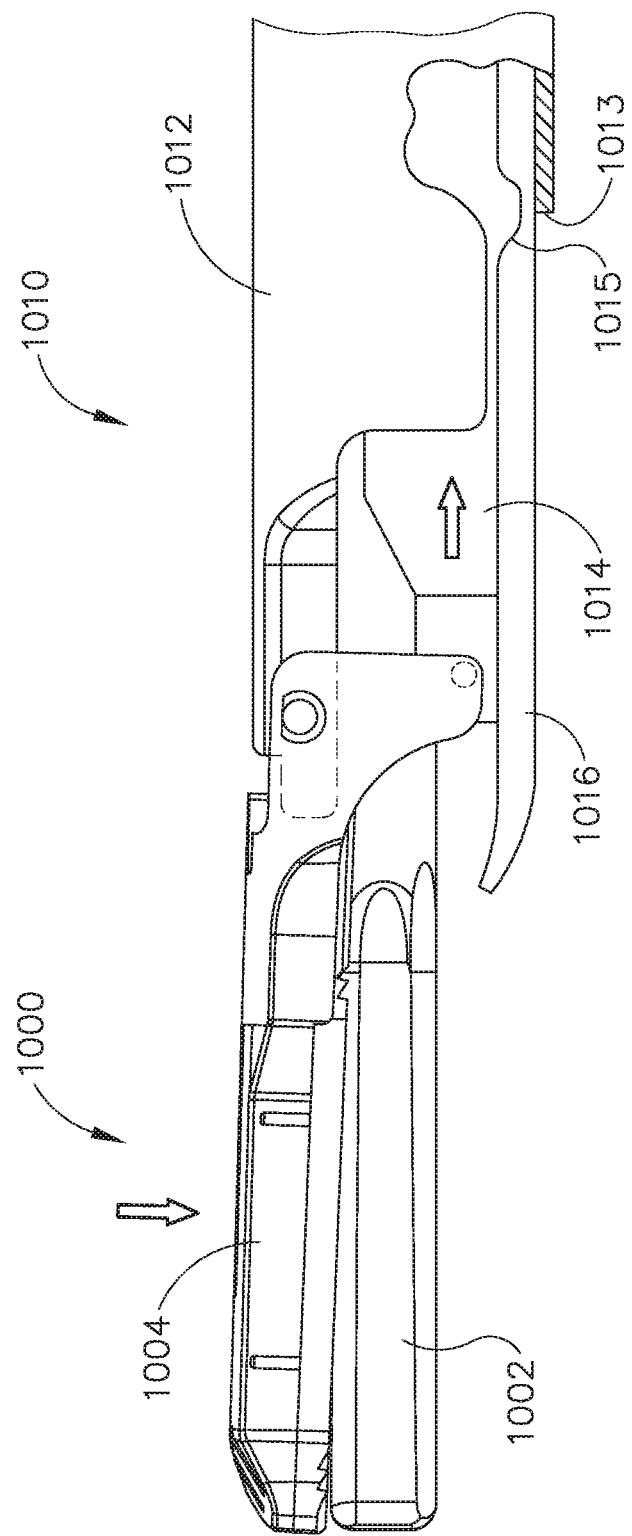
FIG. 55B depicts a partial cross-sectional side view of the fluid delivery system of FIG. 55A, with the inner tube of FIG. 55A moved to a second longitudinal position thereby pinching a fluid line of the fluid delivery system.

FIGS. 55A and 55B illustrate an exemplary end effector (1000) and shaft assembly (1010) that are configured to provide liquid coolant to an ultrasonic blade (1002). End effector (1000) is configured to operate substantially similar to end effectors (140, 240) discussed above except for the differences discussed below. It should therefore be understood that end effector (1000) may be readily substituted for end effectors (14, 240). End effector (1000) of this example includes an ultrasonic blade (1002) and a pivoting clamp arm (1004) selectively pivotable toward and away from blade (1002) to selectively clamp tissue between clamp arm (1004) and blade (1002). Clamp arm (1004) is pivotably coupled to an outer sheath (1012) of shaft assembly (1010). Clamp arm (1004) is further pivotably coupled to an inner tube (1014) of shaft assembly (1010) such that as inner tube (1014) translates longitudinally within outer sheath (1012) relative to outer sheath (1012), clamp arm (1004) is selectively pivoted toward and away from blade (1002). In particular, clamp arm (1004) is coupled with outer sheath (1012) and inner tube (1014) such that clamp arm (1004) is pivotable toward blade (1002) in response to proximal longitudinal translation of inner tube (1014) relative to outer sheath (1012); and such that clamp arm (1004) is pivotable away from ultrasonic blade (1002) in response to distal longitudinal translation of inner tube (1014) relative to outer sheath (1012). Various suitable ways in which clamp arm (1004) may be coupled with outer sheath (1012) and inner tube (1014) will be apparent to those of ordinary skill in the art in view of the teachings herein. In some versions, one or more resilient members are used to bias clamp arm (1004) to the open position shown in FIG. 55A.

Shaft assembly (1010) comprises a tube (1016) disposed within shaft assembly (1010) between outer sheath (1012) and inner tube (1014). Tube (1016) is fluidly coupled to a fluid reservoir (not shown) and is operable to provide liquid coolant from the fluid reservoir to ultrasonic blade (1002). By way of example only, the fluid reservoir may be configured and operable similar to fluid reservoir (270) described above. As another merely illustrative example, the proximal end of tube (1016) may be closed by a one-way valve that permits atmospheric air to be drawn into tube (1016) yet prevents liquid coolant from escaping the proximal end of tube (1016), such that tube (1016) may serve as its own fluid reservoir. Alternatively, the fluid reservoir may take any other suitable form. Tube (1016) extends distally from shaft assembly (1010) such that a distal end of tube (1016) is positioned adjacent to blade (1002). Thus, as liquid coolant is released from tube (1016), the liquid coolant is directed toward ultrasonic blade (1002).

Inner tube (1014) comprises a projection (1015) extending from an exterior surface of inner tube (1014). Inner tube (1014) is oriented such that projection (1015) is positioned distally of a distal edge (1013) of outer sheath (1012). As shown in FIG. 55A, with clamp arm (1004) in an open position, sufficient clearance is provided between projection (1015) of inner tube (1014) and distal edge (1013) of outer sheath (1012) such that liquid coolant is able to flow through tube (1016). As shown in FIG. 55B, as inner tube (1014) is translated longitudinally proximally, clamp arm (1004) is pivoted toward blade (1002). Additionally, as inner tube (1014) is translated longitudinally proximally, projection (1015) of inner tube (1014) is translated longitudinally proximally toward distal edge (1013) of outer sheath (1012) thereby pinching tube (1016) between projection (1015) and distal edge (1013) to thereby prevent the flow of liquid coolant within tube (1016). In the present example, the liquid coolant in tube (1016) is pressurized. Thus, when clamp arm (1004) is opened, the pressurized liquid coolant is allowed to flow through tube (1016) to cool ultrasonic blade (1002). When clamp arm (1004) is closed, the liquid coolant is prevented from flowing through tube (1016).

O. Exemplary Shaft Assembly with Seal Ring

Figure 56A:
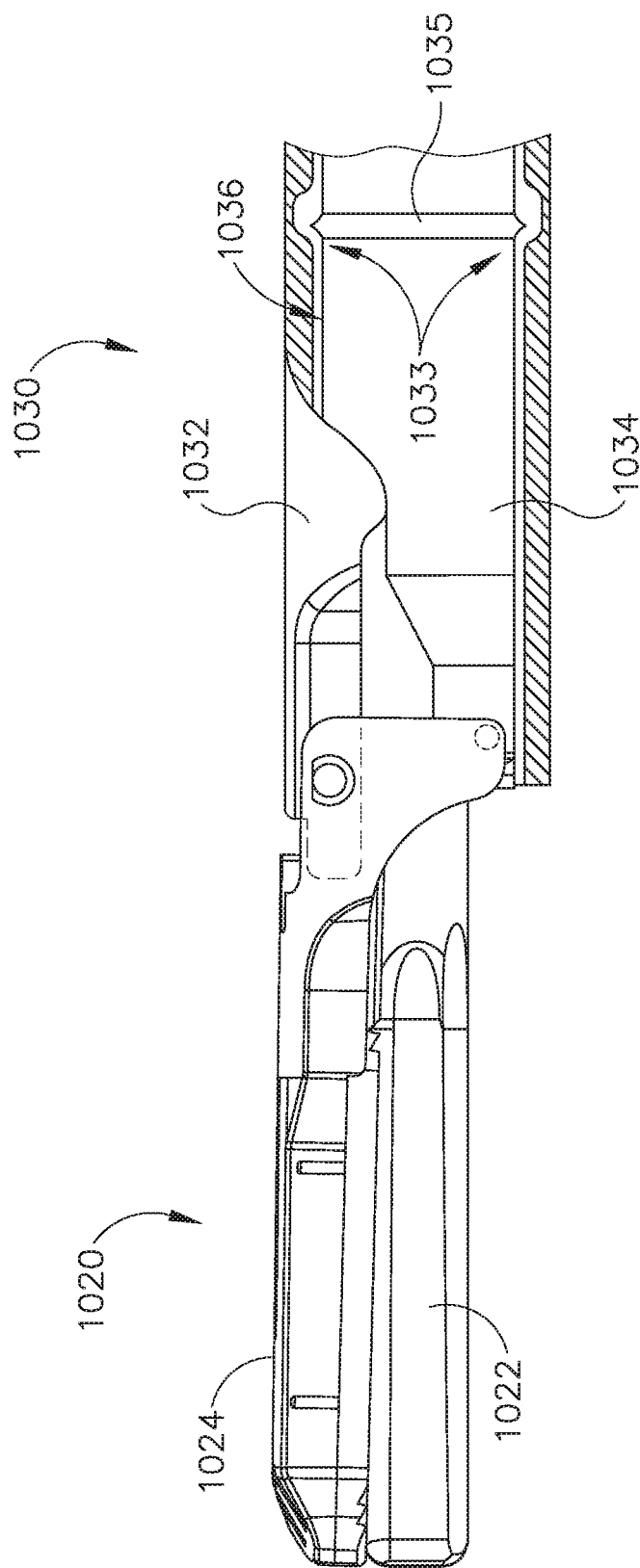
FIG. 56A depicts a partial cross-sectional side view of yet another exemplary fluid delivery system operable for use with any of the instruments described herein, with an inner tube of a shaft assembly in a first longitudinal position.
Figure 56B:
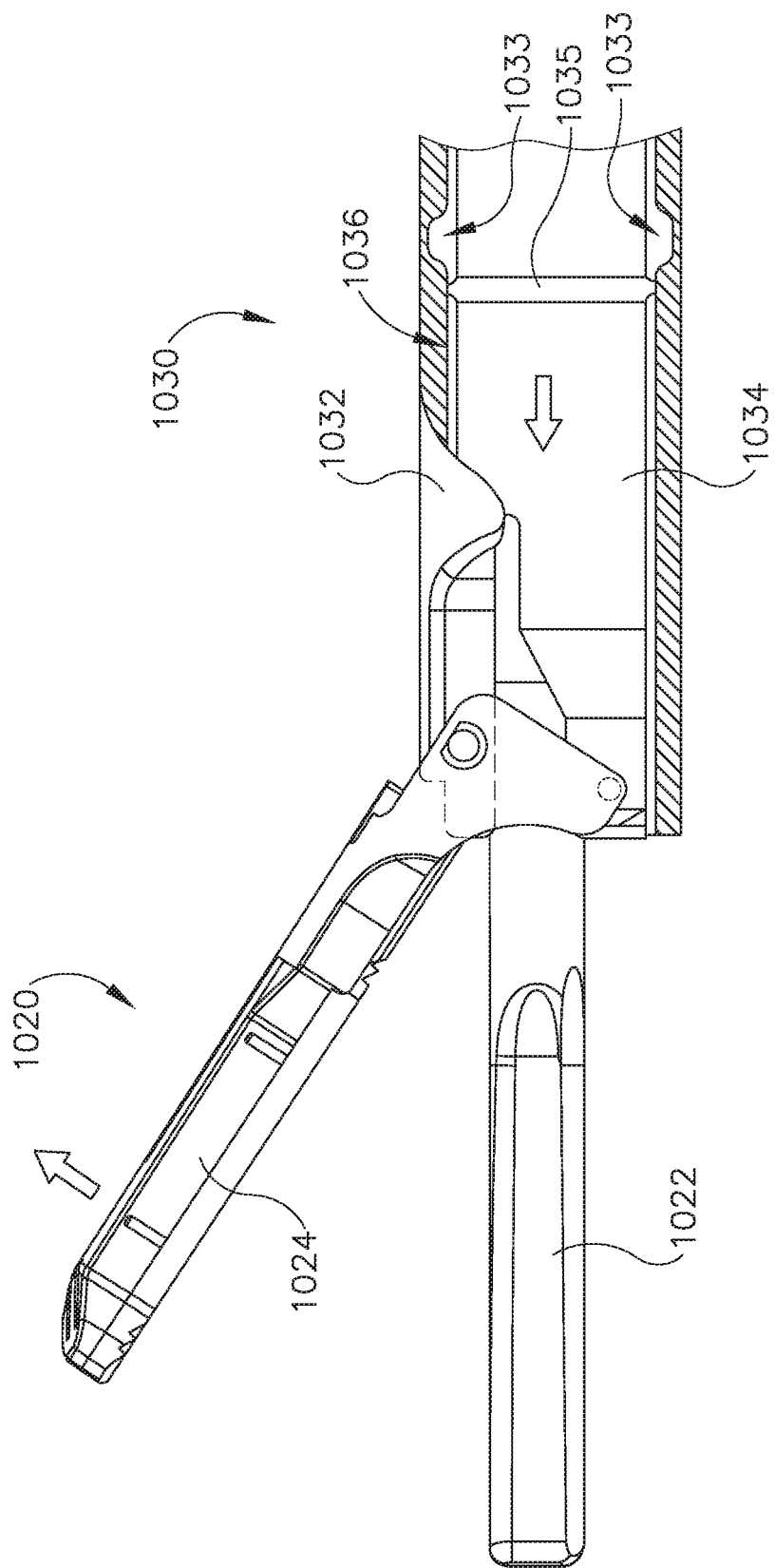
FIG. 56B depicts a partial cross-sectional side view of the fluid delivery system of FIG. 56A, with the inner tube of FIG. 56A moved to a second longitudinal position thereby shutting of fluid flow between an outer tube and an inner tube.

FIGS. 56A and 56B illustrate an exemplary end effector (1020) and shaft assembly (1030) that are configured to provide liquid coolant to an ultrasonic blade (1022). End effector (1020) is configured to operate substantially similar to end effectors (140, 240) discussed above except for the differences discussed below. It should therefore be understood that end effector (1020) may be readily substituted for end effectors (14, 240). End effector (1020) of this example includes an ultrasonic blade (1022) and a pivoting clamp arm (1024) that is selectively pivotable toward and away from blade (1022) to selectively clamp tissue between clamp arm (1024) and blade (1022). Clamp arm (1024) is pivotably coupled to an outer sheath (1032) of shaft assembly (1030). Clamp arm (1024) is further pivotably coupled to an inner tube (1034) of shaft assembly (1030) such that as inner tube (1034) translates longitudinally within outer sheath (1032) relative to outer sheath (1032), clamp arm (1024) is selectively pivoted toward and away from blade (1022). In particular, clamp arm (1024) is coupled with outer sheath (1032) and inner tube (1034) such that clamp arm (1024) is pivotable toward blade (1022) in response to proximal longitudinal translation of inner tube (1034) relative to outer sheath (1032); and such that clamp arm (1024) is pivotable away from ultrasonic blade (1022) in response to distal longitudinal translation of inner tube (1034) relative to outer sheath (1032). Various suitable ways in which clamp arm (1024) may be coupled with outer sheath (1032) and inner tube (1034) will be apparent to those of ordinary skill in the art in view of the teachings herein. In some versions, one or more resilient members are used to bias clamp arm (1024) to the open position shown in FIG. 56B.

An interior space (1036) is defined between an exterior surface of inner tube (1034) and an interior surface of outer sheath (1032). Interior space (1036) is in fluid communication with a fluid reservoir (not shown) and is operable to provide liquid coolant from the fluid reservoir to ultrasonic blade (1022). By way of example only, the fluid reservoir may be configured and operable similar to fluid reservoir (270) described above. Alternatively, the fluid reservoir may take any other suitable form. It should be appreciated that flow within interior space (1036) may be provided by any manner described herein or in any manner apparent to one of ordinary skill in the art. A distal end of outer sheath (1032) is positioned adjacent to blade (1022) such that as liquid coolant is released from interior space (1036), the liquid coolant is directed toward ultrasonic blade (1022).

Outer sheath (1032) comprises an annular recess (1033) formed in an interior surface of outer sheath (1032). Inner tube (1034) comprises a fluid seal (1035) disposed about an exterior surface of inner tube (1034). Inner tube (1034) is oriented such that fluid seal (1035) may be positioned within annular recess (1033) of outer sheath (1032). As shown in FIG. 56A, with clamp arm (1024) in a closed position, fluid seal (1035) is positioned within annular recess (1033) and sufficient clearance is provided between fluid seal (1035) and an interior surface of annular recess (1033) such that liquid coolant is able to flow through interior space (1036). As shown in FIG. 56B, as inner tube (1034) is translated longitudinally distally, clamp arm (1024) is pivoted away from blade (1022). Additionally, as inner tube (1034) is translated longitudinally distally, fluid seal (1035) of inner tube (1034) is translated longitudinally distally until fluid seal (1035) is no longer positioned within annular recess (1033). In this state, fluid seal (1035) engages an interior surface of outer sheath (1032) to thereby provide a fluid seal between inner tube (1034) and outer sheath (1032) and to thereby prevent the flow of liquid coolant within interior space (1036). In the present example, the liquid coolant in interior space (1036) is pressurized. Thus, when clamp arm (1024) is closed, the pressurized liquid coolant is allowed to flow through interior space (1036) to cool ultrasonic blade (1022). When clamp arm (1024) is opened, the liquid coolant is prevented from flowing through interior space (1036).

P. Exemplary Clamp Arm with Fluid Sponge

Figure 57A:
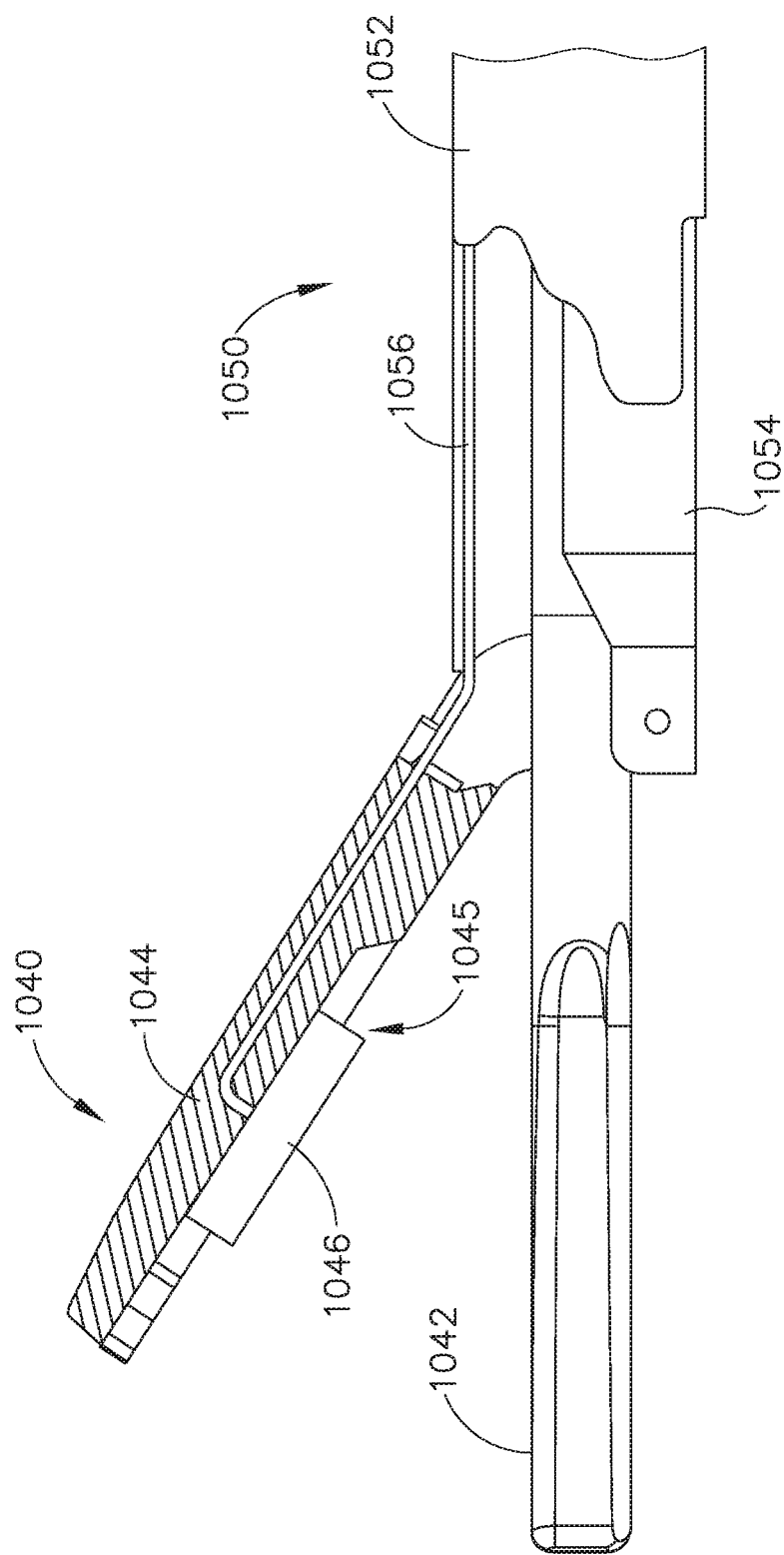
FIG. 57A depicts a partial cross-sectional side view of yet another exemplary fluid delivery system operable for use with any of the instruments described herein, with a clamp arm of an end effector in an open position.
Figure 57B:
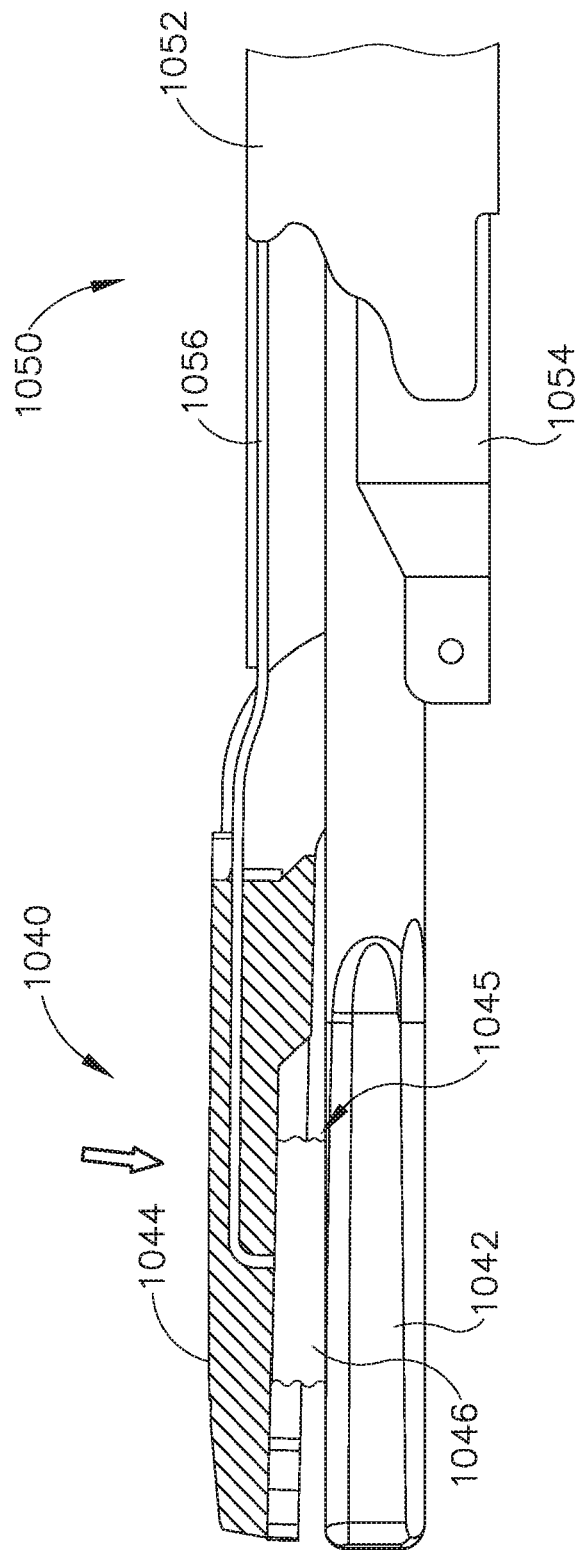
FIG. 57B depicts a partial cross-sectional side view of the fluid delivery system of FIG. 57A, with the clamp arm of FIG. 57A moved to a closed position thereby compressing a sponge/bladder of the fluid delivery system.

FIGS. 57A and 57B illustrate an exemplary end effector (1040) and shaft assembly (1050) that are configured to provide liquid coolant to an ultrasonic blade (1042). End effector (1040) is configured to operate substantially similar to end effectors (140, 240, 340) discussed above except for the differences discussed below. It should therefore be understood that end effector (1040) may be readily substituted for end effectors (14, 240). End effector (1040) of this example includes an ultrasonic blade (1042) and a pivoting clamp arm (1044) that is selectively pivotable toward and away from blade (1042) to selectively clamp tissue between clamp arm (1044) and blade (1042). Clamp arm (1044) is pivotably coupled to an outer sheath (1052) of shaft assembly (1050). Clamp arm (1044) is further pivotably coupled to an inner tube (1054) of shaft assembly (1050) such that as inner tube (1054) translates longitudinally within outer sheath (1052) relative to outer sheath (1052), clamp arm (1044) is selectively pivoted toward and away from blade (1042). In particular, clamp arm (1044) is coupled with outer sheath (1052) and inner tube (1054) such that clamp arm (1044) is pivotable toward blade (1042) in response to proximal longitudinal translation of inner tube (1054) relative to outer sheath (1052); and such that clamp arm (1044) is pivotable away from ultrasonic blade (1042) in response to distal longitudinal translation of inner tube (1054) relative to outer sheath (1052). Various suitable ways in which clamp arm (1044) may be coupled with outer sheath (1052) and inner tube (1054) will be apparent to those of ordinary skill in the art in view of the teachings herein. In some versions, one or more resilient members are used to bias clamp arm (1044) to the open position shown in FIG. 57A.

Clamp arm (1044) of the present example defines a rectangular recess (1045) formed in a bottom surface of clamp arm (1044). Clamp arm (1044) further comprises a porous sponge (1046) disposed within rectangular recess (1045). Sponge (1046) is configured to absorb and selectively retain a liquid coolant. Shaft assembly (1050) comprises a tube (1056) that is disposed within shaft assembly (1050) adjacent to outer sheath (1052). Tube (1056) is fluidly coupled to a fluid reservoir (not shown) and is operable to provide liquid coolant from the fluid reservoir to ultrasonic blade (1042). By way of example only, the fluid reservoir may be configured and operable similar to fluid reservoir (270) described above. Alternatively, the fluid reservoir may take any other suitable form. It should be appreciated that flow within tube (1056) may be provided by any manner described herein or in any manner apparent to one of ordinary skill in the art. Tube (1056) extends distally from shaft assembly (1050) and passes through clamp arm (1044) such that a distal end of tube (1056) is fluidly coupled within sponge (1046). Tube (1056) is in fluid communication with sponge (1046) such that liquid coolant within tube (1056) is passed from tube (1056) to sponge (1046). By way of example only, sponge (1046) may draw liquid coolant from tube (1056) through a capillary action or wicking action. In addition or in the alternative, the liquid coolant may be pressurized such that the fluid pressure drives the liquid coolant through tube (1056) to sponge (1046).

As shown in FIG. 57A, with clamp arm (1044) in an open position, liquid coolant is provided to sponge (1046) via tube (1056) such that sponge (1046) is substantially filled with liquid coolant. In some versions, sponge (1046) is fully saturated with liquid coolant. As shown in FIG. 57B, as inner tube (1054) is translated longitudinally proximally, clamp arm (1044) is pivoted toward blade (1042). As clamp arm (1044) is pivoted toward blade (1042), sponge (1046) is compressed against blade (1042) thereby releasing the liquid coolant from within sponge (1046) onto blade (1042) to thereby cool blade (1042). As clamp arm (1044) is pivoted away from blade (1042), sponge (1046) returns to its original shape and absorbs liquid coolant from tube (1056) until sponge (1046) is substantially filled or saturated with liquid coolant once again. It should be understood that as sponge (1046) returns to its original shape and absorbs liquid coolant, sponge (1046) may provide a suction force at the distal end of tube (1056) to thereby draw liquid coolant through tube (1056).

Q. Exemplary Clamp Arm with Fluid Sponge and Segmented Clamp Pad

Figure 58A:
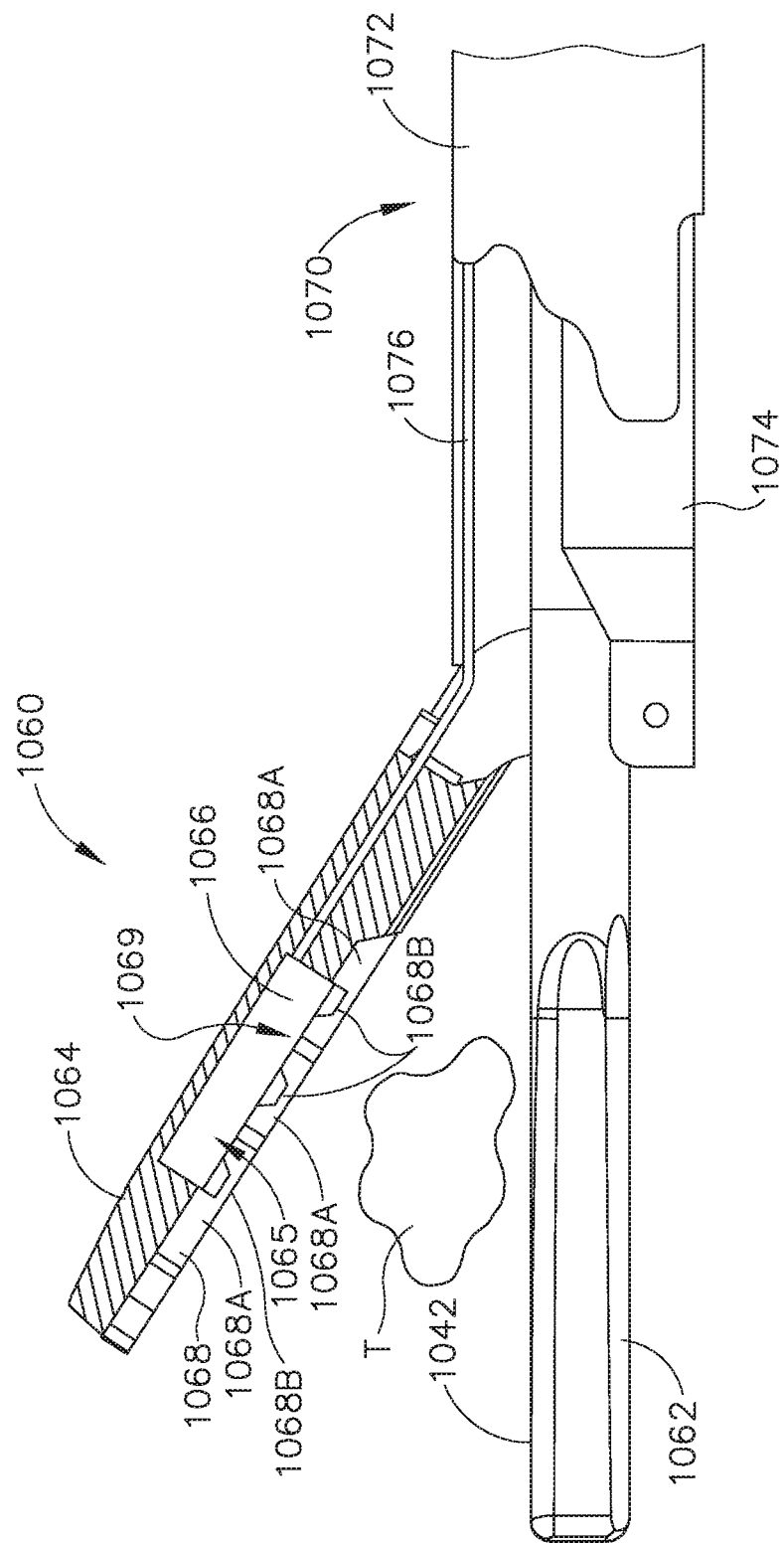
FIG. 58A depicts a partial cross-sectional side view of yet another exemplary fluid delivery system operable for use with any of the instruments described herein, with a clamp arm of an end effector in an open position.
Figure 58B:
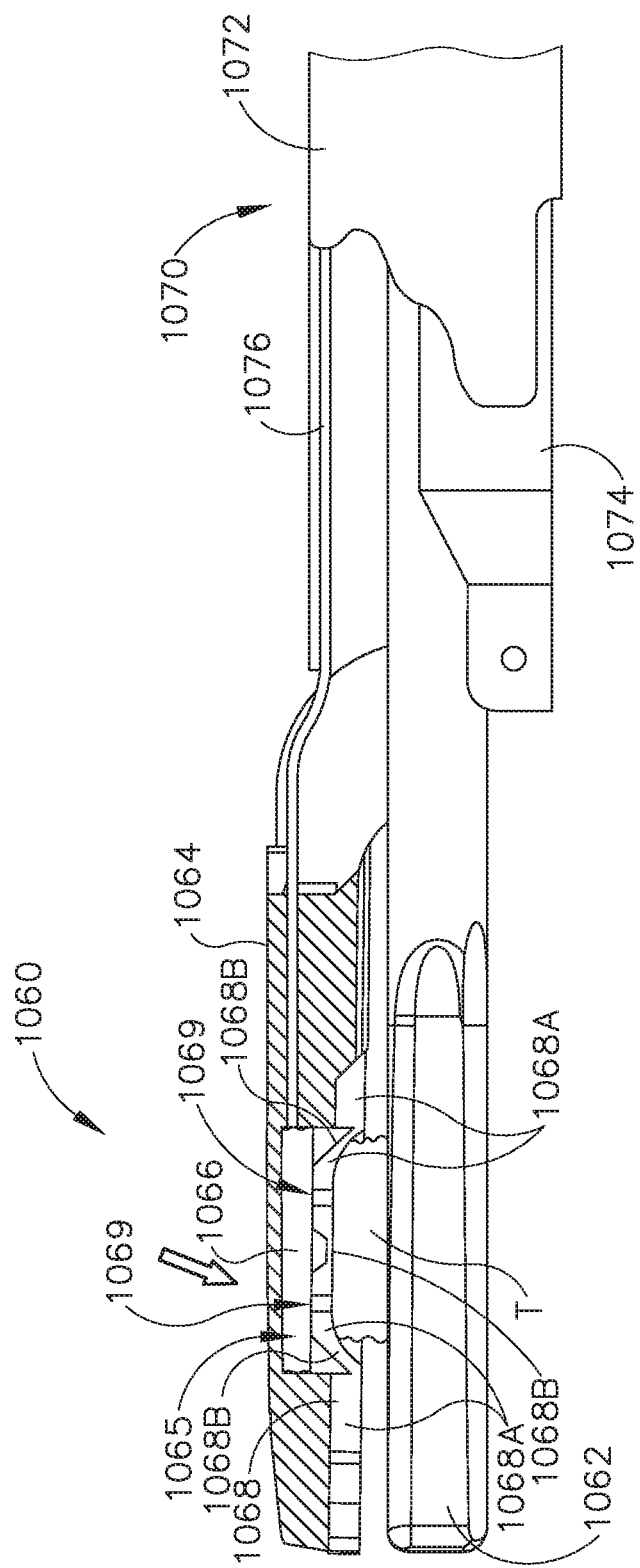
FIG. 58B depicts a partial cross-sectional side view of the fluid delivery system of FIG. 58A, with the clamp arm of FIG. 58A moved to a closed position thereby compressing a fluid source of the fluid delivery system.

FIGS. 58A and 58B illustrate an exemplary end effector (1060) and shaft assembly (1070) that are configured to provide liquid coolant to an ultrasonic blade (1062). End effector (1060) is configured to operate substantially similar to end effectors (140, 240) discussed above except for the differences discussed below. It should therefore be understood that end effector (1060) may be readily substituted for end effectors (14, 240). End effector (1060) of this example includes an ultrasonic blade (1062) and a pivoting clamp arm (1064) that is selectively pivotable toward and away from blade (1062) to selectively clamp tissue between clamp arm (1064) and blade (1062). Clamp arm (1064) is pivotably coupled to an outer sheath (1072) of shaft assembly (1070). Clamp arm (1064) is further pivotably coupled to an inner tube (1074) of shaft assembly (1070) such that as inner tube (1074) translates longitudinally within outer sheath (1072) relative to outer sheath (1072), clamp arm (1064) is selectively pivoted toward and away from blade (1062). In particular, clamp arm (1064) is coupled with outer sheath (1072) and inner tube (1074) such that clamp arm (1064) is pivotable toward blade (1062) in response to proximal longitudinal translation of inner tube (1074) relative to outer sheath (1072); and such that clamp arm (1064) is pivotable away from ultrasonic blade (1062) in response to distal longitudinal translation of inner tube (1074) relative to outer sheath (1072). Various suitable ways in which clamp arm (1064) may be coupled with outer sheath (1072) and inner tube (1074) will be apparent to those of ordinary skill in the art in view of the teachings herein. In some versions, one or more resilient members are used to bias clamp arm (1064) to the open position shown in FIG. 58A.

Clamp arm (1064) of the present example defines a rectangular recess (1065) formed in a bottom surface of clamp arm (1064). Clamp arm (1064) further comprises a segmented clamp pad (1068) which covers recess (1065). Segmented clamp pad (1068) comprises a plurality of segments (1068A) coupled together by a plurality of living hinges (1068B). Thus, it should be understood that segmented clamp pad (1068) is configured to flex inwardly and outwardly relative to recess (1065) as will be discussed in more detail below. Also as will be discussed in more detail below, segmented clamp pad (1068) comprises openings (1069) that are configured to permit liquid coolant to flow from within recess (1065) through segmented clamp pad (1068). Clamp arm (1064) further comprises a porous sponge (1066) disposed within rectangular recess (1065). Sponge (1066) is configured to absorb and selectively retain a liquid coolant.

Shaft assembly (1070) further comprises a tube (1076) that is disposed within shaft assembly (1070) adjacent to outer sheath (1072). Tube (1076) is fluidly coupled to a fluid reservoir (not shown) and is operable to provide liquid coolant from the fluid reservoir to ultrasonic blade (1062). By way of example only, the fluid reservoir may be configured and operable similar to fluid reservoir (270) described above. Alternatively, the fluid reservoir may take any other suitable form. Tube (1076) extends distally from shaft assembly (1070) and passes through clamp arm (1064) such that a distal end of tube (1076) is fluidly coupled within sponge (1066). Tube (1076) is in fluid communication with sponge (1066) such that liquid coolant within tube (1076) is passed from tube (1076) to sponge (1066). By way of example only, sponge (1066) may draw liquid coolant from tube (1076) through a capillary action or wicking action. In addition or in the alternative, the liquid coolant may be pressurized such that the fluid pressure drives the liquid coolant through tube (1076) to sponge (1066).

As shown in FIG. 58A, with clamp arm (1064) in an open position, segmented clamp pad (1068) is substantially straight and liquid coolant is provided to sponge (1066) via tube (1076) such that sponge (1066) is substantially filled with liquid coolant. In some versions, sponge (1066) is fully saturated with liquid coolant. As shown in FIG. 58B, as inner tube (1074) is translated longitudinally proximally, clamp arm (1064) is pivoted toward blade (1062) thereby positioning openings (1069) of segmented clamp pad (1068) adjacent to blade (1062). As clamp arm (1064) is pivoted toward blade (1062), segmented clamp pad (1068) flexes inwardly relative to recess (1065) due to contact between segmented clamp pad (1068) and tissue (T). As segmented clamp pad (1068) flexes inwardly relative to recess (1065), sponge (1066) is compressed thereby expelling the liquid coolant from within sponge (1066) through openings (1069) of segmented clamp pad (1068) onto blade (1062) to thereby cool blade (1062). As clamp arm (1064) is pivoted away from blade (1062), segmented clamp pad (1068) returns to its substantially straight orientation as shown in FIG. 58A. Sponge (1066) thus returns to its original shape and absorbs liquid coolant from tube (1076) until sponge (1066) is substantially filled or saturated with liquid coolant once again. It should be understood that as sponge (1066) returns to its original shape and absorbs liquid coolant, sponge (1066) may provide a suction force at the distal end of tube (1076) to thereby draw liquid coolant through tube (1076).

R. Exemplary Clamp Arm with Fluid Sponge and Roller

Figure 60A:
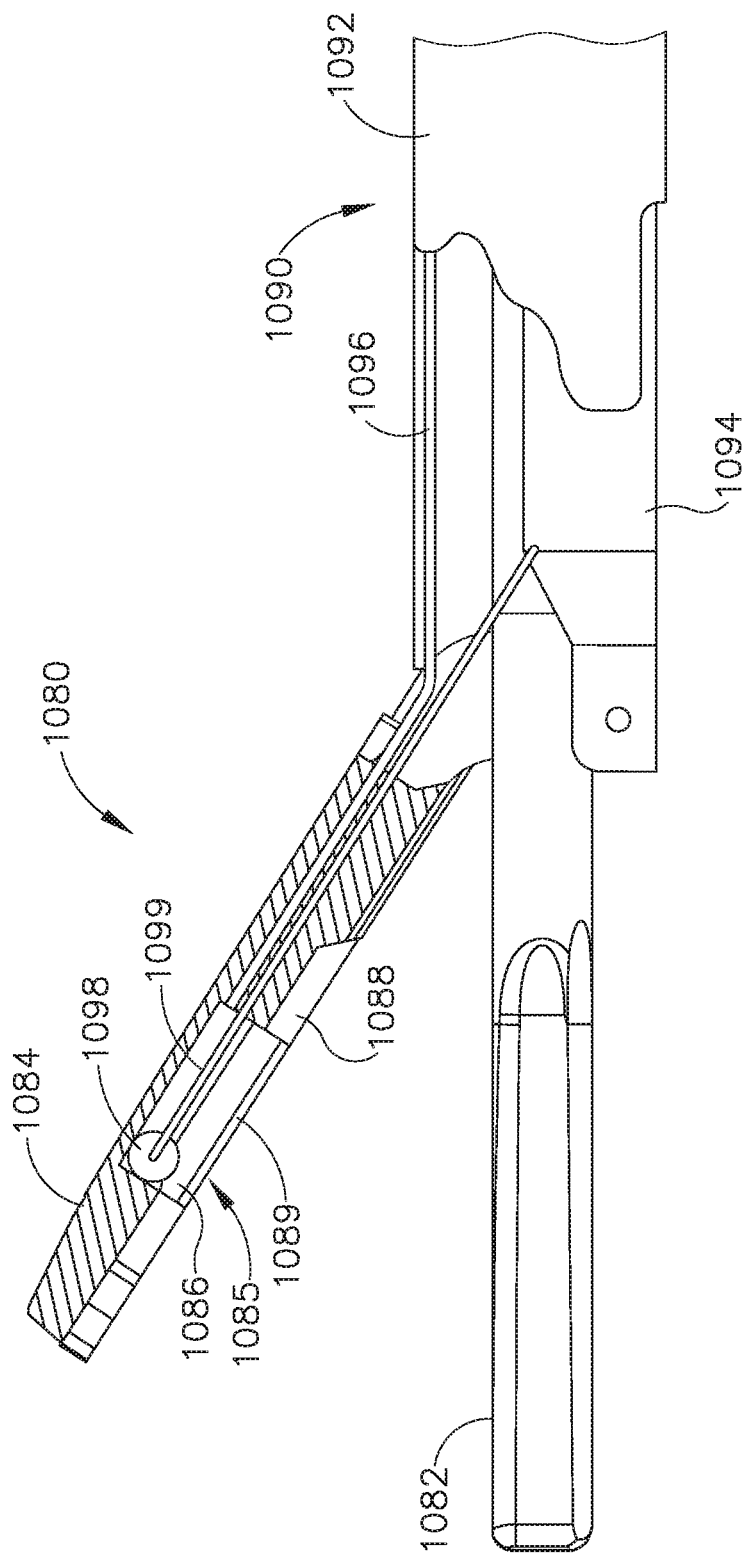
FIG. 60A depicts a partial cross-sectional side view of yet another exemplary fluid delivery system operable for use with any of the instruments described herein, with a clamp arm of an end effector in an open position, and with the roller of FIG. 59 in a first longitudinal position.
Figure 60B:
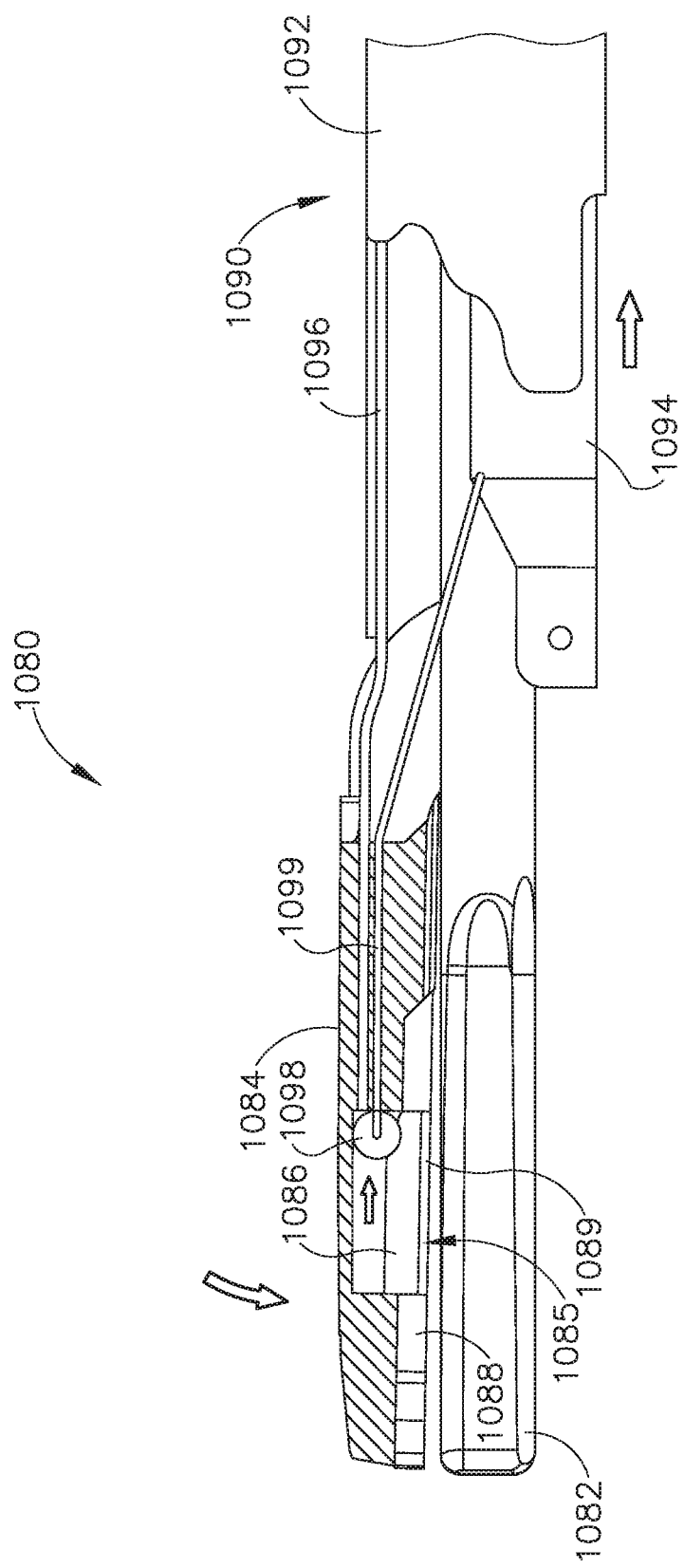
FIG. 60B depicts a partial cross-sectional side view of the fluid delivery system of FIG. 60A, with the roller of FIG. 59 moved to a second longitudinal position by movement of the clamp arm of FIG. 60A to a closed position thereby compressing a fluid source of the fluid delivery system.

FIGS. 59-60B illustrate an exemplary end effector (1080) and shaft assembly (1090) that are configured to provide liquid coolant to an ultrasonic blade (1082). End effector (1080) is configured to operate substantially similar to end effectors (140, 240) discussed above except for the differences discussed below. It should therefore be understood that end effector (1080) may be readily substituted for end effectors (14, 240). End effector (1080) of this example includes an ultrasonic blade (1082) and a pivoting clamp arm (1084) that is selectively pivotable toward and away from blade (1082) to selectively clamp tissue between clamp arm (1084) and blade (1082). Clamp arm (1084) is pivotably coupled to an outer sheath (1092) of shaft assembly (1090). Clamp arm (1084) is further pivotably coupled to an inner tube (1094) of shaft assembly (1090) such that as inner tube (1094) translates longitudinally within outer sheath (1092) relative to outer sheath (1092), clamp arm (1084) is selectively pivoted toward and away from blade (1082). In particular, clamp arm (1084) is coupled with outer sheath (1092) and inner tube (1094) such that clamp arm (1084) is pivotable toward blade (1082) in response to proximal longitudinal translation of inner tube (1094) relative to outer sheath (1092); and such that clamp arm (1084) is pivotable away from ultrasonic blade (1082) in response to distal longitudinal translation of inner tube (1094) relative to outer sheath (1092). Various suitable ways in which clamp arm (1084) may be coupled with outer sheath (1092) and inner tube (1094) will be apparent to those of ordinary skill in the art in view of the teachings herein. In some versions, one or more resilient members are used to bias clamp arm (1084) to the open position shown in FIG. 60A.

As shown in FIGS. 60A and 60B, clamp arm (1084) defines a rectangular recess (1085) formed in a bottom surface of clamp arm (1084). Clamp arm (1084) further comprises clamp pad (1088) having a porous portion (1089) that covers recess (1085). Porous portion (1089) of clamp pad (1088) is configured to permit liquid coolant to flow from within recess (1085) through clamp pad (1088). Clamp arm (1084) further comprises a porous sponge (1086) disposed within rectangular recess (1085). Sponge (1086) is configured to absorb and selectively retain a liquid coolant.

Shaft assembly (1090) comprises a tube (1096) disposed within shaft assembly (1090) adjacent to outer sheath (1092). Tube (1096) is fluidly coupled to a fluid reservoir (not shown) and is operable to provide liquid coolant from the fluid reservoir to ultrasonic blade (1082). By way of example only, the fluid reservoir may be configured and operable similar to fluid reservoir (270) described above. Alternatively, the fluid reservoir may take any other suitable form. Tube (1096) extends distally from shaft assembly (1090) and passes through clamp arm (1084) such that a distal end of tube (1096) is fluidly coupled within sponge (1086). Tube (1096) is in fluid communication with sponge (1086) such that liquid coolant within tube (1096) is passed from tube (1096) to sponge (1086). It should be appreciated that flow within tube (1096) may be provided by any manner described herein or in any manner apparent to one of ordinary skill in the art. By way of example only, sponge (1086) may draw liquid coolant from tube (1096) through a capillary action or wicking action. In addition or in the alternative, the liquid coolant may be pressurized such that the fluid pressure drives the liquid coolant through tube (1096) to sponge (1086).

End effector (1080) further comprises a compression roller (1098) disposed within rectangular recess (1085). As best seen in FIG. 59, roller (1098) comprises an axle (1097) and a pair of rods (1099) extending proximally from both ends of axle (1097). A shown in FIGS. 60A and 60B, roller (1098) is disposed within rectangular recess (1085) atop sponge (1086). Rods (1099) of roller (1098) extend proximally through clamp arm (1084) and are coupled with a distal portion of inner tube (1094) such that longitudinal translation of inner tube (1094) causes concurrent longitudinal translation of roller (1098) within recess (1085) between a distal position (FIG. 60A) and a proximal position (FIG. 60B).

As shown in FIG. 60A, with clamp arm (1084) in an open position, roller (1098) is in the distal position within recess (1085) atop sponge (1086) and liquid coolant is provide to sponge (1086) via tube (1096) such that sponge (1086) is substantially filled or saturated with liquid coolant. As shown in FIG. 60B, as inner tube (1094) is translated longitudinally proximally, clamp arm (1084) is pivoted toward blade (1082) thereby positioning porous portion (1089) of clamp pad (1088) adjacent to blade (1082). Additionally, as inner tube (1094) is translated longitudinally distally, roller (1078) is drawn proximally into the distal position within recess (1085) atop sponge (1086). As roller (1098) is drawn from the distal position (FIG. 60A) to the proximal position (FIG. 60B) roller bears against sponge (1086) such that sponge (1086) is compressed, thereby releasing the liquid coolant from within sponge (1086) through porous portion (1089) of clamp pad (1088) onto blade (1082) to thereby cool blade (1082). As clamp arm (1084) is pivoted away from blade (1082), roller (1098) is driven from the proximal position (FIG. 60B) to the distal position (FIG. 60A) and sponge (1086) returns to its original shape and absorbs liquid coolant from tube (1096) until sponge (1086) is substantially filled with liquid coolant once again. It should be understood that as sponge (1086) returns to its original shape and absorbs liquid coolant, sponge (1086) may provide a suction force at the distal end of tube (1096) to thereby draw liquid coolant through tube (1096).

S. Exemplary Porous Clamp Pad

Figure 61:
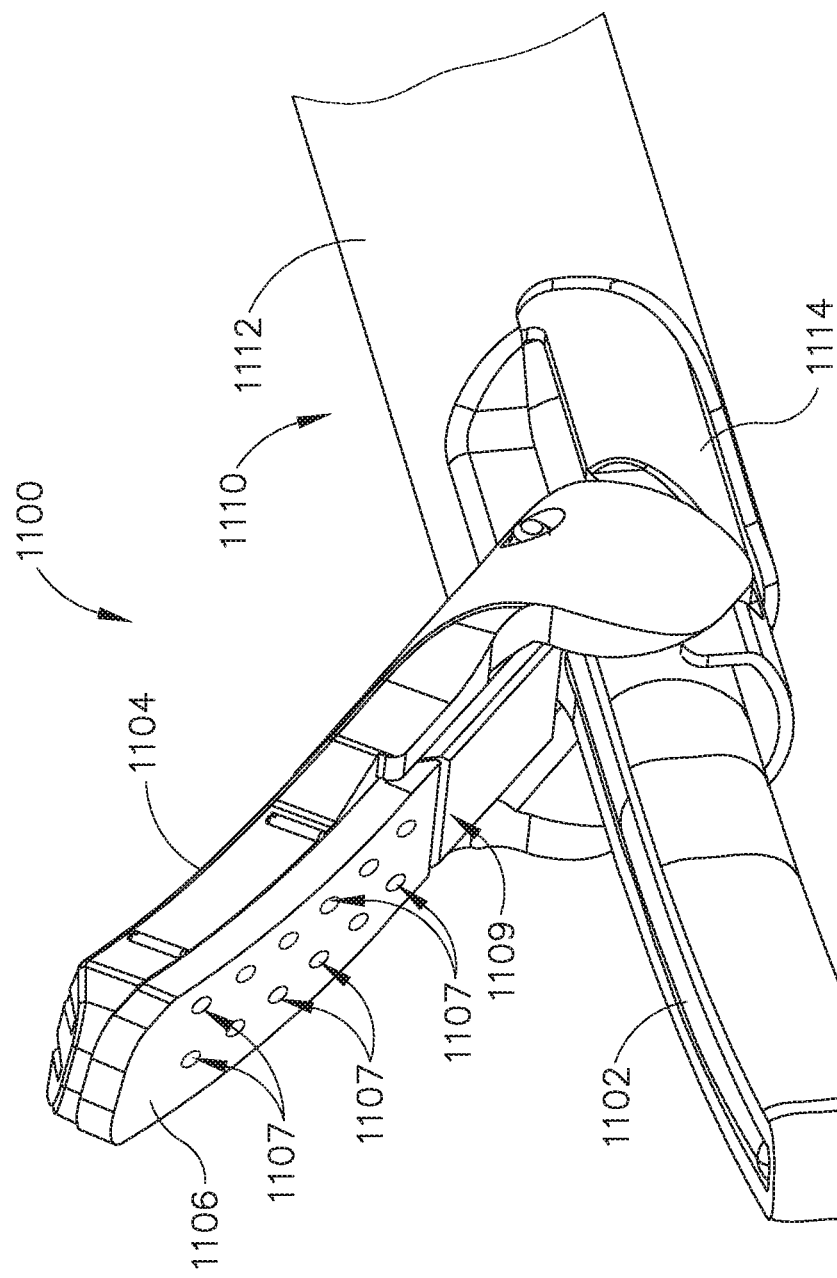
FIG. 61 depicts a perspective view of yet another exemplary fluid delivery system.
Figure 62:
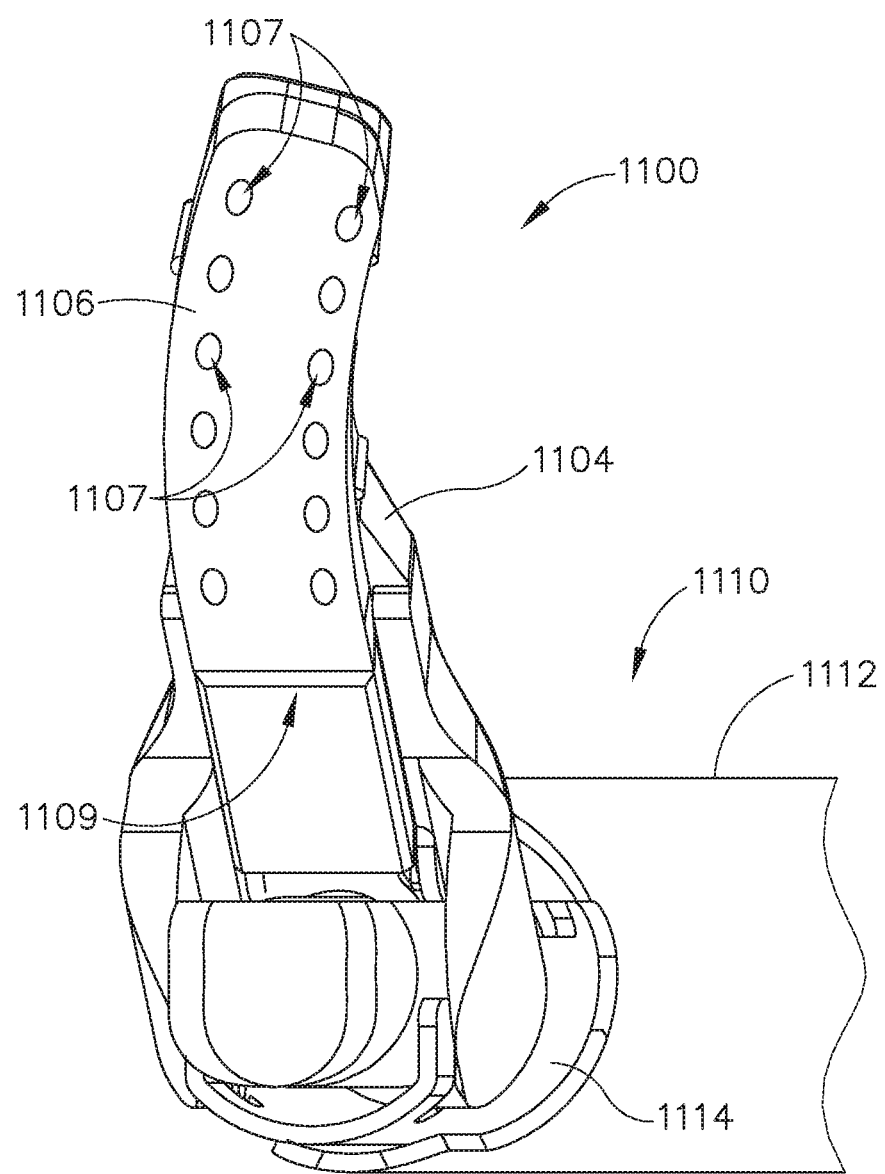
FIG. 62 depicts another perspective view of the fluid delivery system of FIG. 61.
Figure 63:
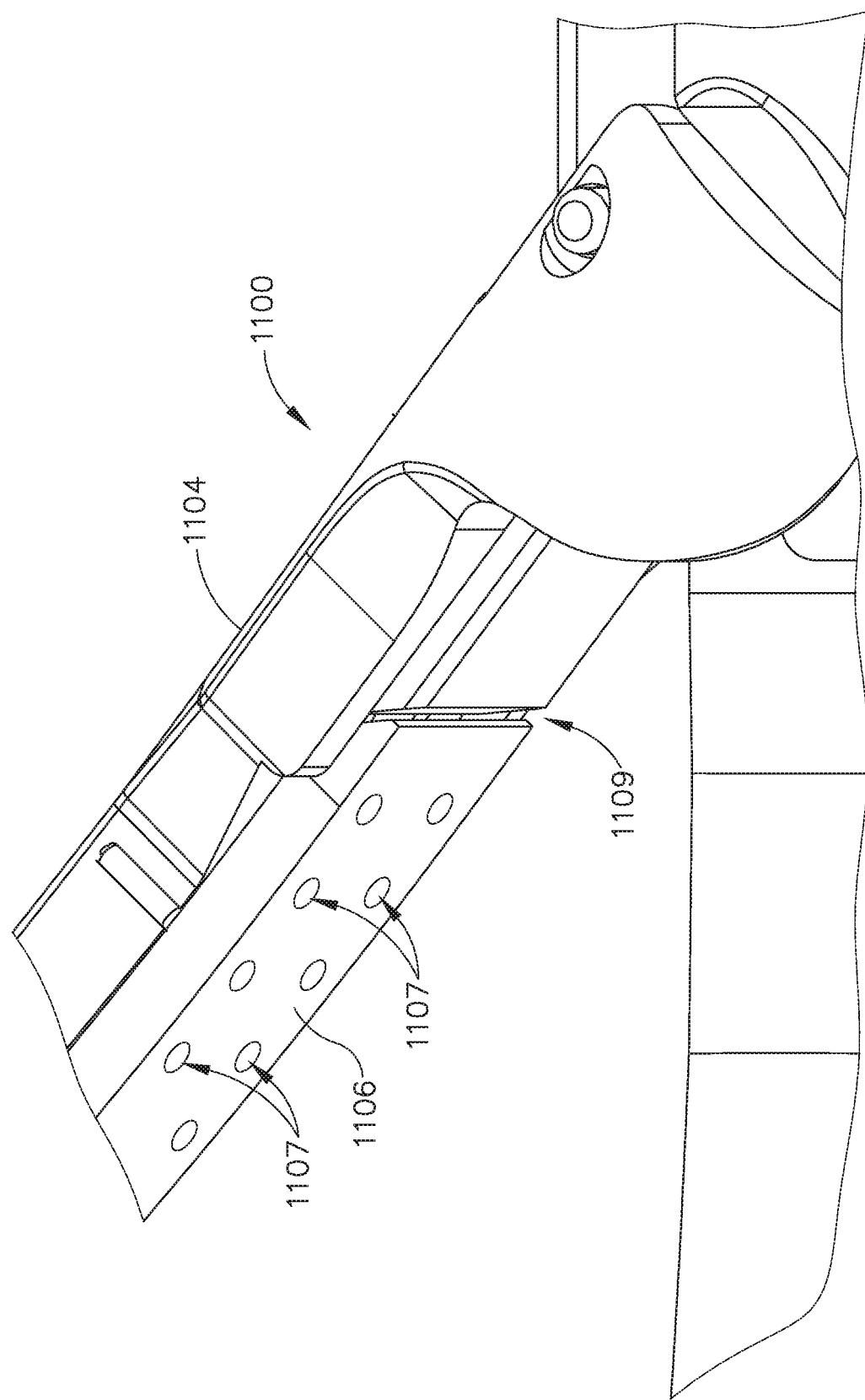
FIG. 63 depicts a detailed perspective view of the fluid delivery system of FIG. 61.

FIGS. 61-63 illustrate an exemplary end effector (1100) and shaft assembly (1110) that are configured to provide liquid coolant to an ultrasonic blade (1102). End effector (1100) is configured to operate substantially similar to end effectors (140, 240) discussed above except for the differences discussed below. It should therefore be understood that end effector (1100) may be readily substituted for end effectors (14, 240). End effector (1100) of this example includes an ultrasonic blade (1102) and a pivoting clamp arm (1104) that is selectively pivotable toward and away from blade (1102) to selectively clamp tissue between clamp arm (1104) and blade (1102). Clamp arm (1104) is pivotably coupled to an outer sheath (1112) of shaft assembly (1110). Clamp arm (1104) is further pivotably coupled to an inner tube (1114) of shaft assembly (1110) such that as inner tube (1114) translates longitudinally within outer sheath (1112) relative to outer sheath (1112), clamp arm (1104) is selectively pivoted toward and away from blade (1102). In particular, clamp arm (1104) is coupled with outer sheath (1112) and inner tube (1114) such that clamp arm (1104) is pivotable toward blade (1102) in response to proximal longitudinal translation of inner tube (1114) relative to outer sheath (1112); and such that clamp arm (1104) is pivotable away from ultrasonic blade (1102) in response to distal longitudinal translation of inner tube (1114) relative to outer sheath (1112). Various suitable ways in which clamp arm (1104) may be coupled with outer sheath (1112) and inner tube (1114) will be apparent to those of ordinary skill in the art in view of the teachings herein. In some versions, one or more resilient members are used to bias clamp arm (1104) to the open position shown in FIGS. 61-63.

Clamp arm (1104) of the present example comprises a clamp pad (1106). Clamp pad (1106) comprises a plurality of openings (1107) that extend through clamp pad (1106) and provide fluid access to a chamber defined between clamp pad (1106) and clamp arm (1104). Openings (1107) are configured to permit fluid that is evaporated during use of end effector (1100) (e.g., fluid evaporated from tissue) to travel through openings (1107) into the chamber defined between clamp pad (1106) and clamp arm (1104). This evaporated fluid condenses within this chamber. When clamp arm (1104) is moved to the open position shown in FIGS. 61-63, the condensed fluid would travel proximally within clamp arm (1104) and through a slot (1109) formed in a proximal portion of clamp arm (1104). As this condensed fluid passes through slot (1109), the fluid is dropped onto blade (1102) thereby cooling blade (1102). In addition to or in lieu of traveling through slot (1109), the condensate may pass through openings (1107) to reach blade (1102). Additionally, the evaporated fluid within the chamber that condenses may reapply itself through openings (1107) back on to blade (1102) for cooling as the tissue is cut through and blade (1102) touches clamp pad (1106) at the end of the transection of tissue, due to the vibrational movement of blade (1102).

IV. Miscellaneous

In some exemplary versions, the same vibrational movement that is used to drive an ultrasonic blade (24, 160) during tissue cutting/sealing may drive liquid distally along blade (24, 160). As yet another merely illustrative example, fluid may be communicated to and/or along blade (24, 160) in accordance with at least some of the teachings of U.S. Pub. No. 2011/0152759, entitled "Use of Biomarkers and Therapeutic Agents with Surgical Devices," published Jun. 23, 2011, now U.S. Pat. No. 8,591,459, issued Nov. 26, 2013, the disclosure of which is incorporated by reference herein. It should be understood that the teachings in U.S. Pub. No. 2011/0152759, now U.S. Pat. No. 8,591,459, issued Nov. 26, 2013, relating to dispensation of medical fluids may be readily adapted to provide communication of cooling fluid. It should also be understood that the teachings herein may be readily combined with the teachings of U.S. Pub. No. 2016/0143657, published May 26, 2016, issued as U.S. Pat. No. 10,206,705 on Feb. 19, 2019, entitled "Features for Communication of Fluid through Shaft Assembly of Ultrasonic Surgical Instrument," the disclosure of which is incorporated by reference herein; U.S. Pub. No. 2016/0143659, published May 23, 2016, issued as U.S. Pat. No. 10,433,863 on Oct. 8, 2019, entitled "Ultrasonic Surgical Instrument with Blade Cooling through Retraction," the disclosure of which is incorporated by reference herein; and U.S. Pub. No. 2015/0148832, published May 28, 2015, issued as U.S. Pat. No. 10,034,685 on Jul. 31, 2018, entitled "Features to Apply Fluid to an Ultrasonic Blade of a Surgical Instrument," the disclosure of which is incorporated by reference herein.

In addition to or as an alternative to using fluid to reduce heat in a version of instrument (10, 100), one or more shielding features may be used to avoid direct contact between a hot portion of instrument (10, 100) and tissue (or other structures). A gap may be defined between the shielding feature and the corresponding hot portion of instrument (10, 100), to avoid or minimize communication of heat from the hot portion of instrument (10, 100) and the shielding feature. Such a gap may be filled with liquid, air or some other gas, a solid insulating material, and/or any other suitable kind of filler, including combinations thereof. It should also be understood that various kinds of structural features may be interposed between the hot portion of instrument (10, 100) and the shielding feature, including but not limited to a roughened surface, grooves, dimples, pimples, nubs, knurling, a honeycomb structure, etc. Such structural features may minimize transfer of heat from the hot portion of instrument (10, 100) and the shielding feature. Similarly, a shielding feature (and/or a hot feature of instrument (10, 100)) may include external surface structures such as a roughened surface, grooves, dimples, pimples, nubs, knurling, a honeycomb structure, etc., to minimize transfer of heat from the shielding feature (or hot feature) to adjacent tissue, etc. Various merely illustrative examples of shielding features are described in U.S. Provisional Patent App. No. 61/908,920, the disclosure of which is incorporated by reference herein; and also in U.S. Pub. No. 2015/0148833, published May 28, 2015, issued as U.S. Pat. No. 9,993,260 on Jun. 12, 2018, entitled "Shielding Features for Ultrasonic Blade of a Surgical Instrument," the disclosure of which is incorporated by reference herein; and also in U.S. Pub. No. 2015/0148835, published May 28, 2015, issued as U.S. Pat. No. 10,004,528 on Jun. 26, 2018, entitled "Sleeve Features for Ultrasonic Blade of a Surgical Instrument," the disclosure of which is incorporated by reference herein. It should be understood that the teachings herein may be readily combined with the teachings of those references and the various other references cited herein. Other suitable examples will be apparent to those of ordinary skill in the art in view of the teachings herein.

In some instances, the heating at an end effector (40, 140) may be caused or hastened by direct contact between clamp pad (46, 146) and blade (42, 142) while clamp arm (44, 144) is closed and blade (42, 142) is activated, etc. Such direct contact may occur at regions where tissue is not interposed between clamp pad (46, 146) and blade (42, 142). Some operators may position tissue just between the distal portion of clamp pad (46, 146) and the distal portion of blade (42, 142). This may occur when end effector (40, 140) is used to transect relatively small vessels. When this occurs, the distal portions of clamp pad (46, 146) and blade (42, 142) may both contact the tissue compressed between clamp pad (46, 146) and blade (42, 142); yet the proximal portions of clamp pad (46, 146) and blade (42, 142) may just directly contact each other. When blade (42, 142) is activated in such instances, clamp pad (46, 146) and blade (42, 142) may rapidly generate a significant amount of heat at the proximal portions where the direct contact occurs.

It may therefore be desirable to minimize the amount of direct contact between clamp pad (46, 146) and blade (42, 142), particularly at the proximal regions of clamp pad (46, 146) and blade (42, 142). In other words, it may be desirable to provide staged engagement between clamp pad (46, 146) and blade (42, 142), such that the distal regions of clamp pad (46, 146) and blade (42, 142) engage first; then the proximal regions of clamp pad (46, 146) and blade (42, 142). Various examples of how an end effector (40, 140) may provide such staged engagement are described in U.S. Provisional Patent App. No. 61/908,920, the disclosure of which is incorporated by reference herein; and also in U.S. Pub. No. 2015/0148834, published May 28, 2015, issued as U.S. Pat. No. 10,004,527 on Jun. 26, 2018, entitled "Ultrasonic Surgical Instrument with Staged Clamping," the disclosure of which is incorporated by reference herein. It should be understood that the teachings herein may be readily combined with the teachings of those references and the various other references cited herein. Other examples will be apparent to those of ordinary skill in the art in view of the teachings herein.

It should be understood that any of the versions of instruments described herein may include various other features in addition to or in lieu of those described above. By way of example only, any of the instruments described herein may also include one or more of the various features disclosed in any of the various references that are incorporated by reference herein. It should also be understood that the teachings herein may be readily applied to any of the instruments described in any of the other references cited herein, such that the teachings herein may be readily combined with the teachings of any of the references cited herein in numerous ways. Other types of instruments into which the teachings herein may be incorporated will be apparent to those of ordinary skill in the art.

It should also be understood that any ranges of values referred to herein should be read to include the upper and lower boundaries of such ranges. For instance, a range expressed as ranging "between approximately 1.0 inches and approximately 1.5 inches" should be read to include approximately 1.0 inches and approximately 1.5 inches, in addition to including the values between those upper and lower boundaries.

It should be appreciated that any patent, publication, or other disclosure material, in whole or in part, that is said to be incorporated by reference herein is incorporated herein only to the extent that the incorporated material does not conflict with existing definitions, statements, or other disclosure material set forth in this disclosure. As such, and to the extent necessary, the disclosure as explicitly set forth herein supersedes any conflicting material incorporated herein by reference. Any material, or portion thereof, that is said to be incorporated by reference herein, but which conflicts with existing definitions, statements, or other disclosure material set forth herein will only be incorporated to the extent that no conflict arises between that incorporated material and the existing disclosure material.

Versions of the devices described above may have application in conventional medical treatments and procedures conducted by a medical professional, as well as application in robotic-assisted medical treatments and procedures. By way of example only, various teachings herein may be readily incorporated into a robotic surgical system such as the DAVINCI™ system by Intuitive Surgical, Inc., of Sunnyvale, Calif. Similarly, those of ordinary skill in the art will recognize that various teachings herein may be readily combined with various teachings of U.S. Pat. No. 6,783,524, entitled "Robotic Surgical Tool with Ultrasound Cauterizing and Cutting Instrument," published Aug. 31, 2004, the disclosure of which is incorporated by reference herein.

Versions described above may be designed to be disposed of after a single use, or they can be designed to be used multiple times. Versions may, in either or both cases, be reconditioned for reuse after at least one use. Reconditioning may include any combination of the steps of disassembly of the device, followed by cleaning or replacement of particular pieces, and subsequent reassembly. In particular, some versions of the device may be disassembled, and any number of the particular pieces or parts of the device may be selectively replaced or removed in any combination. Upon cleaning and/or replacement of particular parts, some versions of the device may be reassembled for subsequent use either at a reconditioning facility, or by an operator immediately prior to a procedure. Those skilled in the art will appreciate that reconditioning of a device may utilize a variety of techniques for disassembly, cleaning/replacement, and reassembly. Use of such techniques, and the resulting reconditioned device, are all within the scope of the present application.

By way of example only, versions described herein may be sterilized before and/or after a procedure. In one sterilization technique, the device is placed in a closed and sealed container, such as a plastic or TYVEK bag. The container and device may then be placed in a field of radiation that can penetrate the container, such as gamma radiation, x-rays, or high-energy electrons. The radiation may kill bacteria on the device and in the container. The sterilized device may then be stored in the sterile container for later use. A device may also be sterilized using any other technique known in the art, including but not limited to beta or gamma radiation, ethylene oxide, or steam.

Having shown and described various embodiments of the present invention, further adaptations of the methods and systems described herein may be accomplished by appropriate modifications by one of ordinary skill in the art without departing from the scope of the present invention. Several of such potential modifications have been mentioned, and others will be apparent to those skilled in the art. For instance, the examples, embodiments, geometrics, materials, dimensions, ratios, steps, and the like discussed above are illustrative and are not required. Accordingly, the scope of the present invention should be considered in terms of the following claims and is understood not to be limited to the details of structure and operation shown and described in the specification and drawings.

We claim:

1. An apparatus for operating on tissue, the apparatus comprising:
   (a) a body;
   (b) a trigger movably coupled with the body;
   (c) a shaft assembly extending distally from the body, wherein the shaft assembly comprises an acoustic waveguide configured to couple with an ultrasonic transducer;
   (d) an end effector, wherein the end effector comprises:
      (i) an ultrasonic blade in acoustic communication with the acoustic waveguide, and
      (ii) a clamp arm, wherein the clamp arm is pivotable toward and away from the ultrasonic blade to clamp tissue therebetween; and
   (e) a blade cooling system operatively coupled with the trigger, wherein the blade cooling system is operable to deliver liquid coolant to the ultrasonic blade,
   wherein in response to movement of the trigger in a first direction, the clamp arm is configured to pivot toward the ultrasonic blade,
   wherein in response to movement of the trigger in a second direction, the clamp arm is configured to pivot away from the ultrasonic blade and the blade cooling system is configured to simultaneously deliver liquid coolant to the ultrasonic blade.

2. The apparatus of claim 1, wherein the movement of the trigger in the first direction comprises movement of the trigger toward the body, wherein the movement of the trigger in the second direction comprises movement of the trigger away from the body.

3. The apparatus of claim 1, wherein the blade cooling system further comprises a fluid pump, wherein the fluid pump is operable to direct liquid coolant toward the ultrasonic blade in response to movement of the trigger in the second direction.

4. The apparatus of claim 3, wherein the fluid pump comprises a peristaltic pump.

5. The apparatus of claim 4, wherein the peristaltic pump comprises a resilient tube configured to contain liquid coolant, and a roller positioned to contact the resilient tube, wherein the roller is configured to deform the resilient tube to thereby direct liquid coolant toward the ultrasonic blade in response to movement of the trigger in the second direction.

6. The apparatus of claim 4, wherein the peristaltic pump is configured to assume an inactive state during movement of the trigger in the first direction.

7. The apparatus of claim 1, further comprising a blade cover extending along the ultrasonic blade, wherein the blade cover is positioned to define a gap between an inner surface of the blade cover and an outer surface of the ultrasonic blade, wherein the blade cooling system is operable to deliver liquid coolant distally to the ultrasonic blade through the gap.

8. The apparatus of claim 7, wherein the blade cover has a closed distal end disposed about a distal tip of the ultrasonic blade.

9. The apparatus of claim 7, wherein the blade cover has an open distal end configured to expose a distal tip of the ultrasonic blade.

10. The apparatus of claim 1, wherein the shaft assembly further comprises:
(i) an inner tube,
(ii) an outer tube, and
(iii) an interior space extending longitudinally between the inner tube and the outer tube, wherein the blade cooling system is in fluid communication with the interior space,
wherein the blade cooling system is operable to direct liquid coolant distally through the interior space and toward the ultrasonic blade in response to movement of the trigger in the second direction.

11. The apparatus of claim 10, further comprising a blade cover extending along the ultrasonic blade, wherein the blade cover is positioned to define a gap between an inner surface of the blade cover and an outer surface of the ultrasonic blade, wherein the gap is in fluid communication with the interior space, wherein the blade cooling system is operable to deliver liquid coolant distally to the ultrasonic blade through the interior space and the gap.

12. The apparatus of claim 10, wherein the inner tube and the outer tube are configured to rotate relative to the body, wherein one of the inner tube or the outer tube is operable to translate relative to the other of the inner tube or the outer tube to pivot the clamp arm relative to the ultrasonic blade.

13. The apparatus of claim 1, wherein the blade cooling system comprises a compressible reservoir configured to store liquid coolant, wherein the compressible reservoir is configured to compress and thereby direct liquid coolant to the ultrasonic blade in response to movement of the trigger in the second direction.

14. The apparatus of claim 1, wherein the blade cooling system is configured to deliver liquid coolant to the ultrasonic blade through the clamp arm.

15. The apparatus of claim 14, wherein the clamp arm includes a fluid inlet opening and a fluid outlet opening arranged proximal to the fluid inlet opening.

16. An apparatus for operating on tissue, the apparatus comprising:
(a) a body;
(b) a shaft assembly extending distally from the body, wherein the shaft assembly comprises an acoustic waveguide configured to couple with an ultrasonic transducer;
(c) an end effector, wherein the end effector comprises:
(i) an ultrasonic blade in acoustic communication with the acoustic waveguide, and
(ii) a clamp arm, wherein the clamp arm is pivotable toward and away from the ultrasonic blade to clamp tissue therebetween; and
(d) a blade cooling system operable to deliver liquid coolant to the ultrasonic blade, wherein the blade cooling system comprises a compressible reservoir arranged within the shaft assembly and configured to store liquid coolant,
wherein the compressible reservoir is configured to compress and thereby direct liquid coolant to the ultrasonic blade in response to movement of the clamp arm relative to the ultrasonic blade.

17. The apparatus of claim 16, wherein the compressible reservoir is arranged within a distal portion of the shaft assembly.

18. The apparatus of claim 16, wherein the compressible reservoir comprises at least one of a sponge or a bladder.

19. An apparatus for operating on tissue, the apparatus comprising:
(a) a body;
(b) a shaft assembly extending distally from the body, wherein the shaft assembly comprises an acoustic waveguide configured to couple with an ultrasonic transducer;
(c) an end effector, wherein the end effector comprises:
(i) an ultrasonic blade in acoustic communication with the acoustic waveguide, and
(ii) a clamp arm, wherein the clamp arm is pivotable toward and away from the ultrasonic blade to clamp tissue therebetween; and
(d) a blade cooling system operable to deliver liquid coolant to the ultrasonic blade, wherein the blade cooling system comprises an outlet opening provided by the clamp arm, wherein the blade cooling system is operable to direct liquid coolant through the outlet opening and toward the ultrasonic blade in response to movement of the clamp arm away from the ultrasonic blade.

20. The apparatus of claim 19, wherein the blade cooling system further comprises:
(i) an inlet opening provided by the clamp arm and arranged distally of the outlet opening, and
(ii) an interior chamber of the clamp arm,
wherein the interior chamber is configured to receive evaporated fluid through the inlet opening when the clamp arm is pivoted toward the ultrasonic blade,
wherein the interior chamber is further configured to condense the evaporated fluid into liquid and direct the liquid through the outlet opening toward the ultrasonic blade to thereby cool the ultrasonic blade when the clamp arm is pivoted away from the ultrasonic blade.

* * * * *